United States Patent
Amano et al.

(10) Patent No.: US 6,890,304 B1
(45) Date of Patent: May 10, 2005

(54) DEVICE FOR DIAGNOSING PHYSIOLOGICAL STATE AND DEVICE FOR CONTROLLING THE SAME

(75) Inventors: Kazuhiko Amano, Suwa (JP); Kazuo Uebaba, Yokohama (JP); Hitoshi Ishiyama, Toride (JP)

(73) Assignee: Seiko Epson Corporation, Tokyo (JP)

( * ) Notice: Subject to any disclaimer, the term of this patent is extended or adjusted under 35 U.S.C. 154(b) by 681 days.

(21) Appl. No.: 09/587,049

(22) Filed: Jun. 2, 2000

Related U.S. Application Data

(62) Division of application No. 08/765,465, filed on Apr. 2, 1997.

(30) Foreign Application Priority Data

| May 12, 1995 | (JP) | 7-114996 |
| May 12, 1995 | (JP) | 7-114997 |
| May 12, 1995 | (JP) | 7-114998 |
| May 12, 1995 | (JP) | 7-114999 |
| May 12, 1995 | (JP) | 7-115000 |

(51) Int. Cl.$^7$ .............................................. A61B 5/00
(52) U.S. Cl. ............................ 600/500; 606/65; 606/66
(58) Field of Search ........................ 600/485, 500–503, 600/300–301, 490, 493–496, 455, 453–6, 544–5; 604/65–67

(56) References Cited

U.S. PATENT DOCUMENTS

| 4,080,966 A | * | 3/1978 | McNally ...................... 600/486 |
| 4,425,920 A | * | 1/1984 | Bourland et al. ............ 600/500 |
| 4,533,346 A | * | 8/1985 | Cosgrove, Jr. et al. ....... 604/66 |
| 4,664,127 A |   | 5/1987 | Ikeyama |

(Continued)

FOREIGN PATENT DOCUMENTS

| DE | 3826943 | 2/1990 |
| EP | 0 434 399 | 6/1991 |
| EP | 0 627 191 | 7/1994 |

(Continued)

*Primary Examiner*—Robert L. Nasser, Jr.
(74) *Attorney, Agent, or Firm*—Mark P. Watson

(57) ABSTRACT

The present invention relates to a device for diagnosing physiological state based on blood pulse waves detected in the body. It is the objective of the present invention to provide a device which correctly diagnoses the current physiological state based on changes in physiological state measured over a specified period of time in the past while taking into consideration the cyclical variation exhibited in physiological state. In order to realize this objective, the device according to the present invention has as its main components: blood pulse wave detector 381 and stroke-volume-per-beat measurer 382 which respectively detect blood pulse wave and stroke volume in the body; blood pulse wave extraction memory 386 which extracts characteristic information from the detected blood pulse wave; memory 383 in which the physiological state calculated from the stroke volume and this characteristic information is stored; output portion 385 which outputs an alarm; and microcomputer 387 which controls each part inside the device. The microcomputer calculates the circulatory parameters based on characteristic information obtained from the waveform extraction memory, and stores the parameters in memory at specified time intervals. At these times, microcomputer 387 calculates the circulatory parameters from the stroke volume per beat and the characteristic information of the blood pulse wave at specified time intervals, and stores the parameters in memory 383. Further, microcomputer 387 reads out from memory 383 the circulatory parameters from a specified time interval in the past, and calculates the average value and standard deviation. Microcomputer 387 then determines whether or not the current circulatory parameters are within a specified range determined by their average value and standard deviation. When the circulatory parameters are determined to be outside this range, microcomputer 387 controls output portion 385 to sound an alarm.

23 Claims, 93 Drawing Sheets

U.S. PATENT DOCUMENTS

| | | | |
|---|---|---|---|
| 4,703,760 A | | 11/1987 | Miyawaki et al. |
| 5,002,055 A | * | 3/1991 | Merki et al. ................. 600/345 |
| 5,007,430 A | | 4/1991 | Dardik |
| 5,101,831 A | * | 4/1992 | Koyama et al. ............ 600/500 |
| 5,103,833 A | | 4/1992 | Apple |
| 5,153,827 A | * | 10/1992 | Coutre et al. ................. 604/66 |
| 5,256,157 A | * | 10/1993 | Samiotes et al. ............. 604/67 |
| 5,298,021 A | * | 3/1994 | Sherer .......................... 604/66 |
| 5,311,872 A | | 5/1994 | Apple |
| 5,357,427 A | * | 10/1994 | Langen et al. .............. 600/300 |
| 5,417,220 A | | 5/1995 | Apple |
| 5,438,983 A | | 8/1995 | Falcone |
| 5,464,012 A | | 11/1995 | Falcone |
| 5,474,552 A | * | 12/1995 | Palti ............................ 604/67 |
| 5,551,435 A | * | 9/1996 | Sramek ....................... 600/481 |
| 5,558,640 A | * | 9/1996 | Pfeiler et al. ................. 604/67 |
| 5,730,137 A | * | 3/1998 | Amano et al. .............. 600/500 |
| 5,733,259 A | * | 3/1998 | Valcke et al. ................. 604/66 |

FOREIGN PATENT DOCUMENTS

| | | |
|---|---|---|
| EP | 0 642 992 A2 | 3/1995 |
| EP | 0 642 992 A3 | 3/1995 |
| EP | 0 645 117 | 3/1995 |
| FR | 2 649 512 | 1/1991 |
| FR | 2 694 421 | 2/1994 |
| GB | 2 233 764 | 1/1991 |
| GB | 2 281 781 | 3/1995 |
| JP | 57-66735 | 4/1982 |
| JP | 59-108638 | 7/1984 |
| JP | 60-48714 | 4/1985 |
| JP | 60-128605 | 8/1985 |
| JP | 60-192842 | 12/1985 |
| JP | 61-187835 | 8/1986 |
| JP | 62-155830 | 7/1987 |
| JP | 63-62102 | 4/1988 |
| JP | 63-212327 | 9/1988 |
| JP | 63-290542 | 11/1988 |
| JP | 64-56715 | 4/1989 |
| JP | 01-131648 | 5/1989 |
| JP | 1-126206 | 8/1989 |
| JP | 1-299531 | 12/1989 |
| JP | 01-305962 | 12/1989 |
| JP | 02-001218 | 1/1990 |
| JP | 02-055034 | 2/1990 |
| JP | 02-147047 | 6/1990 |
| JP | 2-246837 | 10/1990 |
| JP | 02-277435 | 11/1990 |
| JP | 3-15502 | 2/1991 |
| JP | 3-41926 | 2/1991 |
| JP | 03-217672 | 9/1991 |
| JP | 3-284236 | 12/1991 |
| JP | 4-250134 | 9/1992 |
| JP | 04-269972 | 9/1992 |
| JP | 4-300562 | 10/1992 |
| JP | 04-300562 | 10/1992 |
| JP | 04-309362 | 10/1992 |
| JP | 04-348759 | 12/1992 |
| JP | 05-237351 | 9/1993 |
| JP | 5-248356 | 9/1993 |
| JP | 06-070898 | 3/1994 |
| JP | 6-131936 | 5/1994 |
| JP | 6-41743 | 6/1994 |
| JP | 6-156112 | 6/1994 |
| JP | 06-201855 | 7/1994 |
| JP | 6-211822 | 8/1994 |
| JP | 06-311973 | 11/1994 |
| JP | 7-76380 | 3/1995 |
| JP | 07-116138 | 5/1995 |
| JP | 7-148253 * | 6/1995 .................. 600/500 |
| WO | WO 94/09912 | 5/1994 |

* cited by examiner

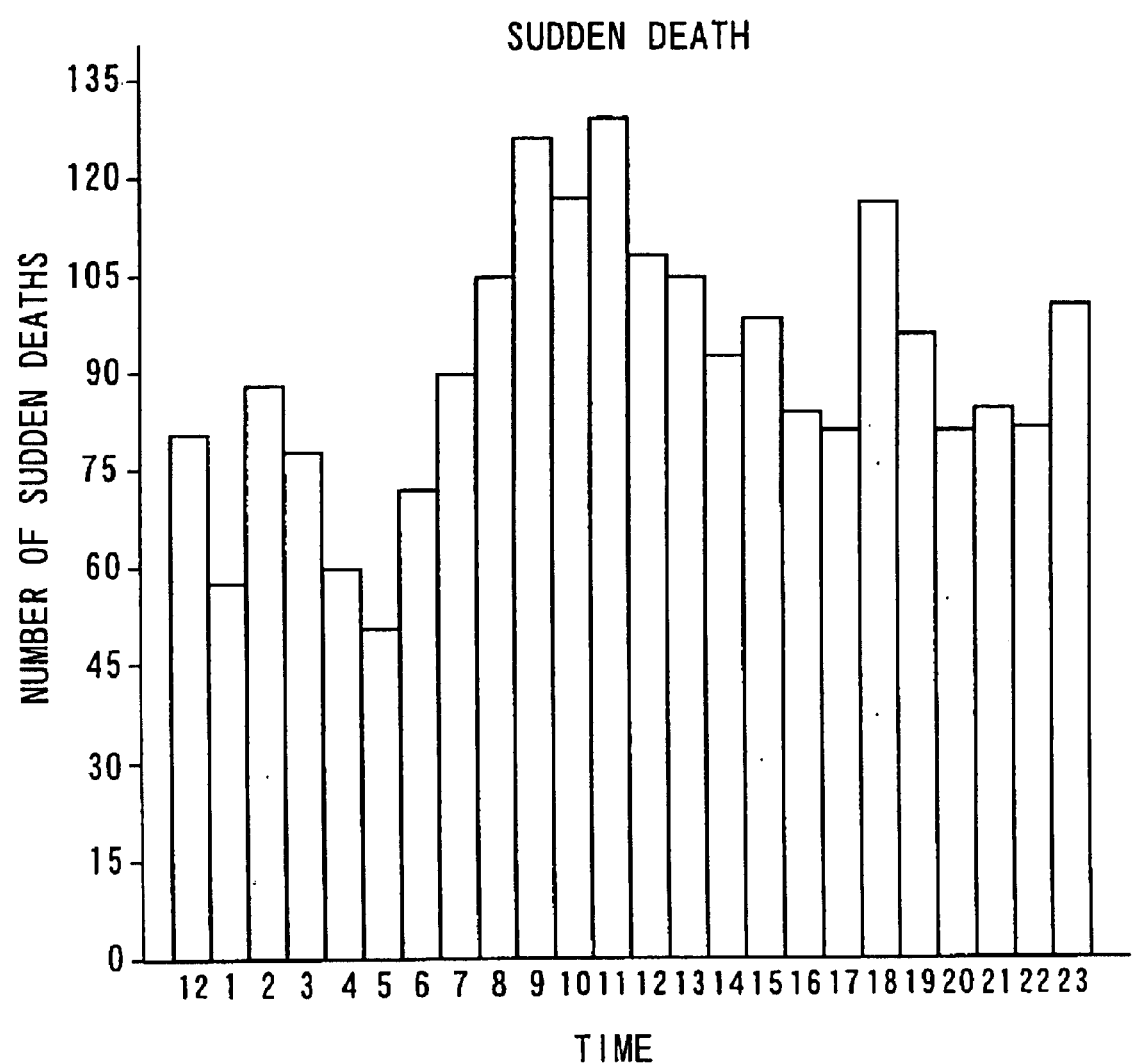

DAILY VARIATION IN Rc

DAILY VARIATION IN Rp

DAILY VARIATION IN L

DAILY VARIATION IN C

DAILY VARIATION IN Rc
(TOTAL AVERAGE)

DAILY VARIATION IN Rp
(TOTAL AVERAGE)

DAILY VARIATION IN C
(TOTAL AVERAGE)

DAILY VARIATION IN L
(TOTAL AVERAGE)

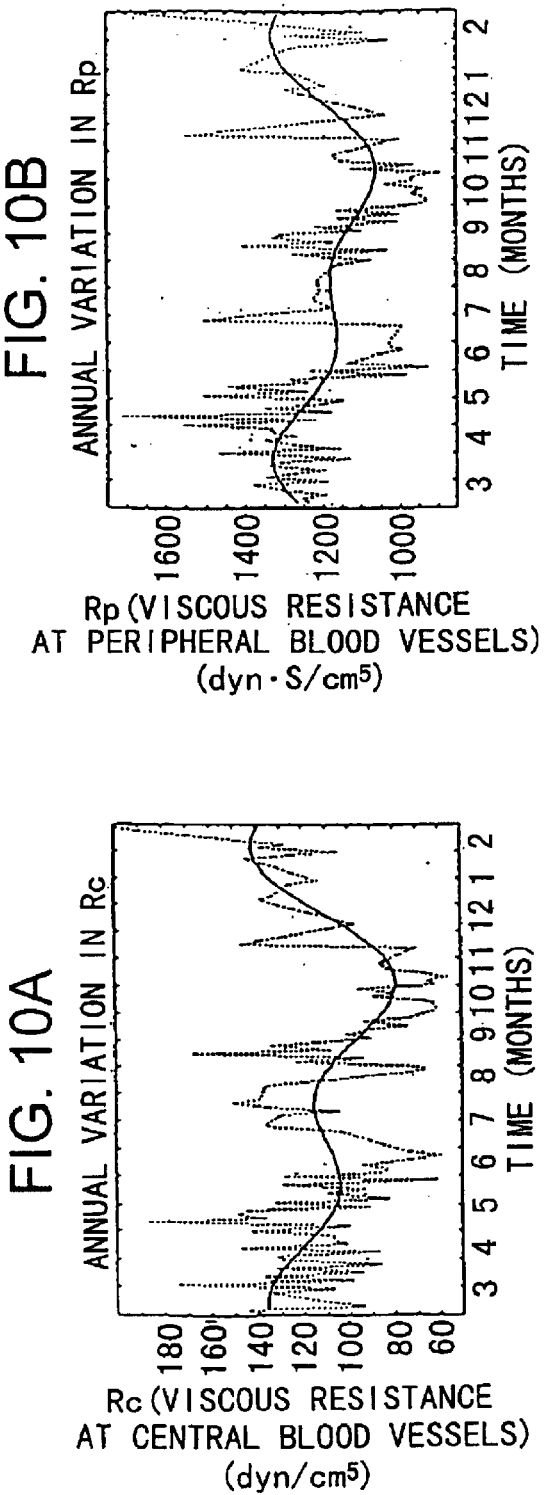
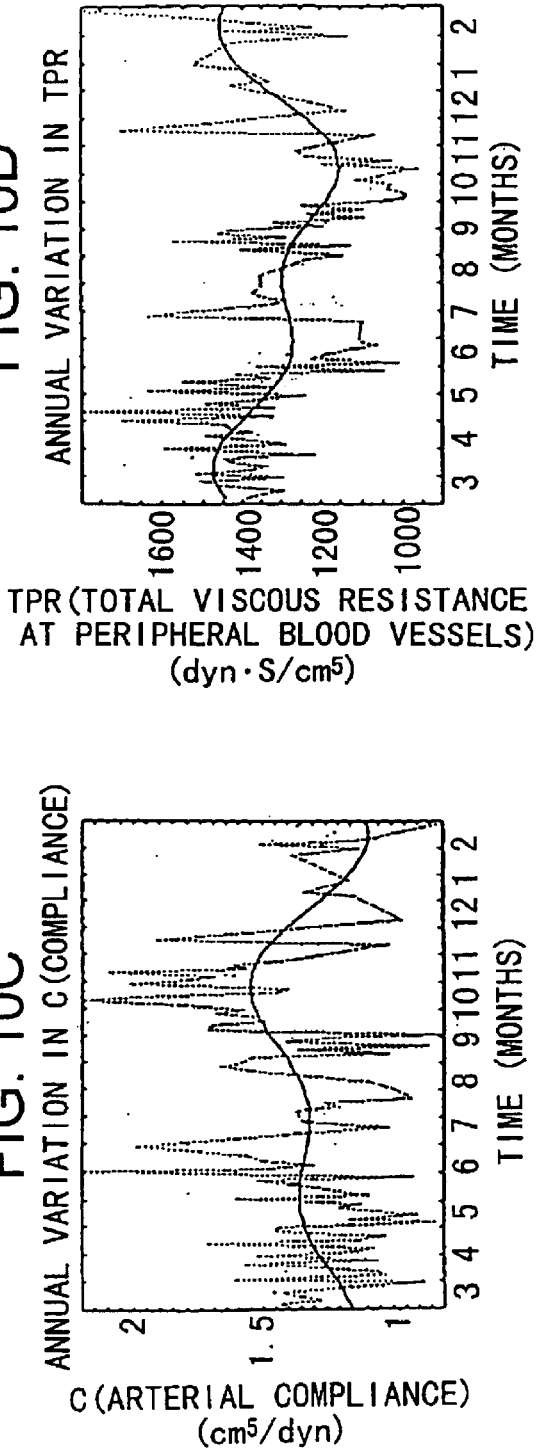
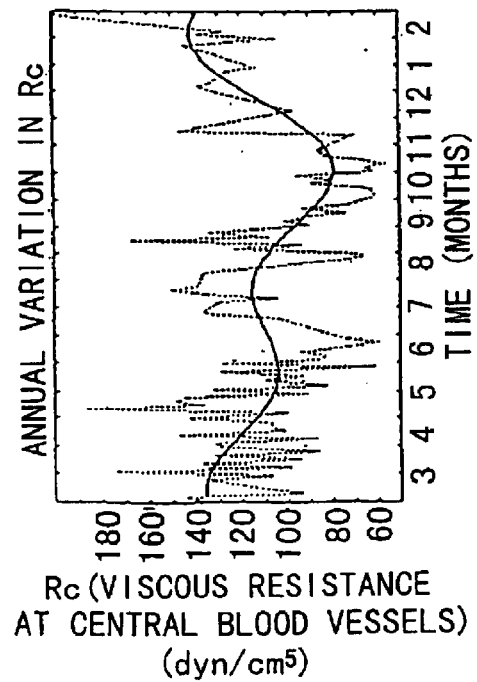
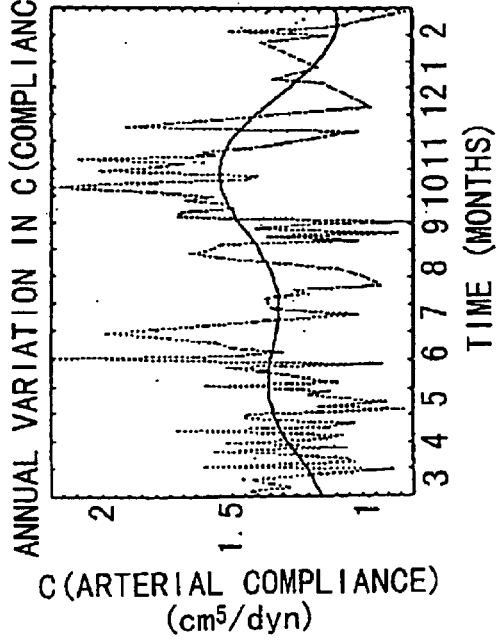

DAILY VARIATION IN PHASE 2 (FFT)

DAILY VARIATION IN PHASE 3 (FFT)

DAILY VARIATION IN PHASE 4 (FFT)

DAILY VARIATION IN AMPLITUDE 3 (FFT)

DAILY VARIATION IN NORMALIZED AMPLITUDE 3 (FFT)

FIG. 38A
CONTROL SIGNAL T
FIG. 38B
CONTROL SIGNAL T
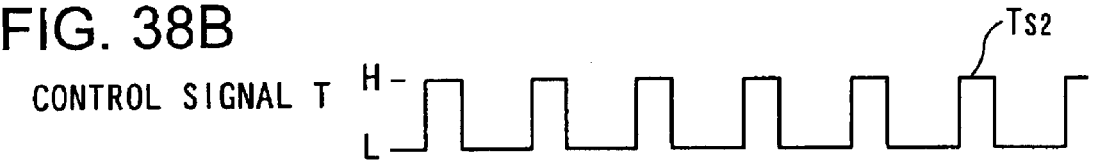
FIG. 38C
CONTROL SIGNAL T
FIG. 38D
CONTROL SIGNAL T
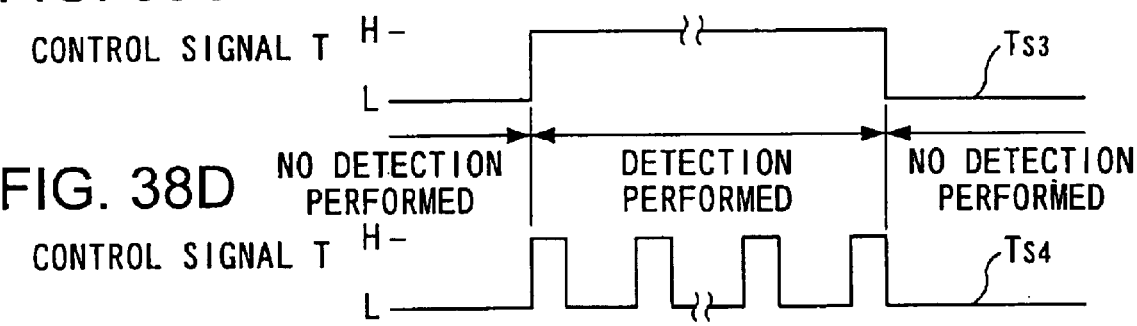
FIG. 38E
BIAS
FIG. 38F
BIAS

| PEAK ADDRESS ADR3 | 0 | 1 | 2 | 3 | 4 |
|---|---|---|---|---|---|
| WAVEFORM VALUE ADDRESS ADR1 | | | | | |
| PEAK CLASSIFICATION B/T | | | | | |
| WAVEFORM VALUE W | | | | | |
| STROKE STRK | | | | | |
| SLOPE INFORMATION SLP | | | | | |

PEAK INFORMATION

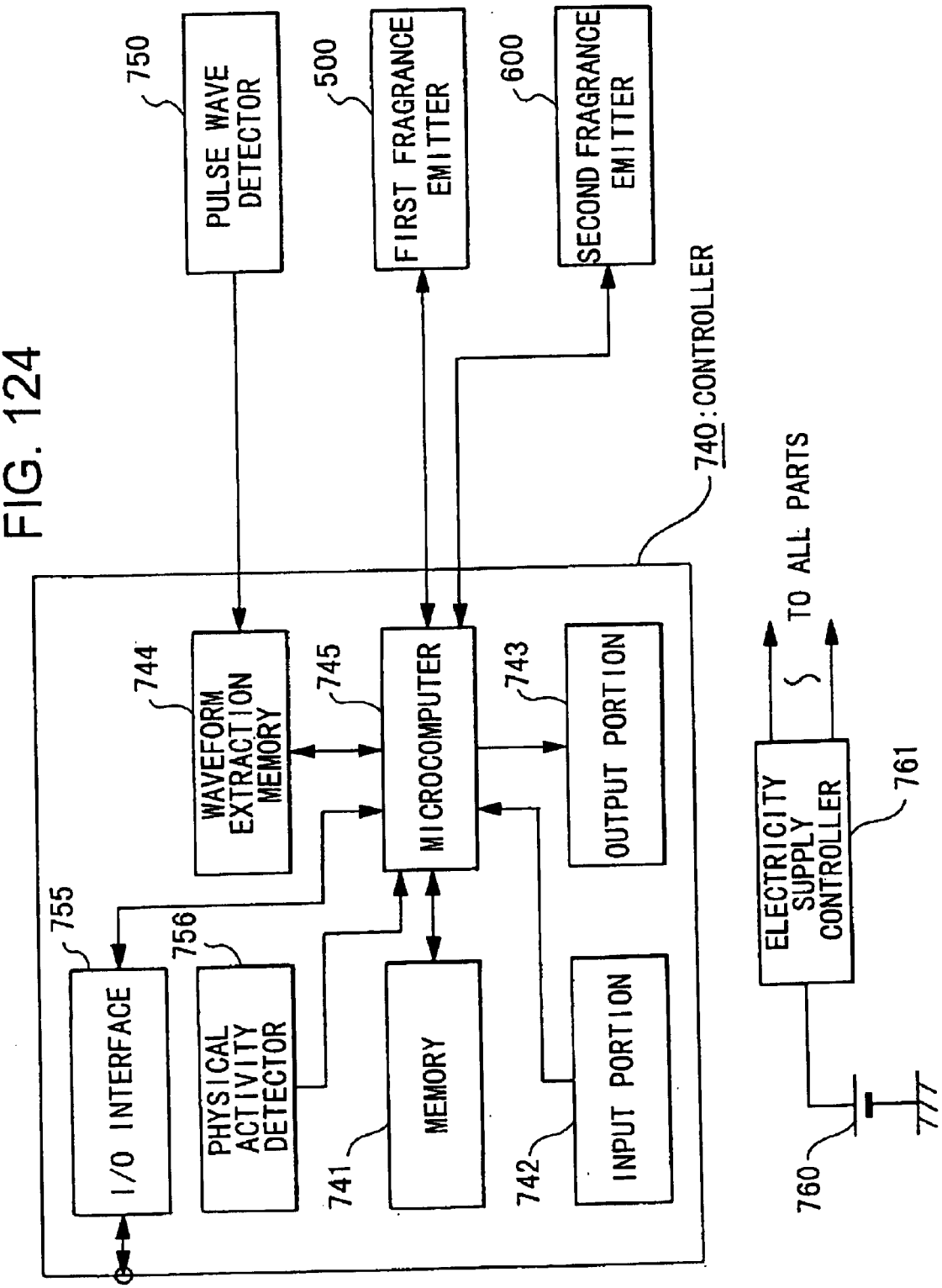

DEVICE FOR DIAGNOSING PHYSIOLOGICAL STATE AND DEVICE FOR CONTROLLING THE SAME

CONTINUING APPLICATION DATA

This application is a divisional of U.S. patent application Ser. No. 08/765,465, filed Apr. 2, 1997, which is 371 of PCT/JP96/01254, filed May 13, 1996, the contents of which applications are incorporated herein in their entirety by reference.

BACKGROUND OF THE INVENTION

1. Field of the Invention

The present invention relates to a device for diagnosing an organism and controlling the physiological state thereof, the devices operating by extracting the physiological state from the organism's pulse waves, diagnosing the condition of the organism and carrying out control of the physiological state thereof after taking into consideration the cyclic fluctuation which occurs naturally in the physiological state of that organism.

2. Description of the Related Art

Blood pressure, heart rate and the like are most typically used when diagnosing the condition of the circulatory system in the human body. Emphasis has conventionally been placed on such easily measured indicators as maximum and minimum blood pressures, blood pulse rate and the like which are obtained from the body, as one type of criterion for determining the state of the circulatory system and, in a wider sense, the condition of the organism. However, when carrying out a more specific diagnosis, it becomes necessary to measure circulatory parameters such as the viscous resistance of the blood vessel, compliance and the like. This will be explained further below.

The pressure waveform and blood flow rate at the proximal portion of the aorta and at the site of insertion of a catheter into an artery are frequently measured in order to measure physiological state indicators such as the circulatory parameters. For this purpose, a direct method of measurement, in which a catheter is inserted into an artery, or an indirect method employing ultrasound waves, may be applied. However, in the case of a method employing catheter insertion into an artery, it is necessary to subject the organism to an invasive and large device. On the other hand, while a method employing ultrasound or the like allows a non invasive observation of blood flow inside the blood vessels, this method is complicated by the fact that it requires training and, moreover, necessitates a large device to carry out the measurements.

As research on blood pulse waves has progressed, it has become clear that a variety of physiological conditions, not obtainable from blood pressure values and blood pulse rate alone, can be gotten by using a variety of methods to analyze blood pulse waveforms obtained from the human body. Diagnosis can then be made based on these physiological states. A "blood pulse wave" is the blood flow wave which is pumped out from the heart and propagates through a blood vessel. It is known that various medical information can be obtained by detecting and analyzing blood pulse waves. In particular, when measuring blood pulse waves at the periphery of an organism's body, the fingertip plethysmogram, the blood pulse wave of the radius artery, or the like are measured. However, there are a variety of other sites on the human body at which the blood pulse wave can be measured. In addition, there are a variety of forms which a blood pulse wave may take, three examples of which are shown in FIGS. 1A through 1C. The Ping mai, Hua mai and Xuan mai shown respectively in FIGS. 1A through 1C may be cited as representative blood pulse waveforms as categorized in Chinese medicine, a medical learning which is recognized in both the East and the West. "Ping mai" as used here indicates the waveform obtained from a healthy subject, with the blood pulse wave example shown in FIG. 1A measured in a 34 year old male test subject. As shown in the figure, a Ping mai is relaxed, and exhibits a constant rhythm without disruption. The Hua mai, on the other hand, is caused by an abnormality in the flow of blood in which the movement of the blood through the vessel becomes extremely smooth due to a mammary tumor, liver or kidney ailment, respiratory ailment, stomach or intestinal ailment, inflammation, or some other illness. The blood pulse wave shown in FIG. 1B is a typical example of a Hua mai, and was taken from a 28 year old male. As shown in the figure, the waveform of a Hua mai exhibits a sharp, rapid rise, and then falls off immediately. The aortic notch is deep, while the peak in the subsequent relaxation period is considerably higher than Ping mai. On the other hand, a Xuan mai is caused by an increase in the tension in the walls of the blood vessels, and is seen in diseases such as liver and gall ailments, dermatological ailments, high blood pressure, and pain ailments. It is believed that tension in the autonomic nervous system causes the walls of the blood vessels to constrict, decreasing elasticity, so that the effect of the blood pulse movement of the pumped blood is not readily expressed, causing this phenomenon. A typical example of a Xuan mai is shown in FIG. 1C and was taken from a 36 year old male. As shown in the figure, the waveform of a Xuan mai rises violently, and does not fall off immediately but remains at a high pressure state for a fixed period of time. In the graphs shown in FIGS. 1A through 1C, blood pressure (BP) measured in mmHG is shown on the vertical axis, while time in sec is displayed on the horizontal axis.

As will be understood from the preceding discussion, by analyzing the waveform of the blood pulse wave and specifying whether the blood pulse wave is, for example, a Ping mai, Hua mai or Xuan mai, it becomes possible to determine the specific ailment, or provide a diagnosis of the patient's condition. It has not been the conventionally practice to carry out qualitative evaluations incorporating this point, however.

Further, as will be explained in greater detail below, the human body's physiological state fluctuates according to a regular rhythm, repeating these rhythms on daily, monthly or annual cycles. This characteristic applies as well to the various indicators of physiological state which can be obtained from the blood pulse wave. Accordingly, if diagnosis and control of an organism's physiological state is carried out without taking into consideration these cyclic fluctuations, then the diagnosis and control of the physiological state are meaningless. However, because a small device able to continuously measure physiological state throughout the daily activities of an organism has not been available previously, it would seem that these cyclic variations in physiological state have not been taken into consideration in the diagnostic technology employed until now.

SUMMARY OF THE INVENTION

Accordingly, it is the object of the present invention to provide the following devices which take into consideration the cyclic variation in physiological state:

1) a diagnostic device which accurately diagnoses the condition of a test subject based on past changes in physiological state which were measured over a past prespecified period of time 2) a diagnostic device which displays a variety of information related to an organism using indicators of blood pulse wave fluctuation 3) a control device for drug administration which monitors the physiological state and carries out the necessary administration of drugs 4) a drug emission device which controls an organism's internal states of arousal or sedation by emitting a fragrance at an appropriate timing 5) a doze prevention device which detects a doze state by analyzing the alertness level in the human body from the activity of the blood pulse wave In order to meet the above-stated objectives, the first aspect of the present invention is characterized in measuring cyclically varying indicators of physiological state in an organism over a fixed period of time, and diagnosing the condition of the organism based on these indicators. Thus, the first aspect of the present invention enables a precise diagnosis of physiological state which takes into consideration the cyclic fluctuations in physiological state.

The second aspect of the present invention is characterized in repeatedly calculating indicators of physiological state; comparing each indicator calculated with an indicator obtained in the past; and outputting the results of the comparison. Thus, by means of the second aspect of the present invention, it is possible to confirm changes in the physiological state by comparing the current indicator and a past indicator.

The third aspect of the present invention is characterized in the provision of a measuring means, a recording means and a control means, wherein:

the measuring means measures indicators of physiological state at a plurality of times every day; and the control means records indicators of physiological state in the recording means at the plurality of times, determines based on the stored data in the recording means whether or not the current indicator is within the range of values displayed by the indicator at the same time of the day over a past fixed period of time, and provides notification of the results of this determination.

Thus, in the forth aspect of the present invention, since it is possible to confirm whether or not the current indicator is within the range of fluctuation displayed by that indicator over a past fixed period of time, it is possible to provide notification when the physical condition on the current day has changed from the physical condition over the recent past several days. In other words, when the current indicator is within the established range of fluctuation, so that the user is notified that his physical condition is good, a sense of psychological reassurance is provided, making this an indicator of quality of life (QOL). On the other hand, when the user is notified that the current indicator is outside the past range of fluctuation, then the user is made aware that his condition is not normal.

The forth aspect of the present invention is provided with a measuring means, recording means, and control means, wherein:

the measuring means measures indicators of physiological state at a plurality of times every day; and the control means stores indicators of physiological state in the recording means at the plurality of times, and provides notification of the deviation in the current indicator from a standard indicator calculated from indicators measured at the same time of the day over an past fixed period of time.

Thus, as a result of the fourth aspect of the present invention, it is possible for the user to accurately know the conditions in his body on the current day.

The fifth aspect of the present invention is characterized in the provision of a measuring means, a recording means and a control means, wherein:

the measuring means measures indicators of physiological state at a plurality of times during the day; and the control means stores these physiological state indicators in the recording means at the plurality of times during the day, determines the mode of change in each of the indicators calculated on the present day and stores this data in the recording means, determines based on the data stored in the recording means whether or not the mode of change in the current indicator is in accordance with the mode of change in the indicator measured at the same time of the day during a past fixed period of time, and provides notification of the results of this determination.

The sixth aspect of the present invention is characterized in the provision of a measuring means, a recording means and a control means, wherein:

the measuring means measures indicators of physiological state at a plurality of times during the day; and the control means stores these physiological state indicators in the recording means at the plurality of times during the day, obtains based on each indicator calculated on the present day the time at which the indicator takes on a large value and stores this data in the recording means, determines based on the data stored in the recording means whether or not the mode of change in the current indicator is in line with the change in the indicator measured at that same time of the day during a past fixed period of time, and provides notification of the results of this determination.

The seventh aspect of the present invention is characterized in the provision of a measuring means, a recording means and a control means, wherein:

the measuring means measures indicators of the physiological state of the organism at a plurality of times during the day; and the control means stores these physiological state indicators in the recording means at the plurality of times during the day, obtains based on each of the indicators calculated on the present day the time at which the indicator takes on a small value and stores this data in the recording means, determines based on the data stored in the recording means whether or not the mode of change in the current indicator is in line with the change in the indicator measured at the same time of the day over a past fixed period of time ; and provides notification of the results of this determination.

Thus, in the above-described sixth and seventh aspects of the present invention, a warning is provided when the rise or fall in a physiological state indicator is not in line with past variation in that indicator, making it possible to catch an abnormal or unnatural variation in physiological state. Further, conversely, since the user is also notified of the good physiological condition when the variation in the indicator is in line with past fluctuation, the user obtains a sense of psychological reassurance concerning his physical state. As a result, the indicator can serve as an indicator of the user's degree of quality-of-life.

The eighth aspect of the present invention is characterized in the provision of a measuring means, a recording means, a first control means, a calculating means, a second control means, and a notifying means, wherein the measuring means measures an indicator showing the physiological state in the organism;

the recording means stores the physiological state indicator;

the first control means uptakes the physiological state indicator measured by the measuring means over a fixed period of time and stores the indicator in the recording means;

the calculating means, upon direction by the user, extracts the indicator stored in the recording means, carries out prespecified calculations, and output the results of this calculation;

the second control means uptakes the indicator upon direction by the user from the measuring means; and the notifying means provides notification of the calculated results and the indicator at the time of the user's direction.

Thus, as a result of the eighth aspect of the present invention, it is possible for the user to obtain information relating to his physical condition at any time.

The ninth aspect of the present invention is characterized in the provision of a measuring means, a recording means, a first control means, a calculating means, a second control means, and a notifying means, wherein:

the measuring means measures an indicator showing physiological state;

the recording means stores the physiological state indicator;

the first control means uptakes the physiological state indicators measured by the measuring means over a fixed period of time and stores the indicators in the recording means;

the calculating means, upon direction by the user, extracts indicators measured over a past prespecified number of days from the recording means, and obtains the maximum value from among these past indicators;

the second control means uptakes the indicator upon direction by the user from the measuring means, compares this indicator to the aforementioned maximum value indicator, and determines that an abnormal state is present when the indicator at the time of direction by the user is larger than the aforementioned maximum value, or determines that an abnormal state is not present when the value of the indicator at the time of direction by the user is not larger than the aforementioned maximum value; and the notifying means provides notification of the results for the determination of the presence or absence of an abnormal state.

The tenth aspect of the present invention is characterized in the provision of a measuring means, a recording means, a first control means, a calculating means, a second control means, and a notifying means, wherein:

the measuring means measures an indicator showing the physiological state;

the recording means stores the physiological state indicator; the first control means uptakes physiological state indicators measured by the measuring means over a fixed period of time, and stores the indicators in the recording means;

the calculating means, upon direction by the user, extracts indicators measured over a past prespecified number of days from the recording means, and obtains the minimum value from among these past indicators;

the second control means uptakes the indicator at the time of direction by the user from the measuring means, compares this indicator to the aforementioned minimum value, and determines that an abnormal state is present when the value of the indicator at the time of direction by the user is smaller than the aforementioned minimum value, or determines that an abnormal state is not present when the value of the indicator at the time of direction by the user is not smaller than the aforementioned minimum value; and the notifying means provides notification of the results for the determination of the presence or absence of an abnormal state.

The above-described ninth and tenth aspects of the present invention provide a warning to the user when his physical condition deviates noticeably from his physical condition over a recent period of time. Further, when a determination is made that there is no abnormal state present, the user is informed that his physical condition is fine, providing him with a sense of psychological reassurance. Accordingly, this can serve an indicator of the level of the user's quality-of-life.

The eleventh aspect of the invention is characterized in the provision of a measuring means, a body movement detection means, a recording means, a first control means, a calculating means, a second control means, and a notifying means, wherein the measuring means measures an indicator showing the physiological state;

the body movement detection means detects movement of the organism's body;

the recording means stores the physiological state indicator and the value measured by the body movement detection means;

the first control means uptakes physiological state indicators from the measurement means and the measured values of the body movement detection means over a fixed period of time, and stores these together in the recording means;

the calculating means, upon direction by the user, up takes the current value of the organism's body movement measured by the body movement detection means, selects from among the values measured by the body detection means stored in the recording means the value closest to the current value for body movement, and reads out and outputs the indicator that was stored together with the selected measured value in the recording means;

the second control means uptakes the indicator upon direction by the user from the measuring means; and the notifying means provides notification of the indicator output by the calculating means and the indicator uptaken by the second control means at the time of direction by the user.

Thus, as a result of the eleventh aspect of the present invention, in the case where the user is carrying out sports training or the like which affects physiological measurements, it is possible to display an indicator which is appropriate to the activity of the user by referencing past data for a similar activity.

The twelfth aspect of the present invention is characterized in measuring cyclically fluctuating physiological state indicators in the body over a fixed period of time, analyzing the state of the organism based on these indicators, and controlling the physiological state in accordance with the results of this analysis so as to affect a desirable state in the organism. Thus, by means of the twelfth aspect of the present invention, it is possible to accurately obtain the condition of the organism by taking into consideration the cyclic fluctuation in the organism's physiological state. As a result, it becomes possible to more accurately carry out control of various types of physiological states in order to affect a desired condition therein.

The thirteenth aspect of the present invention is characterized in the provision of a measuring means, an infusing means, and a drug administration control means; wherein:

the measuring means measures physiological state indicators related to arousal or sedation in a patient;

the infusing means administers a drug to the patient; and the drug administration control means issues a directive to the infusing means for drug administration when the physiological state indicators satisfy specific conditions.

Thus, by means of the thirteenth aspect of the present invention, the circulatory conditions in a patient can be stabilized by monitoring the condition of the patient and automatically administering a drug as necessary. As a result, it is possible to freely control the arousal/sedation state of a patient to affect a desirable condition.

The fourteen aspect of the present invention is characterized in the provision of a measuring means, a recording means, a control means, and an infusing means; wherein:

the measuring means measures physiological state indicators;

the recording means stores the indicators measured up until the current point in time;

the control means determines when a drug is to be infused based on the fluctuations displayed in the rhythm of the indicator over a past prespecified period of time, and outputs a drug infusion directive at the determined time; and the infusing means infuses the drug in accordance with the drug infusion directive.

Thus, by means of the fourteenth aspect of the present invention, since the time of drug infusion is determined based on the fluctuating rhythm of the physiological state, it is possible to automatically carry out the promotion or suppression of arousal or sedation states with the appropriate timing.

The fifteen aspect of the present invention is characterized in the provision of a measuring means, a recording means, a control means, and a drug infusing means; wherein:

the measuring means measures physiological state indicators;

the recording means stores the indicators measured up until the current point in time;

the control means outputs a drug infusion directive based on the current physiological state indicator and on the fluctuating rhythm of the indicator over a past prespecified period of time; and the infusing means infuses a drug in accordance with the drug infusion directive.

Thus, by means of the fifteenth aspect of the present invention, since drug infusion is controlled based on the current physiological state and the fluctuating rhythm of the physiological state in the past, it is possible to carry out drug infusion so as to induce a variation in the rhythm of the physiological state in line with the waveform for a constant rhythmic fluctuation.

The sixteen aspect of the present invention is characterized in the provision of a measuring means, a control means, and a notifying means; wherein:

the measuring means measures physiological state indicators;

the control means determines the user's doze state by comparing the physiological state indicator with a predetermined standard value, and outputs a warning indicator when a doze state is detected; and the notifying means warns the user based on the warning indicator output from the control means.

Thus, as a result of the sixteenth aspect of the present invention, the doze state of a user can be detected with a device employing a relatively simple method, while the device may be incorporated into a portable item which the user can freely carry around at all times.

The seventeenth aspect of the present invention is characterized in the provision of a measuring means, a recording means, a calculating means, a control means, and a notifying means, wherein:

the measuring means measures a physiological state indicator;

the recording means stores the indicators measured over fixed period of time;

the calculating means reads out the indicators showing physiological state over a past prespecified period of time from the recording means, and calculates the moving average of these indicators;

the control means determines the user's doze state by comparing the moving average of the indicators with a predetermined standard value, and outputs a warning indicator when a doze state is detected; and the notifying means warns the user based on the warning indicator output from the control means.

Thus, as a result of the seventeenth aspect of the present invention, it is possible to detect a doze state while taking into consideration the fluctuating rhythms in physiological state, so that the probability of misdetection is reduced.

Other objects and attainments together with a fuller understanding of the invention will become apparent and appreciated by referring to the following description and claims taken in conjunction with the accompanying drawings.

BRIEF DESCRIPTION OF THE DRAWINGS

FIG. 2 is a diagram disclosing the occurrence of sudden death;

FIGS. 10A–10D are a diagram showing the fluctuation in circulatory parameters over one year;

FIGS. 38A to D are all timing diagrams showing examples of the timing of the supply of control signal T to bias circuit 139;

FIGS. 38E to F are diagrams showing the waveform of a fixed current blood pulse from bias circuit 139;

FIG. 109 is a block diagram showing the structure of the drive for driving the same micro pump 501;

FIGS. 110 to 111 are diagrams to explain the operation of micro pump 501;

FIG. 112 is a block diagram showing the first structure of the device for controlling the administration of a drug according to the present invention;

FIGS. 113 to 114 are flow charts showing the operation of an embodiment employing a drug administration control device of the structure shown in FIG. 112;

FIG. 115 is a block diagram showing the second structure of the device for controlling the administration of a drug according to the present invention;

FIG. 116A is a diagram showing the effect of the emission of a fragrance on stroke volume per beat SV;

FIG. 116B is a diagram showing the effect of the emission of a fragrance on peripheral blood vessel resistance Rp;

FIGS. 117 to 123 are diagrams showing the mode of control of fragrance emission;

FIG. 124 is a block diagram showing the structure of the drug administration control device of the present invention;

FIG. 125A is a perspective view showing the mechanical structure of this same device;

FIG. 125B is a section view showing the mechanical structure of this same device;

FIG. 126 is a block diagram showing the structure of the doze prevention device according to the present invention;

Figure 126:
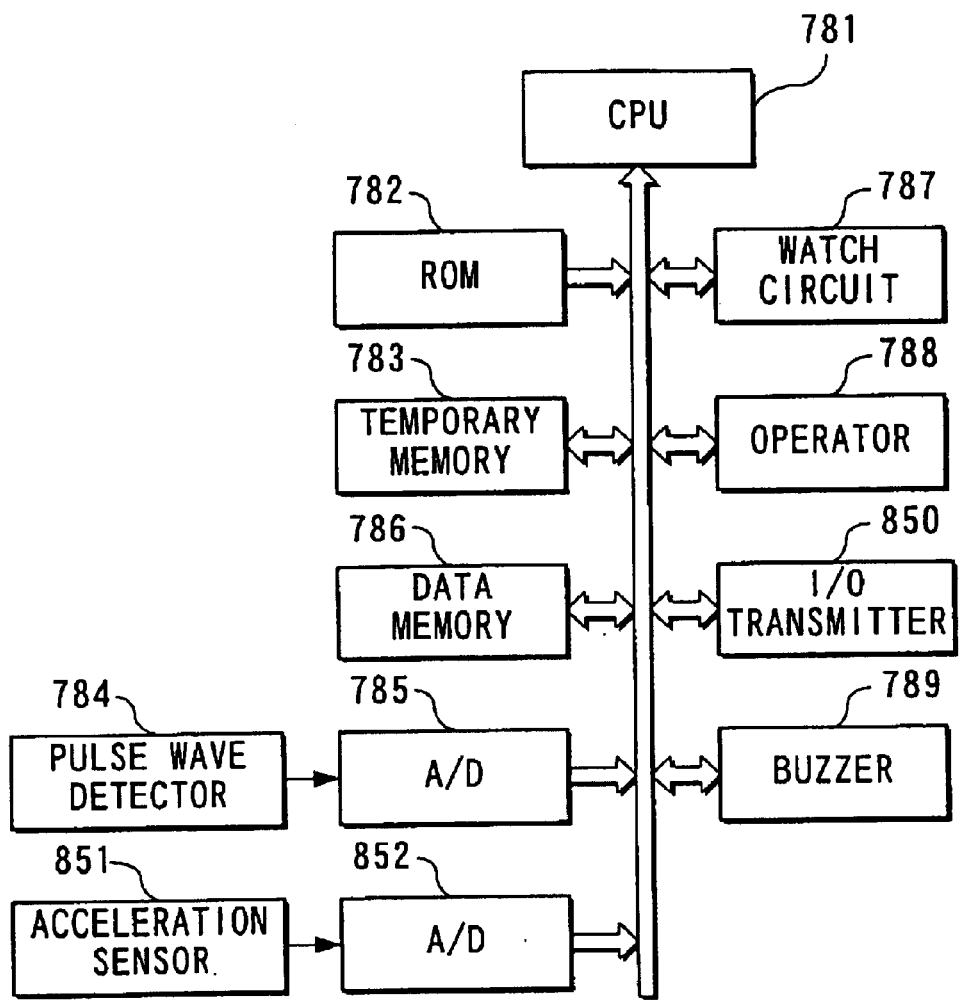
Figure 127:
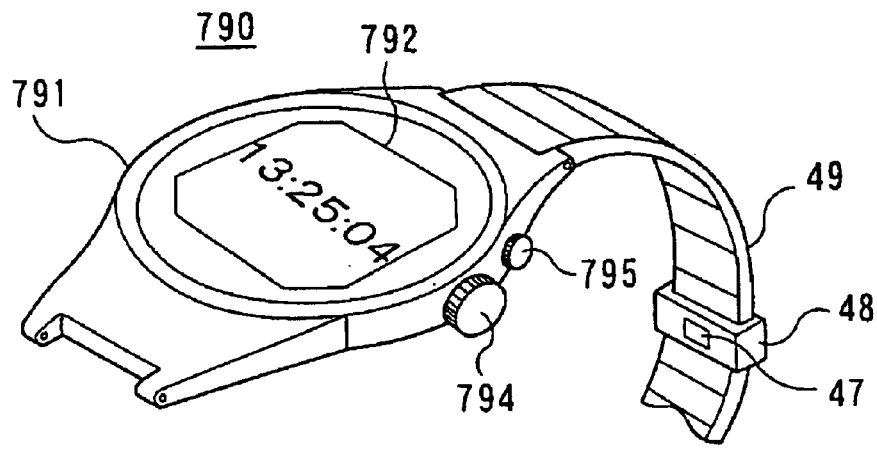
Figure 128:
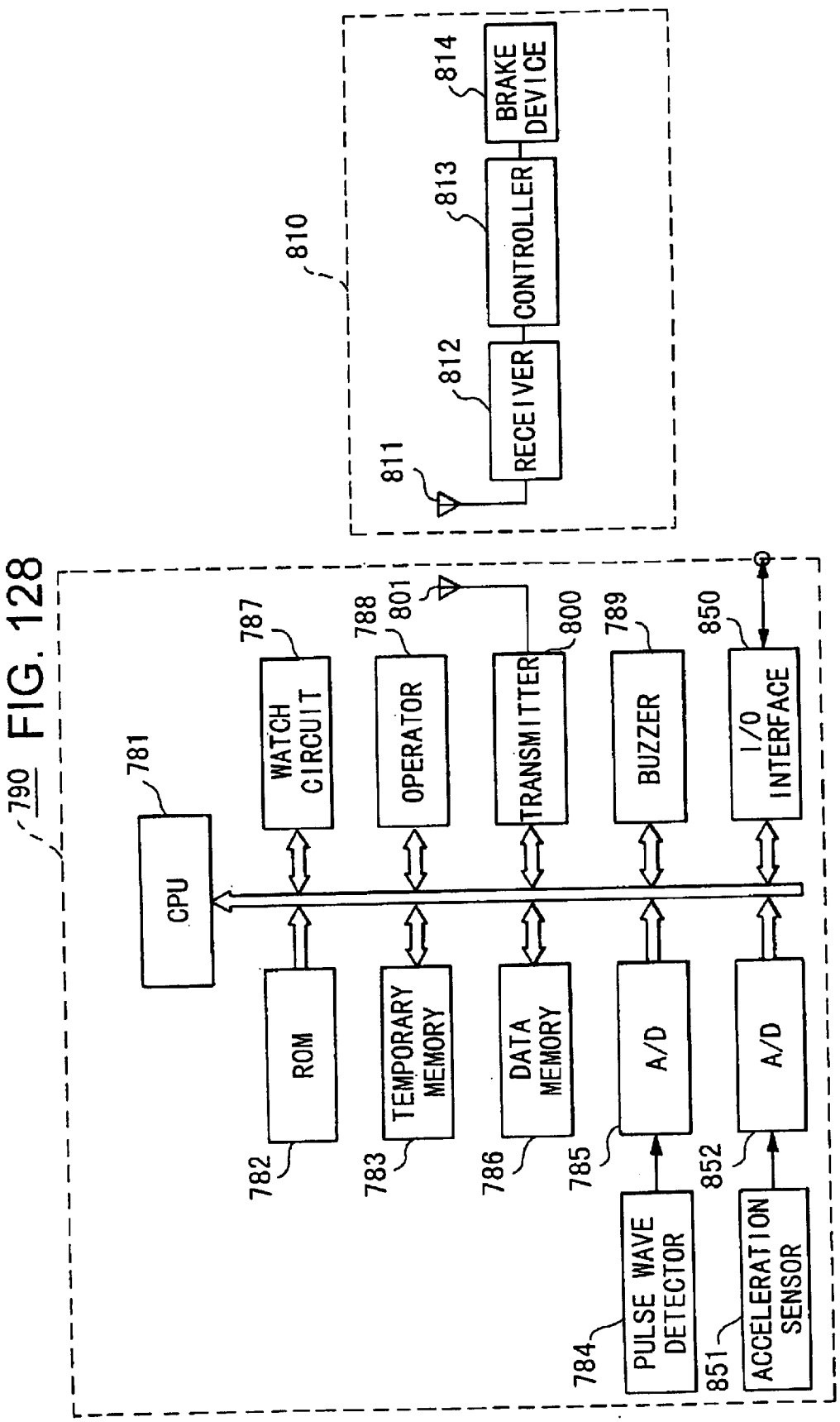

FIG. 127 is a perspective view of wrist watch 790 in which the device in FIG. 126 is incorporated; and FIG. 128 is a block diagram showing an example of another structure of this device.

DESCRIPTION OF THE PREFERRED EMBODIMENTS

Preferred embodiments of the present invention will now be explained below with reference to the figures. The following explanation will be separated into chapters in order to better facilitate the exercise of the present invention by one skilled in the art.

In Chapter 1, the results of experiments on cyclic fluctuation in physiological state, which is the basis of the present invention, will be explained. It is next necessary to provide a means for extracting blood pulse waves from the human body in order to carry out an analysis thereon. Toward this purpose, a variety of sensors for detecting blood pulse waves are explained in Chapter 2. In Chapter 3, a explanation will be made of the means for picking out parameters from the detected blood pulse waves which are appropriate for the blood pulse wave analysis. In Chapter 4, explanations will be made of a variety of physiological states which can be obtained from the blood pulse wave, and methods of analysis of blood pulse waveforms in order to obtain these physiological states.

Chapter 5 concerns input and output means for interfacing between the human body and the device, explaining equipment which can be used in common with each of the devices introduced in Chapter 6. The devices discussed in Chapter 6 will be explained by selecting from among each means a suitable representation thereof. However, the majority of the devices described in Chapter 6 may be substituted by the other means noted in Chapter 5. This also applies to the blood pulse wave detection means in Chapter 2 and the blood pulse wave analysis means in Chapter 3.

Chapter 6 will explain various embodiments realized on the basis of the preceding chapters through Chapter 5.

CHAPTER 1: CYCLIC FLUCTUATION IN PHYSIOLOGICAL STATE

Section 1: Overview

When obtaining a subject's physiological state from blood pulse waves or the like, if one is interested only in the physiological state at the time of each measurement, then a variety of information can be gotten using various blood pulse wave analysis methods, as is described in Chapter 4 below.

However, even in the case of a healthy individual, the body's physiological state fluctuates at a specific rhythm. Accordingly, if analysis or diagnosis of blood pulse waves is carried out while taking these fluctuating rhythms into consideration, it is possible to more accurately ascertain the subject's physiological state. The field-known as "time biology" has gained attention in recent years as a type of research focusing on these physiological rhythms.

Figure 3:
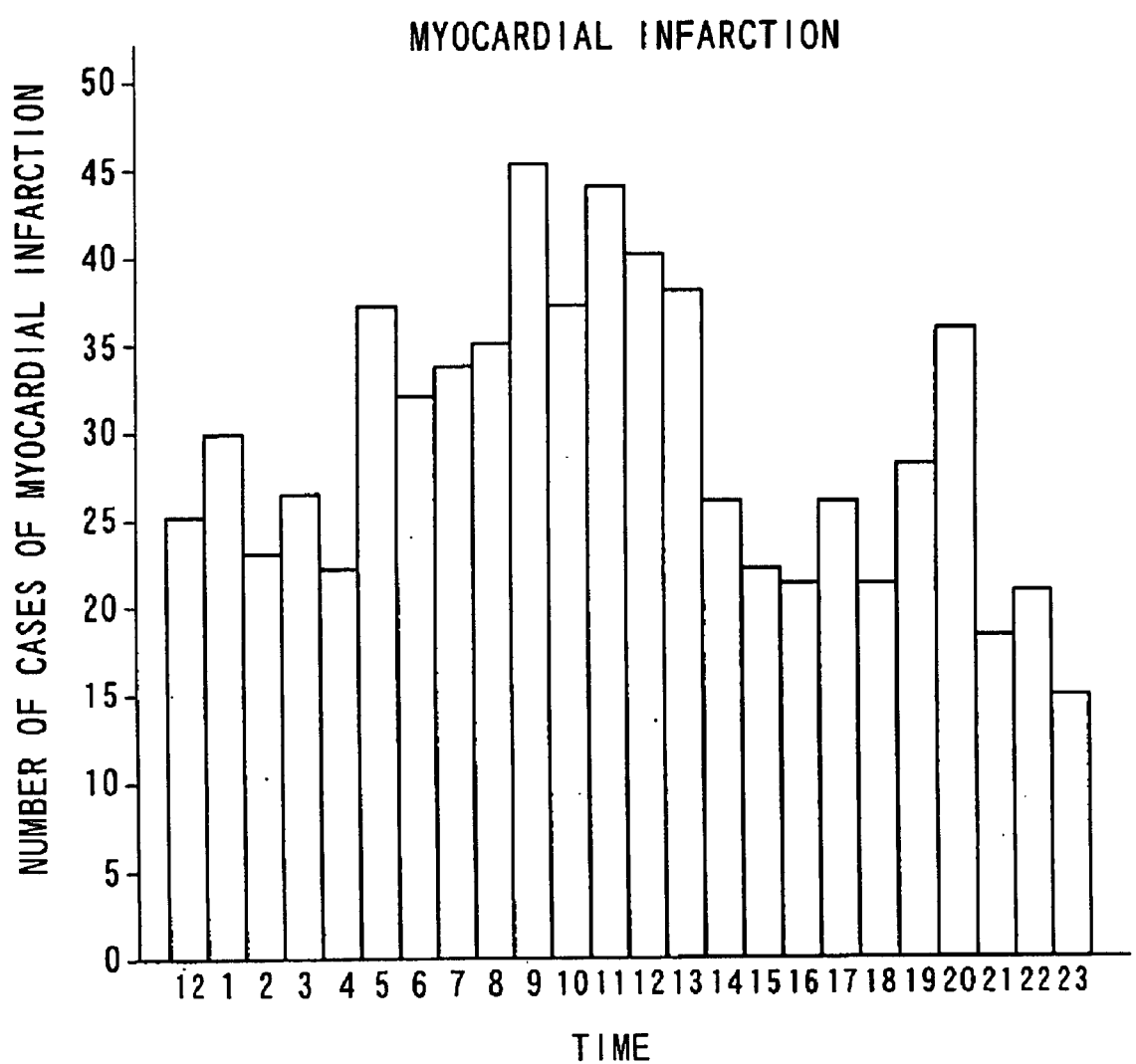
FIG. 3 is a diagram disclosing of the occurrence of acute myocardial infarction.

In addition to fluctuating due to stress, the condition of the circulatory system also fluctuates according to a specific rhythm. More specifically, it has been reported that the circulatory system undergoes cyclic fluctuation over a one day cycle. For example, the incidence of sudden death has also been reported to display cyclic fluctuation throughout the 24 hours of a one day period. Namely, studies have reported that there are time periods in which the sudden death frequency is high and time periods in which the sudden death frequency is low. FIG. 2 shows the fluctuation in the incidence of sudden death cases throughout one day, while FIG. 3 shows the fluctuation in the incidence of cases of acute myocardial infarction throughout one day. This data is disclosed in Muller, J. E., et al: Circulation 79: 733 to 734, 1989.

In addition, blood pressure, blood pulse rate, aortic output, vital output, oxygen consumption, body temperature, hormone secretion, central nervous system activity, time of cell division, sleep, brain waves, pain sensation, body weight, occurrence of angina pectoris, and the like also show rhythmic fluctuations. In fact, there are actually more than 300 body functions which are know to show a physiological rhythm.

The existence of these rhythms may be recognized upon physical activity or arousal, when blood pulse and respiration become rapid. Similarly, irregularity or abnormality in these rhythms during illness or the like, may also be clearly seen. Further, while sleep depravation is partly to blame for the sense of malaise one may feel following an extremely late night, a discrepancy between the body temperature and physical activity rhythms after a drop in body temperature may also cause this sensation. In addition, abnormality in these rhythms are most easily recognized in the so-called "jet-lag" phenomenon which occurs when one moves quickly between time zones which differ by more than 4 hours. Jet-lag occurs when the rhythm of the body's "clock" becomes out of sync with the rhythm of the external environment. Moreover, coping with this phenomenon may be a commonplace requirement when living in particularly large countries such as the United States.

Accordingly, as may be elucidated from the preceding discussion, it is extremely difficult to carry out an accurate determination of physiological state simply by carrying out a diagnosis during a given time period since the physiological state demonstrates natural fluctuation according to a fixed rhythm. For example, while examination of a patient at a certain time of the day may yield favorable results, it is not accurate to deduce that the patient's condition has improved due to treatment since these improved results may simply be due to the natural fluctuation in the physiological state. Similarly, if examination of the patient at a certain time of the day indicates a slight elevation in aortic output, it may not necessarily be accurate to conclude that the patient's condition is particularly dangerous, since the elevated result could be a natural fluctuation in this physiological state indicator. On the other hand, measurements of the physiological state might reveal an unnatural change which departs from the daily natural rhythms expected. For example, a rise in aortic output during a time period when aortic output should be declining might be detected. In such a case, even if the aortic output value is within the normal range, an unexpected shift in the mode of change in the indicator (i.e., rising rather than falling) may point to some abnormal change in the body requiring prompt attention. In such a case, for example, making a diagnosis or providing treatment without taking into consideration the body's physiological rhythms (i.e., cyclic fluctuation in physiological state), may be not only inappropriate, but dangerous.

Accordingly, by carrying out experiments on cyclic fluctuation in physiological state obtained from blood pulse waves in the human body, the present inventors were able to confirm the presence of such cyclic fluctuations. A detailed explanation of the substance and results of these experiments on cyclic fluctuation in physiological state follows below.

Figure 4:
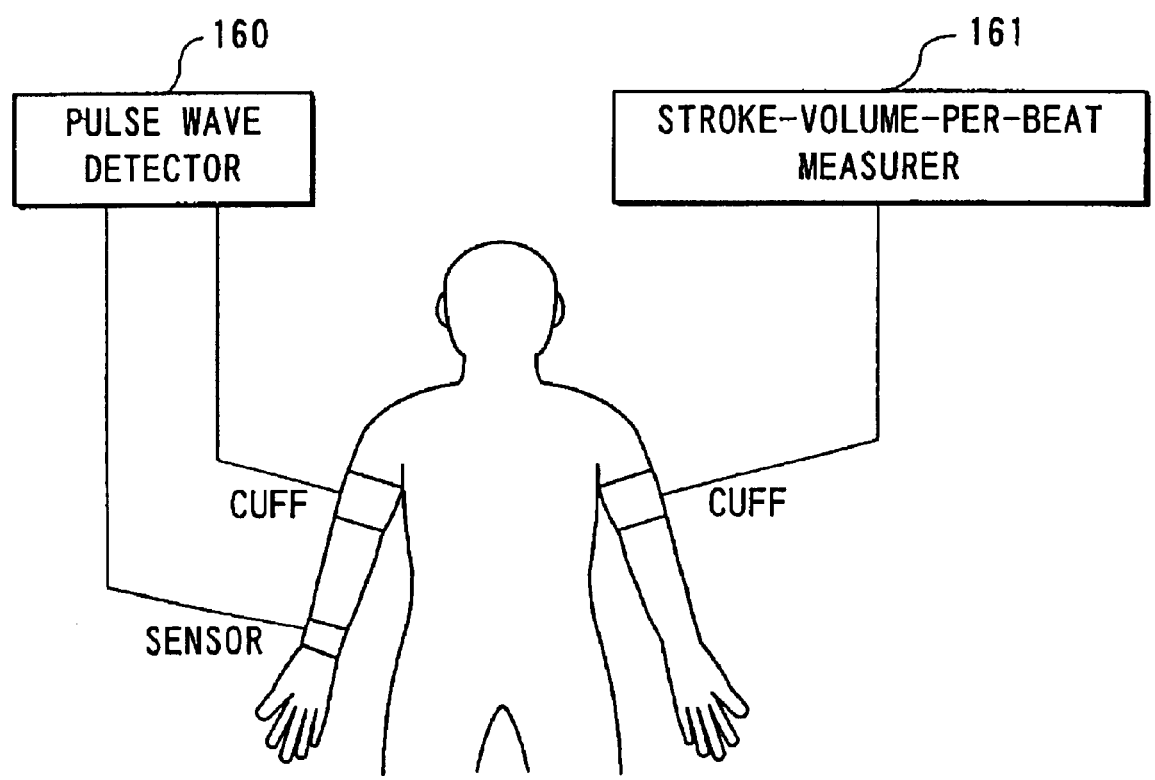
FIG. 4 is a diagram showing the arrangement for carrying out measurements in an experiment measuring cyclic fluctuations in physiological state.

Section 2: Daily Fluctuation in Circulatory Parameters (1) Structure of Device Used in Experiments The structure of the device employed in these experiments is shown in FIG. 4. In this figure, blood pulse wave detector 160 detects the waveform of the radius artery via a pressure sensor attached to the right wrist of a test subject, and detects the blood pressure via a cuff attached to the upper arm of the test subject. Blood pulse wave detector 160 then outputs an electric signal showing the waveform after correcting the radius artery waveform by using blood pressure. Further, stroke-volume-per-beat measurer 161 measures the stroke volume per beat in the test subject, and outputs an electric signal indicating this result. These parts are explained in greater detail in Chapter 2, Sections 2 through 3. In addition to the above-described device, a personal computer (omitted from the figures) was employed to carry out control of these devices and analysis of the measured results. The term "stroke volume per beat" as used here is intended to indicate that volume of blood which is pumped out from the heart per heartbeat.

(2) Test Conditions for Measurement 13 healthy males subjects, aged 21±9 years, were required to carry out identical activities in the same facility for a 36 hour period spanning 2 days. Ambient temperature was maintained in the range of 24.0° to 24.5° C., with humidity held in the range of 40 to 50%.

Figure 5:
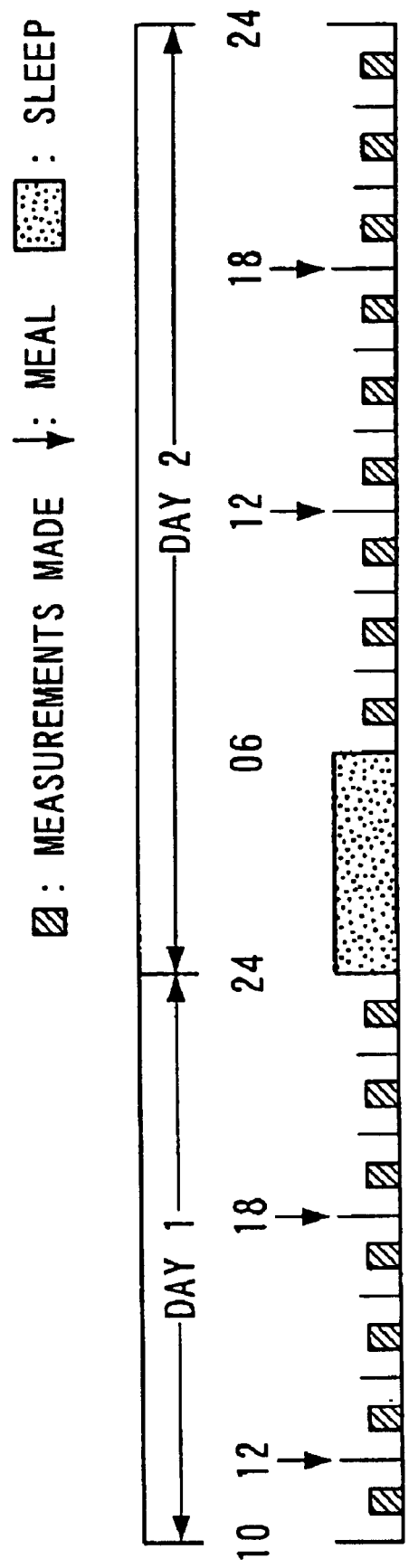
FIG. 5 is a diagram showing the schedule for the aforementioned experiment.
Figure 6A:
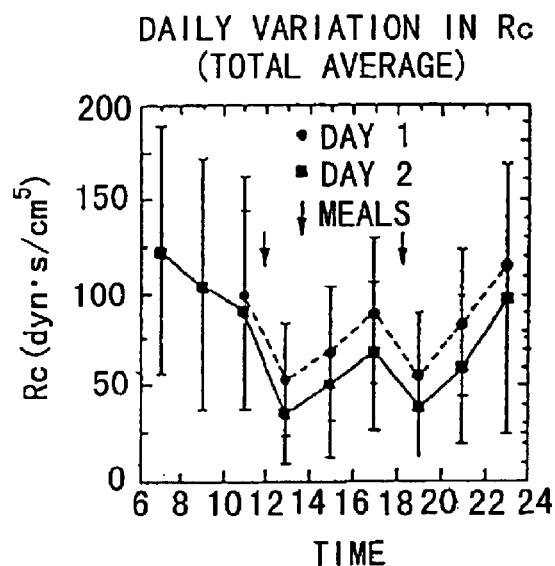
FIGS. 6A–6D are a diagram showing the fluctuations in circulatory parameters over one day.
Figure 6B:
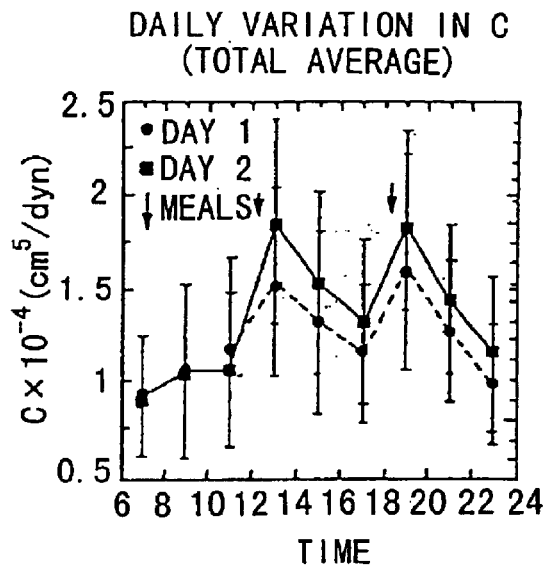
Figure 6C:
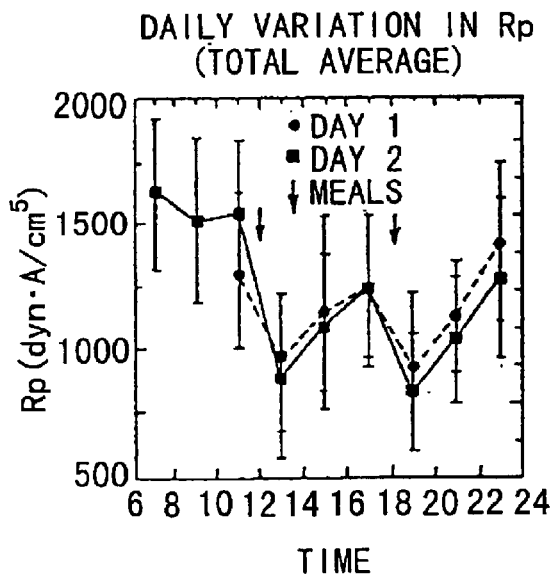
Figure 6D:
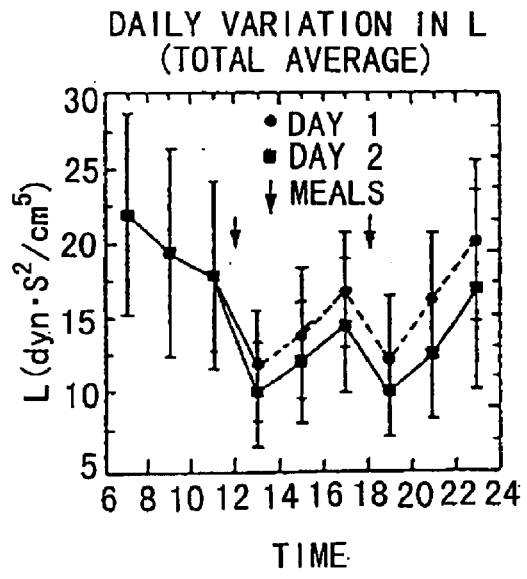

The schedule for the experiments is shown in FIG. 5. As shown in this schedule, meals were provided at noon and 6 PM, with the same menu used on both days. The meals provided approximately 1, 700 kcal per day. The subjects were allowed to sleep 6 hours, going to bed at midnight and rising at 6 am. The waveforms at the radius artery and stroke volume per beat were measured every 2 hours.

The subjects were required to assume a state of repose 15 minutes prior to making any the measurements. While measurements were being taken, the subjects were required to breath at a regular rate in time with a 0.25 Hz metronome. The average summed waveform per beat was obtained using measurements from sets of 10 heart beats counted from the start of measurement (i.e., from to), and 10, 20, 30, 40 and 50 seconds after the start of measurement (i.e., at $t_{10sec}$, $t_{20sec}$, $t_{30sec}$, $t_{40sec}$, and $t_{50sec}$). This result was analyzed as will be explained below.

(3) Analysis

The present inventors supposed that the circulatory parameters in the human body form a lumped four parameter model. In order to confirm how each element in this lumped four parameter model fluctuates over time, the present inventors obtained values for circulatory parameters corresponding to the radius artery blood pulse wave and the stroke volume per beat measured in each test subject. The lumped four parameter model, as will be explained in Chapter 4 below, indicates an electric model which substitutes for the circulatory system in the human body. This electric model is composed of resistances Rc and Rp, capacitance C, and inductance L. These components are equivalent to the circulatory parameters which show the state of the circulatory system in the human body.

(4) Results

1. Comparison of Day 1 and Day 2

FIG. 6 shows the change over time in resistances Rc and Rp, capacitance C, and inductance L of the lumped four parameter model during the two day period. In the figure, the plot indicated by black dots shows the average value for each of the model components of the 13 test subjects taken on the first day. The plot indicated by black squares shows the average values for each of the components taken on the second day. It may be understood from FIG. 6 that the values of each of the components in the lumped four parameter model demonstrated almost the same change over time on day 2 as on day 1.

2. Analysis of the Rhythm of Daily Fluctuation

Figure 7:
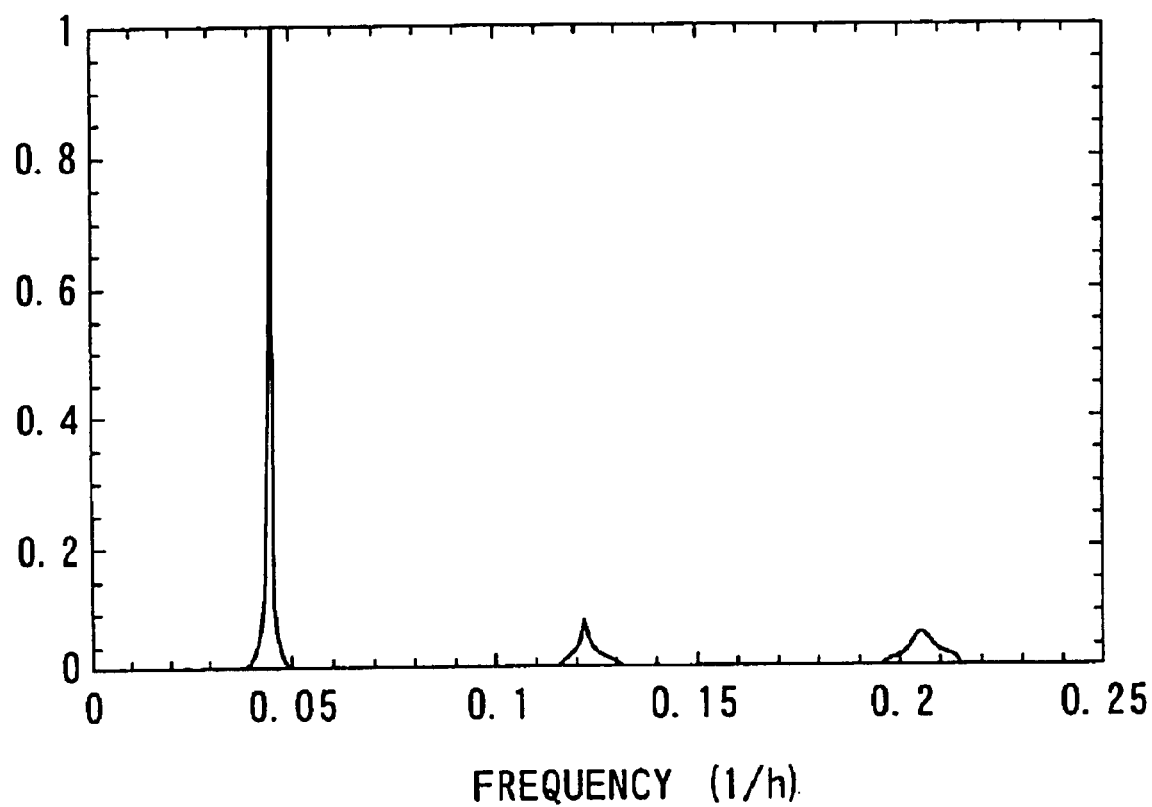
FIG. 7 is a spectral diagram of the fluctuations in the waveforms of the circulatory parameters over one day.
Figure 8A:
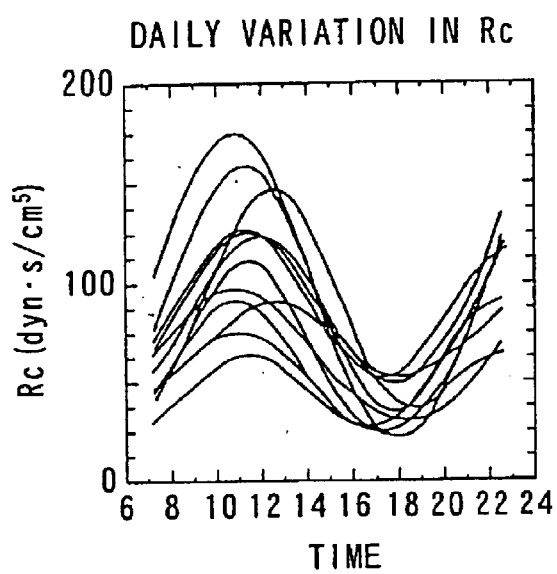
FIGS. 8A–8D are a diagram showing the fundamental wave spectrum of the fluctuations in waveforms of the circulatory parameters over one day.
Figure 8B:
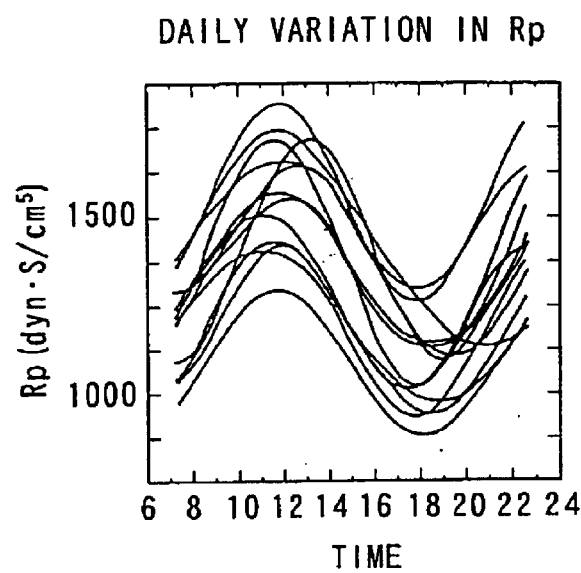
Figure 8C:
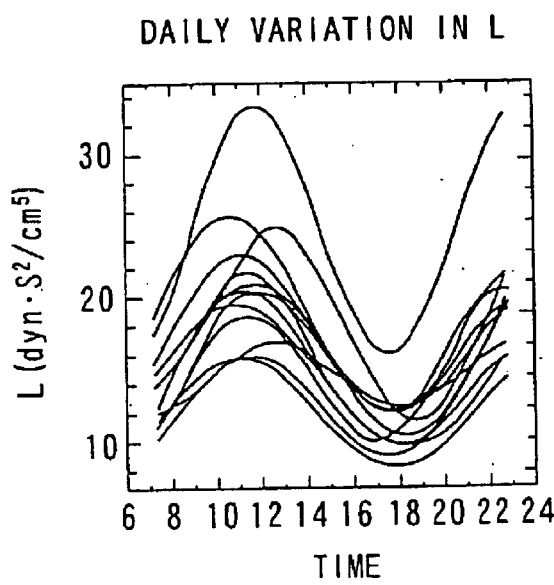
Figure 8D:
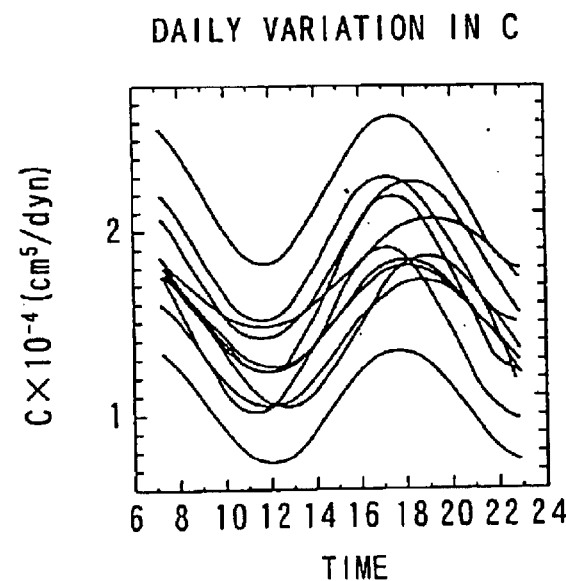
Figure 9A:
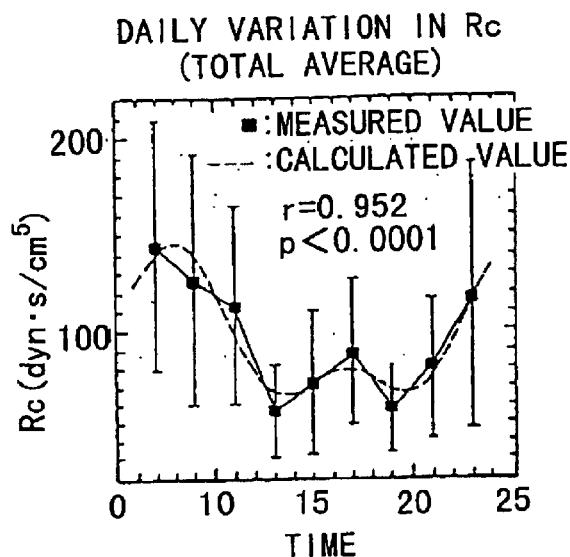
FIGS. 9A–9D are a diagram showing the fluctuation in circulatory parameters over one day.
Figure 9B:
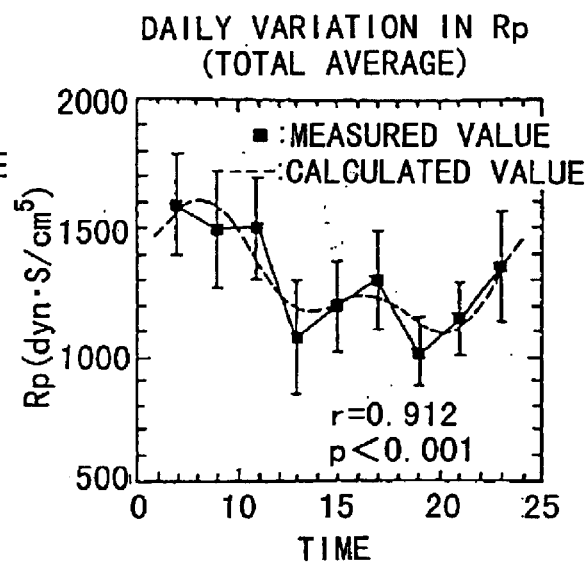
Figure 9C:
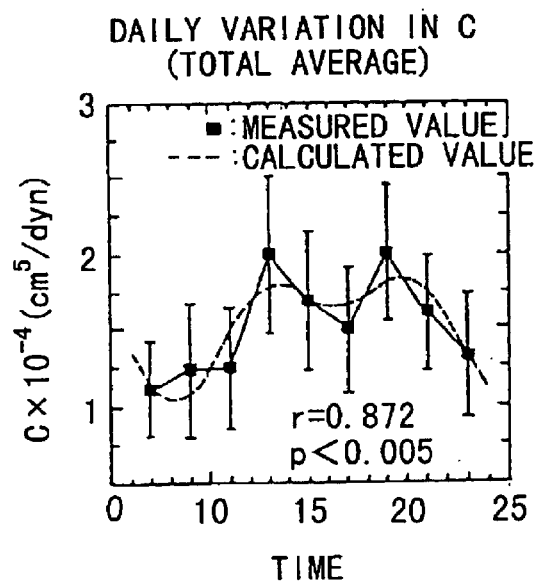
Figure 9D:
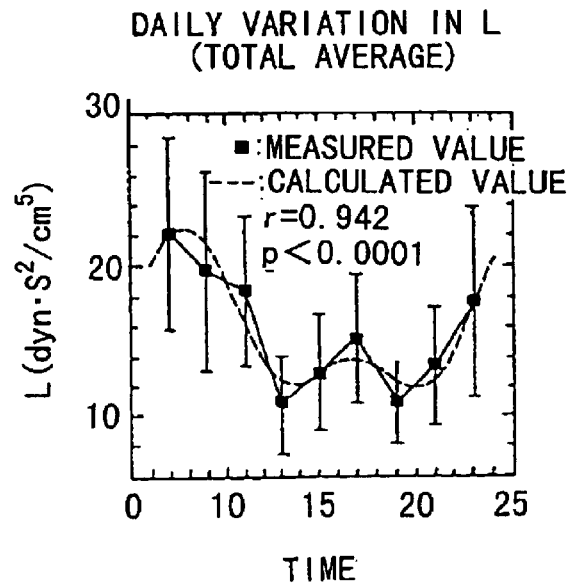

An analysis was made of the rhythm of the change over time in the average value of the resistance Rc in blood vessels at the center of the circulatory system for the 13 test subjects. These results are shown in FIG. 7. As shown in this figure, the waveform of the daily fluctuation in resistance Rc consists of a fundamental spectrum having a period of around 20 hours, and its high harmonic wave spectrum. Further, while omitted from the figure, the fundamental spectrum for the daily fluctuations in the waveforms of the other components Rp, C, and L also has a period of around 20 hours.

FIG. 8 shows the waveform of the fundamental wave spectrum of the waveform of daily fluctuations of the lumped four parameter model components Rc, Rp, C, and L in each of the test subjects. From these figures, it may be understood that individual differences exist in the amplitude and phase of these daily fluctuations in the circulatory parameters.

FIG. 9 shows a comparison between the average value of the lumped four parameter model components Rc, Rp, C, and L for the 13 test subjects, and the waveform of daily fluctuation synthesized from the second harmonic wave spectrum and the fundamental wave spectrum obtained from rhythm analysis.

3. Characteristics of Daily Fluctuations in Circulatory State

From the above experimental results, it may be understood that, despite individual differences in the waveform of daily fluctuations for the circulatory parameters Rc, Rp, C, and L, all of the test subjects' results exhibited certain common characteristics. Namely, the values of Rc, Rp, and L were large in the morning, fell gradually throughout the afternoon, and began to rise again after a small peak in the evening. The value of C, on the other hand, was high during the first half of the day, but showed a decreasing trend throughout the second half of the day.

Section 3: Annual Fluctuation in Circulatory Parameters

Figure 11:
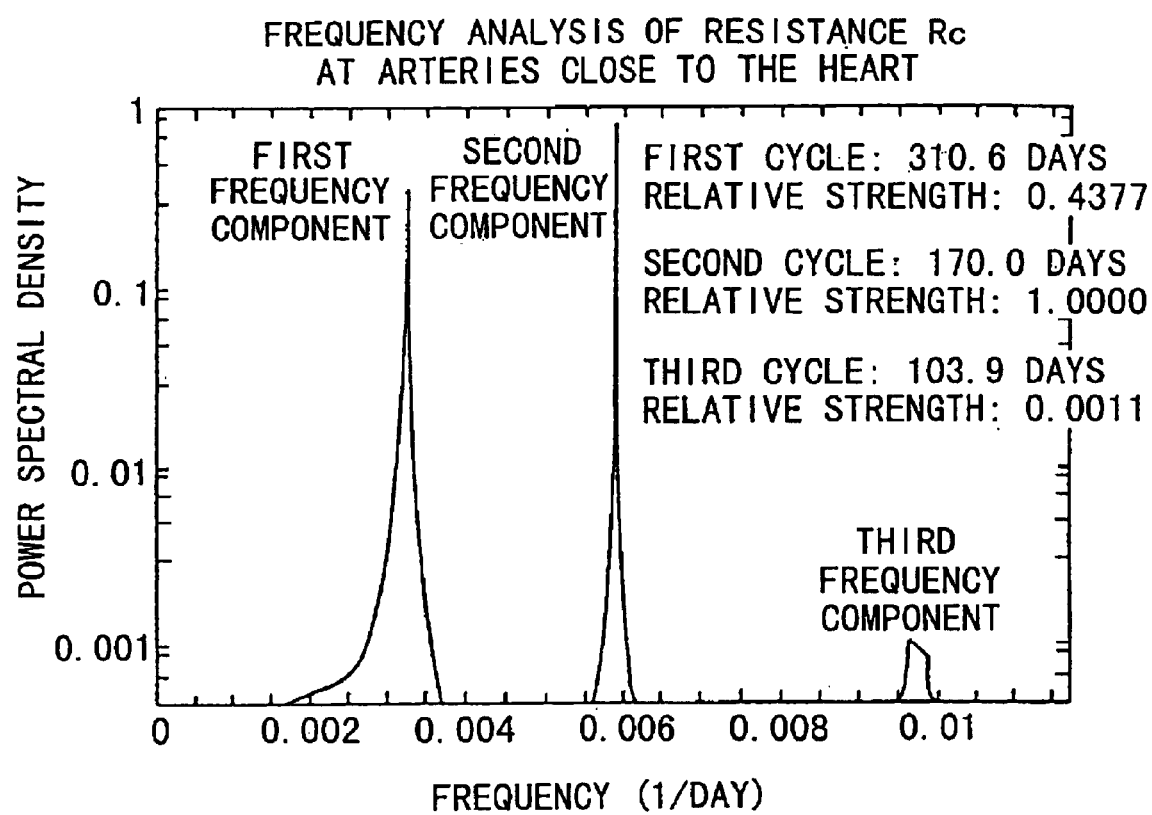
FIG. 11 is a diagram showing the results of a frequency analysis of resistance Rc in blood vessels at the center of the circulatory system.

In addition to daily fluctuations, circulatory parameters also demonstrate gentle rhythmic fluctuation following a one year cycle. For example, compliance C rises in the summer and falls in the winter. FIG. 10 is a graph showing one example of the annual variation in circulatory parameters, while FIG. 11 is a graph showing the results of spectral analysis of viscous resistance Rc at the center area of the circulatory system, near the heart.

Section 4: Daily Variation in the Blood Pulse Wave Spectrum

When a frequency analysis of the waveform of the blood pulse wave is carried out and the spectrum is observed, it becomes clear that the blood pulse wave spectrum exhibits the same type of daily fluctuation described above in the case of the circulatory-parameters. From experiments performed by the present inventors, it was understood that the phase of the fourth harmonic wave (i.e., the phase based on the rise in the blood pulse wave) changes significantly in response to changes in the body's physical condition.

Figure 12A:
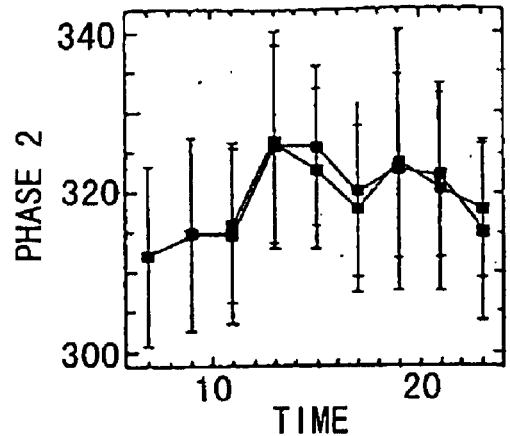
FIG. 12A is a diagram showing the fluctuation in the second harmonic phase of the blood pulse wave over one day.
Figure 12B:
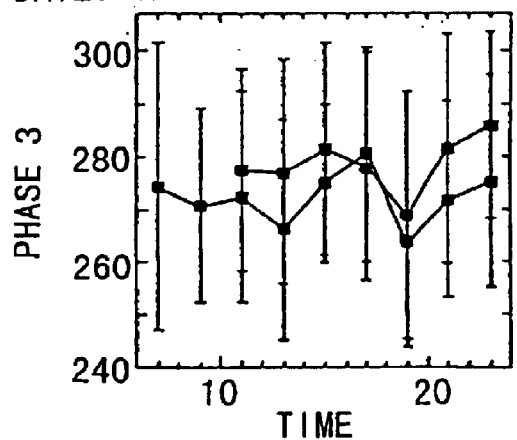
FIG. 12B is a diagram showing the fluctuation in the third harmonic phase of the blood pulse wave over one day.
Figure 12C:
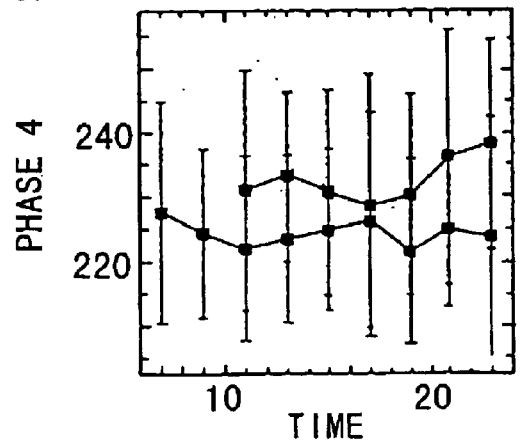
FIG. 12C is a diagram showing the fluctuation in the fourth harmonic phase of the blood pulse wave over one day.
Figure 13A:
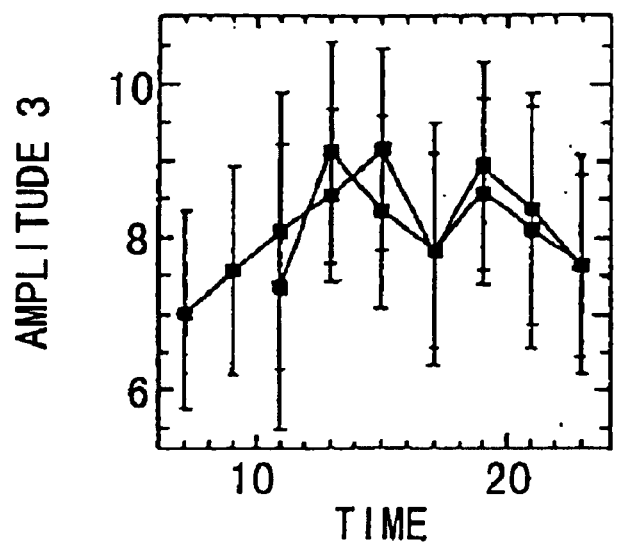
FIG. 13A is a diagram showing the fluctuation in the third harmonic amplitude of the blood pulse wave over one day.
Figure 13B:
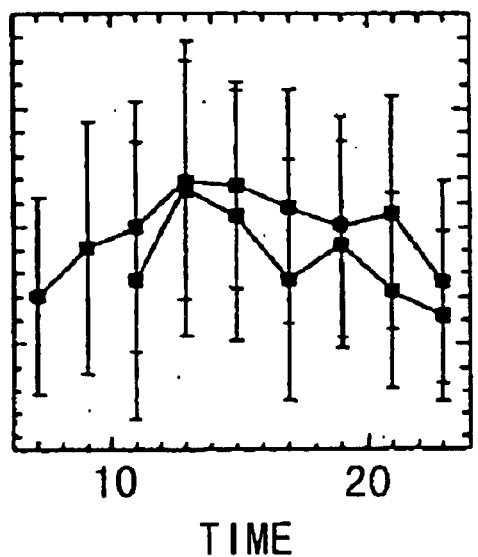
FIG. 13B is a diagram showing the fluctuation in a normalized third harmonic amplitude of the blood pulse wave over one day.

FIGS. 12A to C are graphs which respectively show examples of the daily fluctuation in the second, third and fourth harmonic wave phases of a blood pulse wave. FIG. 13A shows an example of the daily fluctuation in the amplitude of the third harmonic wave, while FIG. 13B shows an example of the daily fluctuation in the normalized amplitude of the third harmonic wave.

Section 5: Conclusion

By obtaining the condition of the human body based on cyclic fluctuations in indicators of physiological state as explained above, it becomes possible to extremely accurately obtain the physiological state, while at the same time detecting any anomalies in the body's condition.

The preceding discussion employed as an example the spectrums obtained from frequency analysis of the blood pulse waveforms and the circulatory parameters as indicators of physiological state. However, it is believed that there are also daily and annual fluctuations in the various other physiological states explained above.

CHAPTER 2

Blood Pulse Wave Detector and Stroke-volume-per-beat MEASURER

In this chapter, an explanation will be provided of the various sensors (blood pulse wave detectors) which the various apparatuses of the present invention use in blood pulse wave measurements. In the diagnosis based on the analysis of the blood pulse wave and the results of this analysis, the stroke volume per beat is sometimes required. Since this stroke volume per beat was measured together with blood pulse wave, an explanation and the method of measurement therefor will also be explained here.

Section 1: Blood Pulse Wave Detector
Part 1 Blood Pulse Wave Sensor Employing Distortion Gauge
(1) Test Product 1

Figure 14A:
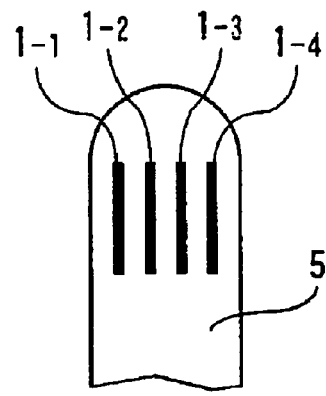
FIG. 14A is a plan view of a first blood pulse wave sensor employing a distortion gauge.

The present inventors prepared for testing purposes the blood pulse wave sensor shown in FIG. 14A. In the example in the figure, wire-like distortion gauges 1-1 to 1-4 are fixed to the finger pad portion of a surgical rubber glove 5. This rubber glove 5 is worn over one hand, and the fingertips thereof are pressed against the arm of the test subject to measure the resistance values on each of the distortion gauges 1-1 to 1-4. In this way, the blood pulse wave can be detected.

(2) Test Product 2

Figure 14B:
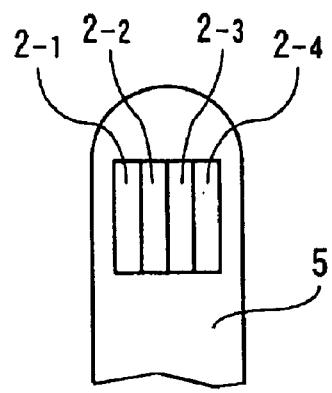
FIG. 14B is a plan view of a second blood pulse wave sensor employing a distortion gauge.

Next, the blood pulse wave sensor shown in FIG. 14B was prepared. In the blood pulse wave sensor of test product 1, it was sufficient that the sensor be one which measured just the distortion along the length of the finger and the strength of the blood pulse. In contrast, the blood pulse wave sensor in FIG. 14B detects the distortion along not only the length but also the width of the finger. In the example shown in the figure, belt-like distortion gauges 2-1 to 2-4 are fixed in parallel to the finger pad portion of the rubber glove 5. These distortion gauges 2-1 to 2-4 are formed in a unitary manner.

(3) Improved Blood Pulse Wave Sensor

Each of distortion gauges 2-1 to 2-4 in the composition of test product 2 are formed in a unitary manner, making it possible for interference to arise between the individual distortion gauges. Accordingly, the present inventors developed the following sensor. This sensor can detect the pressure distribution across the width of the finger, and is able to carry out a highly accurate blood pulse wave detection easily.

Figure 15:
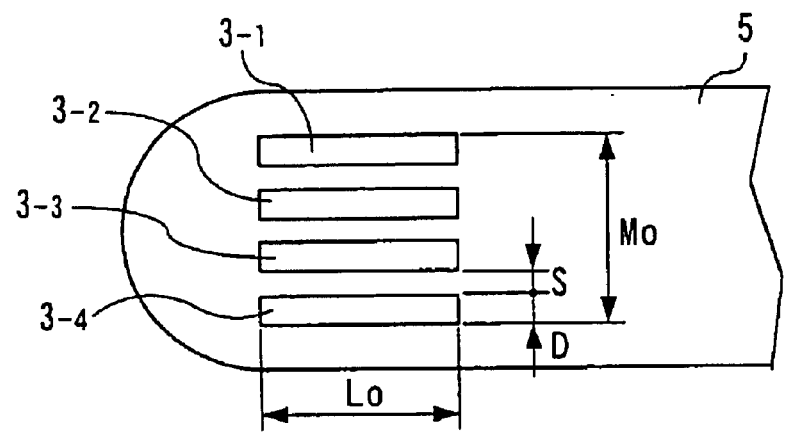
FIG. 15 is a plan view of a third blood pulse wave sensor employing a distortion gauge.

FIG. 15 shows a plan view of the improved blood pulse wave sensor. In this figure, 3-1 to 3-4 are thin belt-like gauges which are disposed in parallel along the length of the fingerpad area of rubber glove 5. The thickness of rubber glove 5 is about 200 $\mu$m, while an adhesive agent used for gauges may be employed as a means for affixing distortion gauges 3-1 to 3-4 to rubber glove 5.

A detailed explanation will now be made of distortion gauges 3-1 to 3-4. Distortion gauges 3-1 to 3-4 are thin gauges, having a gauge rate of 2.1, a resistance of 120 ohms, a width D of 2.8 mm, a length Lo of 9.4 mm, and a thickness of 15 μm. The total width Mo of distortion gauges 3-1 to 3-4 is designed to be 12 mm, corresponding to the contact width when the finger of the diagnostician is lightly pressed against the arm of the test subject. Accordingly, the space between gauges is about 0.27 mm.

(Modifications)

Figure 16:
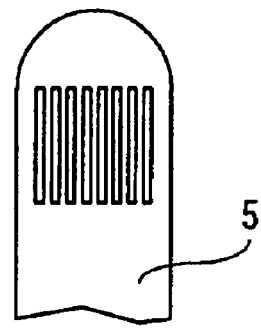
FIG. 16 is a plan view of a modification of the blood pulse wave sensor employing a distortion gauge.

1. Number of Distortion Gauges (a) Although four distortion gauges were provided to each of the fingers in the preceding discussion, the present invention is not limited thereto. For example, if 5 or more distortion gauges are provided as shown in FIG. 16, it becomes possible to realize even more reliable blood pulse wave detection. Conversely, four or fewer distortion gauges may also be employed.

2. Characteristics of Distortion Gauge

The characteristics of distortion gauges 3-1 to 3-4 are not limited to the description above. For example, the gauge rate may of course take on a range of values in addition to a rate of 2.1 employed above. In addition, the dimensions of distortion gauges 3-1 to 3-4 may be varied within a range which still enables measurement. For example, the following device is available.

Figure 17:
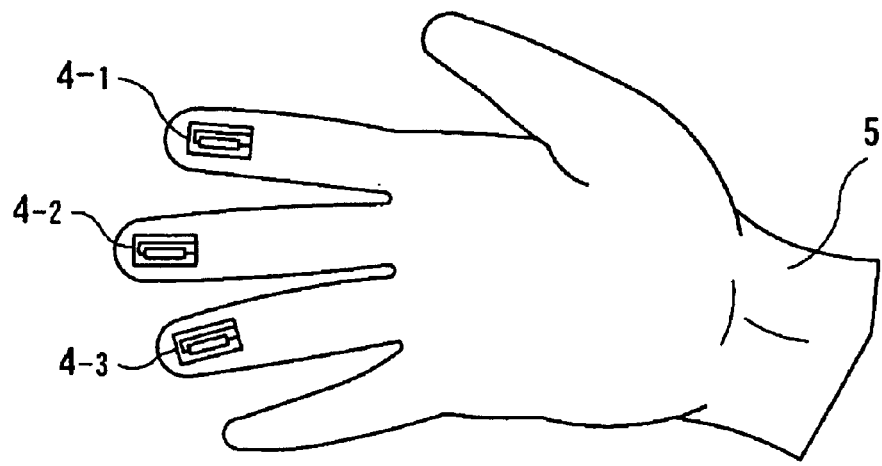
FIG. 17 is a diagram showing a arrangement in which a blood pulse wave sensor is attached to a rubber surgical glove.

FIG. 17 shows a blood pulse wave sensor attached to a rubber glove. In the figure, the numeric symbol 5 indicates a rubber surgical glove as described above. Distortion gauges 4-1 to 4-3 have been attached to the finger pad portions of the first muscle of the second, third and fourth fingers. The distortion gauges employed here use a different arrangement than the distortion gauges described above. Namely, distortion gauges 4-1 to 4-3 are thin gauges, with a gauge rate of 170, a resistance of 2 K½, a width of 0.5 mm and a length of 4 mm. Each of gauges 4-1 to 4-3 is affixed to a flexible thin base which is 4 mm by 11 mm, and is affixed together with this thin base to rubber glove 5.

By using this type of sensor, it becomes possible to detect the pushing force of the finger together with the blood pulse wave. Further, since the rubber glove is attached to a sensor, it is possible to simultaneously carry out diagnosis based on the measurements from the sensor and the diagnostician's sense of touch.

3. Structure of the Distortion Gauge

Figure 18:
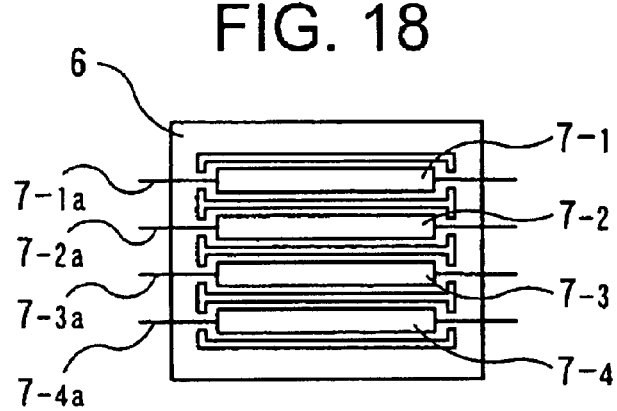
FIG. 18 is a plan view of another modification of a blood pulse wave sensor employing a distortion gauge.

In FIG. 15, the distortion gauge structure is complicated because it is necessary to affix the distortion gauges 3-1 to 3-4 to the rubber glove 5 at a fixed interval of spacing. Accordingly, the distortion gauge may also have the structure shown in FIG. 18. In this figure, the numeric symbol 6 indicates a lattice-type thin film from which thin slits have been punched out. Distortion gauges 7-1 to 7-4 are affixed to respective lattices. Further, the ends of each lattice are provided with a width which is narrow enough to permit the disposition of lead wires 7-1a to 7-4a for each gauge.

By means of this structure, it is possible to dispose distortion gauges 7-1 to 7-4 at a fixed interval of spacing merely by affixing thin film 6 to rubber glove 5. Further, since each of the gauges 7-1 to 7-4 on thin film 6 are separated by a punched out area, and the width of the lattice narrows at the edge of the distortion gauges, it is possible to prevent interference between each of the gauges 7-1 to 7-4 through the thin film 6.

4. Position of Attachment of Distortion Gauge

Blood pulse wave sensors such as distortion gauges may be attached not only to the hand of an examiner, but also to measurement jigs. In other words, these blood pulse wave sensors may be designed so as to carry out measurements by attaching the measurement jig to the blood pulse point of a test subject. Further, the blood pulse wave sensor may also be designed to attach to a robot hand so that automatic measurements may be carried out.

Part 2 Blood Pulse Wave Detector for Distortion Gauge Blood Pulse Wave Sensor

An explanation will now be made of the blood pulse wave detector which carries out detection of the blood pulse wave using a blood pulse wave sensor consisting of the distortion gauges described in Part 1 above.

Embodiment 1

Circuit Structure

The structure of a blood pulse wave detection circuit employing distortion gauges 3-1 to 3-4 will be explained with reference to FIG. 19. In this figure, distortion gauge 3-1 and resistor 12 are connected in series, and a prespecified direct current voltage E is impressed from power source 11. Accordingly, a voltage Vi in response to the resistance ratio of these resistances is generated at both ends of distortion gauge 3-1. Further, the numeric symbol 13 indicates a direct current blocking filter which outputs the voltage Vi after removing the direct current component.

The output signal of direct current blocking filter 13 is amplified via amplifier 14, and an output voltage Vo is output via a low pass filter 15 which has a blocking frequency of 20 Hz.

Figure 19:
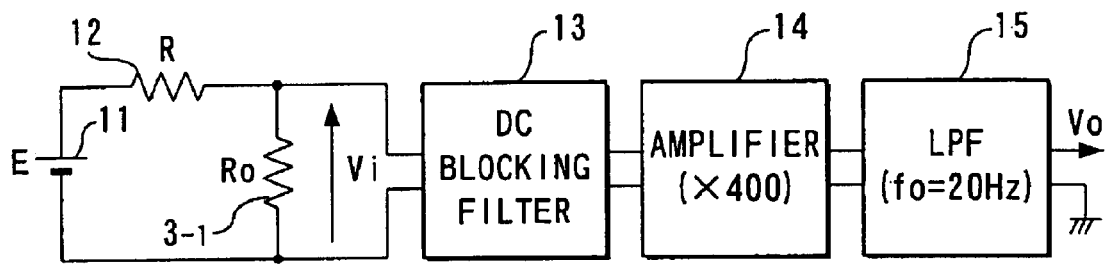
FIG. 19 is a block chart of a blood pulse wave detector employing a distortion gauge.

FIG. 19 shows the device relative to distortion gauge 3-1, however, equivalent circuits are provided to each of the other three distortion gauges 3-2 to 3-4.

Circuit Operation

In order for the circuit to operate correctly, rubber glove 5 is placed on one hand and the sensor is pressed against the site of blood pulse wave detection. Various voltages Vi are then output from the distortion gauges in response to the blood pulse wave. The respective direct current components of these voltages are then removed by the corresponding direct current blocking filter 13. Each of these modified voltages Vi are then output after passing through their corresponding amplifiers 14 and low pass filters 15.

(Modifications)

1. Correction of Temperature Drift

In the circuit shown in FIG. 19, the blood pulse wave is detected by directly measuring the voltage Vi expressed at each end of distortion gauge 3-1. However, it is also possible to form a bridge circuit which employs distortion gauge 3-1 as one arm, and detect the blood pulse wave by detecting the voltage at diagonal corners of the bridge circuit. In other words, a bridge circuit may be formed by affixing a distortion gauge 3-1 and three thin film resistors having the same resistance-temperature coefficient to rubber glove 5. Then, as a result, temperature drift caused by changes in body temperature and the like can be corrected, improving sensitivy.

2. Supply of Current to the Distortion Gauge

While current is continuously supplied to the distortion gauge 3-1 in the circuit shown in FIG. 19, it is also possible to carry out current supply intermittently. Namely, in the circuit shown in the figure, the only frequency components of voltage Vi that are ultimately detected as a blood pulse wave are those components of 20 Hz or less. As a result, it is possible to sufficiently regenerate the blood pulse wave based on sampling results at a frequency of 40 Hz, for example.

By supplying electrical current intermittently in this way, the electric power consumed is decreased. Accordingly, this design is particularly suitable for use in portable apparatus.

Embodiment 2

A blood pulse way detector which detects blood pulse waves using the distortion gauges shown in FIG. 17 will now be explained.

Circuit Structure

Figure 20:
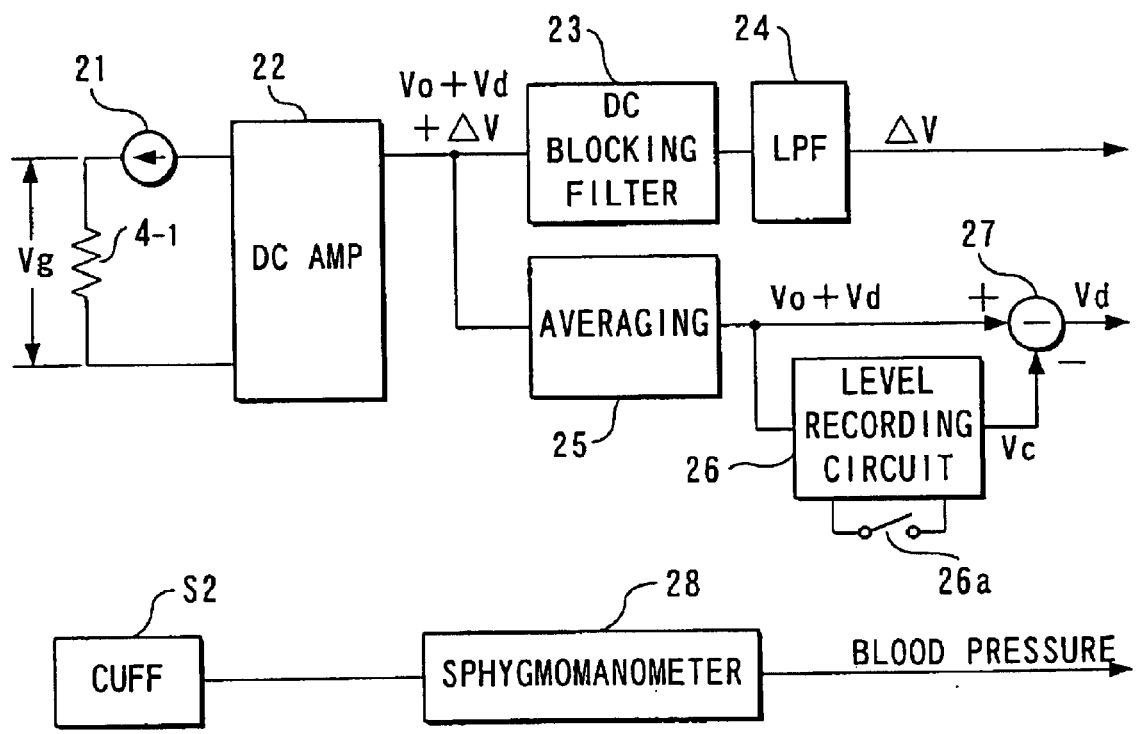
FIG. 20 is a block chart of a blood pulse wave detector employing the blood pulse wave sensor shown in FIG. 17.

The structure of the circuit employed in this embodiment will be explained with reference given to FIG. 20. In the figure, the numeric symbol 21 is a fixed electric current source which supplies a fixed electric current to the above-described distortion gauge 4-1. As a result, a voltage Vg is generated at both ends of distortion gauge 4-1 in response to the physical distortion thereof. This voltage Vg is amplified via a DC amp 22, and supplied to direct current blocking circuit 23 and averaging circuit 25.

The voltage output from DC amp 22 may be expressed as:

$$Vo+Vd+\Delta V$$

where, voltage Vo is the voltage generated when rubber glove 5 is placed over the hand, voltage Vd is the voltage generated by the pressure when the finger is pressed against the arm, and voltage V is the alternating current voltage arising from the blood pulse pressure.

Voltage Vo and voltage Vd, which are direct current components, are removed at direct current blocking circuit 23, while the alternating current component V, i.e., the blood pulse wave signal, is output. This blood pulse wave signal passes through low cut filter 24, which has a blocking frequency of 20 Hz, so that noise component thereof is removed. This blood pulse signal is then output from low cut filter 24.

Averaging circuit 25 detects local maximums of voltage [Vo+Vd+$\Delta$V], defines the time duration between successive local maximums to be one period, and then averages the voltage [Vo+Vd+$\Delta$V] over several periods. As a result, the alternating current component voltage $\Delta$V is removed, and only the direct current component [Vo+Vd] is output.

The numeric symbol 26 in the figure indicates a level recording circuit. The voltage level output from averaging circuit 25 is stored when switch 26a is depressed, and thereafter continually outputs voltage of the stored level.

The numeric symbol 27 in the figure indicates a subtracter. Subtracter 27 subtracts the output voltage of level recording circuit 26 from the output voltage of averaging circuit 25, and then outputs the results of this calculation.

The numeric symbol 28 in the figure indicates a conventional sphygmomanometer. While sphygmomanometer 28 is not directly related to blood pulse wave detection, it may be employed to measure and output blood pressure in a test subject via a cuff S2 when necessary.

Each of the parts indicated by numeric symbols 21 through 27 are provided to distortion gauge 4-1 in FIG. 17. In practice, however, equivalent circuits are provided to distortion gauges 4-2 and 4-3.

Circuit Operation

A voltage Vo is output from DC amp 22 when the rubber glove 5 is placed over the hand. When switch 26a is depressed in this embodiment, the voltage Vo is stored in level recording circuit 26. When the tip of a finger on the gloved hand is pressed against the arm, a voltage (Vo+Vd) is output from averaging circuit 25. This voltage passes through substracter 27 and a voltage Vd corresponding to the pushing force is output. At the same time, a voltage $\Delta$V corresponding to the blood pulse wave is output after sequentially passing through direct current blocking circuit 23 and low blocking filter 24.

Figure 21:
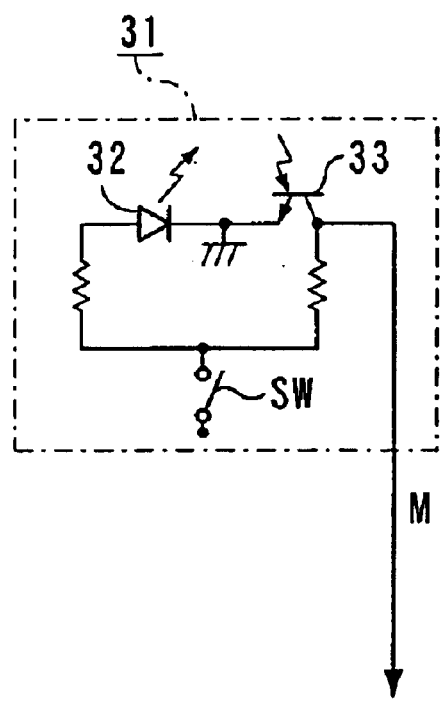
FIG. 21 is a circuit diagram for photoelectric blood pulse wave sensor 31.

Part 3 Photoelectric (Optical) Blood Pulse Wave Sensor (1) Structure and Operation Photoelectric blood pulse wave sensors are available as one example of blood pulse wave sensors employing light. FIG. 21 shows the structure of a photoelectric blood pulse wave sensor 31. In this figure, light generating element 32 is formed of an infrared light generating diode having a wavelength of 940 nm, for example. Optical sensor 33 is formed of a photo transistor or the like.

The light emitted from infrared light generating diode 32 is absorbed by the hemoglobin in the blood cells traveling through the blood vessels directly beneath the skin which is in contact with photoelectric blood pulse wave sensor 31. The quantity of light reflected by the hypodermic tissue will vary. This reflected light is received by optical sensor 33, with a blood pulse wave detection signal M obtained as a photoelectric converted result.

(2) Reduction in Power Consumption

In the case where the blood pulse wave sensor is combined with a battery operated wrist watch, in order to reduce the power consumption to a low value, it is desirable to operate the electric source for photoelectric blood pulse wave sensor 31 only when it is necessary to measure the blood pulse wave. For this purpose, a switch such as indicated by SW in FIG. 21 may be provided along the line which supplies the electric source to the blood pulse wave. Further, a switch drive circuit, not shown in the figures, switches the ON/OFF state of each switch, so that electricity is intermittently supplied to a sensor, etc.

For example, when a battery operated wrist watch is operated as a regular watch only, switch SW is in the OFF state, and an electric source is not supplied to photoelectric blood pulse wave sensor 31. On the other hand, when it becomes necessary to measure the blood pulse waves, switch SW is turned to the ON state, and an electric source is supplied to photoelectric blood pulse wave sensor 31.

Figure 22A:
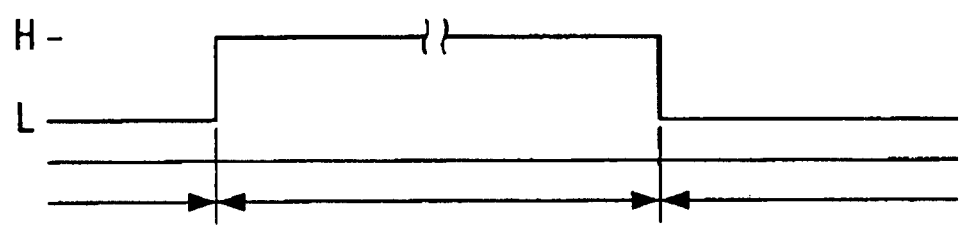
FIG. 22A is a diagram showing the drive timing of the blood pulse wave sensor and the pressure detection sensor.

FIG. 22A shows a timing signal for switching the ON/OFF state of each switch, the signal entering a high level state H only in the mode for measuring the blood pulse wave (denoted as "analysis mode" in the figure). In this figure, this timing signal enters a low level state L during non-analysis modes (i.e., when the battery operated wrist watch is employed as a watch only). In this case, switch SW is switched OFF, and the electric source is not supplied to the sensor. Once the analysis mode is initiated, this timing signal enters the H state, switch SW is turned ON, and the electric source is again supplied to the sensor. When the analysis mode concludes, the timing signal again enters the L state. Switch SW is turned OFF and the supply of the power source to the sensor ceases.

Accordingly, by means of the above design in which a timing signal is employed so that electric current is supplied to the sensor only when measurement of blood pulse waves is required, it is possible to conserve electric power consumption in the case where the device's function as a watch constitutes the majority of its use.

(3) Modifications

1. In view of the signal noise ratio, a blue light generating diode is even more preferable for the light generating diode employed in the light generating element.

Figure 22B:
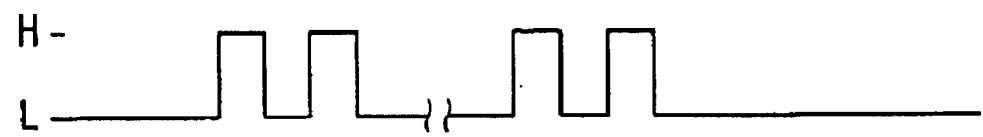
FIG. 22B is a diagram showing another example of the drive timing of the blood pulse wave sensor and the pressure detection sensor.

2. As an additional strategy to conserve electricity, as shown in FIG. 22B, the ON/OFF state of switch SW may be switched based on the timing of a blood pulse signal such as one which enters the H state only when a blood pulse wave detection signal is actually uptaken in the analysis mode.

3. The ON/OFF state of switch SW may be switched based on the timing of a blood pulse signal such as one which enters the H state only when a detection signal from the sensor is employed, irrespective of whether or not the device is operating in the analysis mode.

Part 4 Pressure-type Blood Pulse Wave Sensor

A blood pulse wave detector in which a blood pulse wave sensor is combined with a portable device will now be explained. However, the present invention is not limited to the arrangements described below, but may be combined with a variety of devices worn on the body daily.

Figure 23:
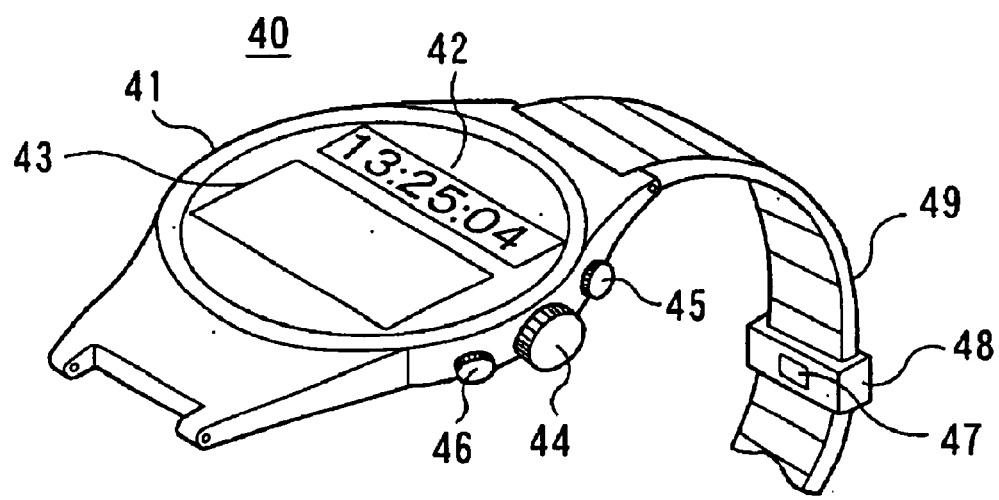
FIG. 23 is a perspective view of a wrist watch in an embodiment in which a pressure-type blood pulse wave detector is incorporated into a wrist watch.

An explanation of an embodiment in which a pressure-type sensor is combined with a wrist watch will now be explained with reference to FIG. 23. In this FIG., 40 indicates a wrist watch, 41 is the main body of the wrist watch, and 42 and 43 are the display portions for carrying out various displays. Further, 44 through 46 are buttons, the functions of which vary depending on the type of device as will be explained below. Accordingly, the functions of these buttons will be explained for each of the devices as they appear below. Numeric symbol 47 indicates a pressure sensor and 48 is a fastener. Pressure sensor 47 and fastener 48 comprise a blood pulse wave detector for detecting blood pulse waves.

Pressure sensor 47 is attached to the surface of fastener 48, and fastener 48 is attached in a freely sliding manner to wrist watch band 49. When wrist watch 40 is worn on the wrist, pressure sensor 47 is pressed against the radius artery with a suitable pressure. This pressure sensor 47 is comprised of distortion gauges, for example. A blood pulse wave signal expressing the waveform of the radius artery is obtained as an analog quantity from the terminals (not shown) provided to both ends of pressure sensor 47. This blood pulse wave signal is output to the main area of a device housed inside the main body 41 of the wrist watch via a signal line (omitted from the figure) embedded inside wrist watch band 49.

Part 5 Push-type Blood Pulse Wave Sensor
(1) Structure and Operation

Figure 24:
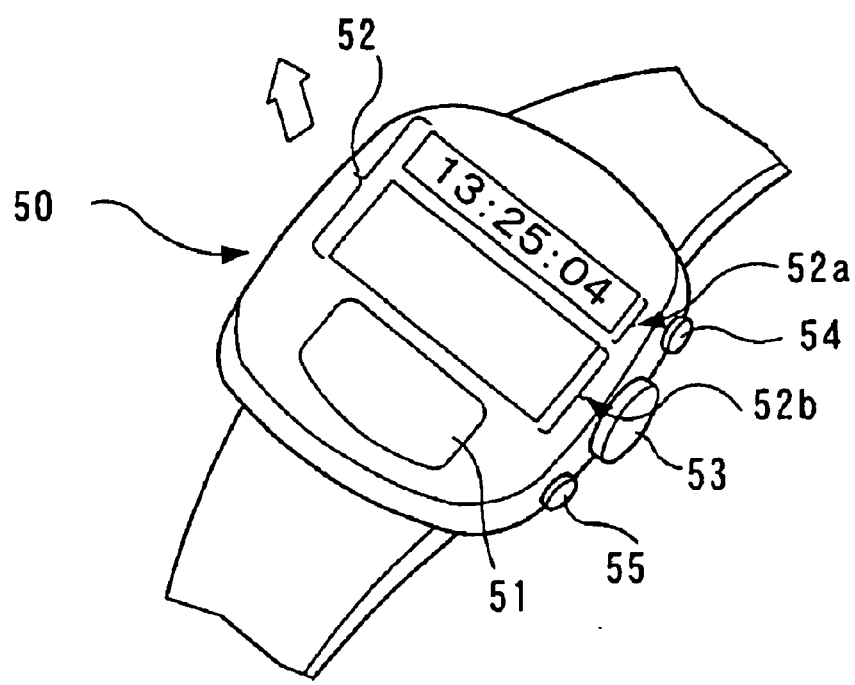
FIG. 24 is a perspective view of a wrist watch in an embodiment in which a pressure-type blood pulse wave detector is incorporated into a wrist watch.

An explanation will now be made of an embodiment in which a blood pulse wave detector employing a push-type blood pulse wave sensor is incorporated in a wrist watch. FIG. 24 shows the mechanical structure of a blood pulse wave detector. In this figure, 50 indicates the main body of a wrist watch, and is provided with a finger contact pad 51 and a variety of buttons and displays. The fingertip of, for example, the second finger on the hand not wearing the watch is pressed against finger contact pad 51. The functions of displays 52, 52*a*, 52*b* and buttons 53 through 55 vary in each device employing the blood pulse wave sensor. The arrow in FIG. 24 indicates the visual field direction of the displays.

Figure 25:
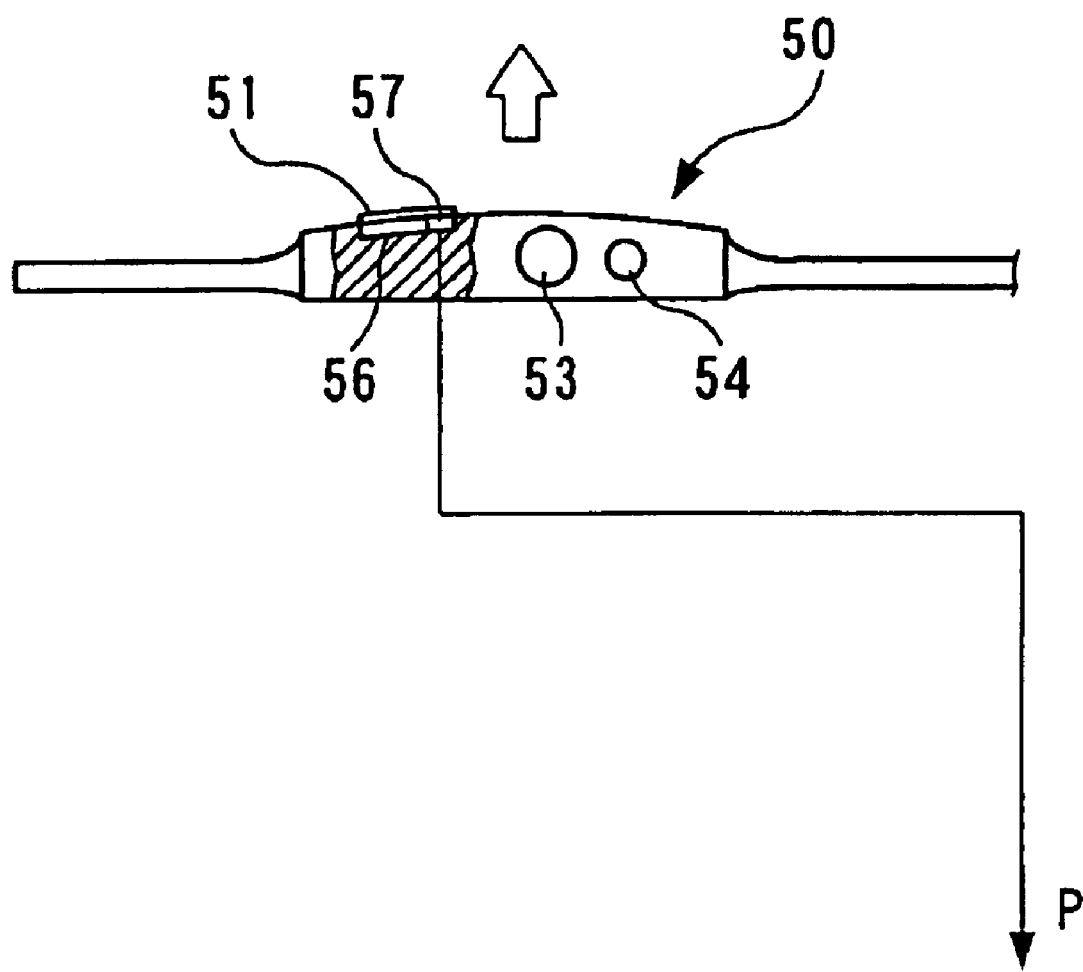
FIG. 25 is a sectional view showing the detailed structure of the wrist watch shown in FIG. 24.

FIG. 25 shows the structure of this blood pulse wave detector in greater detail. In this figure, a photoelectric blood pulse wave sensor 56 and a distortion gauge 57 are provided to the rear of finger contact pad 51. Photoelectric blood pulse wave sensor 56, which has the structure as described above, outputs a blood pulse wave detection signal M. The resistance value of distortion gauge 57 varies in response to distortion, so that a pressure signal P responding to the pressing pressure of the user's finger via finger contact pad 51 is output.

This pressure signal P is employed in order for the user to adjust the pressing pressure of his finger so that the value of the blood pulse wave detection signal M obtained from photoelectric blood pulse wave sensor 56 reaches a maximum. In other words, the device connected to the blood pulse wave detector uptakes the pressure signal P, and displays whether or not the pressing pressure of the finger is within a suitable range. The user then increases or decreases the pushing force of his finger so that the press pressure is within this range.

(2) Modifications

1. The pushing force detection means is not limited to a distortion gauge. In addition, for example, finger contact pad 51 may be formed as a moveable mechanism by means of a spring, with the pushing force detected from the degree of expansion in the spring.

2. The part of the body brought into contact with finger contact pad 51 is not limited to the fingertip. Rather, press pressure measurement may be carried out in the same way at the toes or other body periphery.

3. A window may be provided in the rear surface of main body 50 of the wrist watch, sandwiched between plastic plates or the like, with photoelectric blood pulse wave sensor 56 exposed via this window. As a result, the blood pulse wave of the blood vessels directly beneath the skin surface which is in contact with the plastic plate attached to the rear surface of main body 50 may be obtained.

4. In the above explanation, a switch for reducing electric power consumption was provided to photoelectric blood pulse wave sensor 56. However, if an equivalent switch is provided to distortion gauge 57, then a conservation of energy can be similarly effected.

Part 6 Use of Blood Pulse Wave Detector in Other Portable Devices

An explanation will now be made of the case in which the blood pulse wave sensor is incorporated into various portable devices, other than a wrist watch.

(1) Blood Pulse Wave Detector Incorporated in Necklace

Figure 26:
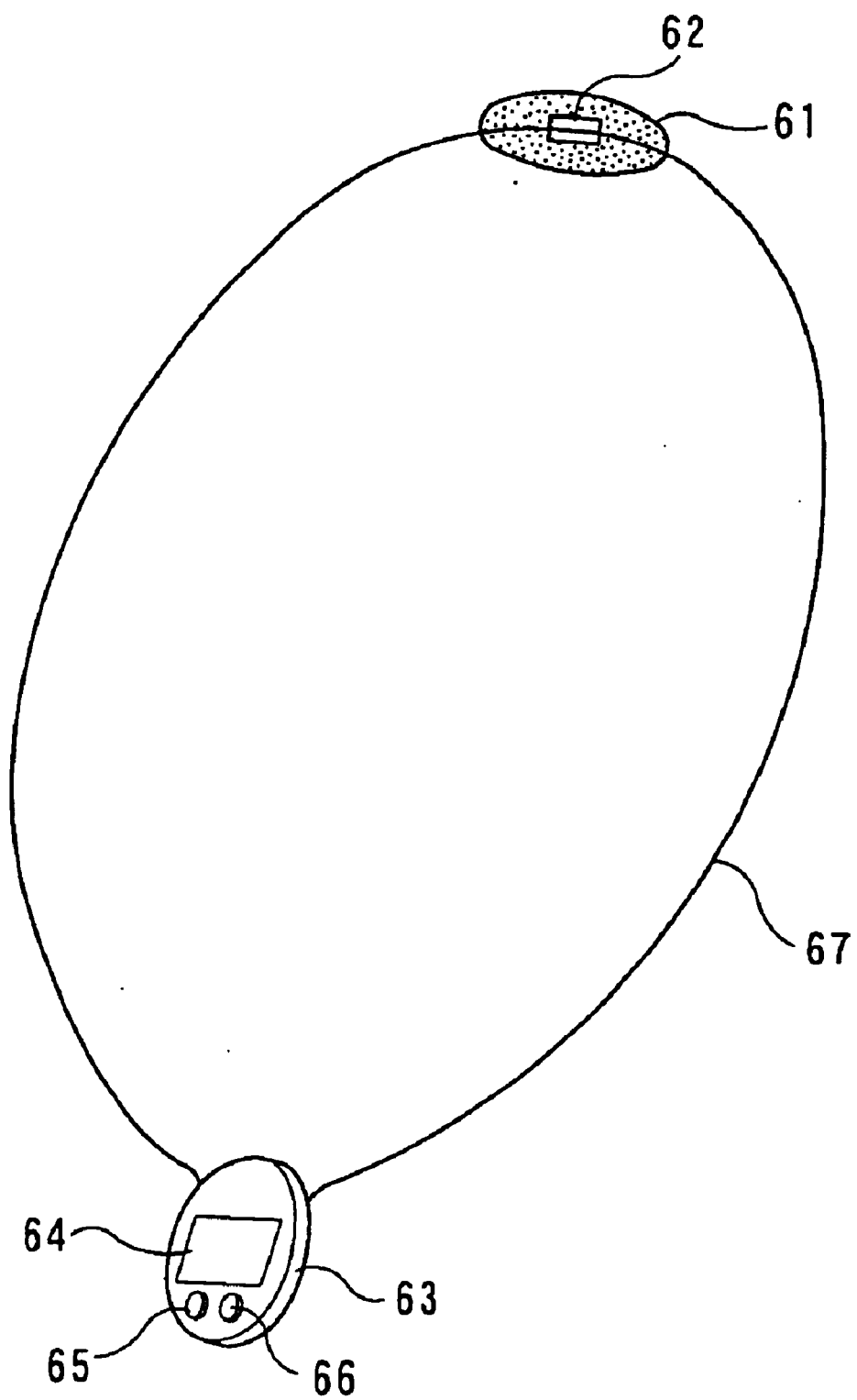
FIG. 26 is a diagram showing the case where a photoelectric blood pulse wave sensor is incorporated into a necklace.

The case where an photoelectric blood pulse wave sensor is incorporated in an accessory worn on the body will now be explained. The necklace shown in FIG. 26 will be taken as a representative example of an accessory for this purpose. In this figure, 61 is a sensor pad, and is comprised, for example, of a shock absorbing material such as a sponge. An photoelectric blood pulse wave sensor 62 is attached in the middle of sensor pad 61 so as to come in contact with the skin surface. As a result, when this necklace is worn around the neck, photoelectric blood pulse wave sensor 62 comes in contact with the skin at the back of the neck, enabling measurement of the blood pulse wave.

The main portion of the device incorporating this blood pulse wave detector is incorporated inside main body 63 which is hollow. This main body 63 is a brooch-shaped case, and is provided on the front surface thereof with a graphic displays and buttons. The functions of this display 64 and buttons 65, 66 differs in each device incorporating the blood pulse wave detector.

Photoelectric blood pulse wave sensor 62 and main body 63 are attached respectively to a chain 67, and are electrically connected via a lead wire (not shown) embedded inside chain 67.

(Modifications)

1. The device may be incorporated in other accessories in addition to a necklace.

Figure 27:
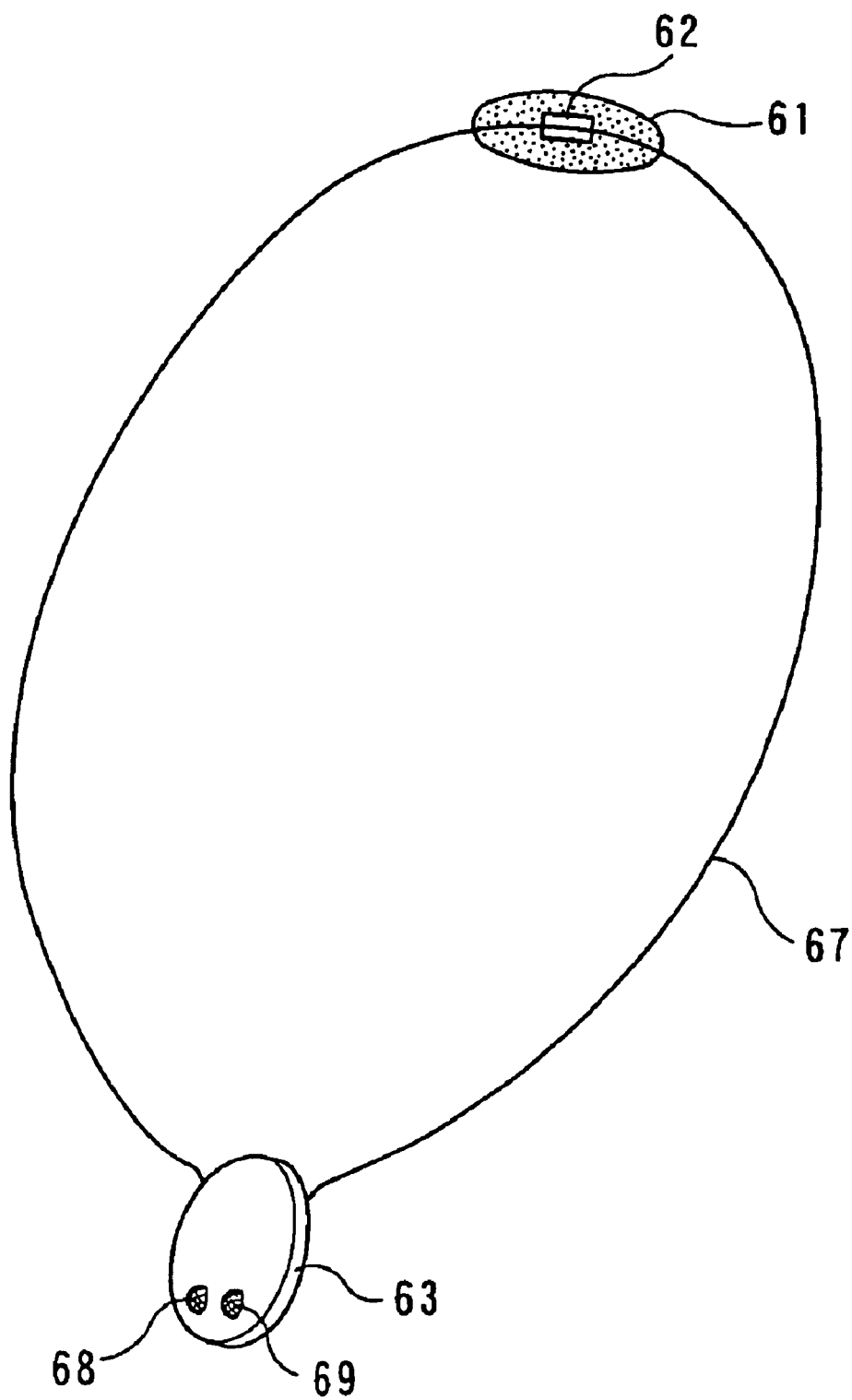
FIG. 27 is a diagram showing an embodiment in which a photoelectric blood pulse wave sensor is incorporated into a necklace, and a fragrance jet hole is provided.
Figure 28:
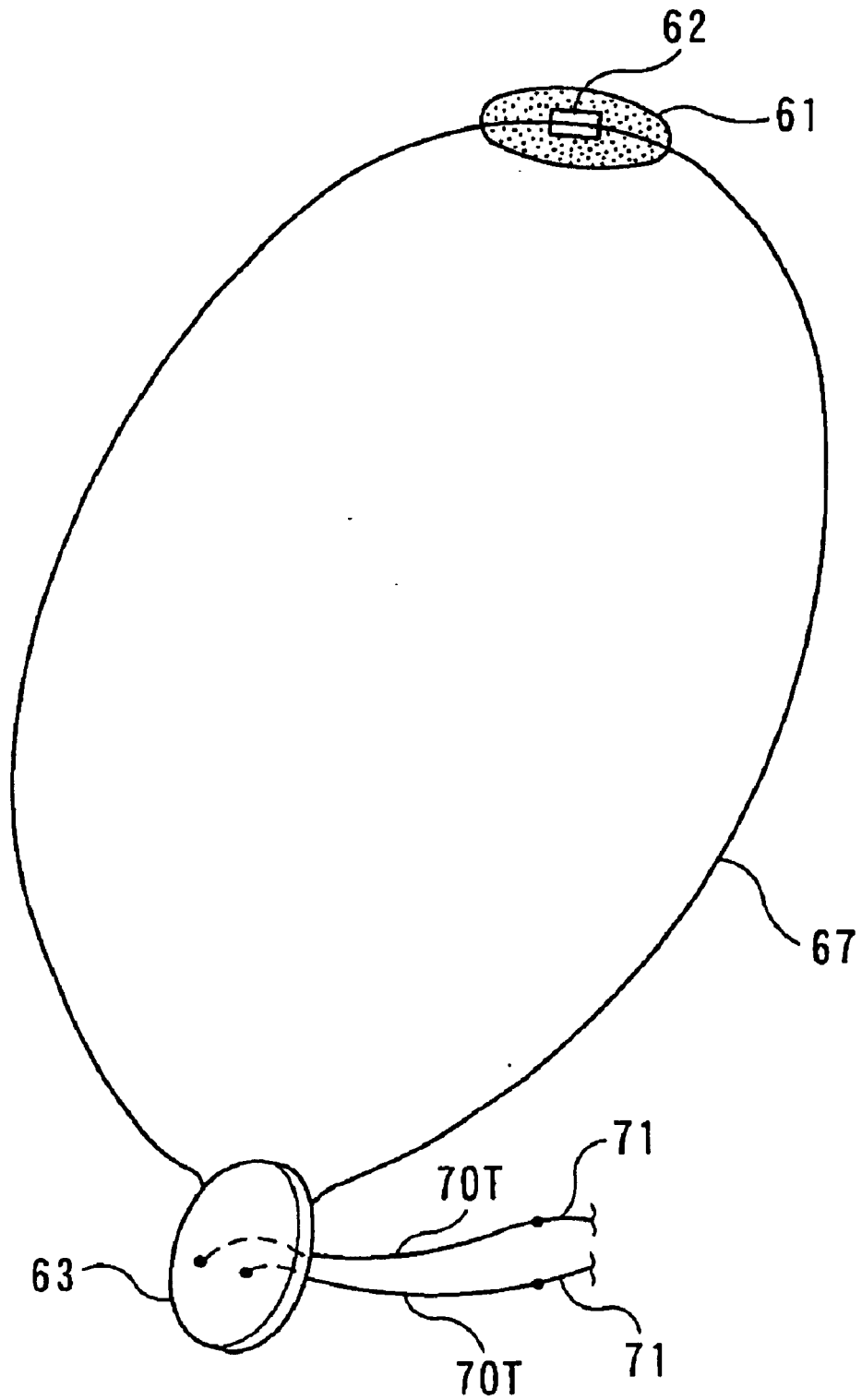
FIG. 28 is a diagram showing an embodiment in which a photoelectric blood pulse wave sensor is incorporated into a necklace, and tube for administering a drug is provided.

2. When this embodiment is employed to infuse a drug, as will be explained below, then jet holes 68, 69 may be provided to the front surface of main body 63 as shown in FIG. 27. Alternatively, drug jet holes 68, 69 may be provided to the rear surface of main body 63, designed so as to directly infuse the drug to the skin surface.

3. As will be explained below, in the case where this embodiment is employed to administer a drug, then syringe needles 71, 71 may to attached to the front surface of main body 63 via drug administration tubes 70T, 70T.

4. Jet holes 68, 69, tubes 70T or a variety of buttons may be attached to main body 63.

5. In the various devices to be discussed below, an acceleration sensor may be employed for the purpose of measuring the user's physical activity. This acceleration sensor may be attached adjacent to photoelectric blood pulse wave sensor 62.

(2) Blood Pulse Wave Detector Incorporated in Eyeglasses

An explanation will now be made of the case where a photoelectric blood pulse wave sensor is incorporated in a pair of eyeglasses. Further, this embodiment employs a structure in which a display device is also incorporated as a notifying means for notifying the user. Accordingly, the function of this display device will be explained together with the function of the blood pulse wave detector.

Figure 29:
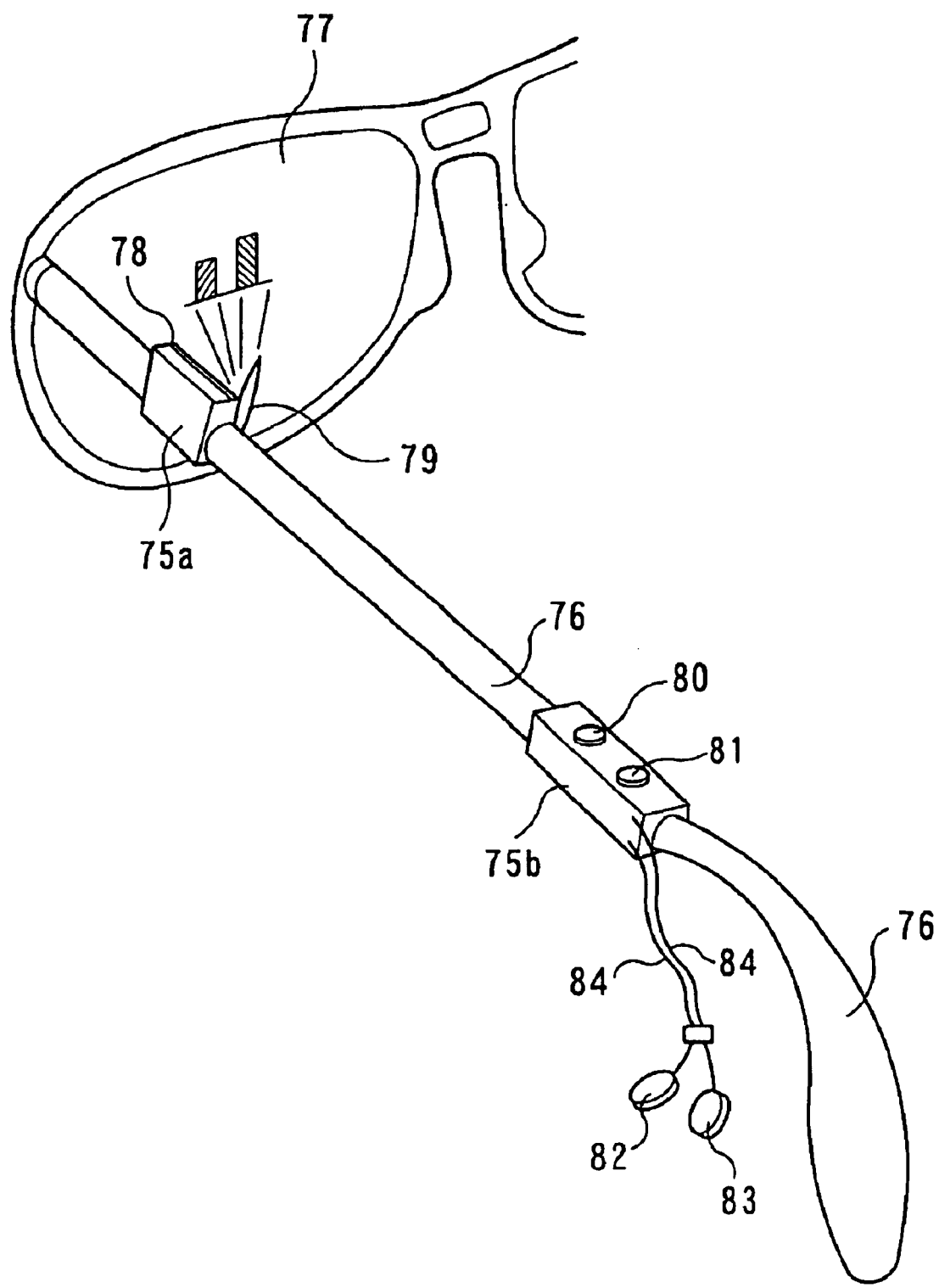
FIG. 29 is a diagram of the case where a photoelectric blood pulse wave sensor is incorporated into a pair of eyeglasses.

FIG. 29 is a perspective view showing a arrangement in which a device connected to a blood pulse wave detector is attached to a pair of eyeglasses. As shown in this figure, the main body of the device is divided into main body 75a and main body 75b which are attached respectively to the stems 76 of the eyeglasses. These main bodies are electrically attached via a lead wire embedded inside stems 76.

Main body 75a houses a display control circuit. A liquid crystal panel 78 is provided across the entire lateral surface of the lens side of main body 75a. A mirror 79 is fixed at a specific angle at one edge of this lateral surface. A drive circuit for liquid crystal panel 78 which includes a light source (not shown) and a circuit for creating display data are incorporated in main body 75a. The light emitted from this light source passes via liquid crystal panel 78, and is reflected at mirror 79 to incident on lens 77 of the eyeglasses. Further, the main portion of the device is incorporated in main body 75b, with a variety of buttons provided on the top surface thereof. The functions of these buttons 80, 81 differ in each device.

The infrared light generating diode and the optical sensor (see FIG. 21) which form the photoelectric blood pulse wave sensor are housed in pads 82, 83, with pads 82, 83 fixed to the ear lobes of the user. These pads 82, 83 are electrically connected by lead wires 84, 84 which are pulled out from main body 75b.

(Modifications)

Figure 30:
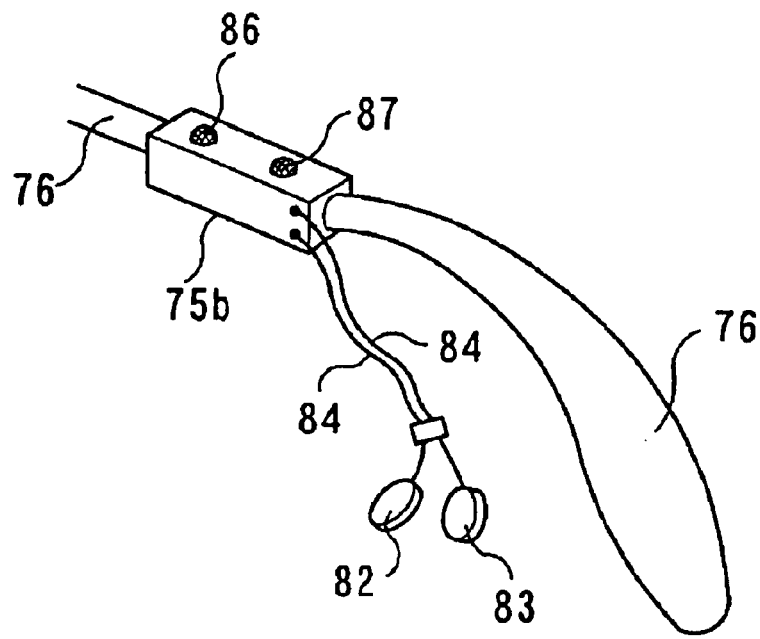
FIG. 30 is a diagram of an embodiment in which a photoelectric blood pulse wave sensor is incorporated into a pair of eyeglasses, and a fragrance jet hole is provided.
Figure 31:
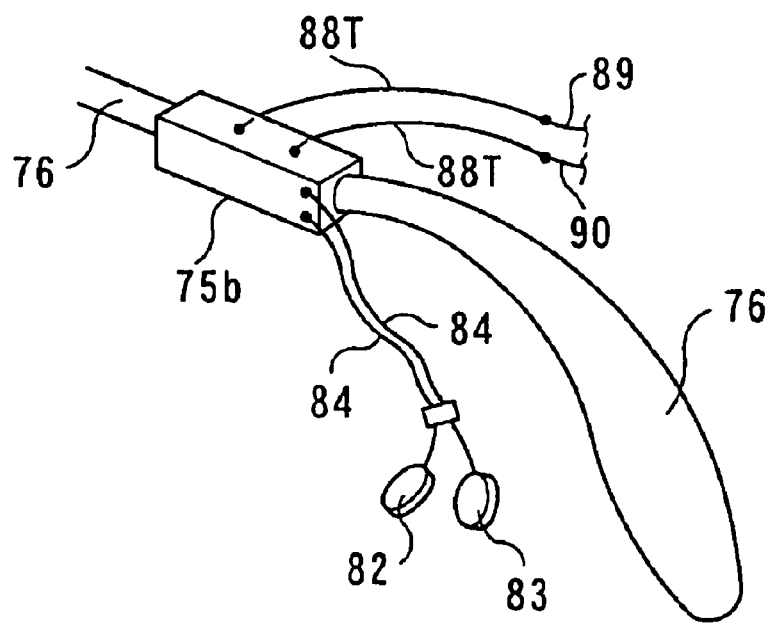
FIG. 31 is a diagram of an embodiment in which a photoelectric blood pulse wave sensor is incorporated into a pair of eyeglasses, and a tube for administering a drug is provided.

1. The lead wire which connects main bodies 75a and 75b may lie along stems 76.
2. In the above explanation, the main body of the device was divided into a main body 75a and a main body 75b, however, the main body may be formed in a unitary fashion.
3. When this embodiment is employed to infuse a drug, then drug jet holes 86, 87 may be provided to the upper surface of main body 75b as shown in FIG. 30.
4. When this embodiment is employed in a fragrance emission device, jet holes 86, 87 are attached to the lateral surface of main body 75b which face the side of the user's head, and the fragrance is emitted to the skin surface.
5. When this embodiment is employed to administer a drug, syringes 89, 90 are attached to the upper surface of main body 75b via drug administration tubes 88T, 88T, as shown in FIG. 31. Syringes 89, 90 are attached to the tips of drug administration tubes 88T, 88T.
6. Jet holes 86, 87, tube 88T and a variety of buttons may be attached anywhere to main body 75b.
7. Mirror 79 may be moveable so as to enable adjustment of the angle between the mirror 79 and liquid crystal panel 78 by the user.

Part 7 Wrist Watch-type Blood Pulse Wave Detector in Which Sensor is Attached to Base of Finger An explanation will now be made using FIGS. 32 through 34 of an embodiment in which the blood pulse wave sensor itself is attached to the finger when the detector is incorporated in a wrist watch.

First, the detailed structure of a wrist watch actually employed by one of the present inventors will be explained. As shown in FIG. 32, the device connected to this blood pulse wave detector comprises a main body 100 having a wrist watch mechanism, a cable 101 connected to the device main body 100, and a sensor unit 102 provided to an end of the cable.

The wrist watch is wrapped around the wrist of the user from the 12 o'clock position. A wrist band 103 which is fixed at the 6 o'clock position of the wrist watch is attached to the device main body 100. This device main body 100 is designed to be freely detachable from the arm of the user by means of wrist band 103.

Sensor unit 102 is blocked from light by a band 104 for fixing the sensor in place, and is attached between the base and the second joint of the index finger. When sensor unit 102 is attached in this way to the base of the finger, cable 101 can be made shorter, making it less likely to be a hindrance to the user during exercise, for example. When the temperature distribution is measured from the palm to the fingertip at a cool ambient temperature, it is clear that the temperature at the fingertip falls noticeably while the temperature at the base of the finger does not fall. Accordingly, if the sensor unit 102 is attached to the base of the finger, accurate measurements may still be obtained even on a cold day when the user is exercising outdoors.

A connector 105 is provided to the surface of the wristwatch at; the 6 o'clock position. Connector piece 106, which is provided to an end of cable 101, is attached to connect 105 provided so as to be freely detachable. By releasing connector piece 106 from connector 105, the device may be used as a regular wristwatch or stopwatch. Further, with the intention of protecting connector 105, a prespecified type of connector cover may be attached when cable 101 and sensor unit 102 are released from connector 105. A component formed in the same way as connector piece 106 may be employed for the connector cover, with the exception that electrodes and the like are omitted from this connector cover component.

In the above connector construction, connector 105 is disposed on the side of the watch which is nearer the user's body. Thus, it is easily manipulated by the user. Further, since connector 105 does not extend outward from the 3 o'clock side of device main body 100 of the wrist watch, the user can freely move his wrist during exercise. Even if the user falls during exercise, the back of the hand does not hit the connector 105.

Figure 32:
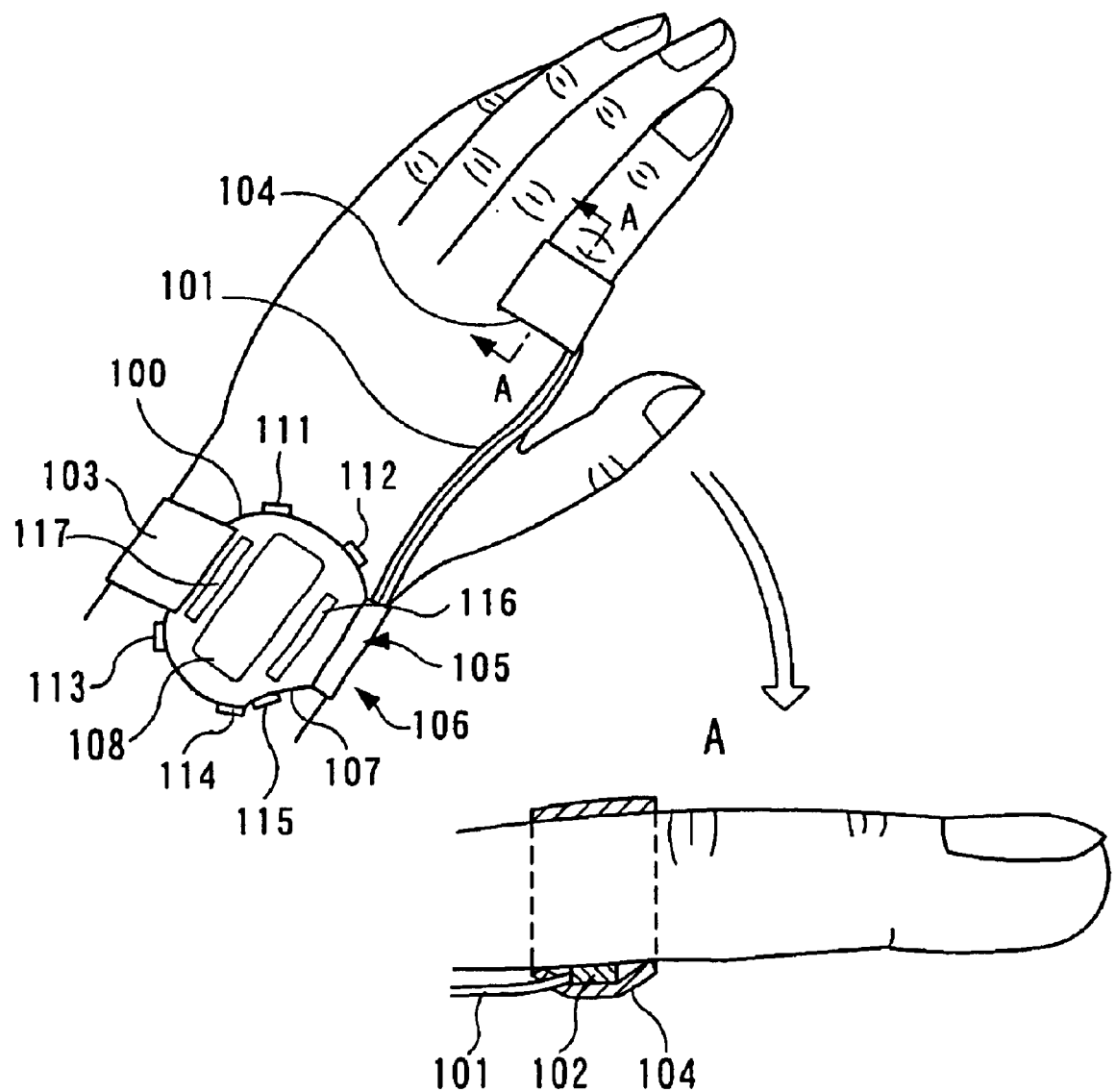
FIG. 32 is a diagram of an embodiment in which the photoelectric blood pulse wave sensor is incorporated into a wrist watch, with the photoelectric blood pulse wave sensor attached to the base of the finger.
Figure 33:
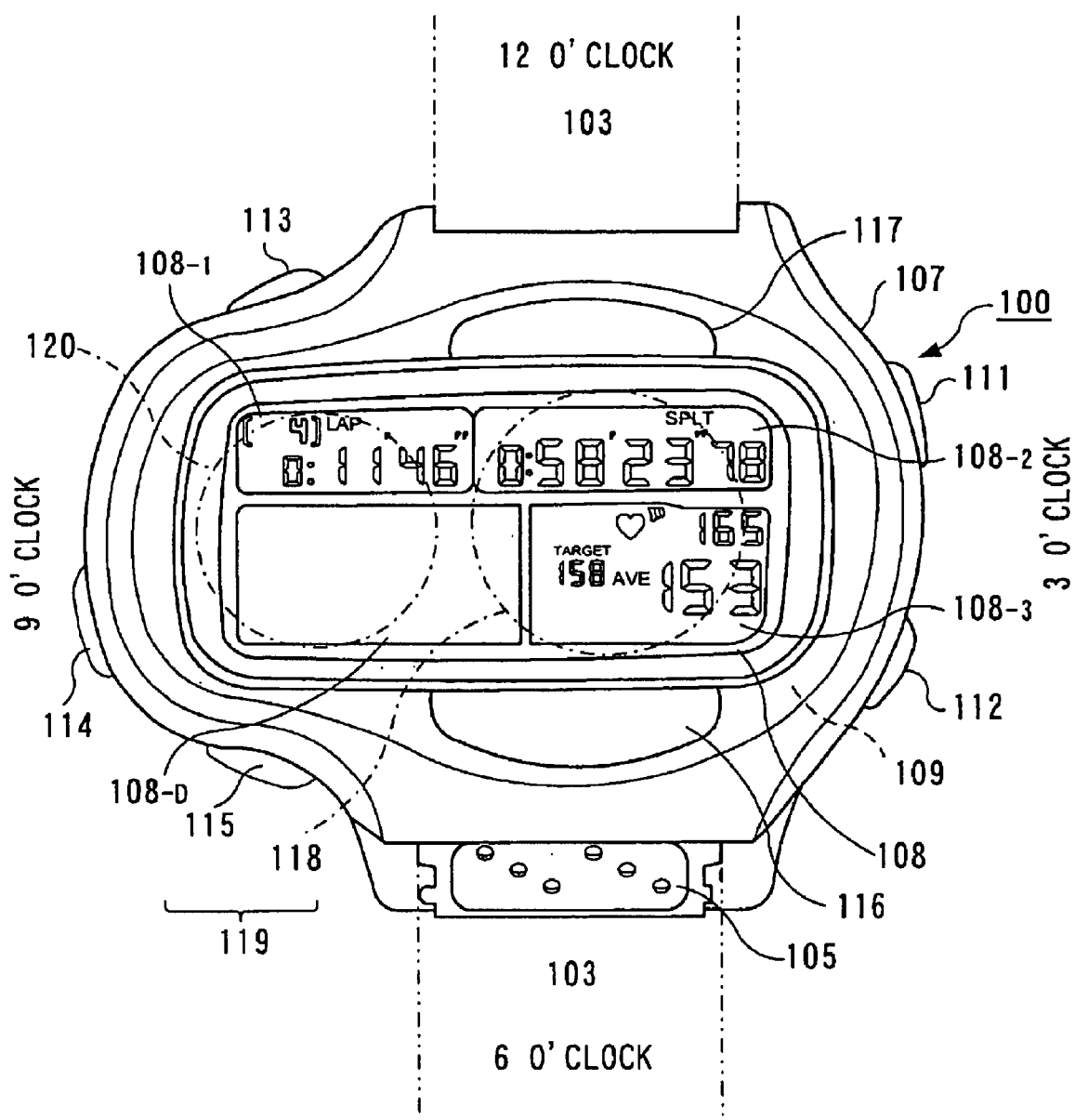
FIG. 33 is a plan view showing in greater detail the structure of the wrist watch in the embodiment shown in FIG. 32.

FIG. 33 will now be used to provide an explanation of the other parts shown in FIG. 32. FIG. 33 shows the main body 100 of the device in this embodiment in greater detail, with cable 101 and wrist band 103 detached. In this figure, parts which are identical to those shown in FIG. 32 are noted by the same numerals, and an explanation thereof is omitted.

In FIG. 33, device main body 100 is equipped with a watch case 107 formed of a resin material. A liquid crystal display device 108 is provided to the surface of watch case 107 for displaying the current time and date, as well as blood pulse rate and other blood pulse wave information in digital form. LCD device 108 is comprised of first, second, and third segment display regions 108-1, 108-2, and 108-3, respectively, and a dot display region 108-D. First segment display region 108-1 is positioned at the upper left area of the display panel; second segment display region 108-2 is positioned at the upper right area of the display panel; third segment display region 108-3 is positioned at the lower right area of the display panel; and dot display region 108-D is positioned at the lower left area of the display panel.

In this example, the date, day of the week and current time are displayed in first segment region 108-1, while the passage of time when carrying out various time measurements is displayed in second segment region 108-2. A variety of values measured during the measurement of blood pulse waves are displayed in third segment region 108-3. Finally, various information can be graphically displayed in dot display region 108-D, in addition to a variety of other displays such as the mode display, which indicates which mode the device is in at a particular time, blood pulse waveform display, bar graph display, and the like.

The term "mode" as used here refers to a variety of modes such as a mode for setting the time and date, a mode for using the device as a stop watch, and a mode for operating the device to analyze or diagnosis the blood pulse wave. Since these modes and the content of the displays in each of the aforementioned regions will differ depending upon the application, these will be explained as necessary.

A controller 109 for carrying out signal processing for display on LCD device 108 is housed inside watch case 107. A one chip micro computer, or a general microprocessor composed of a central processing unit (CPU), random access memory (RAM), read-only-memory (ROM), and the like, is suitable for use as controller 109. Controller 109 includes a watch circuit for carrying out watch functions. Further, an ordinary time display may be used for LCD device 108, however, live time or split time displays for use when the device is operated as a stop watch are also possible.

Button switches 111 to 117 are provided to the outer periphery and surface of watch case 107. One example of the function of these button switches will be explained hereafter, however, these functions will differ according to the type of device incorporated into the wrist watch.

When button switch 111, which is at the 2 o'clock position on the wrist watch, is pressed, an alarm is set to sound one hour thereafter.

Button switch 112, which is at the 4 o'clock position on the wrist watch, is provided for directing switching of the device's various modes.

When button switch 113, which is at the 11 o'clock position on the wrist watch, is pressed, an electroluminescence (EL) back light on liquid crystal display device 108 is turned on for 3 sec, for example, after which it automatically turns off.

Button switch 114, which is at the 8 o'clock position on the wrist watch, switches between the various graphic displays which are to be displayed on dot display region 108-D

By pressing button switch 115, which is at the 7 o'clock position on the wrist watch, the form of time and date display (i.e., time displayed in seconds/minutes/hours, 12 or 24 hour display, etc.) can be switched in the day and date correction mode.

Button switch 116, which is positioned below LCD display 108, can be used when correcting time or date, by decreasing the setting by one. Additionally, when timing a lap, button switch 116 can be used as a switch for informing controller 109 of the completion each lap.

Button switch 117, which is positioned above LCD 108, is employed for indicating the initiation or termination of operation of the device as a blood pulse wave analysis or diagnostic device. In addition to being used to increase the time and date setting by one, button switch 117 can also be used to indicate the initiation or termination of a variety of time elapse measurements.

A button-shaped battery 118 is housed in watch case 107 and serves as an power source for the watch. Cable 101 shown in FIG. 32 supplies electric power from battery 118 to sensor unit 102, and sends the detection results from sensor unit 102 to controller 109.

It becomes necessary to enlarge device main body 100 as the functions of the watch itself are increased. Device main body 100 cannot be enlarged in the 6 or 12 o'clock directions, however, since a limitation on size is imposed because the watch must be worn on the arm. Therefore, in this embodiment, a horizontally long watch case 107 is employed which is longer in the horizontal, (i.e., 3 o'clock to 9 o'clock) direction, than in the vertical (i.e., 6 o'clock to 12 o'clock) direction.

In this embodiment, wrist band 103 is connected to a watch case 107 at a position shifted toward the 3 o'clock side of the watch. As seen from wrist band 103, a large overhang 119 is present on the 9 o'clock side the wrist watch, but is absent from the 3 o'clock side of the watch. Accordingly, the user can bend his wrist when using or carrying the horizontally long watch case 107. Further, even if the user falls, he will not hit the watch case with the back of his hand.

A flat piezo element 120 used as a buzzer is disposed inside the watch case 107, at the 9 o'clock position with respect to the battery 118. Battery 118 is heavier than piezo element 120, such that the position of the weight center of device main body 100 shifts toward the 3 o'clock side. Moreover, wrist band 103 is connected to the side of the main body 100 toward which the weight center has shifted. As a result, device main body 100 can be attached to the arm in a stable manner. Further, since battery 118 and piezo element 120 are disposed in the planar direction, device main body 100 may be made thinner. By providing a battery cover to the rear surface of the wrist watch, the user can easily change the battery.

Figure 34:
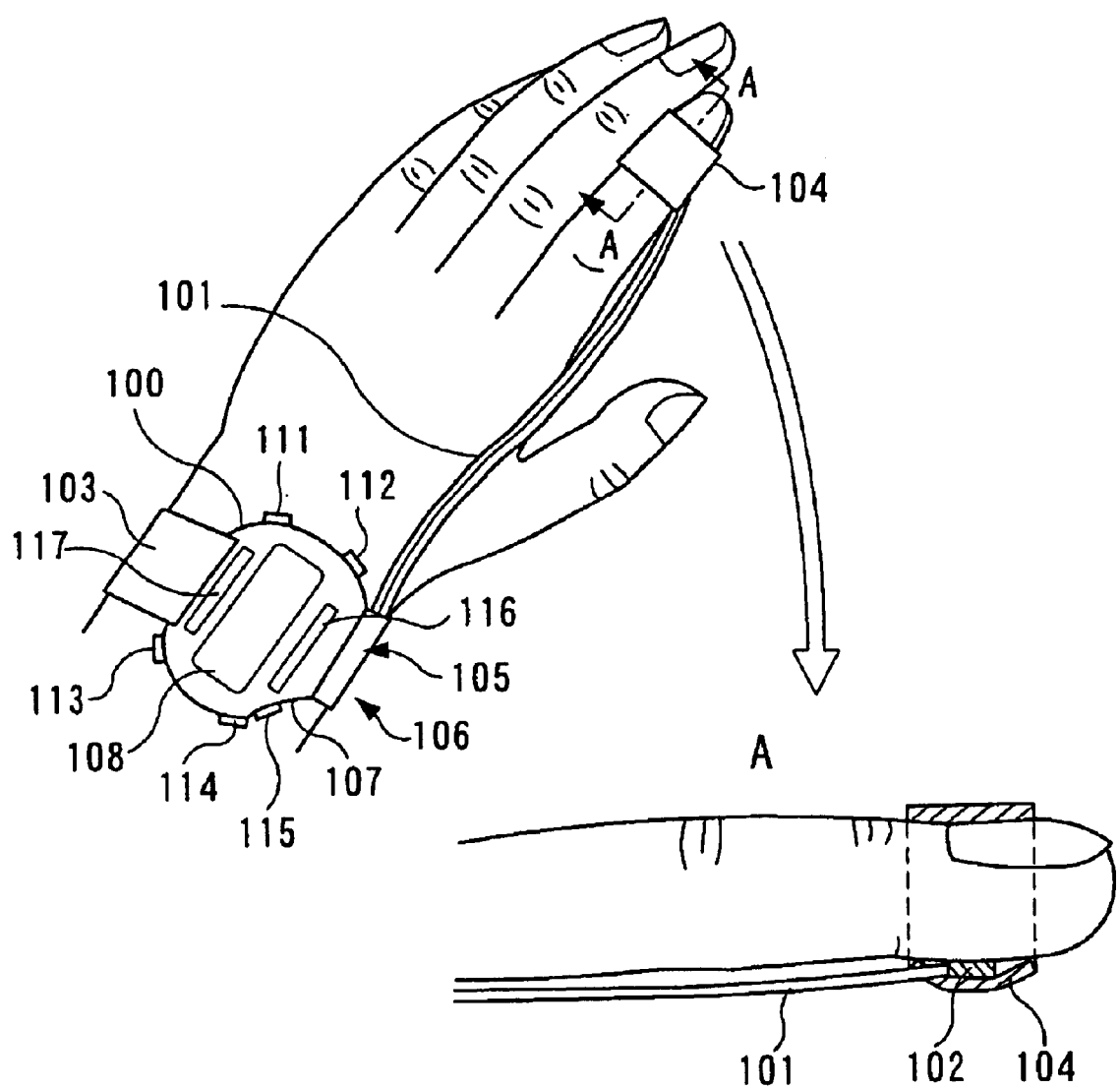
FIG. 34 is a diagram of an embodiment in which a photoelectric blood pulse wave sensor is incorporated into a wrist watch, with the photoelectric blood pulse wave sensor attached to the fingertip.

As shown in FIG. 34, a modification of the above embodiment may be considered, in which the sensor unit 102 and band 104 for fixing the sensor in place are attached to the fingertip, enabling measurement of the fingertip plethysmogram.

Part 8 Blood Pulse Wave Detector Employing Elastic Rubber

The blood pulse wave detector explained below is a pressure sensor for carrying out blood pulse wave detection by detecting pressure vibrations using elastic rubber.

Embodiment 1

(1) Pressure Sensor Structure

Figure 35A:
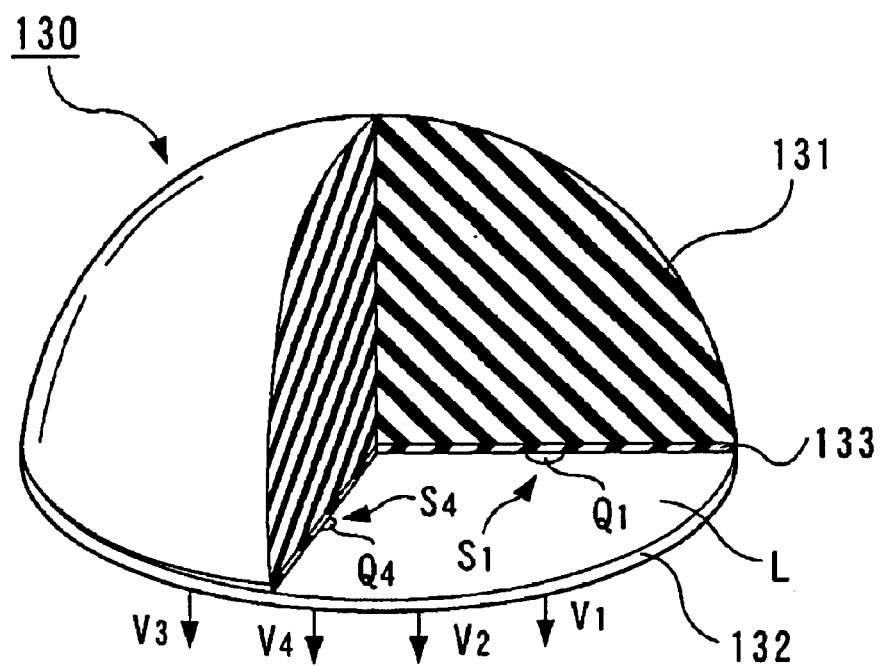
FIG. 35A is a perspective view showing a partial section of the structure of pressure sensor 130.
Figure 35B:
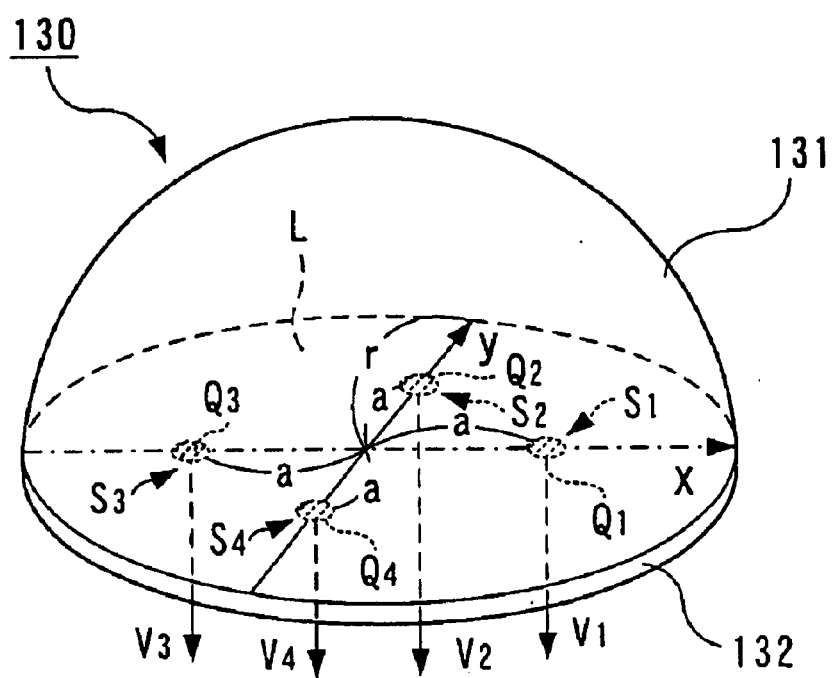
FIG. 35B is a see-through perspective view showing the structure of pressure sensor 130.

Pressure sensor 130 calculates the pressure vibration generated by pressure from the operator on elastic rubber 131, and calculates the generation coordinates of this pressure vibration. FIG. 35A and 35B are, respectively, a perspective view and a see-through perspective view showing the structure of the pressure sensor. FIG. 35A is a partial sectional view provided for explanatory purposes. As shown in these figures, pressure sensor 130 is composed of pressure-sensitive piezo elements S1 to S4 and hemispherical elastic rubber 131. In the explanation to follow, the shape of elastic rubber 131 will be imagined to be a perfect hemispherical surface.

Each of pressure-sensitive piezo elements S1 to S4 are provided to the bottom surface (flat surface) L of elastic rubber 131, and respectively output voltages V1 to V4 proportional to the detection pressure as detection signals. One example of the structure of these pressure-sensitive piezo elements S1 to S4 will be explained below. The coordinates (x, y) of the detection positions Q1 to Q4 of pressure-sensitive elements S1 to S4 are:

$$(a, 0)(0, a)(-a, 0)(0, -a) \tag{a}$$

where the radius of the elastic rubber 131 is r and the center of the bottom surface L is taken as the origin (0, 0), and r>a>0.

In other words, the coordinates at which the pressure is to be detected by pressure-sensitive elements S1 to S4 are on the x and y axes on the lower surface L and are located equidistant from the origin.

Figure 36:
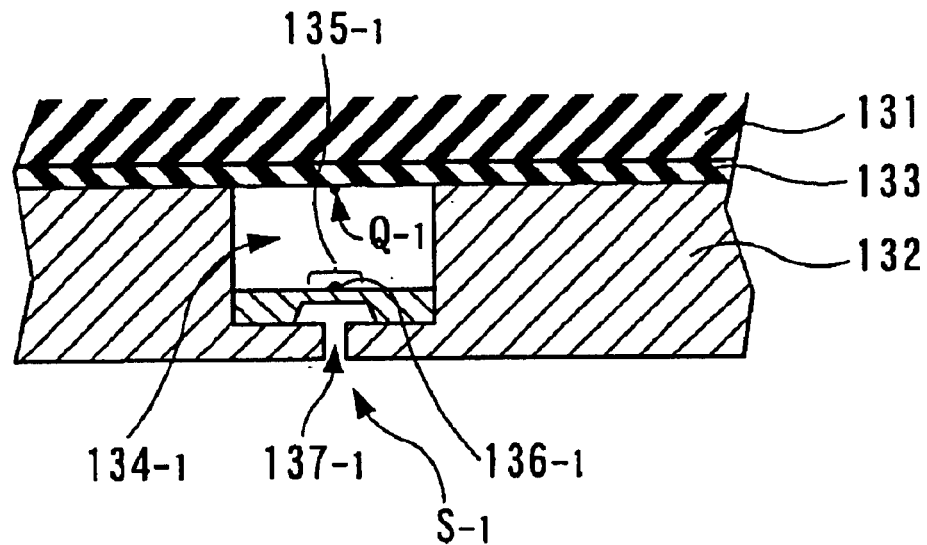
FIG. 36 is a section diagram of a principal component of the present invention, in which the area of joining between elastic rubber 131 and semiconductor substrate 132 in pressure sensor 130 is enlarged.

Joining between the pressure-sensitive element and elastic rubber 131 will now be explained employing pressure-sensitive element S1 as an example. FIG. 36 is a sectional view of a principal component showing the structure of pressure-sensitive element S1.

Semiconductor substrate 132 is bonded to the bottom surface L of elastic rubber 131 by means of an elastic bonding layer 133. Pressure-sensitive element S1 which detects pressure at detection position Q1 is formed to semiconductor substrate 132 along with a hollow chamber 134-1 which is open at the detection position. Pressure-sensitive element S1 is formed of a thin portion 135-1 which is employed as a diaphragm and has a thickness of about 20 to 30 $\mu$m, and a distortion gauge 136-1 which is formed to the surface of this thin portion 135-1.

Pressure-sensitive element S1 is formed using a known technique for etching semiconductors. In particular, distortion gauge 136-1 is formed of a piezo resistance element (p-type resistance layer) which is formed using a selective dispersion technique for impurities (i.e., boron, etc.). When this type of distortion gauge 136-1 bends, the resistance value varies in response to the distortion.

Similarly, pressure-sensitive elements S2 to S4 are formed on top of semiconductor substrate 132, with the resistance values thereof varying respectively in proportion to the pressure at detection positions Q2 to Q4.

When a pressure vibration is generated on the hemispherical surface of elastic rubber 131 in a pressure sensor 130 of the above described structure, it is propagated as an acoustic wave through elastic rubber 131, and becomes respective microvibrations at detection positions Q1 to Q4, causing a change in each of the pressures inside hollow chambers 134-1 to 134-4. In this case, each of distortion gauges 136-1 to 136-4 respectively bend under the difference between the pressure inside hollow chamber 134-1 to 134-4 and the outside pressure introduced by openings 137-1 to 137-4 which are open to the outside environment. As a result, each of the resistance values changes in response to the pressure vibration.

Aluminum electrodes (not shown) for directing the external circuits are deposited to each end of distortion gauges 136-1 to 136-4. The electrodes can be respectively converted between resistance and voltage by means of the circuit described below, with the voltage output as a detected voltage V1 proportional to the pressures at detection positions Q1 to Q4.

As necessary, an alternative design is also possible in which each of hollow chambers 134-1 to 134-4 are not left empty, but are filled with a liquid having a low coefficient of thermal expansion, such as water or alcohol, or a liquid substance, such as gelatin. In this case, the microvibrations generated at detection positions Q1 to Q4 can be converted to detection signals from distortion gauges 136-1 to 136-4 with little loss and greater accuracy.

Figure 37:
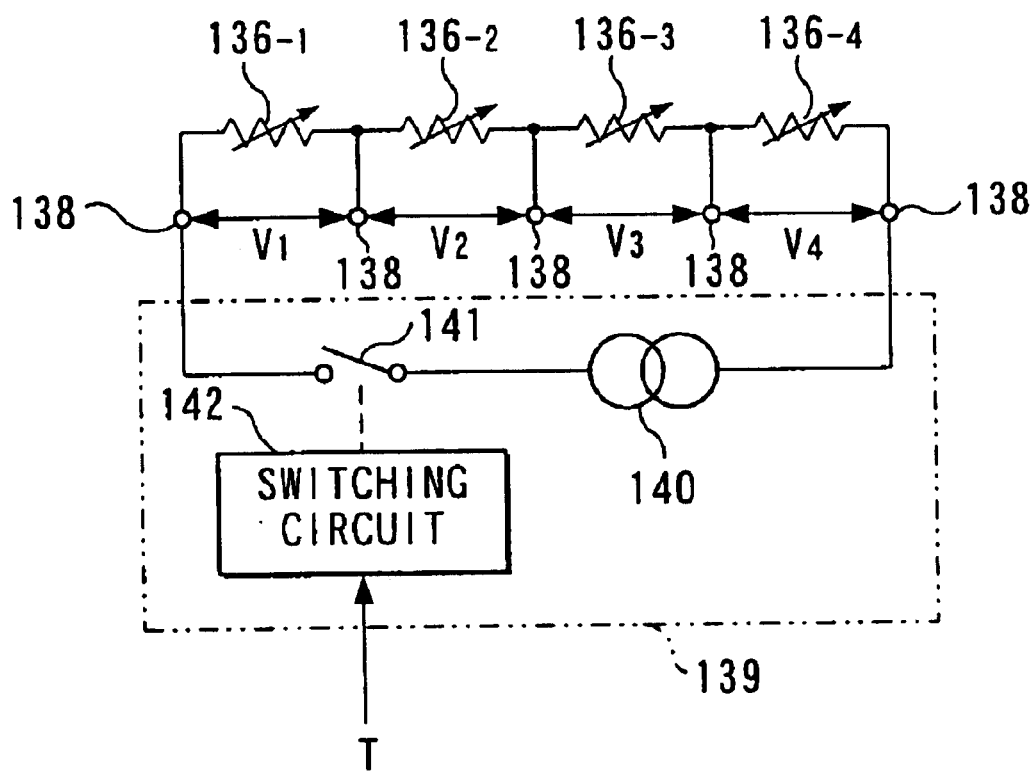
FIG. 37 is a circuit diagram showing the structure of bias circuit 139 provided to pressure sensor 130.

Next, FIGS. 37 and 38 will be used to explain the electrical connection of pressure-sensitive elements S1 to S4 at pressure sensor 130, and the bias method therefor. Each of distortion gauges 136-1 to 136-4 are disclosed equivalently as variable resistors in FIG. 37.

As shown in FIG. 37, each of distortion gauges 136-1 to 136-4 corresponding to pressure-sensitive elements S1 to S4 are connected in series, with output terminals 138, . . . , 138 provided to both ends of each distortion gauge.

The serial terminals of distortion gauges 136-1 to 136-4 are connected to bias circuit 139. This bias circuit 139 is composed of a fixed current circuit 140, a switch 141 for turning the output signals of fixed current circuit 140 on or off, and a switcher circuit 142 for turning on switch 41 when the control signal T has entered the "H" state. In other words, when control signal T is in the H state, the output signal from fixed current circuit 140 is impressed on distortion gauges 136-1 to 136-4.

As explained above, the resistance values of the distortion gauges change in response to the distortion. Thus, if the same fixed current flows through distortion gauges 136-1 to 136-4, the voltages V1 to V4 between each of the output terminals 138, . . . , 138 are proportional to each of the pressures at detection positions Q1 to Q4 and relatively indicate the size of each of the pressures.

However, there are a variety of waveform patterns for control signal T which may be considered by means of altering the arrangement or scale of the device for processing the detection signal of pressure sensor 130. For example, a signal TS1 (see FIG. 38A) which is constantly in the H state regardless of whether or not it is time for measurements to be made; a blood pulse signal TS2 having a specific duty ratio which is intermittently in the H state regardless of whether or not it is time for measurements to be made (see FIG. 38B); a signal TS3 which is in the H state only when it is time for measurements to be made (see FIG. 38C); and a blood pulse signal TS4 having a specific duty ratio which is in the H state intermittently only when it is time for measurements to be made; may be selected for control signal T. "Time for measurements to be made" as used here indicates the time period during which detection of pressure vibration is to be carried out.

Signal TS1 is suitably employed for the control signal T in the case where considerable detection accuracy is demanded of the device for processing the detection signal of pressure sensor 130. On the other hand, if it is desirable to reduce power consumption, then blood pulse signal TS4 is suitably employed for control signal T. Further, in the case where a compromise between detection accuracy and power consumption is desired of the device, then blood pulse signal TS2 or signal TS3 are suitably employed for control signal T. The basis for these selections is as follows.

A slight generation of heat accompanies the provision of a fixed current flow to distortion gauges 136-1 to 136-4. For this reason, a temperature difference occurs between when a bias is impressed and when it is not. This temperature difference gives rise to an extremely slight difference in the resistance values, and may be a cause of error during pressure detection. When signal TS1 is employed as control signal T, a fixed current is impressed on distortion gauges 136-1 to 136-4 even when detection is not taking place. If pressure detection is carried out at a point after the elapse of a set period of time at which heat generation has reached a saturation point, then the errors in measurement caused by the difference in temperature can be held to an extremely small amount.

On the other hand, if blood pulse signal TS4 is employed as control signal T, then a fixed electric current is impressed intermittently on distortion gauges 136-1 to 136-4 only at the time of detection. As a result, the heat generated by the electric current can be reduced, thereby contributing to power conservation. Further, if each part (analog/digital) of the detection signal processing device of pressure sensor 130 is operated in synchronization with blood pulse signal ST4, the power consumption can be reduced even further. To take an extreme case, it is permissible that the flow of electricity to each of these parts be carried out only when blood pulse signal TS4 is in the H state.

Further, a construction is also possible in which fixed current circuit 140 outputs a fixed current blood pulse (see FIG. 38E) for the fixed current bias, this fixed current blood pulse having a shorter interval that is even more sufficient than that provided with blood pulse signal TS2 and TS4. In this case, this signal may of course be combined with signal TS1 to TS4 for use as a control signal T. In particular, when blood pulse signal TS4 is employed, the duration of the impression of the bias on distortion gauges 136-1 to 136-4 becomes extremely short, as shown in FIG. 38F. As a result, it is possible to limit the power consumption to an extremely small value. Similarly, in this case as well, if all the parts in the detection signal processing device in pressure sensor 130 are operated in synchronization with the fixed current blood pulse, the electric power consumed can be reduced even further. Finally, if the flow of electricity through these parts is carried out only during bias impression, then power consumption can be held to an extremely small value.

It is necessary that the interval of bias impression be short enough to sufficiently correspond to changes in pressure vibration (i.e., to satisfy the sampling theorem), but within limits which permit the device receiving the output to respond.

It is preferable that pressure-sensitive elements S1 to S4 are formed on the same semiconductor substrate 132. Disposition of the elements or formation in a unitary manner to the same semiconductor substrate is readily accomplished using semiconductor manufacturing techniques, and is more accurate and convenient than the case where the pressure sensitive elements are formed or disposed to separate semiconductor substrates. In addition, by using semiconductor manufacturing technology, the blood pulse wave detector can be made extremely small and highly accurate.

(2) Principle of Blood Pulse Wave Detection and Coordinate Calculation

Figure 39:
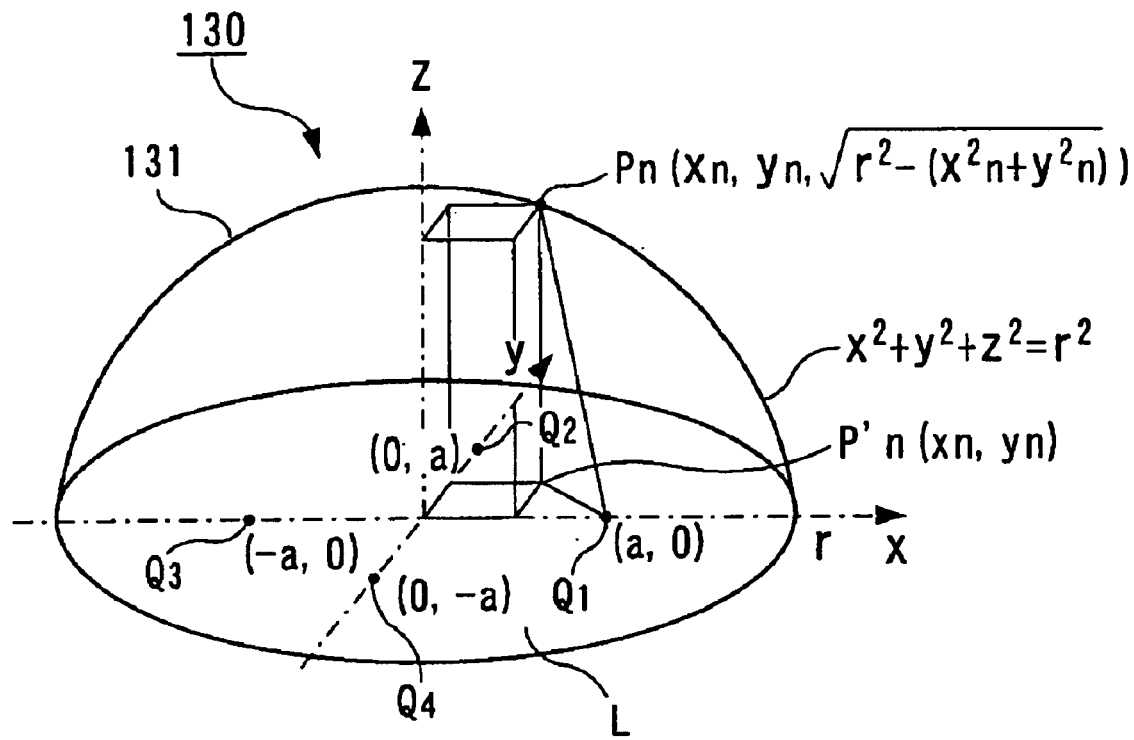
FIG. 39 is a simplified perspective view diagram provided to explain the principle of coordinate detection using pressure sensor 130.

An explanation will now be made of the principle of blood pulse wave detection and coordinate calculation using a pressure sensor 130 of the above-described structure. Additionally, it is assumed that all of the arteries which are the focus of interest in the present invention are under the surface of the skin. FIG. 39 is a perspective view for explaining the principle of blood pulse wave detection and coordinate calculation. For the purpose of simplification, the pressure sensor 130 shown in FIGS. 35A and B is omitted from this figure.

Figure 40:
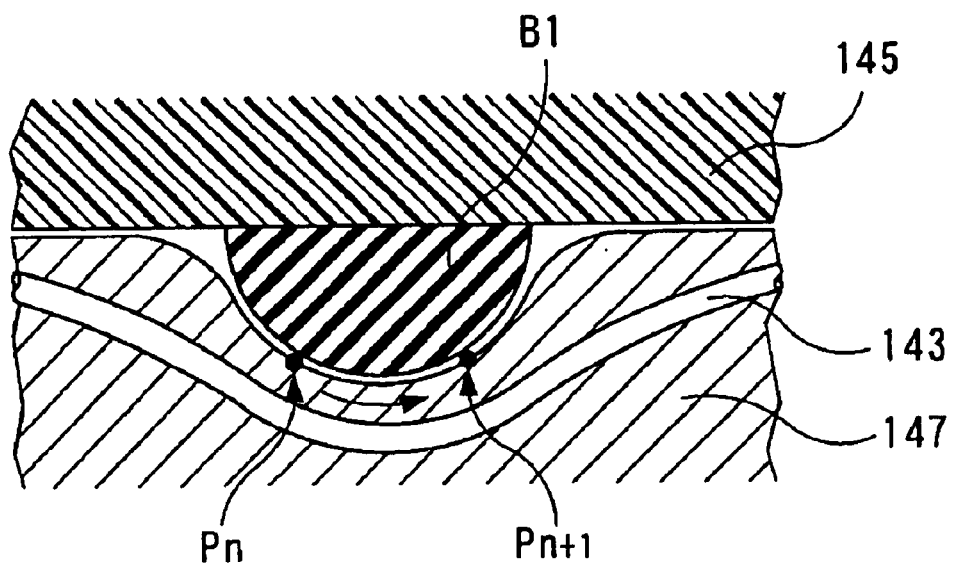
FIG. 40 is a section diagram of a principal component of the present invention provided to explain the principle of blood pulse wave detection using pressure sensor 130.

As shown in FIG. 40, the hemispherical outer surface of elastic rubber 131 is pressed against the vicinity of an artery (radius artery 143 in this explanation). A vibration occurs at point Pn on the hemispherical surface of elastic rubber 131 due to a pressure vibration wave (i.e., blood pulse wave) generated from radius artery 143. In this discussion, point Pn is assumed to be the vibration center. The vibration is propagated through elastic rubber 131, with pressure-sensitive elements S1 to S4 outputting respective electric signals, i.e., detection signals having voltages V1 to V4, which indicate the blood pulse wave.

The principle of coordinate calculation at the pressure vibration point will now be explained.

When the hemispherical surface of elastic rubber 131 is pressed against the vicinity of the artery so that radius artery 143 is projected inside surface L, then, at time t=n, a vibration occurs at point Pn on the hemispherical surface of elastic rubber 131 due to the blood pulse wave generated from radius artery 143. This vibration is propagated through elastic rubber 131, with the vibration attenuating in proportion to the square of the propagation distance. The vibrations are detected by pressure-sensitive elements S1 to S4 as detection signals having voltages V1 to V4 which show the blood pulse wave.

The following equation expresses the spherical surface of elastic rubber 131.

$$x^2+y^2+z^2=r^2 \quad (b)$$

where z>0.

Accordingly, when the values of the coordinates (x, y) of an optional point Pn on the spherical surface of elastic rubber 131 are expressed as $x_n$, $y_n$, then the following may be derived from equation (b):

$$P_n[x_n, y_n, \sqrt{\{r^2-(x_n^2+y_n^2)\}}] \quad (c)$$

Drawing from equation (c) and the above equation (a) for indicating the coordinates of each of the detection positions, the distances between point Pn and each of detection positions Q1 to Q4 of pressure-sensitive elements S1 to S4 may be obtained from the following equations:

$$\overline{P_nQ_1}=\sqrt{(a^2-2axn+r^2)}$$

$$\overline{P_nQ_2}=\sqrt{(a^2-2ayn+r^2)}$$

$$\overline{P_nQ_3}=\sqrt{(a^2-2axn+r^2)}$$

$$\overline{P_nQ_4}=\sqrt{(a^2-2ayn+r^2)} \quad (d)$$

As mentioned above, the vibration generated at point Pn attenuates in proportion to the square of the propagation distance. As a result, the values of voltages V1 to V4 detected by each element are inversely proportional to square of the distance between Pn and the detection position of the corresponding element. Accordingly, the following equivalency equations may be set up.

$$V1\{\sqrt{(a^2-2axn+r^2)}\}^2 = V2\{\sqrt{(a^2-2ayn+r^2)}\}^2 \quad (e)$$
$$= V3\{\sqrt{(a^2+2axn+r^2)}\}^2$$
$$= V4\{\sqrt{(a^2+2ayn+r^2)}\}^2$$

From equation (e), the values $x_n$, $y_y$ of the x and y coordinates of point Pn are as follows.

$$x_n=\{(V1-V3)\cdot(a^2+r^2)\}/2a(V1+V3)$$

$$y_n=\{(V2-V4)\cdot(a^2+r^2)\}/2a(V2+V4) \quad (f)$$

In this way, then, when a pressure vibration due to pressure from a blood pulse wave occurs at point Pn on the hemispherical surface of elastic rubber 131, the coordinate values $x_n$, $y_y$ of point Pn can be obtained from the voltages V1 to V4 detected at pressure-sensitive elements S1 to S4. Obtaining coordinate values $x_n$, $y_n$ is nothing more than obtaining the coordinates of the point P'n (see FIG. 39) which is the vertical projection of the point Pn to the plane. "Flat surface" here indicates the flat surface (i.e., x-y plane) on which the detection positions of pressure-sensitive elements S1 to S4 are located, i.e., the bottom surface L of elastic rubber 131.

In equation (f), the coordinate value $x_n$ is obtained from voltages Vi and V3 of pressure-sensitive elements S1 and S3 provided along the x axis, while the coordinate value $y_y$ is obtained from voltages V2 and V4 of pressure-sensitive elements S2 and S4 provided along the y axis. Further, coordinate values $x_n$ and $y_n$ can be obtained independently of one another, so that it is possible to eliminate any mutual effect when calculating coordinates.

As may be understood from equation (e), the voltage necessary to obtain coordinate values $x_n$, $y_n$ may be obtained using just three of the four pressure-sensitive elements S1 to S4. However, in this case, when calculating values of one set of coordinates, the other coordinate values exert an influence. For example, to calculate coordinate values $x_n$, $y_n$ using only pressure-sensitive elements S1 to S3, coordinate value $x_n$ is first calculated from voltages V1 and V3. Coordinate value $y_n$ can then be calculated from voltage V2 by substituting coordinate value $x_n$ into equation (e). However, since coordinate value $y_n$ is dependent on voltages V1 to V2 in this case, it is not possible to obtain an accurate coordinate calculation when there is a difference in the output characteristics of the pressure-sensitive elements.

In contrast, when four pressure-sensitive elements are provided, the pressure detection positions are disposed to be mutually symmetrical about the center of the bottom surface of elastic rubber 131. For this reason, even if the point at which a pressure vibration is generated on the exposed surface moves, the attenuation characteristics of elastic rubber 131 are equivalent with respect to each of the pressure-sensitive elements. Further, if the direction of movement of the pressure vibration point is such that it passes through the apex of elastic rubber 131 and moves along one of the positional axes of a detection position, then the distance of propagation of the elastic wave can be minimized, thus enabling an even more accurate pressure detection.

(3) Operation of Blood Pulse Wave Detector

1. Mode of Measurement

A simple explanation will now be made of the mode of measurement when carrying out detection of a pressure vibration at a radius artery of a test subject.

Figure 41:
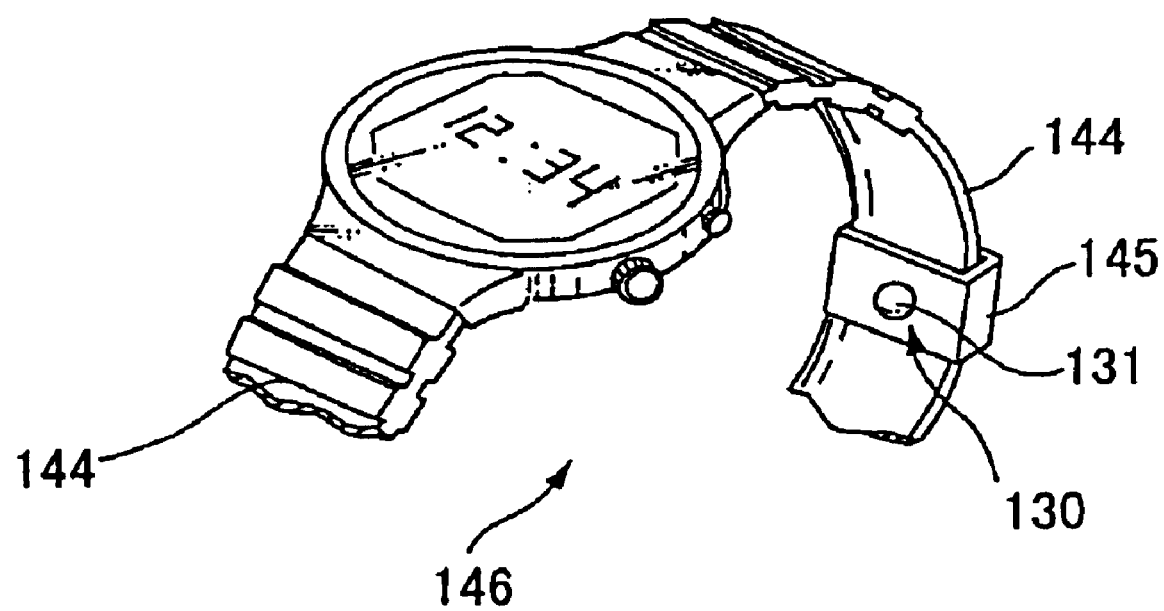
FIG. 41 is a perspective view showing the external structure of wrist watch 146 which incorporates a device employing pressure sensor 130.

FIG. 41 is a perspective view showing the external structure of an embodiment in which a pressure sensor 130 is incorporated into a wrist watch. As shown in the figure, the elastic rubber 131 of pressure sensor 130 projects outward from the fastening side of a belt-shaped fastener 145 which is provided to one of a pair of wrist watch bands 144, 144. Although not shown in detail in the figure, the band 144 provided with belt-shaped fastener 145 has a structure wherein the FPC (flexible printed circuit) substrate which is to supply the detection signal from pressure sensor 130 is coated with a soft plastic.

2. Operation

Figure 42A:
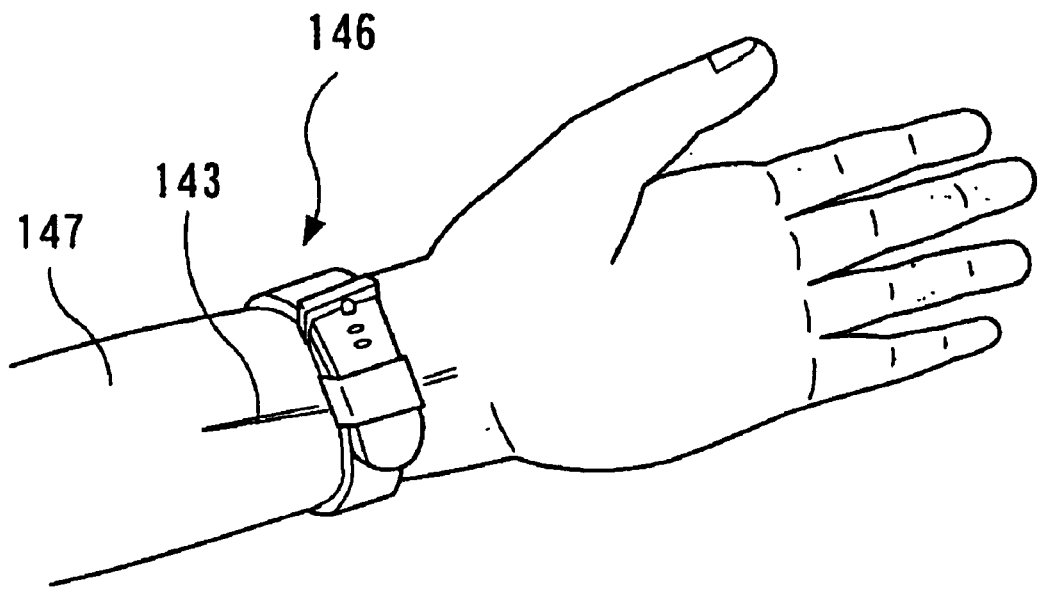
FIG. 42A is a perspective view showing the state of attachment of wrist watch 146.
Figure 42B:
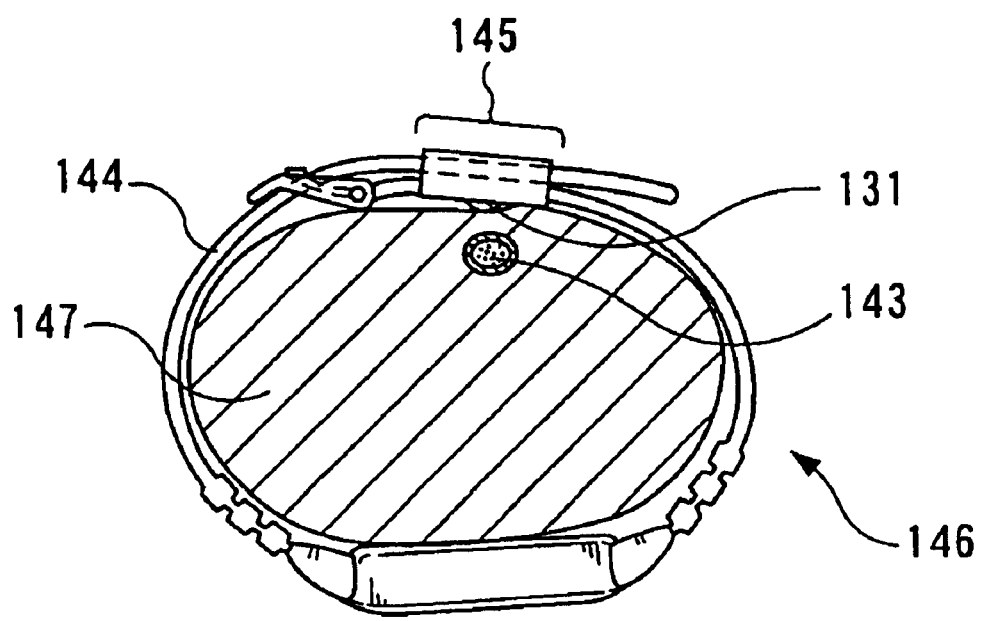
FIG. 42B is a section view showing the state of attachment of wrist watch 146.

As shown in FIGS. 42A and 42B, when in use, wrist watch 146 incorporating this blood pulse wave detector is wrapped around the left wrist 147 of a test subject so that the elastic rubber 131 provided to belt-shaped fastener 145 is positioned in the vicinity of radius artery 143, enabling constant detection of blood pulse wave. Further, the operation to wrap this device around the arm of the user is equivalent to that when using an ordinary wrist watch.

When elastic rubber 131 is pressed against the vicinity of the subject's radius artery, vibrations centered on point Pn on the hemispherical surface of elastic rubber 131 are generated by the change in blood flow (i.e., blood pulse wave) in the artery. These vibrations are propagated from point Pn through elastic rubber 131 to detection positions Q1 to Q4, and become pressure waves in hollow chambers 134-1 to 134-4. Pressure sensitive elements S1 to S4 then detect these pressure waves as voltages V1 to V4.

A variety of analytic processing is carried out in the device connected to the blood pulse wave detector once the detected voltages have been converted into digital values. However, when this blood pulse wave detector is employed only for the purpose of detecting blood pulse waves, it is not necessary to convert all of the voltages V1 to V4 into digital values. Rather, just one of the voltages V1 to V4, such as that with the largest value, may be converted. It is also acceptable to convert any number of the voltages, for one to all, to digital values.

(Structural Modifications)

Figure 43A:
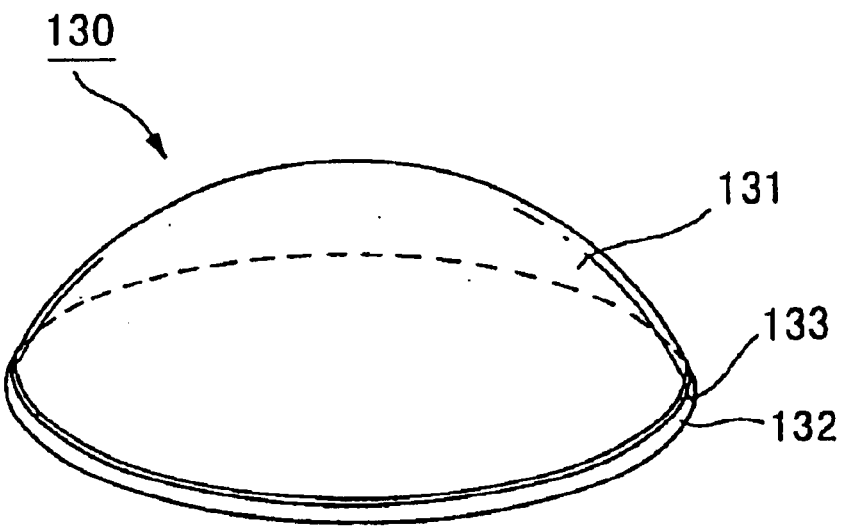
FIGS. 43A and B are perspective views showing modified structures of pressure sensor 130.
Figure 43B:
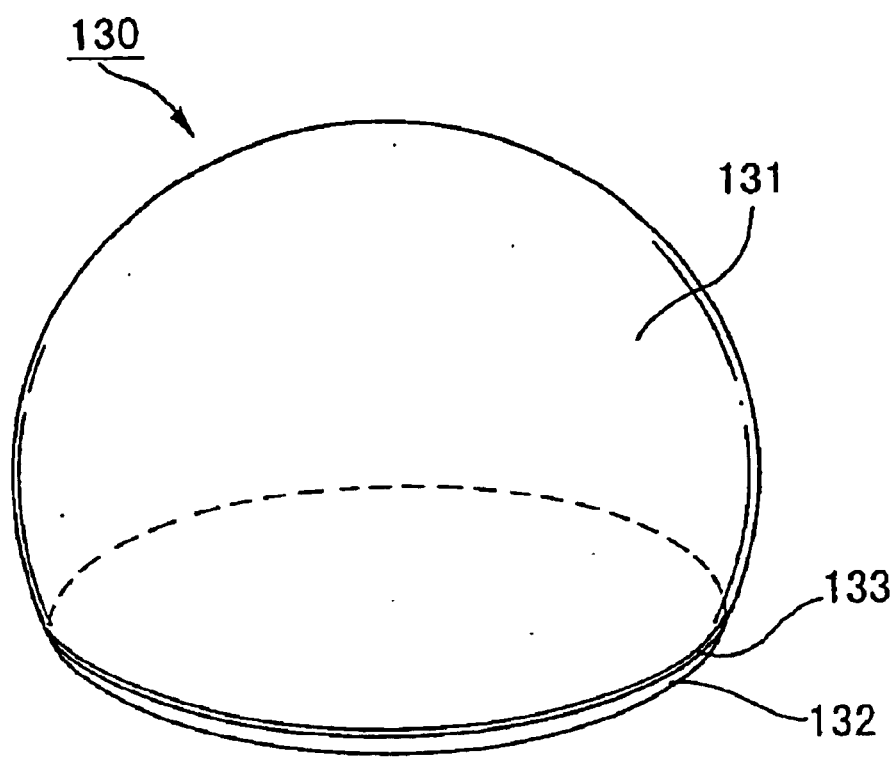

1. Equations (b) through (f) which are employed here to obtain the coordinates $x_n$, $y_n$ of point P'n assume that elastic rubber 131 is a perfect hemisphere, i.e., the shape obtained when a sphere is cut along a plane through its center. However, with a view toward improving the sensation imparted the user of the device to which pressure sensor 130 is attached, the shape of elastic rubber 131 is preferably formed in the approximately convex shape shown in FIG. 43A. Moreover, from a manufacturing standpoint, as well, it is extremely difficult to manufacture pressure sensor 130 in the shape of a perfect hemisphere. Instead, due to the difficulty of the slicing operation and the like, numerous sensors which deviate from this ideal are produced. FIGS. 43A and 43B show two extreme examples in which the sensor produced deviates substantially from a perfect hemisphere. However, even in this case, provided that the deviation is within limits which still permit accurate measurement, then coordinate values $x_n$, $y_n$ may be obtained using equation (f) as an approximation.

An explanation of this approximation will now be made, using the case where the shape of elastic rubber 31 is an approximate hemisphere formed by slicing a perfect sphere along a plane which deviates an amount $\Delta z$ from the center thereof. In this case, the coordinates (x, y, z) of detection positions Q1 to Q4 of pressure-sensitive elements S1 to S4 when the radius of elastic rubber 131 is r and are the center of the hemisphere is defined as the origin (0, 0, 0) are expressed as follows:

Q1(a, 0, $\Delta z$)

Q2(0, a, $\Delta z$)

Q3(−a, 0, $\Delta z$)

Q4(a, −0, $\Delta z$)

Accordingly, the square of the distance between point Pn and each of the detection positions Q1 to Q4 may be obtained as in the case of equations (d) above, with the respective equations resulting as follow:

$$\overline{P_nQ_1}^2 = (xn-a)^2 + yn^2 + (zn-\Delta z)^2$$

$$\overline{P_nQ_2}^2 = xn^2 + (yn-a)^2 + (zn-\Delta z)^2$$

$$\overline{P_nQ_3}^2 = (xn+a)^2 + yn^2 + (zn-\Delta z)^2$$

$$\overline{P_nQ_4}^2 = xn^2 + (yn+a)^2 + (zn-\Delta z)^2 \quad (g)$$

Where, in the above equations:

$$zn^2 = \sqrt{\{r^2 - (xn^2 + yn^2)\}} \quad (h)$$

The vibration generated at point Pn in this case attenuates in proportion to the square of the propagation distance in elastic rubber 131. Therefore, the values of voltages V1 to V4 which are detected by each of the sensors are inversely proportional to the square of the distance between point Pn and the detection position of the corresponding sensor. In other words, the product of the square of each of the distances in equation (g) and the detection voltages V1 to V4 are mutually equal, so that the coordinate values $x_n$, $y_n$ of the x and y coordinates of point Pn are as follows:

$$xn=\{(V1-V3)\cdot(a^2+r^2-2zn\cdot\Delta z+(\Delta z)^2)\}/2a(V1+V3)$$

$$yn=\{(V2-V4)\cdot(a^2+r^2-2zn\cdot\Delta z+(\Delta z)^2)\}/2a(V2+V4) \qquad (i)$$

In equation (i), $(\Delta z)^2$ may be ignored if $(\Delta z)$ is sufficiently small with respect to the z axis. Further, as may be understood from equation (i), $(z_n\cdot\Delta_z)$ may be ignored by making the sensor's distance a from the origin as large as possible while remaining within the limits for the radius r. As a result, equation (i) essentially becomes equivalent to equation (f).

2. The coordinate values $x_n$ and $y_n$ of point P'n can be obtained by substituting the voltages V1 to V4 of each of the detection signals in equation (f). However, these coordinate values may also be obtained from the following equation.

Namely, a fixed vibration is generated experimentally on the exposed surface of elastic rubber 131, and the relationship between the coordinates at which the vibration was applied and the ratio of voltages V1 to V4 is measured in advance. A table showing this relationship is then created. In order to obtain coordinate values xn, yn of point P'n, the coordinates corresponding to the ratio of voltages V1 to V4 can be read off from this table.

As a result, it is not necessary to for elastic rubber 131 in the shape of a hemisphere. Rather, elastic rubber 131 may have a convex shape which is easily pressed against the surface at which measurements are carried out.

Embodiment 2

Figure 44A:
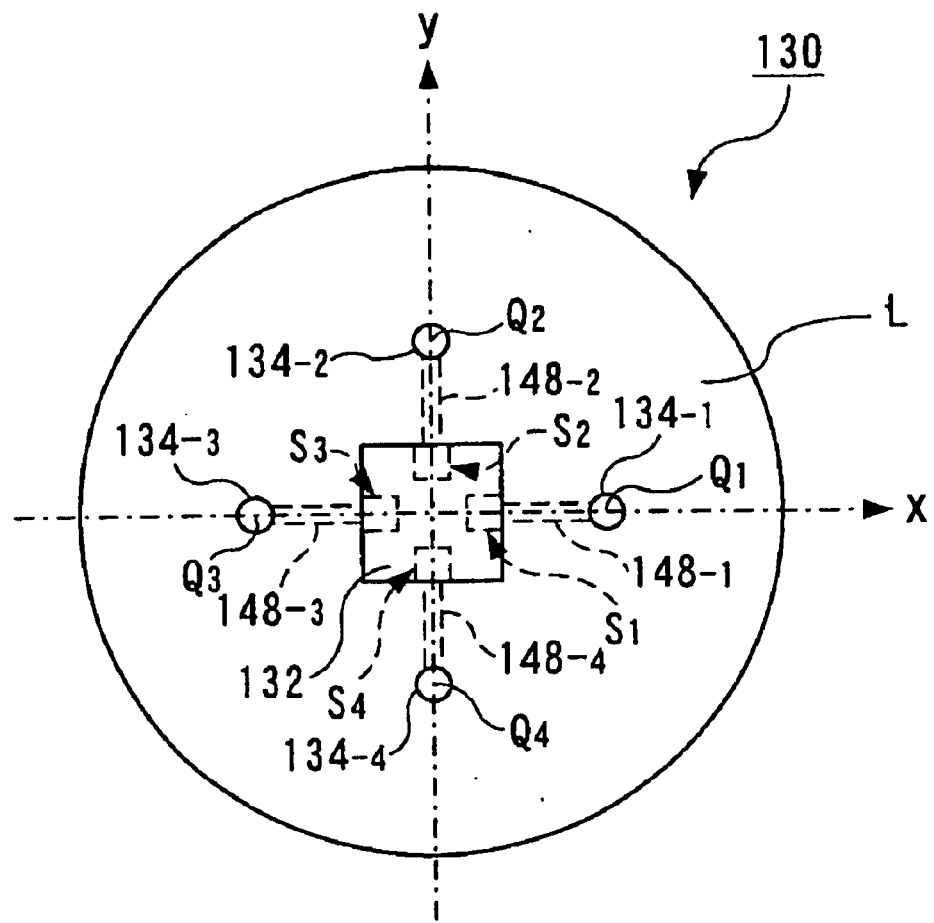
FIG. 44A is a plan view showing another example of pressure sensor 130.
Figure 44B:
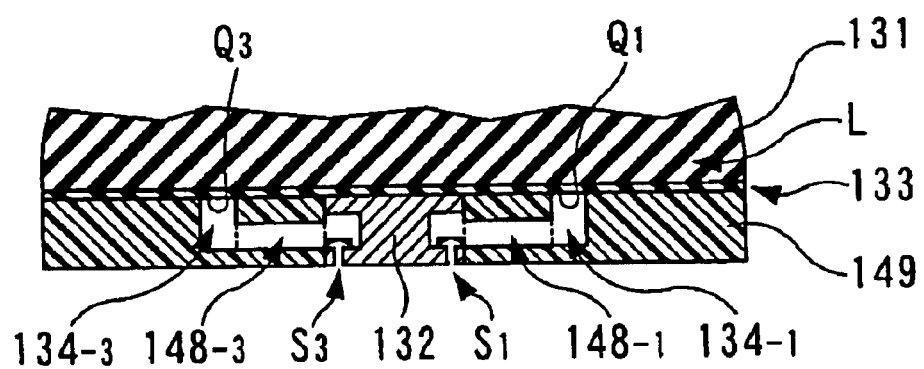
FIG. 44B is an enlarged section view of a principal component of the present invention showing the structure of the area of joining between elastic rubber 131 and semiconductor substrate 132 in the same example.

Another structural example of the pressure sensor will now be explained. FIG. 44A is an approximate plan view provided to explain the structure in this example. FIG. 44B is a section view of a principal component shown along the x axis in FIG. 44A. Parts which are equivalent to those shown in FIGS. 35 and 36 are denoted with the same numbers in this figure, and an explanation thereof is omitted.

As shown in these figures, a hollow chamber 134-1 which is open at detection position Q1 is provided to pressure sensor 130. A hollow tube 148-1, which opens to the lateral wall of hollow chamber 134-1 extends toward the center of flat surface L, and is connected to semiconductor substrate 132. Hollow chambers 134-2 to 134-4 are similarly provided to detection positions Q2 to Q4, respectively, while respective hollow tubes 148-2 to 148-4 similarly extend toward the center of flat surface L. Pressure-sensitive elements S1 to S4 are provided to semiconductor substrate 132, and are connected with their ends left open to hollow tubes 148-1 to 148-4 which extend outward from the center of pressure sensor 130 in the four directions as indicated.

In this case, it is preferable that hollow chambers 134-1 to 134-4 and hollow tubes 148-1 to 148-4 have a different composition than that of semiconductor substrate 132. For example, hollow chambers 134-1 to 134-4 and hollow tubes 148-1 to 148-4 may be formed of a rigid body 149 such as hard plastic or metal. In such a case, pressure sensitive elements S1 to S4 may be intensively formed on semiconductor substrate 132 without giving consideration to detection positions Q1 to Q4. As a result, this offers the advantage of reducing costs by increasing the number of pressure sensitive elements which can be present within the same surface area.

In this construction, as well, hollow chambers 134-1 to 134-4 and hollow tubes 148-1 to 148-4 may be filled with a liquid having a low thermal expansion coefficient, such as water or alcohol, or a liquid substance, such as gelatin.

Pressure sensor 130 may employ a construction wherein a convention distortion gauge is directly adhered to detection positions Q1 to Q4 on bottom surface L, with vibrations at these positions detected as distortion. In this structure, however, distortion from extremely small deformations during pressing of elastic rubber 131 appear in the direct output. Accordingly, a more preferable construction is one in which detection of the acoustic wave (pressure wave) is carried out via adhesive layer 133 and hollow chamber 134-1. In this case, it is possible to prevent extremely slight displacements of elastic rubber 131 from being directly applied to pressure-sensitive elements S1 to S4, thereby improving detection accuracy.

Additionally, while the above example employed four pressure sensitive elements, three elements are also acceptable, as state above. In other words, the number of elements provided is sufficient so long as each of the detection positions for the pressure sensitive elements is on the bottom surface of the hemisphere, such that the distance between each detection position and a point on the hemispherical surface of elastic rubber 131 can be specified.

Embodiment 3

In the pressure sensor 130 of the preceding two examples, the acoustic wave arising from a vibration at point Pn is propagated not only the direction of detection positions Q1 to Q4, but is also propagated almost equivalently in all directions of elastic rubber 131. For this reason, the pressure generated at detection positions Q1 to Q4 becomes small with respect to the size of the vibration generated at point Pn. Each of the values of voltages V1 to V4 also tends to become small in response to this. Accordingly, there is a disadvantage in these examples in that the S/N ratio deteriorates easily. Therefore, the examples explained in the current and next embodiments incorporate an improvement in the S/N ratio.

Figure 45:
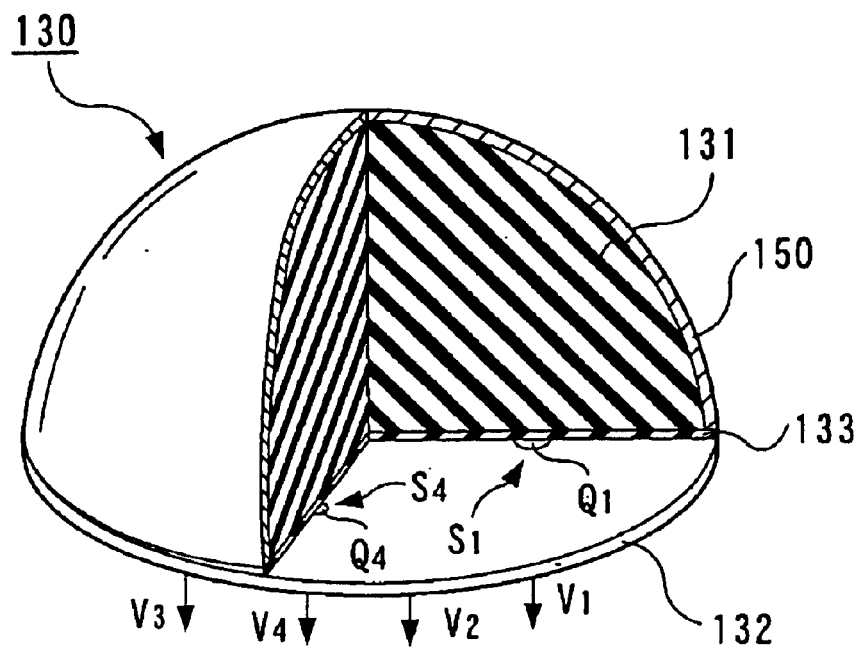
FIG. 45 is a perspective view showing a partial section of the another example of the structure of pressure sensor 130.

The present inventors experimentally confirmed that when a member 150 having a higher elasticity coefficient than elastic rubber 131 (for example, solid plastic, metal, or the like) is coated to the hemispherical surface of elastic rubber 131 as shown in FIG. 45, the voltages V1 to V4 output from pressure sensitive elements S1 to S4 is larger than in the case where this member 150 coating is not employed. This is believed to be because the presence of member 150 makes it more difficult for surface acoustic waves to propagate along the hemispherical surface of elastic rubber 131, so that some of the waves propagate toward the center instead. As a result, this portion of the waves contributes to an increase in pressure at detection positions Q1 to Q4, so that the output voltage of the pressure-sensitive elements becomes even larger. In other words, it is believed that the transfer function showing the propagation of an acoustic wave from the hemispherical surface toward a detection position is improved.

Furthermore, due to the presence of the member 150 covering, there is no direct contact between the user/test subject and elastic rubber 131. Thus, degradation of elastic rubber 131 by skin oils or the like is prevented.

Embodiment 4

Figure 46:
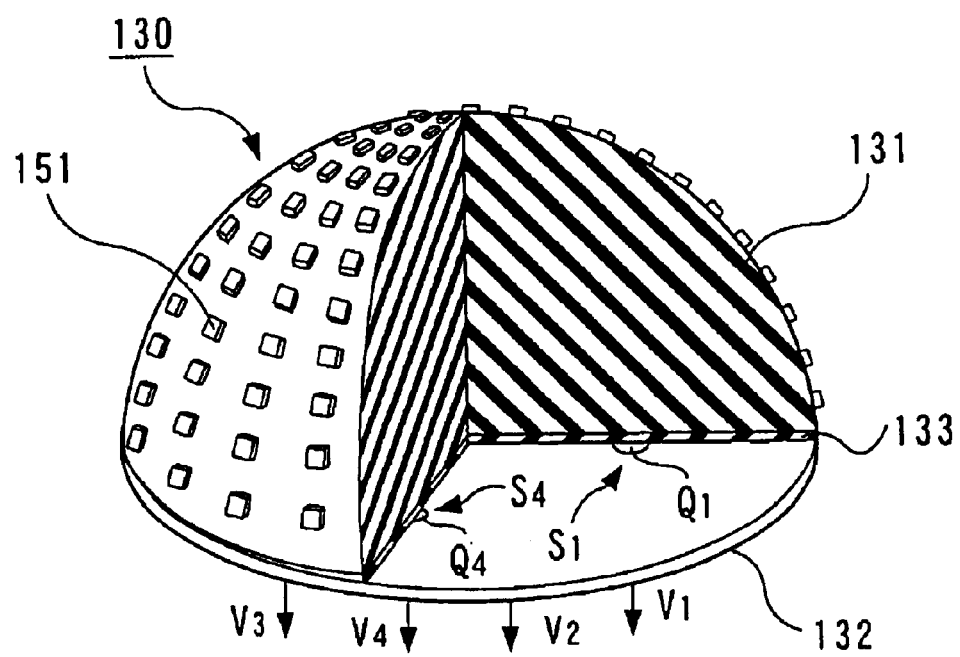
FIG. 46 is a perspective view showing a partial section of the still another example of the structure of pressure sensor 130.

As shown in FIG. 46, a plurality of small pieces 151 of member 150 may be provided dispersed across the hemispherical surface of elastic rubber 131. Small pieces 151 may be embedded or adhered to the surface of the hemisphere (small pieces 151 are shown adhered in FIG. 46)

Waves propagating from small pieces 151 to a detection position provide a greater improvement in the acoustic wave's transfer function than do waves propagating from the exposed surface of elastic rubber 131 to the detection position. For this reason, vibration point Pn on the surface of the hemisphere tends to be selectively limited by the positions at which small pieces 151 are set. Thus, a problem arises in that the coordinate values of point Pn become the dispersion values at which the positions of small pieces 151 are projected onto bottom surface L. However, since the output voltages V1 to V4 of the pressure-sensitive elements S1 to S4 can be made large, this is beneficial when the resolution during blood pulse wave detection is comparatively rough. Additionally, this problem can also be resolved by disposing numerous small pieces 151 efficiently.

(Modifications)

1. The difference in the output characteristics of pressure-sensitive elements S1 to S4 can be canceled by the following method. This method employs the technique of calculating coordinate values for point P'n using three pressure-sensitive elements as discussed above in "Principle of Blood pulse Wave Detection and Coordinate Calculation," under Section 1, Part 8-(2) of this chapter.

First, three of the four pressure-sensitive elements are selected and the coordinate values $x_n$, $y_n$ are calculated using just these pressure-sensitive elements. Next, a different combination of the pressure-sensitive elements is selected and the coordinate values $x_n$, $y_n$ are calculated in the same way. When selecting three item from among of four different items, there are four different possible combinations ($=_4C_3$). Accordingly, two more different combinations of three pressure-sensitive elements are selected and used to calculate coordinate values $x_n$, $y_n$ in the same way. The coordinate values $x_n$, $y_n$ which where independently calculated from each of these different combinations should be equivalent if the output characteristics of the pressure-sensitive elements S1 to S4 are all the same. Hypothetically, then, it may be interpreted that the output characteristics of the respective pressure-sensitive elements S1 to S4 are not the same if these coordinate values are not equivalent. If the detected voltage is instead corrected from the calculated coordinates, and the calculated coordinates are made to coincide, it is then possible for the differences in the output characteristics which accompany individual differences in the pressure-sensitive elements to mutually cancel out one another. Thus, it becomes possible to obtain more accurate coordinate values.

2. The preceding example employed a design in which the blood pulse wave of the radius artery was detected using a device incorporated into a wrist watch. However, the present invention is not limited thereto. Namely, in addition to a wrist watch construction, other constructions may be employed for detecting the blood pulse wave, one such example being shown in FIG. 47.

Figure 47:
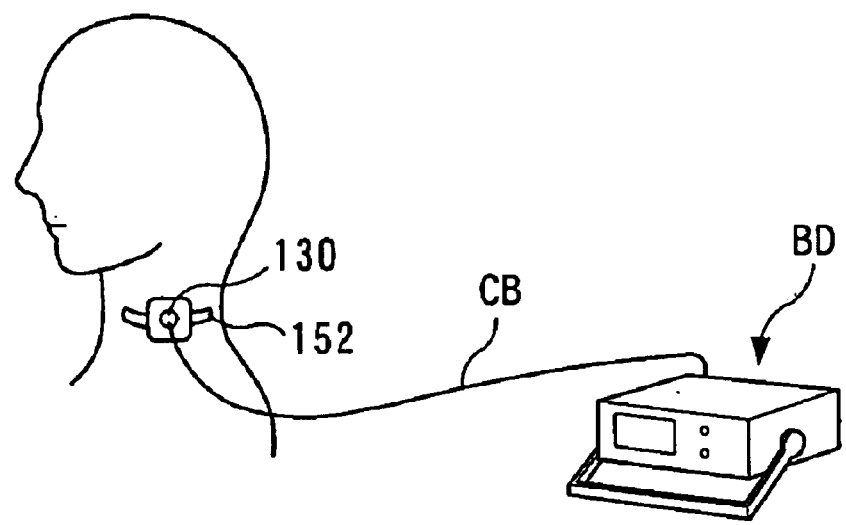
FIG. 47 is a diagram showing another embodiment for measuring blood pulse waves.

In the example in FIG. 47, pressure sensor 130 is pressed against the vicinity of the carotid artery of a test subject using a tape 152, for example. A detection signal from pressure sensor 130 is supplied via a cable CB to device main body BD for analysis of the blood pulse wave.

Section 2: Stroke Volume Per Beat (1) Definition of "Stroke Volume Per Beat"

The stroke volume per beat is the volume of blood which is pumped out from the heart at each heartbeat. This volume is equivalent to the area of the waveform for blood flow from the heart.

(2) Method for Measuring Stroke Volume Per Beat

Figure 48:
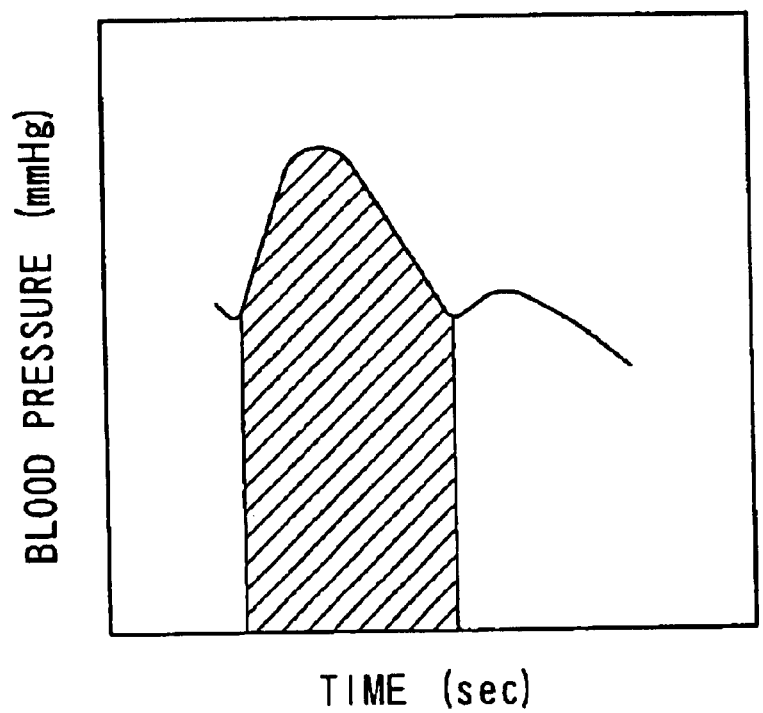
FIG. 48 is a diagram explaining the contraction period area method employed to measure the stroke volume per beat.

The stroke volume per beat can be calculated using the so-called "contraction period area method". In this method, the area S of the waveform of the portion of the blood pulse wave corresponding to the contraction period of the heart is calculated from the measured blood pulse waveform. Using the blood pulse waveform in FIG. 48 as an example, the area of the region extending from the rise in the waveform to the notch (i.e., the hatched area in the figure) is defined as area S. When a prespecified constant is defined at Ksv, then the stroke volume per beat SV can be calculated from the following equation.

stroke volume per beat $SV[ml]$=Area$Ssv$[mmHg s]×constant $Ksv$

Arrangements for measuring stroke volume per beat will be described hereafter, together with the arrangement for measuring the blood pulse wave.

Section 3: Arrangement for Measuring Blood Pulse Wave and Stroke Volume Per Beat A variety of arrangements for detecting blood pulse wave and measuring stroke volume per beat will be explained in this section.

(1) First Arrangement

Figure 49:
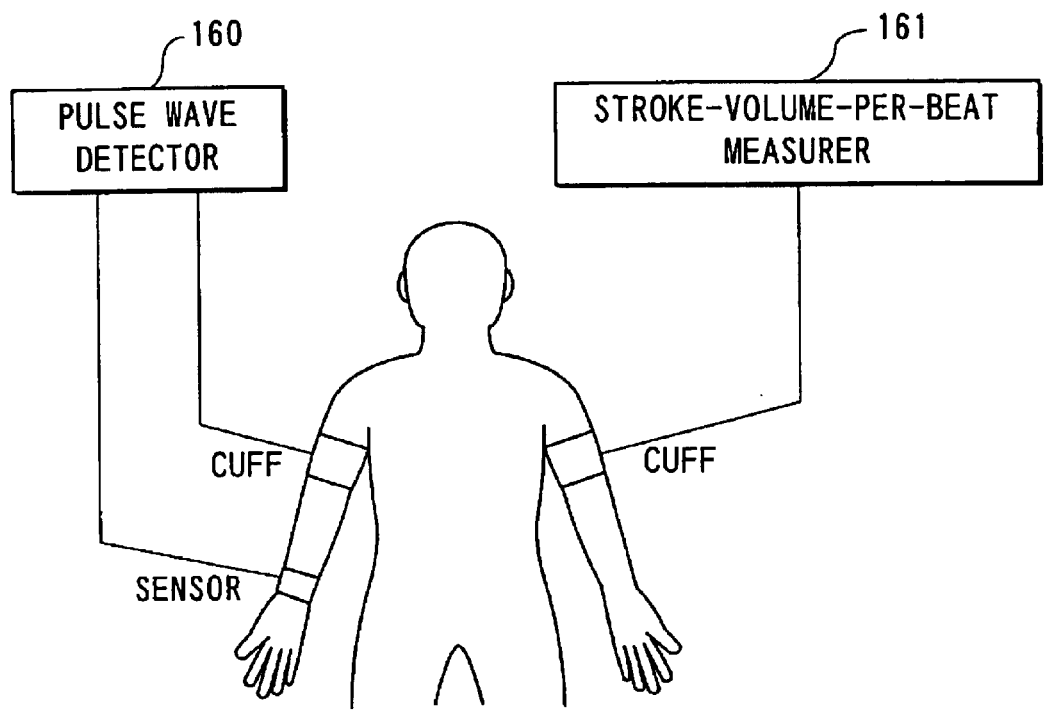
FIG. 49 is a diagram showing the arrangement for measuring stroke volume per beat and detecting the blood pulse wave.

As shown in FIG. 49, blood pulse wave detector 160 and measurer 161 for measuring stroke volume per beat are provided to measure the waveform of the radius artery and the stroke volume per beat in a subject. In other words, in the figure, blood pulse wave detector 160 detects the radius artery waveform via a sensor attached to the wrist of the subject, while detecting the subject's blood pressure via a cuff attached to his upper arm. The radius artery waveform is corrected using blood pressure, and the thus corrected radius artery waveform is output as an electric signal (analog signal). Stroke-volume-per-beat measurer 161, on the other hand, measures the stroke volume per beat in the subject, and outputs an electric signal indicating this result.

(2) Second Arrangement

Figure 50:
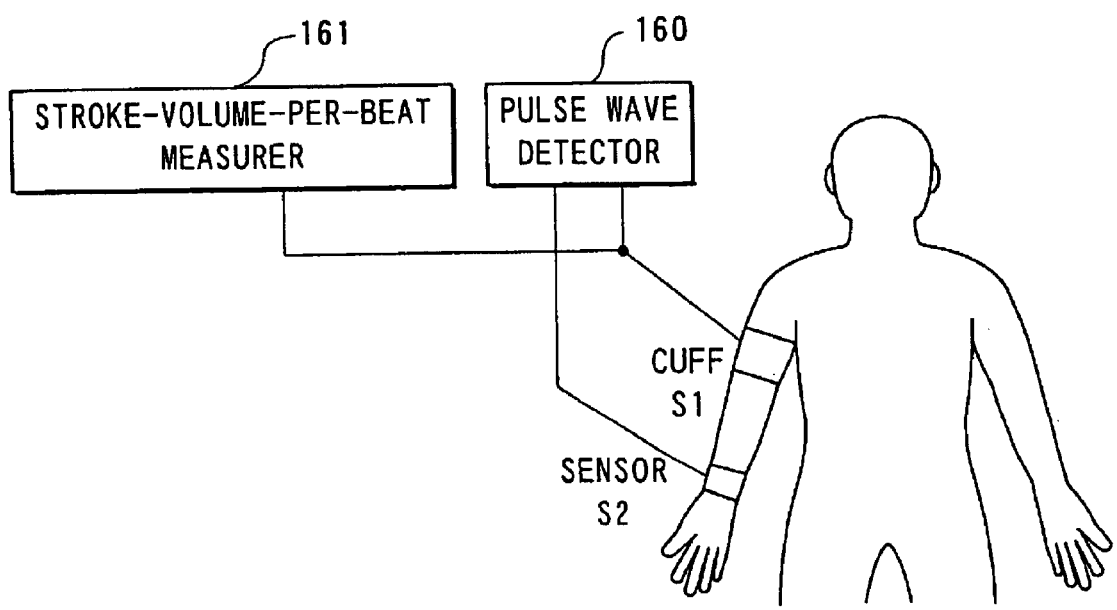
FIG. 50 is a diagram showing another arrangement for measuring stroke volume per beat and detecting the blood pulse wave.

In addition to the construction employing two separate cuffs as shown in FIG. 49, a construction such as shown in FIG. 50 is also possible in which blood pulse wave detector 160 and stroke-volume-per-beat measurer 161 share one cuff S1.

Moreover, the measurement of blood pulse wave and stroke volume per beat are not limited to sites on the body as shown in FIGS. 49 and 50, but may be taken at any location on the subject's body. In other words, while the above discussion concerned an arrangement in which measurements were carried out using a cuff attached to the upper arm of the subject, it is preferable that a cuff not be employed so as to decrease the inconvenience to the subject. Accordingly, third and forth arrangements are proposed as explained below.

(3) Third Arrangement

Figure 51:
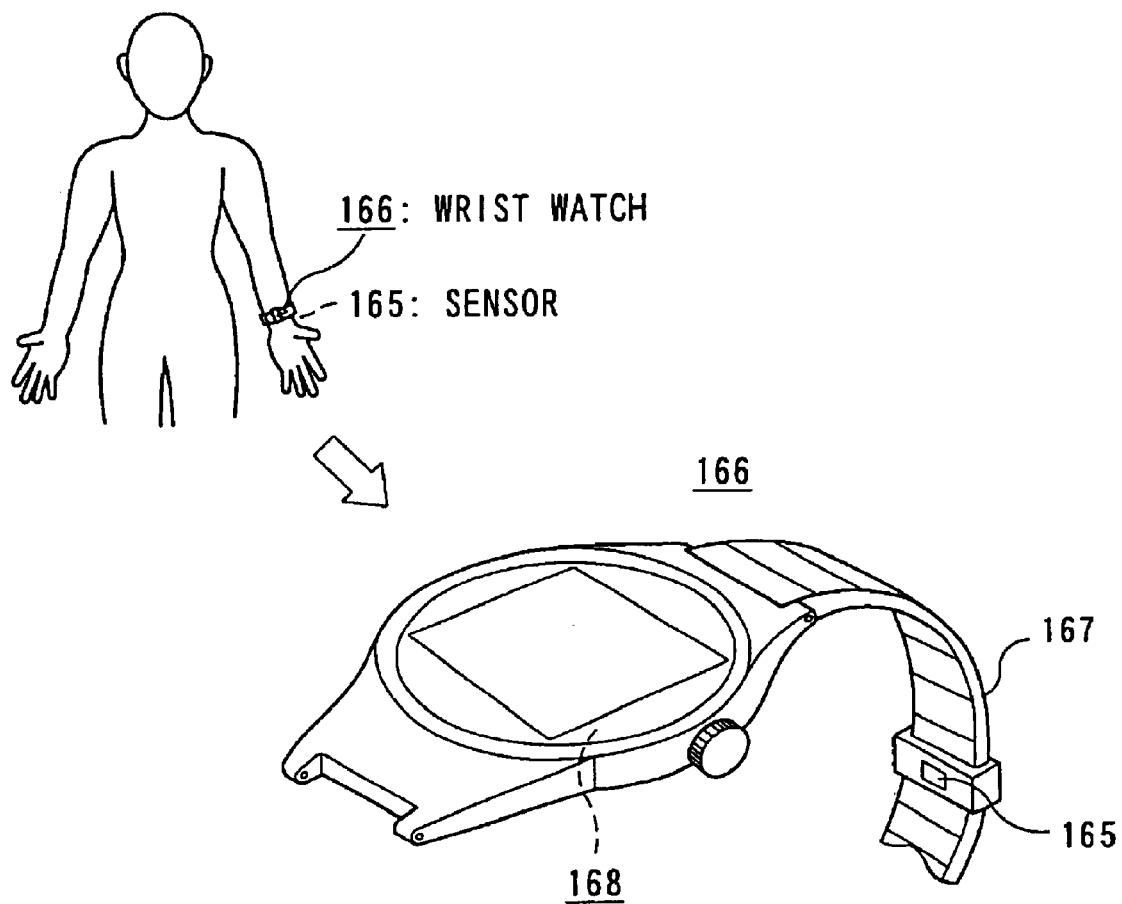
FIG. 51 is a perspective view of an embodiment in which the structural components of the device, excluding the sensor, are housed inside a wrist watch, while the sensor is attached externally to the wrist watch band.

In this arrangement, the radius artery waveform and the stroke volume per beat are both measured at the wrist. As shown in FIG. 51, in this construction, a sensor 165 consisting of a sensor for measuring blood pressure and a sensor for measuring stroke volume per beat is attached to the belt 167 of a wrist watch 166, with the other structural components 168 of the device housed in the main body of wrist watch 166. As shown in the figure, a pressure-type blood pulse wave sensor such as described above may be employed for sensor 165, for example.

(4) Fourth Arrangement

Figure 52:
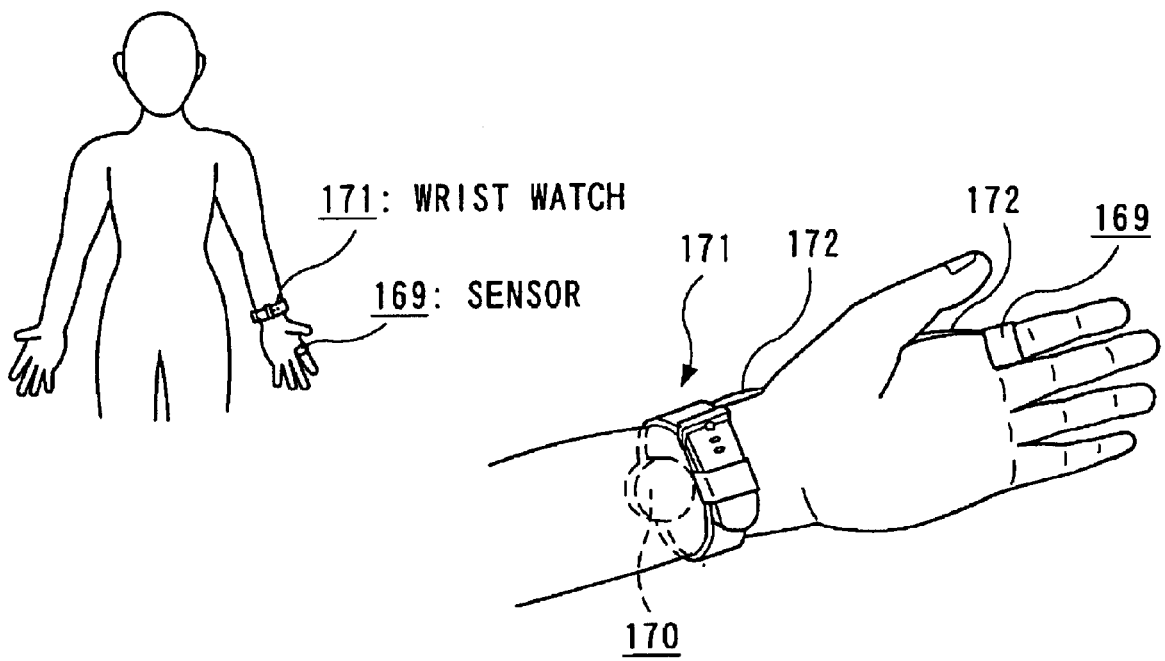
FIG. 52 is a perspective view of an embodiment in which the structural components of the device, excluding the sensor, are housed inside a wrist watch, and the sensor is attached to the base of the finger.

Another arrangement which may be proposed is one in which the blood pulse wave and stroke volume per beat are measured at the finger. A structural example of a device according to this embodiment is shown in FIG. 52. As shown in this figure, a sensor 169 consisting of a sensor for measuring blood pressure and a sensor for measuring stroke volume per beat is attached to the base of the finger (the index finger in the figure), while the other structural components 170 are housed inside a wrist watch 171 and are connected to sensor 169 via lead wires 172, 172.

By combining the third and fourth arrangements for carrying out measurements, it is possible to realize an embodiment in which the stroke volume per beat is measured at the wrist and the blood pulse wave is measured at the fingertip, or, conversely, a arrangement in which the stroke volume per beat is measured at the fingertip and the blood pulse wave of the radius artery is measured at the wrist.

By employing a construction in which a cuff is not used, such as in the third and fourth arrangements discussed above, it is not necessary to roll up the subject's shirt sleeves. Thus, the burden on the subject during measurement is reduced.

(5) Fifth Arrangement

Figure 53:
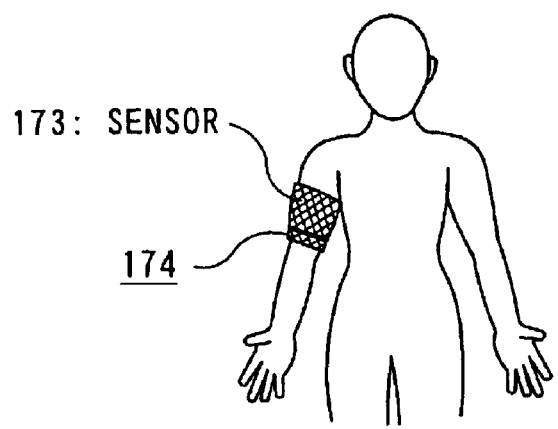
FIG. 53 is a structural diagram of an embodiment in which the sensor and the other structural components of the device excluding the sensor are attached to the upper arm of a subject by means of a cuff.

The structure shown in FIG. 53 may be considered in the case of an embodiment employing only a cuff. As in this figure, sensor 173, consisting of a sensor for measuring blood pressure and a sensor for measuring stroke volume per beat, and all other structural components 174 of the device are attached to the upper arm of the subject by means of a cuff. Accordingly, this is a simpler structure than that shown in FIG. 49.

(6) Sixth Arrangement

Figure 54:
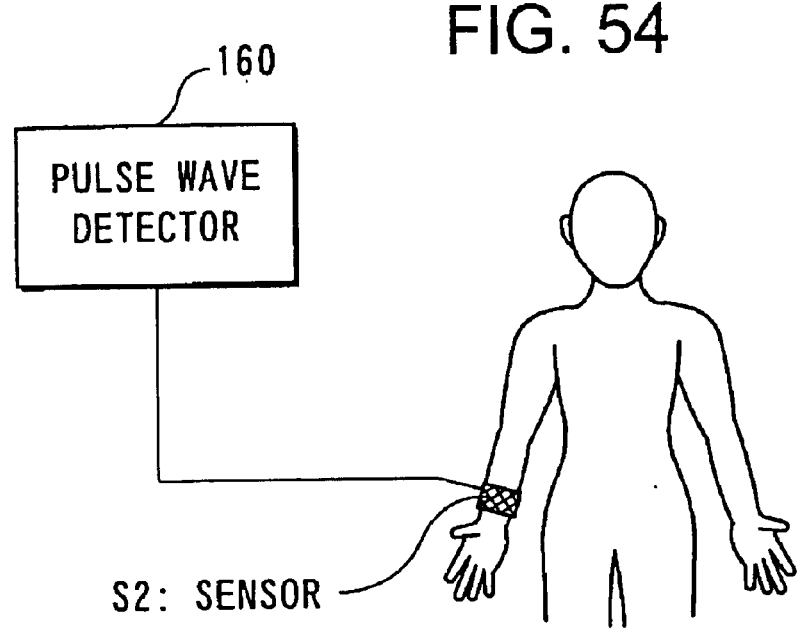
FIG. 54 is a diagram of an embodiment in which only the blood pulse wave detector is attached to the wrist, with the stroke-volume-per-beat measurer omitted.

The nature of this arrangement differs somewhat from the preceding five arrangements. Namely, in this arrangement, the stroke volume per beat can be inferred from the radius artery waveform (refer to Chapter 4, Section 1, Part 1 for details). In this case, a stroke-volume-per-beat measurer 161 such as shown in FIG. 49 is not necessary, and the arrangement for carrying out measurements is as shown in FIG. 54.

(7) Seventh Arrangement

1. When collecting the radius artery blood pulse waves and measuring the stroke volume per beat, a design may be considered in which the user is notified at a prespecified time prior to when the measurements will be carried out. This notification can be affected by means of a chime or the like, and is provided to remind the subject to attach the cuff in preparation for measurements to be made. At all other times, then, the subject is able to move about freely without wearing the cuff.

2. Additionally, the subject may be provided with a portable wireless pager by means of which he may be called when the scheduled time for taking measurements is approaching.

CHAPTER 3

Extraction of Characteristic Information from the Blood Pulse Wave

In order to analyze the blood pulse waveforms taken up by the blood pulse wave detector explained in Chapter 2, it becomes necessary to extract information showing the characteristics of the blood pulse waveform. The technique for extracting this characteristic information is the same for each of the devices explained below. Accordingly, this chapter will explain the details of this characteristic information and the means employed to realize extraction of the characteristic information from the waveform of the blood pulse wave.

Section 1: Waveform Parameters
Part 1 Definition of Waveform Parameters

Figure 55:
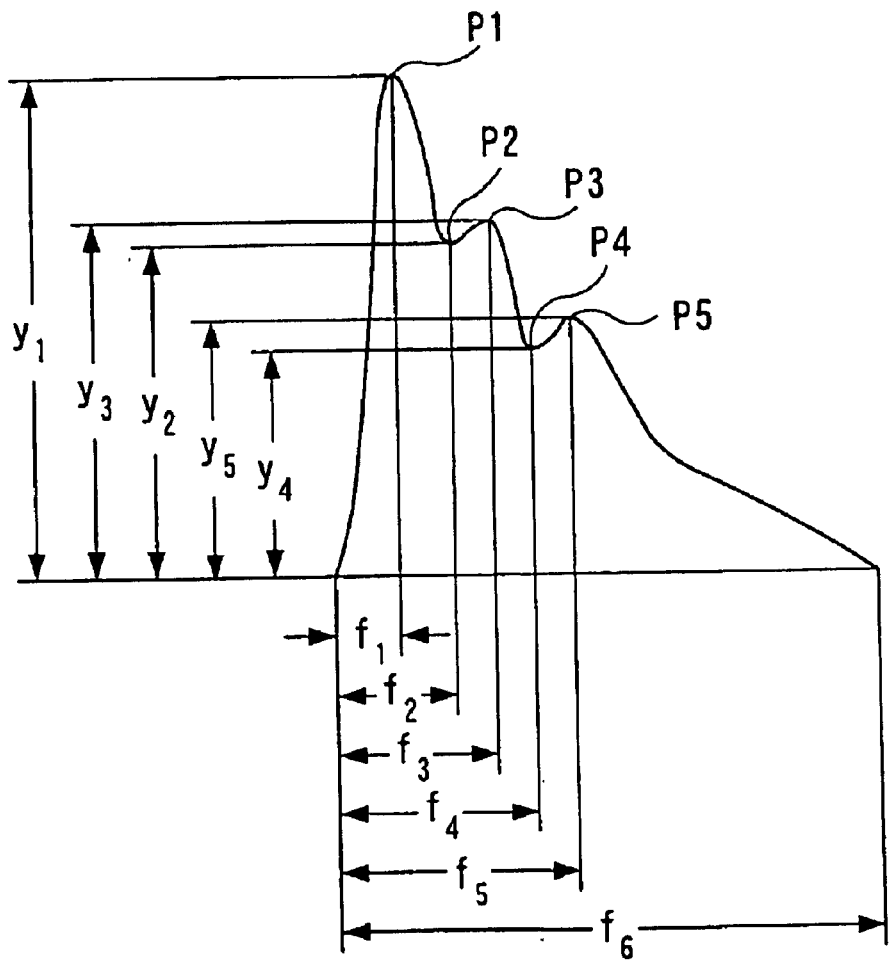
FIG. 55 is a diagram showing the correspondence between the waveform parameters and the waveform of a single blood pulse in the blood pulse wave.

The waveform of one beat of a blood pulse wave has a shape such as shown in FIG. 55. Blood pressure is shown on the vertical axis, while time is measured on the horizontal axis. The waveform parameters for specifying the shape of the waveform of the blood pulse wave are as described below.

1. time $t_6$, the time period between the initiation of rise in consecutive waveforms associated with consecutive beats (hereinafter, this initiation of the rise in the waveform will be referred to as "time of blood pulse wave initiation")

2. blood pressure values $y_1$ to $y_5$ for the maximum point P1, minimum point P2, maximum point P3, minimum point P4 and maximum point P5 which appear sequentially in the blood pulse wave 3. elapsed times $t_1$ to $t_5$, which represent the respective times elapsed from blood pulse wave initiation until each of points P1 through P5, respectively, appear Part 2 Waveform Extraction Memory When calculating waveform parameters, the so-called peak information, i.e., information relating to each of these maximum and minimum points, is extracted. The waveform extraction memory discussed below extracts this peak information from the blood pulse waveforms which have been taken up. Since the details of the peak information are related to the structure and operation of the waveform extraction memory, the peak information will be explained after the circuit structure is explained.

(1) Circuit Structure

Figure 56:
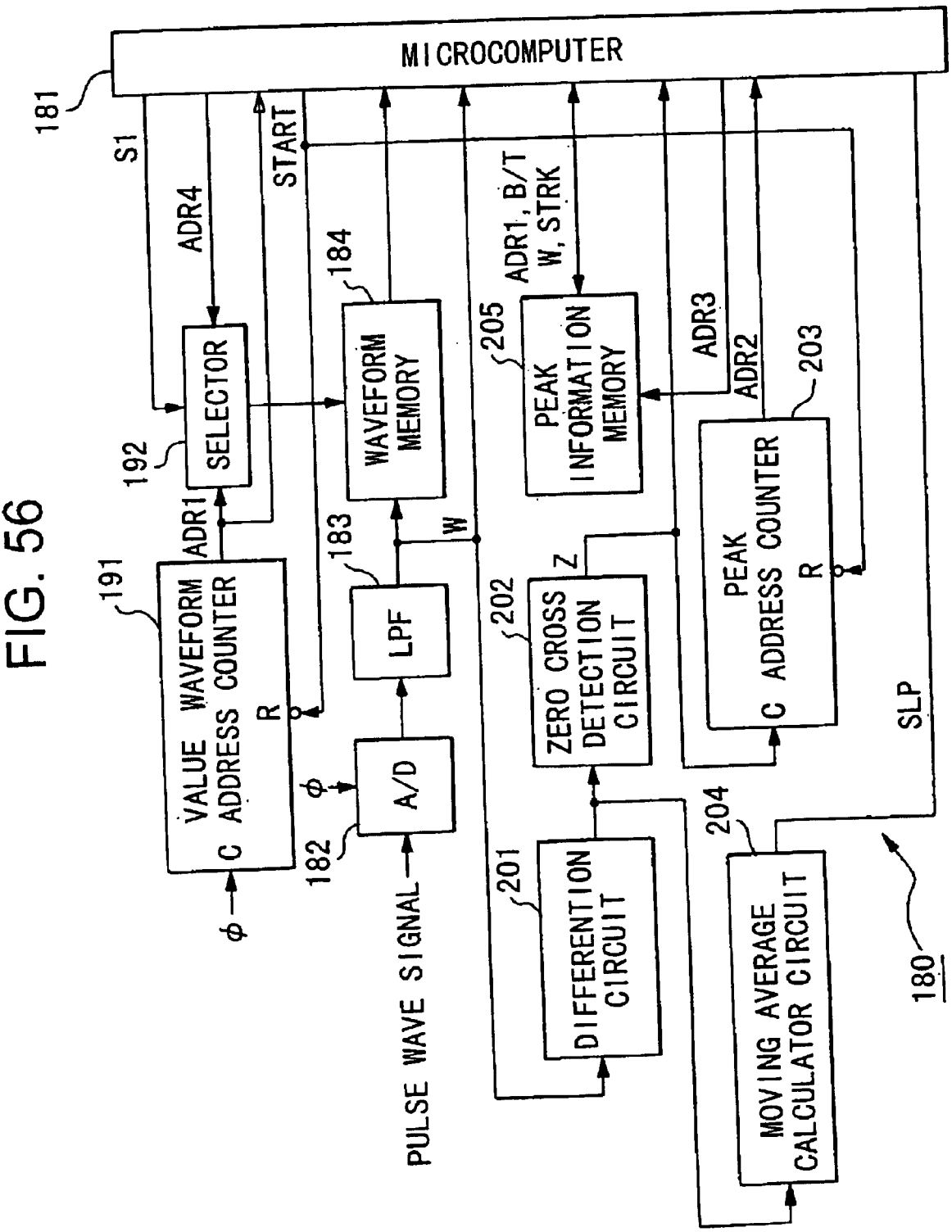
FIG. 56 is a block diagram showing the structure of parameter extractor 180.

The structure of waveform extraction memory 180 will be explained with reference to FIG. 56. In this explanation, waveform extraction memory 180 is assumed to be controlled by a microcomputer 181.

The numeric symbol 182 in this figure is an A/D converter, which converts the blood pulse wave signal output from each of the blood pulse wave detectors described in Chapter 2 to a digital signal in accordance with a fixed cycle sampling clock f.

The numeric symbol 183 indicates a low pass filter which removes from the digital signals sequentially output from A/D converter 182 those components which exceed a specified cut-off frequency, and sequentially outputs this result as waveform value W.

The numeric symbol 184 indicates a waveform memory formed of RAM which sequentially stores the waveform values W supplied via a low pass filter 183.

The numeric symbol 191 is a waveform value address counter which starts counting the sampling clock f during the time period in which microcomputer 181 outputs a START directive to begin collecting the blood pulse waves. Waveform value address counter 191 outputs the counter result as the waveform value address ADR1 at which waveform value W is to be written. This waveform value address ADR1 is monitored by microcomputer 181.

The numeric symbol 192 indicates a selector. When microcomputer 181 is not outputting a select signal S1, selector 192 selects the waveform value address ADR1 output by waveform value address counter 191, and supplies the selected waveform value address ADR1 to the address input terminal of waveform memory 184. In contrast, when a select signal S1 is being output by microcomputer 181, selector 192 selects the readout address ADR4 which is output by microcomputer 181, and supplies the selected readout address ADR4 to the address input terminal of waveform memory 184.

The numeric symbol 201 in the figure is a differentiation circuit which calculates the time differential of the waveform values W which are sequentially output from low pass filter 183. 202 is a zero cross detection circuit which outputs zero cross detection blood pulse Z when the time differential of the waveform value W is O because the waveform value W assumes a maximum or minimum value. More precisely, zero cross detection circuit 202 is provided to detect peaks P1, P2, . . . in the waveform of the blood pulse wave disclosed in FIG. 57. Zero cross detection blood pulse Z is output when waveform values W corresponding to these peaks are input.

203 is a peak address counter. Peak address counter 203 counts zero cross detection blood pulse Z while microcomputer 181 is outputting a START directive to begin collecting the blood pulse waves. Peak address counter 203 then outputs the counted result as peak address ADR2.

204 is a moving average calculator circuit which calculates the average value of the time differential of a fixed number of past waveform values W output from differentiation circuit 201 through the present point in time. The calculated result is output as slope information SLIP indicating the slope of the blood pulse wave up through the current point in time.

Figures 57, 58:
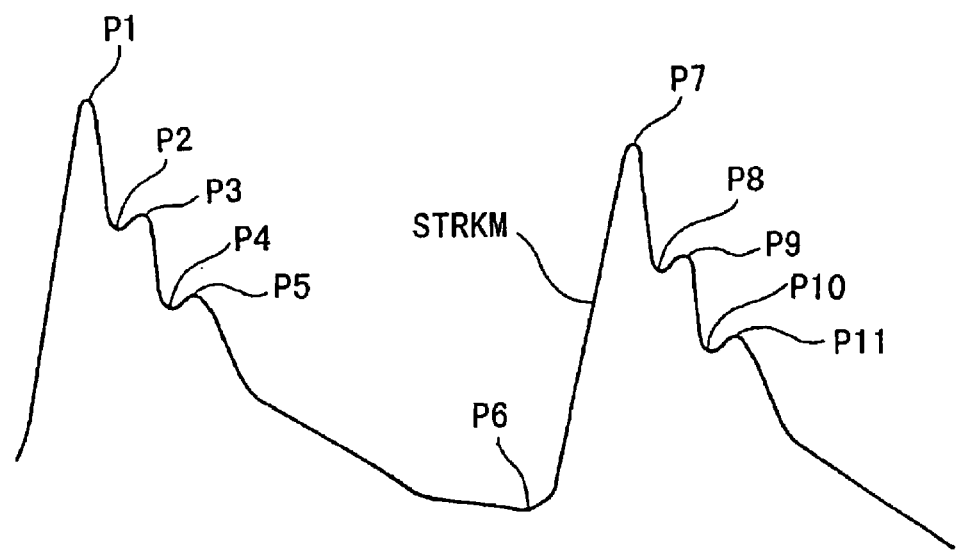
FIG. 57 is a diagram showing the waveform of the radius artery stored in waveform memory 184.
FIG. 58 is a diagram showing the stored details of peak information memory 205.

205 indicates a peak information memory provided to store the peak information explained below. Peak information will be explained in greater detail below. Namely, the details regarding peak information shown in FIG. 58 are listed as follows 1. waveform value address ADR1

The waveform value address ADR1 is the write address output from waveform value address counter 191 when the waveform value W output from low pass filter 183 is a maximum or minimum value. In other words, this is the write address in waveform memory 184 for waveform value W corresponding to a maximum or minimum value.

2. peak type B/T

The peak type is information indicating whether waveform value W which is written in waveform value address ADR1 is a maximum value T (Top) or a minimum value B (Bottom).

3. waveform value W

This is the waveform value corresponding to the maximum or minimum values.

4. stroke information STRK

The stroke information STRK is the amount of change in the waveform value from the immediately preceding peak value to the relevant peak value.

5. slope information SLP

This is the average value of the time differential of a fixed number of past waveform values up through the relevant peak value.

(2) Circuit Operation

An explanation will now be made of the waveform extraction memory 180 under the control of microcomputer 181.

(a) Collecting Waveform and Corresponding Peak Information

When microcomputer 181 outputs a START directive to begin collecting waveforms, waveform value address counter 191 and peak address counter 203 cease to be reset.

As a result, the sampling clock f counter is started by waveform value address counter 191. The counter value is supplied to waveform memory 184 via selector 192 as waveform value address ADR1. The blood pulse wave singles detected from the human body are input to A/D converter 182, and sequentially converted to digital signals in accordance with the sampling clock f. These converted digital signals are then sequentially output via low pass filter 183 as waveform values W. The waveform values W output in this way are sequentially supplied to waveform memory 184, and written in the memory area specified by waveform value address ADR1 at that point in time. As a result of the preceding operations, a continuous waveform value W corresponding to the waveform of the radius artery is stored in waveform memory 184. This continuous waveform value W is shown in FIG. 57.

In parallel to the preceding operation, detection of peak information and writing to peak information memory 205 are carried out as explained below.

First, the time differential of the waveform values W output from low pass filter 183 is calculated at differential circuit 201, and then input to zero cross detection circuit 202 and moving average calculator circuit 204. Moving average calculator circuit 204 calculates the average value (i.e., moving average value) of a specified past number of time differentials each time the time differential of a waveform value W is supplied, and outputs the calculated result as slope information SLP. A positive value will be output for slope information SLP when waveform value W is rising or has reached a maximum value. Conversely, a negative value will be output for slope information SLP when waveform value W is falling or has reached a minimum value.

When waveform value W corresponding to maximum point P1 shown in FIG. 57, for example, is output from low pass filter 183, O is output from differential circuit 201 as the time differential, and zero cross detection blood pulse Z is output from zero cross detection circuit 202.

As a result, microcomputer 181 uptakes at that point in time waveform address ADR1, which is the counter value of waveform value address counter 191; waveform value W; peak address ADR2, which is the counter value of the peak address counter (here, ADR2=0); and slope information SLP. Further, when zero cross detection blood pulse Z is output, the counter value ADR2 of peak address counter 203 becomes 1.

Microcomputer 181 creates peak type B/T based on the sign of the uptaken slope information SLP. In this case, when the waveform value W of maximum value P1 is output, then positive slope information is output at that point in time. As a result, microcomputer 181 sets the value of peak information B/T to one corresponding to a maximum value. Microcomputer 181 indicates as is peak address ADR2 uptaken from peak address counter 203 (here ADR2=0) as write address ADR3, and writes waveform value W, its waveform address ADR1, peak type B/T, and slope information SLP as the first time peak information in peak information memory 205. When writing first time peak information, stroke information STRK is not created or written since there is no immediately preceding peak information.

When waveform value W corresponding to minimum point P2 shown in FIG. 57, for example, is subsequently output from low pass filter 183, zero cross detection blood pulse Z is output in the same way as above, and write address ADR1, waveform value W, peak address ADR2 (=1), and slope information SLP (<0) are taken up by microcomputer 181.

Next, in the same way as above, microcomputer 181 determines the peak type B/T (B, in this case) based on slope information SLP. Next, the address which is 1 less than peak address ADR2 is read out by microcomputer 181, and supplied to peak information memory 205 as address ADR3. Recorded waveform value W written the first time is then read. Next, microcomputer 181 calculates the difference between waveform value W taken up at the current time from the low pass filter 183 and the waveform value W read out from peak information memory 205 that was taken up the first time, thereby obtaining stroke information STRK. The thus obtained peak type B/T and stroke information STRK are written in the recording area corresponding to peak address ADR3=1 in peak information memory 205 as second time peak information together with other information such as waveform value address ADR1, waveform value W and slope information SLP. The same operation is then carried out when peaks P3, P4, . . . , are detected.

Once a specific period of time has elapsed, microcomputer 181 stops outputting the waveform collection directive START, and the collection of waveform value W and peak information terminates.

(b) Blood Pulse Waveform Partitioning Processing

Microcomputer 181 carries out processing to specify from among the various information stored in peak information memory 205 the information corresponding to the waveform of a single beat at which waveform parameter collection is carried out.

First, slope information SLP and stroke information STRK corresponding to each of the peaks P1, P2, . . . are sequentially read out from peak information memory 205. Next, stroke information corresponding to positive slopes are selected from each stroke information STRK (i.e., the corresponding slope information SLP which is positive). A specified number of the largest values are then selected from among this stroke information. Next, stroke information corresponding to medium values is selected from among the selected stroke information, and the stroke information for the rising portion (for example, the rising portion indicated by symbol STRKM in FIG. 57) of the blood pulse wave of one beat at which waveform parameter extraction is to be carried out is obtained. Next, the peak address preceding the peak address of this slope information (i.e., the peak address at point P6, the initiation of the blood pulse wave of one beat at which waveform parameter extraction is to be performed) is obtained.

(c) Extraction of Waveform Parameters

Microcomputer 181 calculates each waveform parameter by referencing each peak information corresponding to the blood pulse wave of one beat recorded in peak information memory 205. This processing may be obtained as follows.

1. blood pressure values $y_1$ to $y_5$

The waveform values corresponding to peaks P7 to P11 are defined as $y_1$ to $y_5$ respectively 2. time $t_1$ The waveform address corresponding to peak P6 is subtracted from the waveform address corresponding to peak P7. $t_1$ is calculated by multiplying the period of the sampling clock f with this result.

3. time $t_2$ to $t_6$

As in the case of $t_1$ above, $t_2$ to $t_6$ are calculated based on the difference in the waveform addresses between each of the corresponding peaks.

Further, each of the waveform parameters obtained in this way are stored in the buffer memory inside microcomputer 181.

(3) Modification

1. The information stored in waveform memory 184 and peak information memory 205 may be employed for a variety of purposes in addition to extraction of the waveform parameters.

In this case, after the above-described circuit operations (a) and (b) have been carried out, microcomputer 181 extracts this information, and carries out a variety of analyses and diagnosis.

2. In addition to the above-described blood pulse waveform parameters, a variety of other modifications may be considered. Accordingly, when this circuit is used in the diagnosis of a human being, modifications may be made in order to obtain the parameters which are most suitable for that diagnosis.

Section 2: Blood Pulse Wave Spectrum

Part 1 Significance of the Blood Pulse Wave Spectrum

It known that the frequency spectrum obtained from frequency analysis of the blood pulse waveform can serve as information indicating the characteristics of the original blood pulse waveforms. More specifically, the amplitude and phase of the frequency spectrum are used as information regarding the characteristics of the blood pulse wave.

Part 2 Frequency Analyzer

FFT (Fast Fourier Transform) and the like are available as general methods for carrying out frequency analysis of waveforms, and accordingly are first considered as methods for carrying out frequency analysis of waveforms. The individual waves which form the waveform of the blood pulse wave do not have the same shape, and, moreover, change over time. In addition, the wavelengths of each wave is not constant. When employing FFT in this case, a method is employed in which FFT is carried out by viewing blood pulse waves which demonstrate this kind of chaotic movement as waveforms having an extremely long period.

When FFT is employed, the wave blood pulse spectrum can be obtained in detail, but the amount of calculations tends to become very large. Therefore, for applications in which the wave blood pulse spectrum generated over time is obtained quickly, the present inventors developed the frequency analyzer explained below. This frequency analyzer, which carries out frequency analysis of the blood pulse waveform, is a spectrum detection circuit for extracting the amplitude and phase of the spectrum obtained. The frequency analyzer is controlled by microcomputer 181 and is operated in sync with waveform extraction memory 180 to quickly detect the blood pulse wave spectrum. As a result, the waveform parameters indicating the characteristics of each wave forming the blood pulse wave can be obtained continuously.

(1) Circuit Structure

Figure 59:
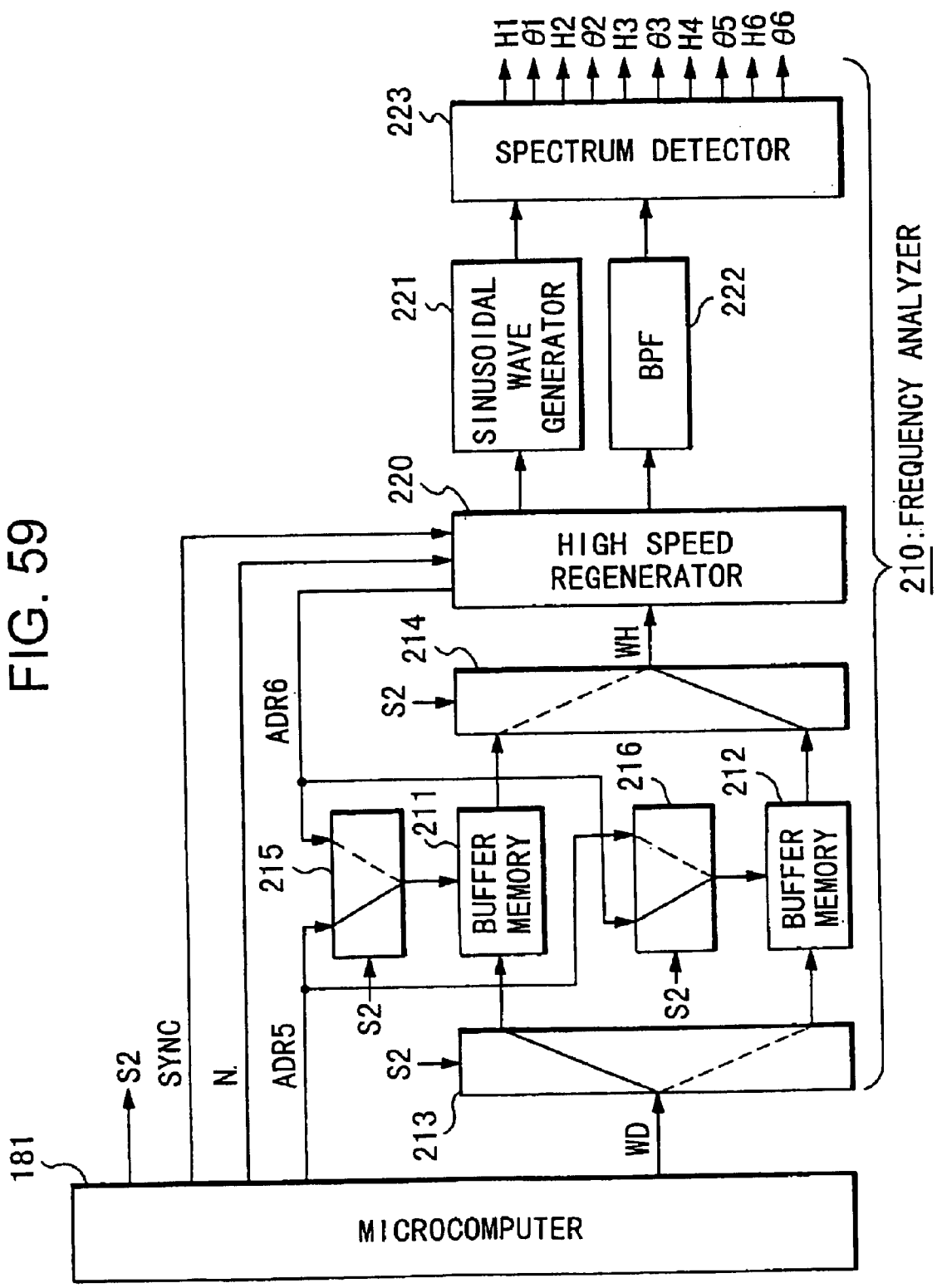
FIG. 59 is a block diagram showing the structure of frequency analyzer 210 for obtaining spectrum information about the wave form of the blood pulse wave.

FIG. 59 is a block diagram showing frequency analyzer 210 in detail. Frequency analyzer 210 receives waveform values WD of the blood pulse wave via microcomputer 181 at each beat. This received waveform value WD is repeatedly regenerated at high speed. Frequency analysis is carried out at each beat, to calculate the spectrum forming the blood pulse wave. Further, frequency analyzer 210 calculates by time segments each spectrum forming the blood pulse wave, starting with the fundamental spectrum of the waveform, and followed by the second harmonic wave spectrum, and so on.

When microcomputer 181 outputs the initial waveform value WD of the blood pulse wave of one beat to frequency analyzer 210, a synchronized signal SYNC and the number N of waveforms WD included in that beat are output, and select signal S2 is switched. Further, while microcomputer 181 is outputting the waveform value WD of one beat, write address ADR5, which changes from 0 to N−1 in time with the transmission of each waveform value WD, is sequentially output.

Buffer memories 211 and 212 are provided to store the waveform values WD output from microcomputer 181 in this way.

Distributor 213 outputs waveform value WD of the blood pulse wave which is supplied via microcomputer 181 to whichever of buffer memories 211 and 212 is indicated by select signal S2.

Selector 214 selects either buffer memory 211 or 212, as indicated by select signal S2, and the waveform value WH read out from the selected memory is output to the high-speed regenerator 220 which will be explained below.

Selectors 215 and 216 select write address ADR5 or read-out address ADR 6 (explained below) regenerated by high-speed regenerator 220 in accordance with select signal S2, and supply the selected address to each of the buffer memories 211 and 212.

In the above-described switching distributor 213, switching between selectors 214 to 216 is controlled based on select signal S2. As a result, during the time in which data is being written in buffer memory 211, data is being read out from buffer memory 212 and supplied to high speed regenerator 220. Similarly, during the time in which data is being written in buffer memory 212, data is being read out from buffer memory 211 and supplied to high-speed regenerator 220.

High-speed regenerator 220 reads out waveform values corresponding to each of the beats from buffer memories 211 and 212. High-speed regenerator 220 varies the read-out address ADR6 within the range of 0 to N−1 (where N is the number of waveform values to be read out), and outputs the result. More specifically, high-speed regenerator 220 generates a read-out address ADR 6 during the time in which each waveform value WD corresponding to a given beat is being written in one of the buffer memories. All waveform values WD corresponding to the beat preceding the given beat are read out from the other buffer memory a plurality of times. In this case, the regeneration of read-out address ADR 6 is controlled so that all of the waveform values WD corresponding to one beat are read out within a fixed period of time. The time period for reading out all waveforms values corresponding to one beat can be changed in correspondence with the order of the spectrum to be detected. For example, the respective time periods can be switched from T, 2T, 3T . . . , when detecting the fundamental spectrum, the second harmonic wave spectrum, third harmonic wave spectrum . . . , respectively. Further, high-speed regenerator 220 contains an interpolator which interpolates the waveform value WH read out from buffer memory 211 or 212, and outputs the interpolated waveform value WH as a waveforms value of a fixed sample frequency m/T (where m is a specific constant).

Sinusoidal wave generator 221 is a frequency convertible waveform generator which sequentially outputs each of the sinusoidal waves for periods T, 2T, 3T, 4T, 5T, and 6T corresponding to the order of the spectrum to be detected. Sinusoidal wave generator 221 is under the control of microcomputer 181.

Band pass filter 222 is a band pass filter in which the center frequency of the pass band is a specific value 1/T.

Spectrum detector 223 detects amplitudes $H_1$ to $H_6$ of each spectrum of the blood pulse wave based on the output level of band pass filter 222, and detects phases $q_1$ to $q_6$ in each spectrum based on the difference in the phase of the detection signal of band pass filter 222 and the phase of the sinusoidal waves output by sinusoidal wave generator 221.

(2) Circuit Operation

As explained above, frequency analyzer 210 detects the waveform spectrum at high speed by coupling its operation to waveform extraction memory 180. Accordingly, the operation of microcomputer 181 and waveform extraction memory 180 will be explained next.

(a) Waveform Partitioning

As explained in the paragraph on the operation of waveform extraction memory 180, when microcomputer 181 outputs the waveform collection directive START, the collection of waveforms and the peak information therefor is carried out. The collected waveforms are stored in waveform memory 184 and the peak information is stored in peak information memory 205 inside waveform extraction memory 180.

When stroke information corresponding to minimum point P2 is created, if the stroke information STRK in the peak information exceeds a specified value, i.e., the stroke value is large enough to consider that it corresponds to the rise in the waveform (see STRKM in FIG. 57), then microcomputer 181 carries out the following operation. Namely, in this case, microcomputer 181 reads out the waveform address of the minimum value which is the initial point of this stroke (see starting point P6 of STRKM in FIG. 57, for example) from peak information memory 205, and writes this waveform address in a shift register housed inside microcomputer 181. Subsequently, the equivalent operation is carried out as peaks P3, P4, . . . , are detected.

(b) Waveform Transmission

Figure 61:
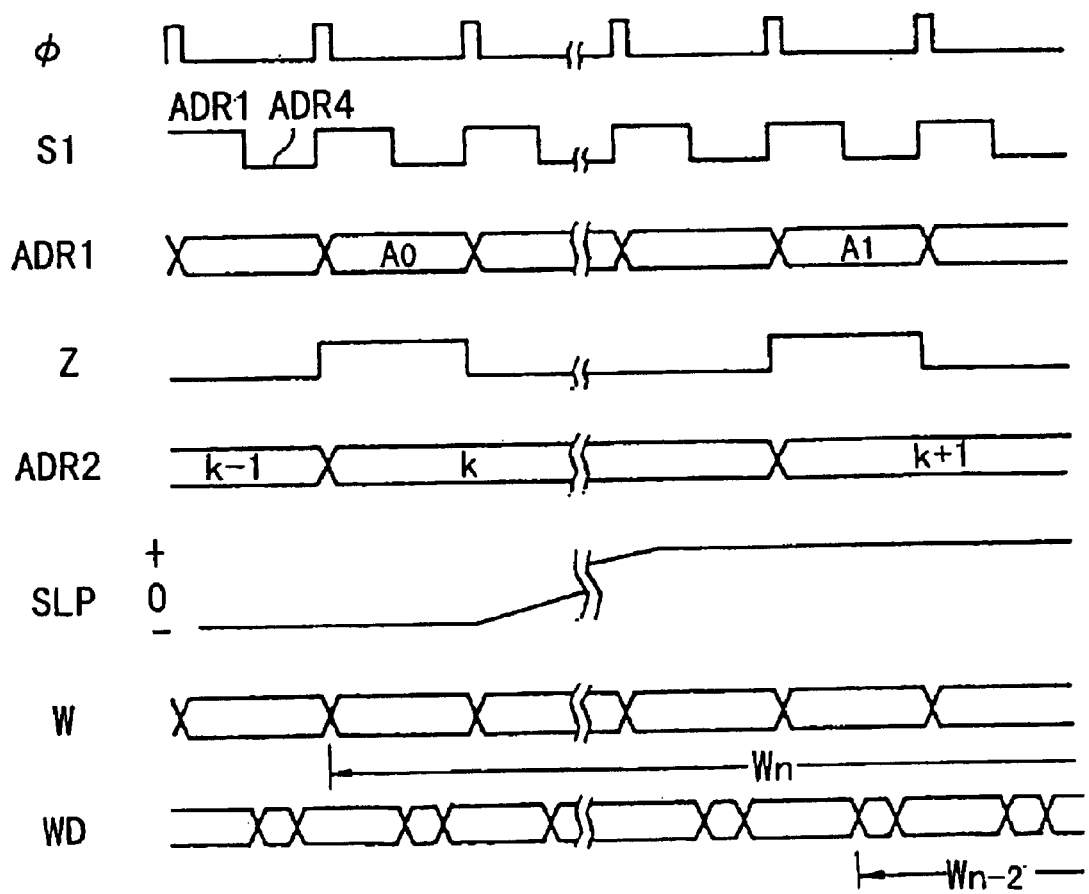
FIG. 61 is a time chart showing the operation inside waveform extraction memory 180.

In parallel with the preceding operation, microcomputer 181 sequentially reads out the waveform values from waveform memory 184 inside waveform extraction memory 180, and transmits these waveforms to frequency analyzer 210 as waveform data WD. As shown in FIG. 61, select signal S1 is switched in time with clock f, while waveform memory 184 switches between the write and read modes in synchronization with the switching of select signal S1.

Figure 60:
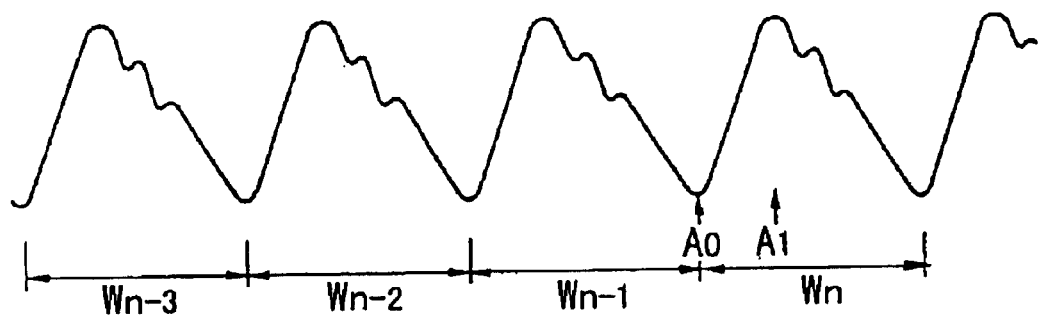
FIG. 60 is a diagram for explaining the waveform transmit timing for transmitting the waveform from waveform extraction memory 180 to frequency analyzer 210.

However, in FIG. 60, when the waveform value of blood pulse wave Wn corresponding to a beat portion of a given beat is input to waveform memory 184, a zero cross detection blood pulse Z is generated when the initial minimum value of the blood pulse wave corresponding to this beat is input. The waveform value address ADR1=Ao is written in peak information memory 205 (refer to FIG. 61). Subsequently, when the maximum value (address A1) is input into waveform extraction memory 180, a zero cross detection blood pulse Z is again generated (see FIG. 61). When the stroke between this maximum value and the immediately preceding minimum value (address Ao) is above a specified value, then minimum value address Ao is written in the shift register inside microcomputer 181. The thus written waveform address is subsequently output from the shift register two beats later and taken up by microcomputer 181 as the initial address of the waveform value WD for the beat portion which is to be transmitted to frequency analyzer 210. In other words, in FIG. 60, when address Wn of a maximum value of waveform Wn corresponding to a given beat is written in the shift address, the initial address (i.e., initial minimum value address) of blood pulse wave Wn−2 from two beats prior to the current beat which was previously written in the shift register is output from the shift register, and detected by microcomputer 181.

At this point, microcomputer 181 references the contents of the shift register, and obtains the difference between the waveform address of the initial minimum value of blood pulse wave Wn−2 and waveform address of the initial minimum value of the next blood pulse wave Wn−1. In other words, microcomputer 181 obtains the number N of waveform values included in blood pulse wave Wn−1 of one beat portion. This result is output along with synchronization signal SYNC to frequency analyzer 210. Select signal S2 is switched in time with synchronization signal SYNC, with the internal connections between distributor 213 and selectors 214 to 216 becoming as shown by the solid line in FIG. 59, for example.

Microcomputer 181 sequentially increases read-out address ADR4 from the initial minimum value waveform address of blood pulse wave Wn-2, and supplies the result to waveform memory 184 via selector 192. Read-out address ADR4 changes at a faster speed (for example, twice as fast) than write address ADR1. This is so that all of the waveform values corresponding to blood pulse wave Wn-2, the blood pulse wave preceding blood pulse wave Wn-1, can be read out prior to the input of the maximum value of blood pulse wave Wn+1, which is associated with the beat proceeding blood pulse wave Wn, to waveform extraction memory 180. In parallel with the storage of blood pulse wave Wn in waveform memory 184, the waveform value WD of blood pulse wave Wn-2 from two beats previous is read out from waveform memory 184 by microcomputer 181, transmitted to frequency analyzer 210, and sequentially supplied to buffer memory 211 via distributor 213. Write address ADR5 is sequentially increased from 0 to N-1 in synchronization with the sequential supply of waveform values WD to buffer memory 211, and is then supplied to buffer memory 211 via selector 215. As a result, each of the waveform values WD corresponding to blood pulse wave Wn-2 is stored in each of the recording areas of addresses 0 to N-1 of buffer memory 211.

(c) High-speed Regeneration

In parallel with the above operation, high-speed regenerator 220 outputs read-out address ADR6, and supplies it to buffer memory 212 via selector 216. As a result, each waveform value WD corresponding to blood pulse wave Wn-3, the beat prior to blood pulse wave Wn-2, is read out from buffer memory 212, and taken up by high-speed regenerator 220 via selector 214.

Figure 62:
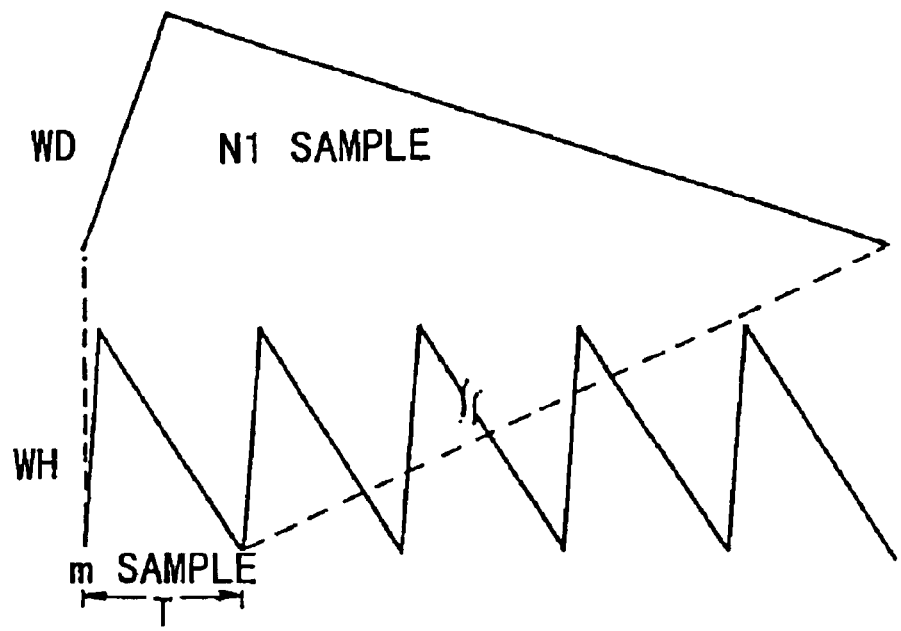
FIGS. 62 to 63 are diagrams provided to explain the operation of high speed regenerator 220.
Figure 63:
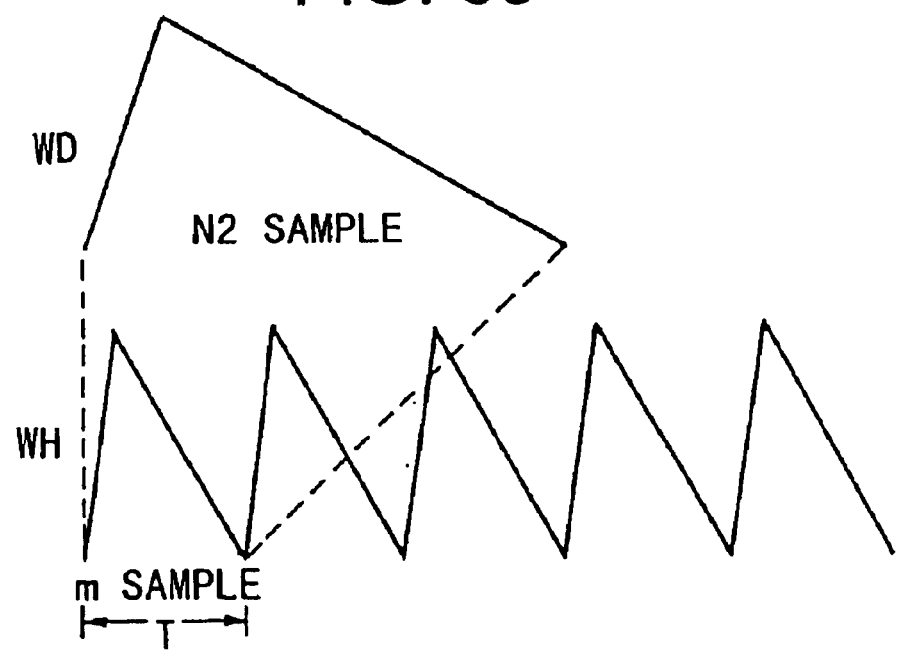

Each waveform value W/D corresponding to blood pulse wave Wn-3 in buffer memory 212 is repeatedly read out at a speed which is faster than the storing of each of the waveform values corresponding to blood pulse wave Wn-2 in buffer memory 211. In this case, the speed at which read-out address ADR6 is increased is controlled so that all of the waveform values WD corresponding to blood pulse wave Wn-3 can be read out within a fixed time period T. In other words, high-speed regenerator 220 increases read-out address ADR6 at a high speed when the number of waveform values WD to be read out from buffer memory 212 is a large value N1, as shown in FIG. 62. Conversely, high-speed regenerator 220 increases read-out address ADR6 at a low speed when the number of waveform values WD to be read out from buffer memory 212 is a small value N2, as shown in FIG. 63. Accordingly, read-out address ADR6 varies from 0 to N1-1 or 0 to N2-1 within a fixed period of time T. Waveform values WD sequentially read out in this way undergo interpolation calculations in high-speed regenerator 220, to become waveform values of a fixed sampling frequency m/T, which are then supplied to band pass filter 222.

(d) Spectrum Detection

Figure 64:
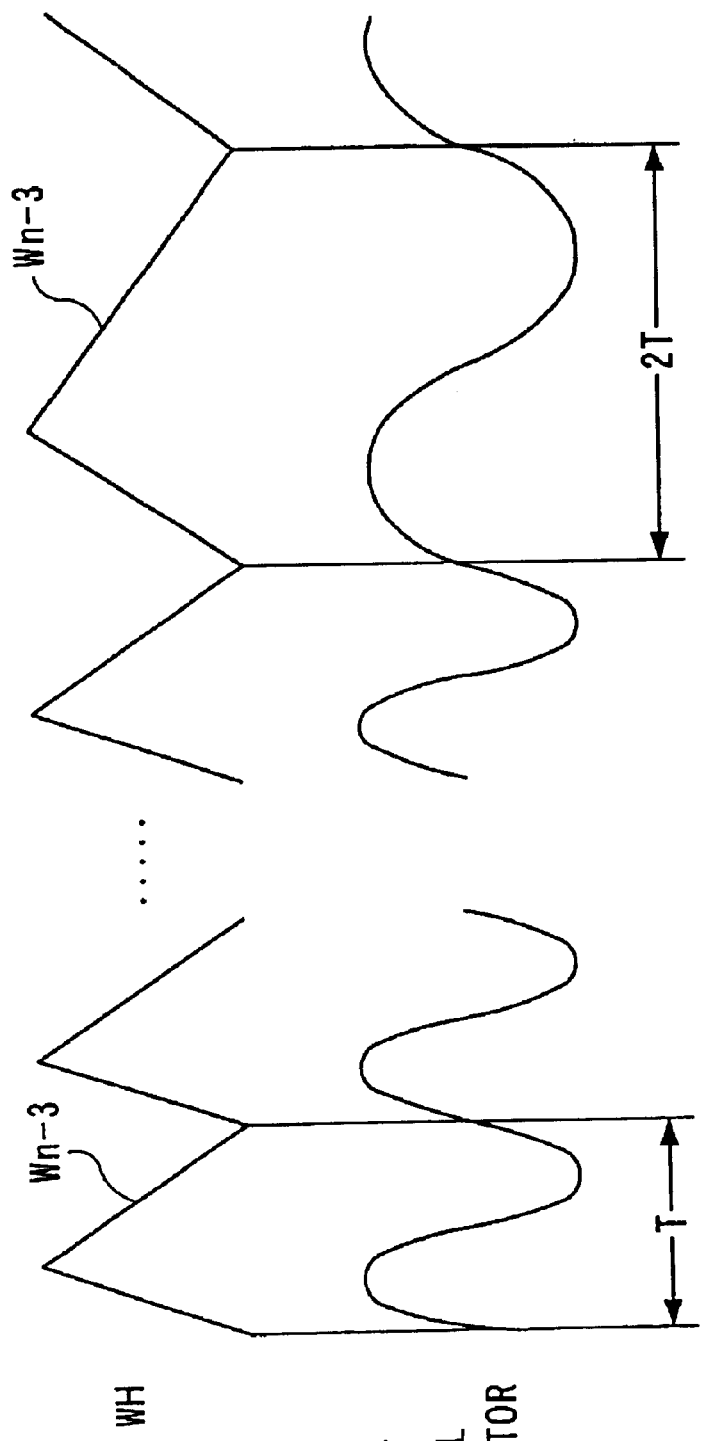
FIG. 64 is a diagram provided to explain the operation of high speed regenerator 220 and sinusoidal wave generator 221.

Band pass filter 222 selects a signal in which the frequency is 1/T from among the time series data of the received waveform values, and passes the signal through to spectrum detector 223. As shown in FIG. 64, sinusoidal wave generator 221 generates a sinusoidal wave in which the frequency is T, and supplies the wave to the spectrum detector 223. Spectrum detector 223 detects the output signal level of band pass filter 222 over several waves, and outputs the representative value as the amplitude H1 of the fundamental wave spectrum of blood pulse wave Wn-3. Spectrum detector 223 also detects over several waves the difference in the phase of the output signal of band pass filter 222 and the phase of the sinusoidal wave output from sinusoidal wave generator 221, and outputs the representative value as the phase $q_1$ of the fundamental wave spectrum of blood pulse wave Wn-3. For each representative value, the moving average value of the phase difference and the output signal level corresponding to each wave prior to the output of the fundamental spectrum, for example, is calculated.

High-speed regenerator 220 sets the speed of the increase in read-out address ADR6 to ½ when detecting the fundamental spectrum, for example, so that all of the waveform values of the blood pulse wave Wn-3 can be read out within a fixed period of time 2T, repeatedly reads outs waveform value WH corresponding to blood pulse wave Wn-3, and supplies the waveform values to band pass fiber 222 (see FIG. 64). From among the time series data comprising waveform values WH, those signals in which the frequency is 1/T, i.e., those signal corresponding to the second harmonic wave of blood pulse wave Wn-3, pass through band pass filter 222 and are supplied to spectrum detector 223. As a result, the amplitude H2 of the second harmonic wave spectrum of blood pulse wave Wn-3 is detected and output by spectrum detector 223. Sinusoidal waveform generator 221 generates sinusoidal waves in which the period is 2T and supplies them to spectrum detector 223 (see FIG. 64). As a result, phase q2 of the fundamental spectrum of blood pulse wave Wn-3 is output by spectrum detector 223.

Thereafter, the speed of increase of read-out address ADR6 is sequentially switched from ⅓, ¼, ⅕ and ⅙ in the case where detecting the fundamental spectrum, while, in concert with this, the period of the sinusoidal wave generated by sinusoidal wave generator 221 is sequentially switched from 3T, 4T, 5T and 6T. The amplitudes $H_3$ to $H_6$ and the phases $q_3$ to $q_6$ of the third through sixth order high harmonic wave spectrum are output from spectrum detector 223 by means of the same operation as above. Each of the spectrums of the thus obtained blood pulse wave Wn-3 is taken up by microcomputer 181. Microcomputer 181 calculates the frequency f=1/(Nt) of the fundamental wave using the period t of the clock f and the number N of waveform values WD corresponding to blood pulse wave Wn-3, and outputs this result together with the aforementioned spectrum.

Next, when blood pulse wave Wn+1, which is one beat after blood pulse wave Wn, starts to rise and the initial maximum value is input into waveform extraction memory 180, a synchronized signal SYNC is generated by microcomputer 181 and the number N of the waveform values WD included in blood pulse wave Wn-2 is output. Further, select signal S2 is inverted, with the internal connections between distributor 213 and selectors 214 to 216 becoming as indicated by the broken line in FIG. 59. In parallel with the storage of blood pulse wave Wn+1 in waveform memory 184, microcomputer 181 reads out from waveform memory 184 the waveform value WD of blood pulse wave Wn-1 from two beats before, and transmits it to frequency analyzer 210. From there, the waveform value WD is sequentially supplied to buffer memory 212 via distributor 213.

In parallel with this operation, each of the waveform values WD corresponding to blood pulse wave Wn-2 from one beat prior to blood pulse wave Wn-1 is read out from buffer memory 211 by high-speed regenerator 220, interpolated by high-speed regenerator 220, and output as waveform value WH. The same processing as carried out on blood pulse wave Wn-3 is applied to the waveform value WH for blood pulse wave Wn-2, to obtain the spectrum therefor.

Subsequently, the equivalent processing as described above is carried out on each of the sequentially arriving blood pulse waves, thereby obtaining a continuous spectrum for each of the blood pulse waves which is then output as parameters corresponding to each beat.

(3) Modifications

1. Rather than detecting all of the amplitudes H1 to H6 and phases q1 to q6, the device may be designed to detect only phase q4, for example, where there is a noticeable change in physical condition.

2. In the above-described circuit, the waveform parameters corresponding to each beat are output in real time as each is obtained. However, the present invention is not limited thereto, but be designed so that microcomputer 181 calculates and outputs the summed average value of the waveform parameters for a specified number of beats (i.e., the moving average value of the waveform parameters), for example.

CHAPTER 4

Analysis of Blood Pulse Waveform

Section 1: Calculation of Circulatory Parameters

As discussed above, circulatory parameters are one important factor determining the behavior of the circulatory system in the human body. The following explanation will concern a variety of methods for deriving the circulatory parameters by analyzing the waveform of a blood pulse wave.

Part 1 Calculation Method Based on Electric Model (Lumped Four Parameter Model)

Employing an electric model to simulate the circulatory system of the human body, the present inventors discovered a method for calculating circulatory parameters by obtaining values for each of the components forming this electric model. By employing this electric model, the circulatory parameters can be calculated using a simple calculation process.

(1) Overview

First, the present inventors employed a lumped four parameter model as an electric model of the arterial system. The model focused on four of the circulatory parameters which determine the behavior of the circulatory system in the human body: 1) inertia due to blood at the center of the arterial system; 2) blood vessel resistance (viscous resistance) due to blood viscosity at the center of the arterial system; 3) compliance (viscoelasticity) of the blood vessels at the center of the arterial system; and 4) blood vessel resistance (viscous resistance) at the periphery of the arterial system. Incidentally, compliance, which is a quantity indicating the pliability of the blood vessels, is equivalent to viscoelasticity.

Figure 65:
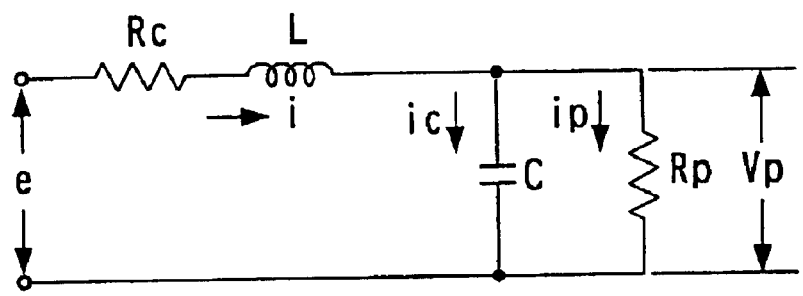
FIG. 65 is a circuit diagram of a lumped four parameter model which models the arterial system in a human being.

FIG. 65 shows the circuit diagram for a lumped four parameter model, and shows the correspondence relationship between each of the following components forming the model and the above-described circulatory parameters.

inductance L:
  inertia due to blood at the center of the arterial system $[dyn \cdot s^2/cm^5]$ capacitance C:
  compliance of the blood vessels at the center of the arterial system $[cm^5/dyn]$ electrical resistance Rc:
  blood vessel resistance due to blood viscosity at the center of the arterial system $[dyn \cdot s/cm^5]$ electrical resistance Rp:
  blood vessel resistance at the periphery of the arterial system $[dyn \cdot s/cm^5]$ Electric current i, ip, and ic flowing through each of the parts of the electric circuit is equivalent to blood flow $[cm^3/s]$ through each of the parts as described. The input voltage e impressed on the electric circuit is equivalent to the pressure at the proximal portion of the aorta. The terminal voltage vp of the capacitance is equivalent to pressure $[dyn/cm^2]$ at the periphery of the arterial system, such as at the radius artery, for example.

(2) Order of Parameter Calculations (a) Approximation of Corresponding Characteristics for Lumped Four Parameter Model A theoretical explanation will now be made of the behavior of the lumped four parameter model shown in FIG. 65. First, the following differential equation may be established for the lumped four parameter model shown in this figure.

$$e=Rci+L(di/dt)+vp \tag{1}$$

where current i can be represented by the formula:

$$i=ic+ip=C(dvp/dt)+(vp/Rp) \tag{2}$$

Thus, equation (1) above can be expressed using the following equation (3).

$$e=LC(d^2vp/dt^2)+\{RcC+(L/Rp)\}(dvp/dt)+\{1+(Rc/Rp)\}vp \tag{3}$$

As is known, the general solution for a second order constant coefficient ordinary differential equation such as shown in equation (3) can be obtained from the sum of the particular solution (steady-state solution) and the transient solution which satisfy the following differential equation.

$$0=LC(d^2vp/dt^2)+\{RcC+(L/Rp)\}(dvp/dt)+(1+(Rc/Rp))vp \tag{4}$$

The solution to differential equation (4) can be obtained as follows. First, the solution to differential equation (4), is assumed to be the damped oscillating waveform expressed by the following equation (5).

$$vp=A\exp(st) \tag{5}$$

Substituting equation (5) into equation (4), equation (4) can be expressed as follows.

$$\{LCs^2+(RcC+(L/Rp))s+(1+(Rc/Rp))\}vp=0 \tag{6}$$

Solving for s in equation (6), $$s=\{(RcC+(L/Rp))6\sqrt{((RcC+(L/Rp))^24LC(1+Rc/Rp)))}\}/2LC \tag{7}$$

Where, when $$(RcC+(L/Rp))^2<4LC(1+(Rc/Rp)) \tag{8}$$

in equation (7), the second term of the equation under the radical becomes negative. In this case, s is expressed as follows:

$$s=\{(RcC+(L/Rp))\pm j\sqrt{(4LC(1+(Rc/Rp))(RcC+(L/Rp))^2)}\}/2LC=-a\pm j\omega \tag{9}$$

$$\alpha=(RcC+(L/Rp))/2LC=(L+RpRcC)/2LCRp \tag{10}$$

$$\omega=\{\sqrt{(4LC(1+(Rc/Rp))(RcC+(L/Rp))^2)}\}/2LC \tag{11}$$

Where, when setting $$A1=LC \tag{12}$$

$$A2=(L+RcRpC)/Rp \tag{13}$$

$$A3=(Rc+Rp)/Rp \tag{14}$$

equations (10) and (11) can be expressed as follows.

$$\alpha = A2/2A1 \tag{15}$$

$$\omega = \sqrt{(A3/A1)\alpha^2} \tag{16}$$

Thus, the value of s is confirmed in this way, and a solution satisfying differential equation (4) is be obtained.

Based on the above then, the present inventors employed equation (5) to approximate the damped oscillation component included in the corresponding waveform of the lumped four parameter model.

Figure 66:
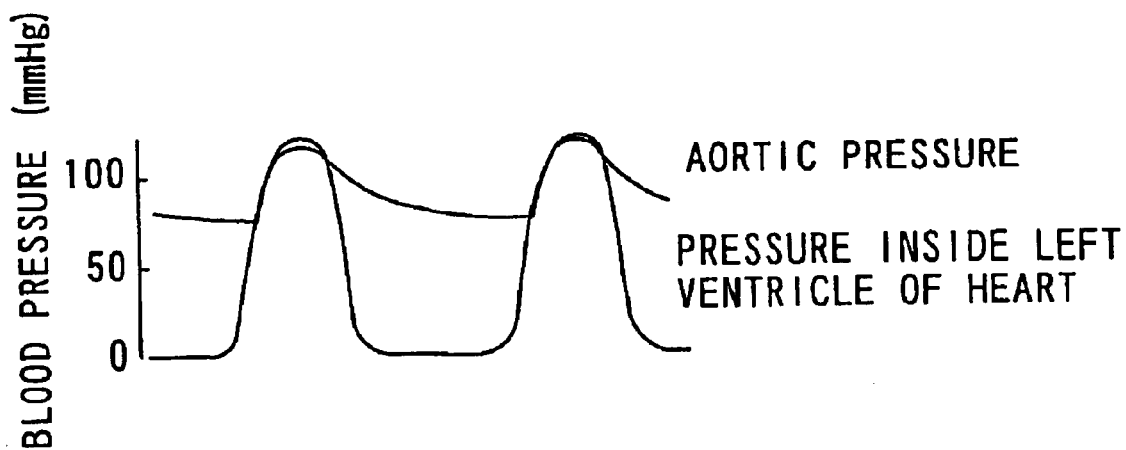
FIG. 66 is a diagram showing the blood pressure waveform at the proximal portion of the aorta in a human being.
Figure 67:
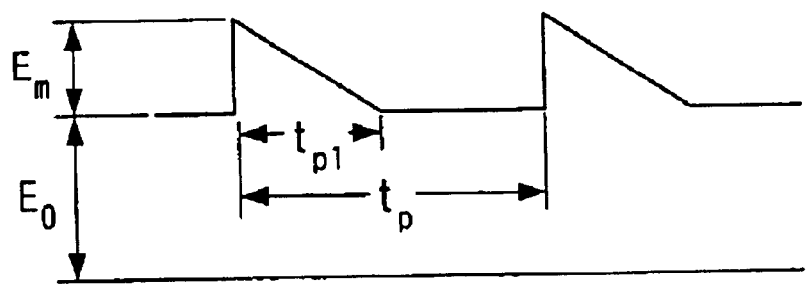
FIG. 67 is a waveform diagram modeling the blood pressure waveform at the proximal portion of the aorta in a human being.

Next, a modeling of the pressure waveform at the proximal portion of the aorta will be carried out. In general, the pressure waveform at the proximal portion of the aorta exhibits a waveform such as shown in FIG. 66. Accordingly, this pressure waveform has been approximated by the triangular-shaped wave shown in FIG. 67. When the amplitude and time of this approximated waveform shown in FIG. 67 are set to Eo, Em, tp, and tp1, arterial pressure e at optional time t can be expressed by the following equation.

At time interval $0^2 t < tp1$:

$$e = Eo + Em(1(t/tp1)) \tag{17}$$

At time interval $tp1^2 t < tp$:

$$e = Eo \tag{18}$$

By modeling the pressure waveform at the proximal portion of the aorta using this simple triangular wave, the circulatory parameters can be calculated using a simple calculating process. Eo is the minimum blood pressure (blood pressure during relaxation), and Eo+Em is the maximum blood pressure (blood pressure during contraction). tp is the time duration of one beat, and tp1 is the time duration from the rise in arterial pressure until that pressure reaches a minimum blood pressure value.

When electric signal e expressed by equations (17) and (18) is input into the equivalency circuit in FIG. 65, response waveform vp (corresponding to the radius artery waveform) is approximated as follows.

At time interval $0^2 t < tp1$:

$$vp = E\min + B(1t/tb) + Dm1 \exp(\alpha t) \sin(\omega t + q1) \tag{19}$$

At time interval $tp1^2 t < tp$:

$$vp = E\min + Dm2 \exp\{\alpha(t-tp1)\} \sin \{\omega(ttp1) + q2\} \tag{20}$$

Where, Emin is the minimum blood pressure value (refer to FIG. 72) in the radius artery waveform.

The third term from the right in equation (19) and the second term from the right in equation (20) are the damping oscillator components (corresponding to equation (5)) already explained. The α and w in these terms are obtained from equations (15) and (16).

B, tb, Dm1, Dm2 are constant values calculated in the order described below.

(b) Relationship Between Radius Artery Waveform and Each Parameter in Lumped Four Parameter Model The following discussion will be directed to the constants in equations (19) and (20), excluding a and w which have already been confirmed.

First, equations (17) and (19) are substituted into differential equation (3) to obtain the following equation (21).

$$Eo + Em(1\{t/tp1\}) = \{1 + (Rc/Rp)\}(E\min + B)(B/tb)RcC + (L/Rp))t + \{LC(\alpha^2\omega^2)Dm1$$

$$\alpha Dm1(RcC + (L/Rp)) + Dm1(1 + Rc/Rp))\} \exp(\alpha$$

$$t) \sin(\omega t + q1) + \{\omega Dm1(RcC + (L/Rp))2$$

$$LC \alpha\omega Dm1\} \exp(\alpha t)\cos(\omega t + q1) \tag{21}$$

The following conditions are necessary in order to establish formula (21):

$$Eo + Em = \{1 + (Rc/Rp)\}(E\min + B) = Eo + A3B - (B/tb)A2 \tag{22}$$

$$Em/tp1 = (B/tb)\{1 + (Rc/Rp)\} = A3 \cdot B/tb) \tag{23}$$

$$LC(\alpha^2 \ \omega^2)\alpha\{RcC + (L/Rp)\} + (1 + Rc/Rp) = 0 \tag{24}$$

$$RcC + (L/Rp) = 2LCa \tag{25}$$

Equations (24) and (25) above restrict and, however, the and obtained from equations (15) and (16) satisfy these equations.

When equations (18) and (19) are substituted into differential equations (3), the following equation (26) is obtained.

$$Eo = \{1 + (Rc/Rp)\}E\min + \{LC$$

$$(\alpha^2\omega^2)Dm2(RcC + (L/Rp))Dm2 +$$

$$(1 + (Rc/Rp))Dm2\} \exp(\alpha(ttp1))\sin(\omega$$

$$(ttp1) + q2) + \{\omega(RcC + (L/Rp))$$

$$Dm2\ 2LC\ \alpha\omega\ Dm2\} \exp(a(t-tp1))\cos(\omega$$

$$(ttp1) + q2) \tag{26}$$

In order to establish equation (26), it is necessary to set up the preceding equations (24) and (25), as well as the following equation (27).

$$Eo = \{1 + (Rc/Rp)\}E\min = A3E\min \tag{27}$$

Each of the constants in equations (19) and (20) are calculated based on the conditional equations (22) to (25) and (27) for setting up the differential equation (3) obtained as above.

From equation (27), $$E\min = E0/A3 \tag{28}$$

From equation (23), B is $$B = (tbEm)/(tp1A3) \tag{29}$$

Next, substituting equation (29) into equation (22) and solving for tb yields:

$$tb = (tp1A3 + A2)/A3 \tag{30}$$

Values are selected for the remaining constants Dm1, Dm2, q1 and q2 which enable the radius artery waveform vp to maintain continuous at t=0, tp1 and tp. In other words, values are selected for the remaining constants Dm1, Dm2, q1 and q2 which satisfy the following conditions.

(1) vp(tp1) in equation (19) and vp(tp1) in equation 20 are equivalent (2) vp(tp) in equation (20) and vp(0) in equation 19 are equivalent (3) differential coefficients at t=tp1 in equations (19) and (20) are equivalent (4) differential coefficients at t=0 in equation (19) and the differential coefficients at t=tp in equation (20) are equal Namely, values are selected for Dm1 and q1 such that $$Dm1=\sqrt{\{D11^2+D12^2\}}/\omega \qquad (31)$$

$$q1=\tan^{-1}(D11/D12) \qquad (32)$$

However, in each of the above equations $$D11=(v01-B-E\min) \qquad (33)$$

$$D12=(v01-B-E\min)a+(B/t0)+(i01/C) \qquad (34)$$

Where, v01 and i02 are the initial values of vp and ic at t=0.

Further, values are selected for Dm2 and q2 such that $$Dm2=\sqrt{(D21^2+D22^2)}/\omega \qquad (35)$$

$$q2=\tan^{1}(D21/D22) \qquad (36)$$

However, in the preceding formulas, $$D21=(v02\,E\min)\omega \qquad (37)$$

$$D22=(v02\,E\min)\alpha+(i02/C) \qquad (38)$$

Where v02 and i02 are the initial values of vp and ic at t=tp1. In this way, each of the constants in equations (19) and (20) are obtained.

Carrying out an inverse operation on the angular frequency w in equation (16), blood vessel resistance Rc at the center of the circulatory system becomes $$Rc=\{L-2Rp\sqrt{(LC(1\,\omega^2LC))}\}/Crp \qquad (39)$$

Where the conditions for Rc to be a real and positive number are $$4RP^2C/\{1+(2\omega RPC)^2\}^2L^21/\omega^2C \qquad (40)$$

Rp is generally on the order of $10^3$ (dyn·s/cm5), while C is around $10^4$ (cm$^5$/dyn). Further, since it is the angular frequency of the oscillation component superimposed on the blood pulse wave, w may be considered to be a value of 10 (rad/s) or more. For this reason, the lower limit for equation (40) is viewed to be about 1/(w$^2$C). Thus, when L is approximated as follows for simplification as $$L=1/((\omega^2 C) \qquad (41)$$

Rc becomes $$Rc=L/(CRp) \qquad (42)$$

From the relationship between equations (41) and (42), the damping constant a in equation (15) becomes $$a=1/(CRp) \qquad (43)$$

Using the relationships between equations (41) through (43), and a, w and one of the four constants, for example blood inertia L, the remaining parameters may be expressed as $$Rc=\alpha L \qquad (44)$$

$$Rp=\omega^2 L/\alpha \qquad (45)$$

$$C=1/(\omega^2 L) \qquad (46)$$

It is clear, then, that the parameters of the model can be confirmed by obtaining α, ω, and L from the above equations (44) through (46). Here, a and w can be obtained from the actual measured waveform of the radius artery waveform. L can be calculated based on stroke volume per beat SV.

An explanation will now be made of the order for calculating L based on the stroke volume per beat SV. First, the average value E01 of the pressure waveform at the proximal portion of the aorta can be obtained from the following equation (47)

$$E01=\{E0tp+(tp1Em/2)\}/tp \qquad (47)$$

Further, the following equation (48) can be established using Rc, Rp, α, ω, and L.

$$Rc+Rp=\alpha L+(w^2L/\alpha)=(\alpha^2+\omega^2)L/\alpha. \qquad (48)$$

Because the average current flowing through the lumped four parameter model, i.e., the quotient of E01 by Rc+Rp, is equivalent to the average value (SV/tp) of the blood flow flowing through the artery at each blood pulse. Accordingly, the following equation (49) can be established.

$$(SV/tp)=1333.22(1/tp)\{E0tp+(tp1Em/2)\}\alpha/\{(\alpha^2+\omega^2)\cdot L\} \qquad (49)$$

The number 1333.22 in equation (49) above is the proportional constant when the units for pressure are converted from [mmHg] to [dyn/cm$^2$].

By solving the thus obtained equation (49) for L, the following equation (50) is obtained for determining L from stroke volume per beat SV.

$$L=1333.22\{E0tp+(tp1Em/2)\}\alpha/\{(\alpha^2+\omega^2)\cdot SV\} \qquad (50)$$

(c) Method for Calculating Parameters in Lumped Four Parameter Model

Figure 71:
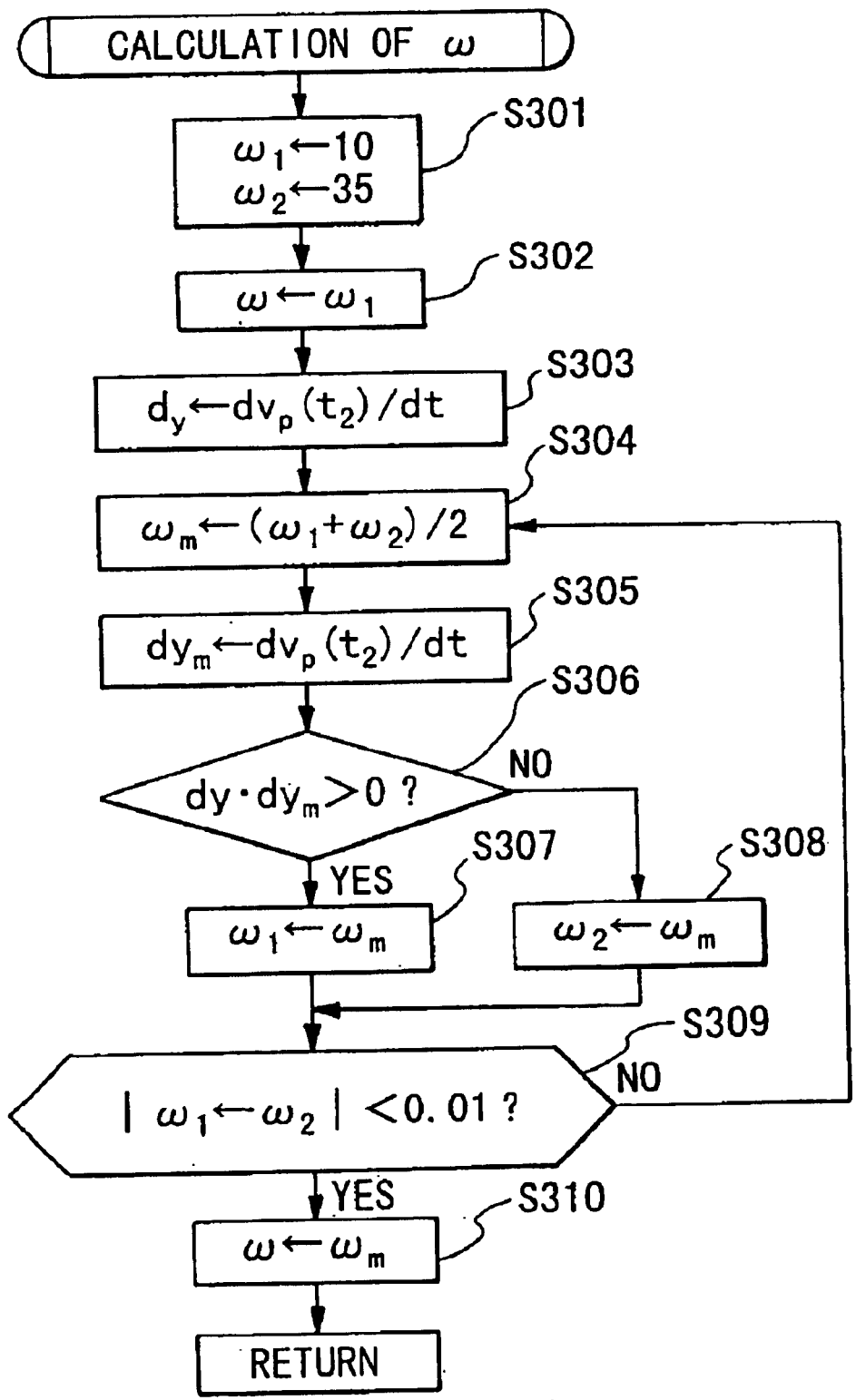
Figure 72:
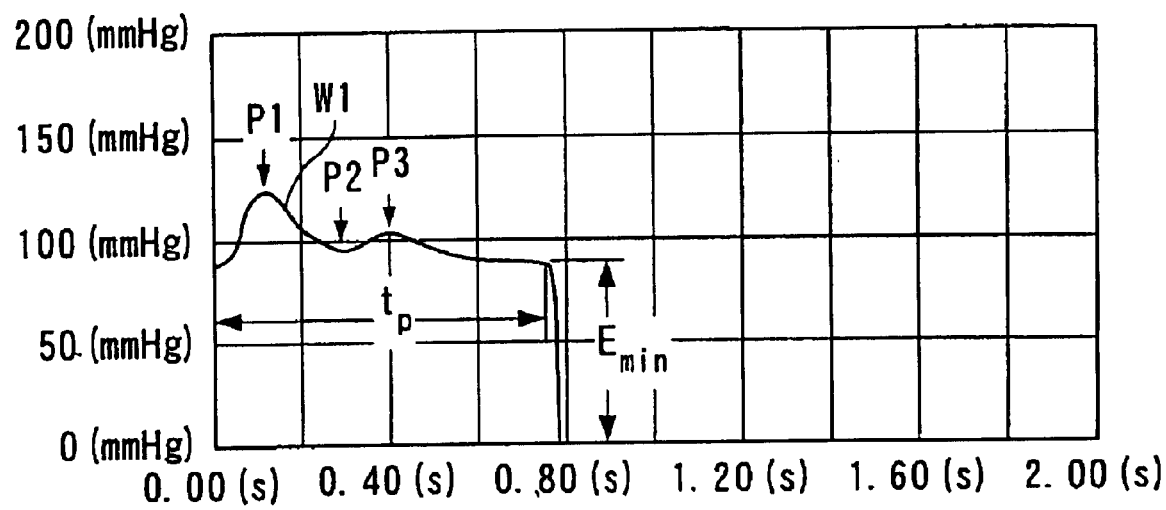
FIG. 72 is a waveform diagram showing an example of the radius artery waveform obtained through an averaging process.

FIGS. 68 through 71 are flow charts showing the operation for parameter calculation. FIG. 72 is a waveform diagram showing the radius artery waveform. An explanation will now be made with reference to these figures of the processing carried out by a microcomputer (not shown) to calculate the parameters.

As preconditions for calculating the parameters, it is assumed that measurements of the blood pulse waveform and the stroke volume per beat SV of the radius artery blood pulse wave are carried out. The details for carrying out these measurements are discussed in Chapter 2, Sections 2 and 3.

Figure 68:
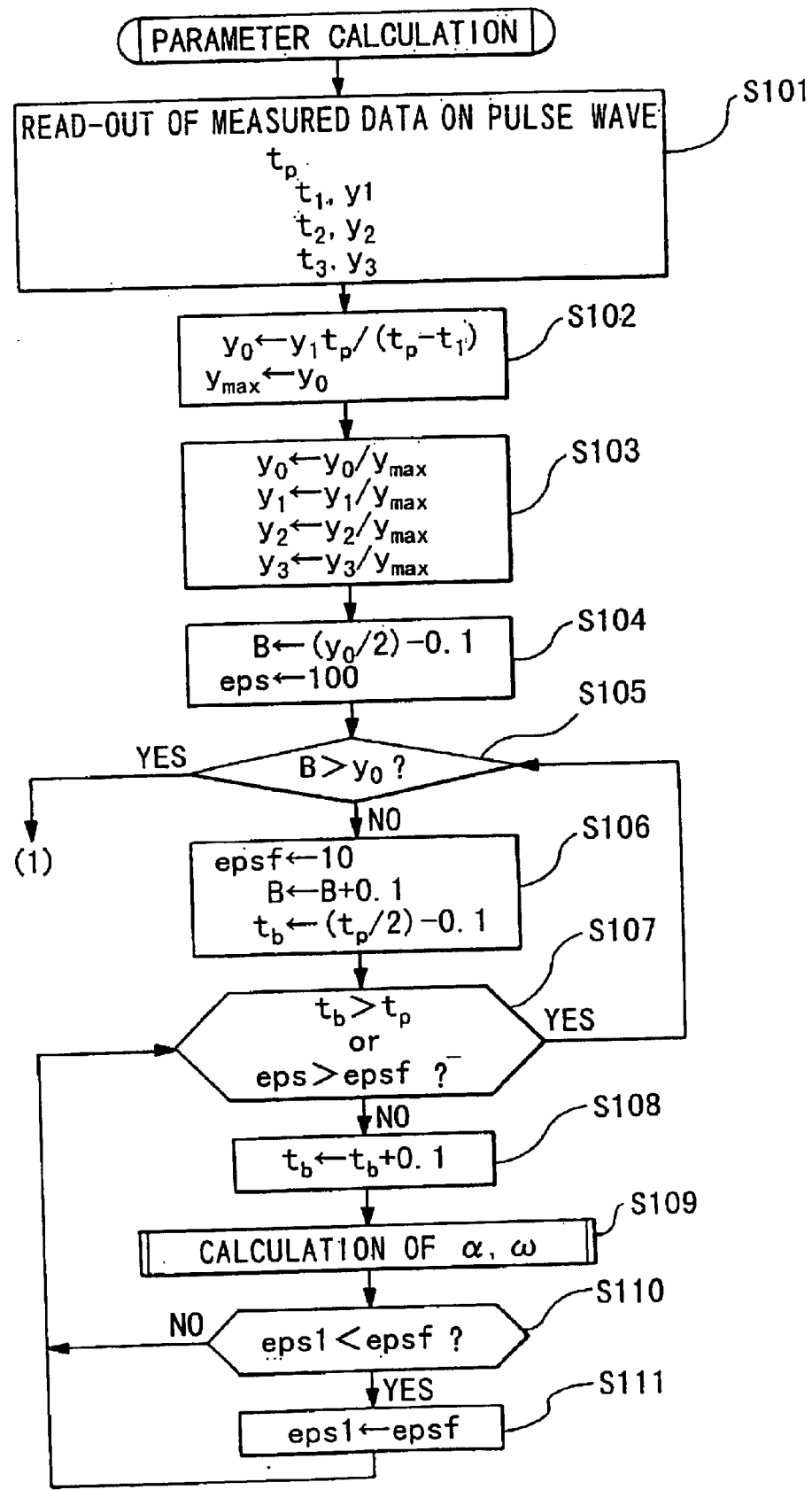
FIGS. 68 to 71 are flow charts showing the operation of the processing to calculate parameters in a lumped four parameter model.
Figure 69:
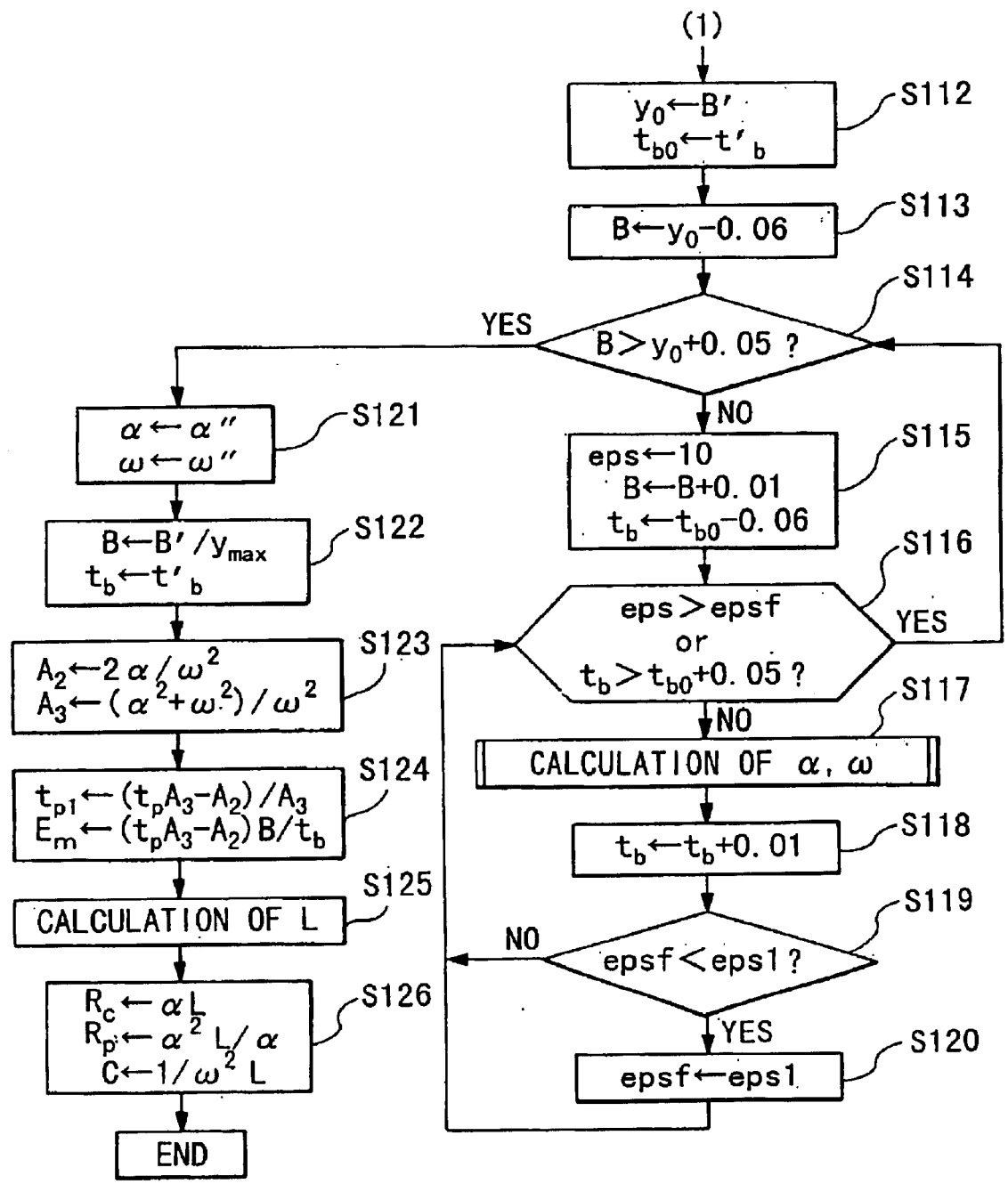
Figure 70:
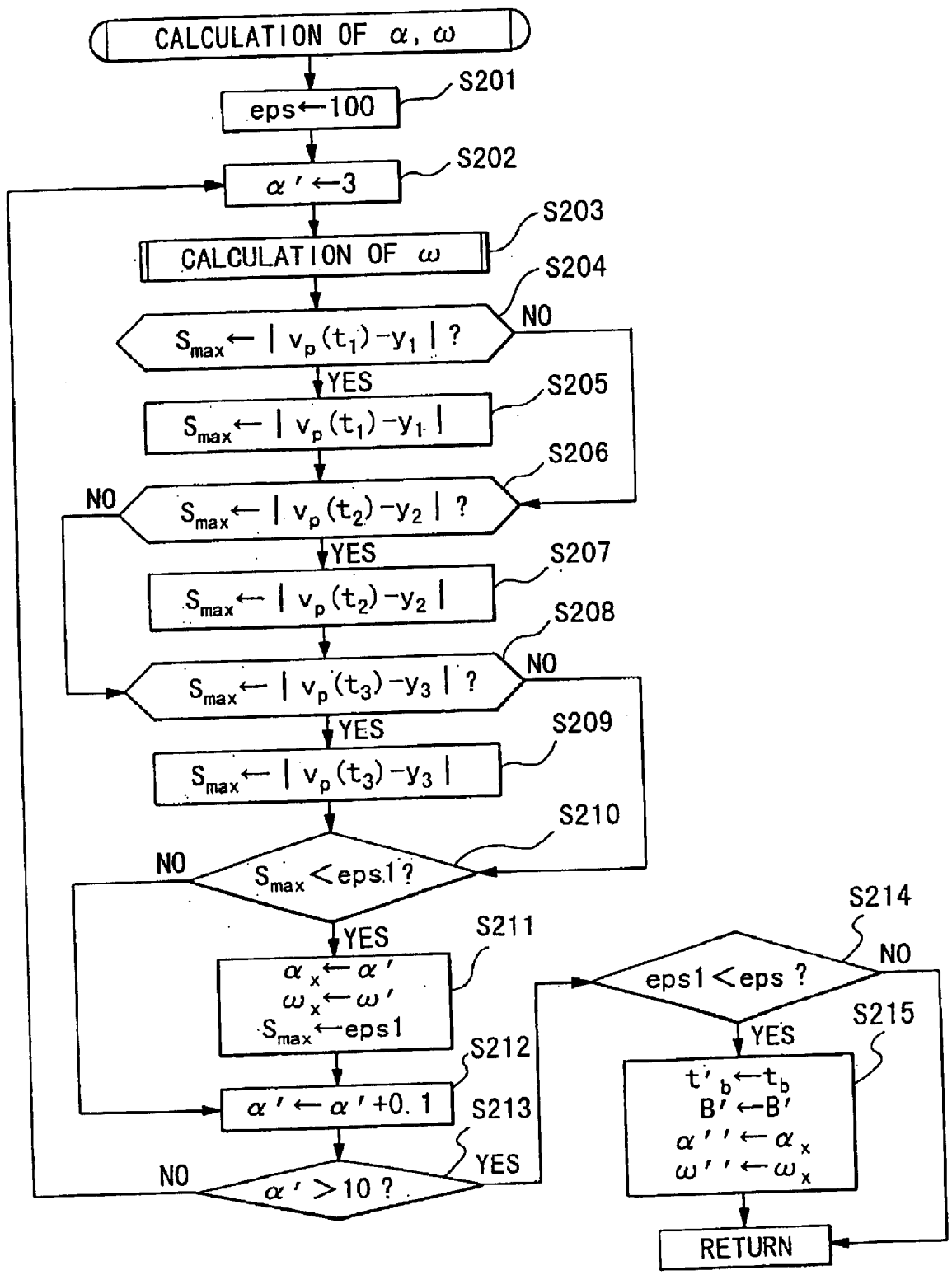

Once measurement of the blood pulse waveform and the stroke volume per beat are completed, the parameter calculation processing routines shown in the flow charts in FIGS. 68 and 69 are executed. Accompanying execution of this routine, the routine shown in FIG. 70 for calculating a and w is carried out (steps S109 and S117). Accompanying the execution of the routine for calculating a and w, the routine for calculating w shown in the flow chart in FIG. 71 is carried out (steps 203). An explanation of the processing in these routines will now be explained.

First, the microcomputer obtains the following for the radius artery waveform of one beat that has been taken up in the microcomputer's internally stored memory. Namely, for this radius artery waveform of one beat, the microcomputer obtains the time t1 and blood pressure y1 corresponding to a first point P1 at which blood pressure reaches a maximum; the time t2 and blood pressure y2 corresponding to a second point where blood pressure has fallen subsequent to the first point; and the time t3 and blood pressure value y3 corresponding to a third point P3 at which there is the second peak. The details of this processing are covered in Chapter 3, Section 1.

Figure 73:
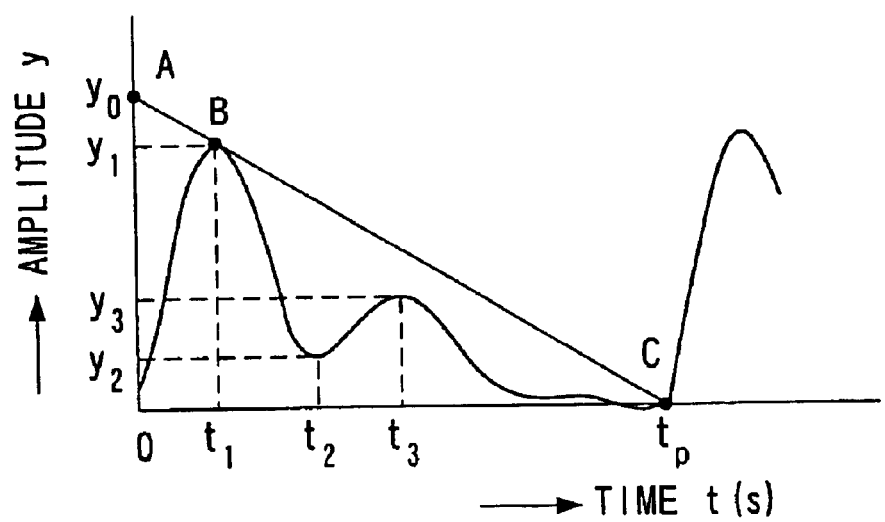
FIG. 73 is a waveform diagram showing an example of the radius artery waveform obtained through an averaging process, along with the details of the processing applied to this waveform.

Time tp of one beat and minimum blood pressure value Emin (equivalent to the first terms in equations (3) and (4))

are obtained for a radius artery blood pulse waveform taken up in memory (step S101). Additionally, in the case of a gentle blood pulse wave for which it is difficult to distinguish between the second point P2 and third point P3, the time interval between second point P2 and third point P3 is set to t2=2t1 and t3=3t1, and the blood pressure at these points is determined In order to simplify the calculations, normalization processing of y1 to y3 utilizing blood pressure value y0 at point A shown in FIG. 73 is carried out (steps S102 and S103), and the value of B is initially set to (y0/2)−0.1 (step S104).

Next, the optimal values of B, tb, a, and w are obtained in the following order.

1. B is varied within the range of y0/2 to y0, tb is varied within the range of tp/2 to tp (at intervals of +0.1), and the a, and w are obtained for each B and tb at which |vp(t1)−y1|, |vp(t2)−y2|, and |vp(t3)−y3| become minimum values.

2. From among the B, tb, a, and w obtained in step 1 above, the B, tb, a, and w at which |vp(t1)−y1|, |vp(t2)−y2|, and |vp(t3)−y3| are minimum values are obtained.

3. Using the B and tb obtained in step 2 above as the standard, the processes in the above steps 1 and 2 are again carried out within the limits of B+0.05 and tb±0.05.

4. When carrying out the processing in the above steps 1 through 3, a is varied within the range of 3 to 10 at intervals of 0.1, and the optimal w is calculated for each a. Further, for each a, a dichotomy is used to obtain the w at which $dvp(t2)/dt=0$ (see FIG. 71). When calculating the value of vp in each of these processings, the initial value v01 in equation (33) is set to zero.

5. tp1, Em and E0 are calculated based on equations (28) through (30) and (44) through (46)(steps S123 and S124).

6. Using equation (50), the value of L is calculated from the stroke volume per beat (step S125), and the values of the remaining parameters are obtained from equations (44) through (46)(steps S126).

Next, direct flow (average value) total peripheral blood vessel resistance TPR is calculated as follows.

$$TPR=Rc+Rp$$

(3) Data Examples

As one example of the data necessary in the processing to calculate parameters, the following were obtained from the radius artery blood pulse waveform shown in FIG. 72.

First Point: t1=0.104 (s), y1=123.4 (mmHg)

Second Point: t2=0.264 (s), y2=93.8 (mmHg)

Third Point: t3=0.38 (s), y3=103.1 (mmHg)

time duration of one blood pulse: tp=0.784 (s)

minimum blood pressure: Emin=87.7 (mmHg)

data of stroke volume per beat: SV=103.19 (cc/beat)

Each of the data are determined as exemplified below by carrying out processing to calculate parameters.

a=4.2 ($s^{-1}$), w=24.325 (rad/s)

B=27.2 (mmHg), tb=0.602 (s)

tp1=0.588 (s)

Em=27.4 (mmHg)

E0=90.3 (mmHg)

As a result, the parameters disclosed below are obtained.

L=7.021 (dyn·$s^2$/$cm^5$)

C=2.407×$10^{-4}$ ($cm^5$/dyn)

Rc=29.5 (dyn·s/$cm^5$)

Rp=958.2 (dyn·s/$cm^5$)

TPR=1018.7 (dyn·s/$cm^5$)

Figure 74:
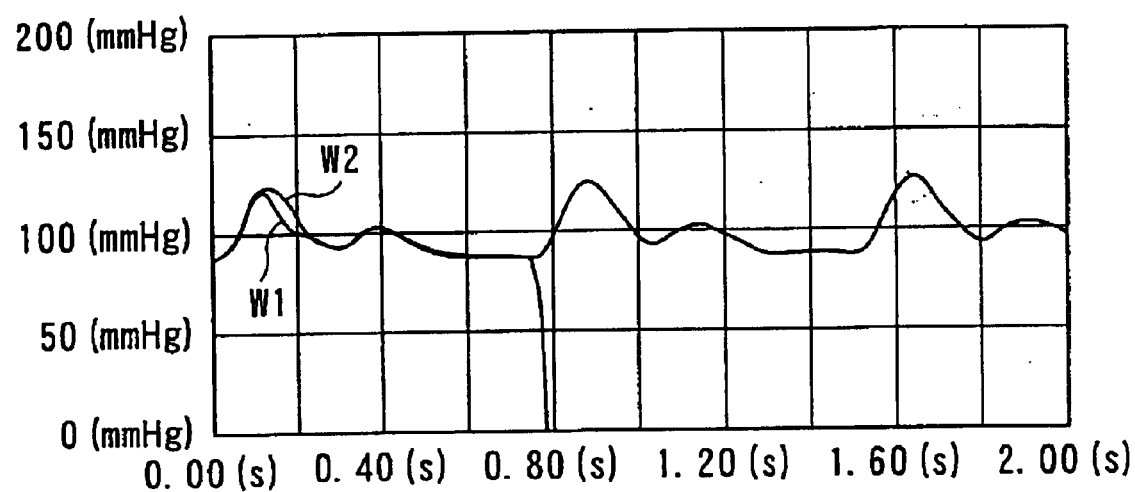
FIG. 74 is a waveform diagram showing the multiple display of the radius artery waveform obtained through a calculating process and the radius artery waveform obtained through an averaging process.

For confirmation purposes, when equation (40) is calculated using the calculated parameters, $$6.969^2L^27.021$$

the approximation of equation (41) may be deemed appropriate. As shown in FIG. 74, the radius artery blood pulse waveform W2 calculated using the calculated parameters coincides extremely well with the waveform W1 (average waveform over 1 minute) of the waveform actually measured.

(4) Modifications

1. Calculation of Inductance L

By measuring the blood flow volume, the value equivalent to the average current $(1/tp)\{E0tp+(tp1)Em/2)\}$ in equation (49) above is obtained. Inductance L may be calculated based on this result. Known devices for measuring blood flow volume include a device employing an impedance method, Doppler method or the like, may be used. Further, in the case of a blood flow measuring device using the Doppler method, devices employing ultrasound, laser or the like are available.

2. Parameter Calculation Method Not Carrying Out Measurement of Stroke Volume Per Beat An embodiment may be considered in which circulatory parameters are obtained without measuring stroke volume per beat SV. Namely, from among the four circulatory parameters, inductance L is set to a fixed value, and the other circulatory parameter values are calculated based on only the waveform of the measured radius artery blood pulse wave. As a result, it is possible to eliminate the stroke volume per beat measurer (see FIGS. 50 and after) for measuring the stroke volume per beat.

However, when inductance L is set to a fixed value in this way, there is a decrease in the accuracy of the circulatory parameters obtained as compared to a method employing an actually measured value for stroke volume per beat. Therefore, to compensate for this, a monitor may be provided as shown in FIG. 74 which superimposes and displays radius artery blood pulse waveform W1 (measured waveform) obtained by measurement, and radius artery blood pulse waveform W2 (calculated waveform) obtained by calculation. First, the value of inductance L is set to a fixed value, and calculated waveform W2 is obtained. The degree of coincidence between calculated waveform W2 and measured waveform W1 can be seen by displaying calculated waveform W2 on the monitor. Next, the diagnostician sets a suitable value which is different from the aforementioned fixed value as inductance L. Calculated waveform W2 is again obtained and its degree of coincidence with the measured waveform W1 is viewed on the monitor. Next, the diagnostician determines a number of suitable values for inductance L in the same manner as above, and calculated waveforms W2 are obtained for each of the inductance L values. Each of the thus obtained calculated waveforms W2 is displayed on the monitor and compared to measured waveform WI. Next, the one waveform W2 which best coincides with measured waveform WI is selected from among the aforementioned calculated waveforms W2, and the value of the inductance L at that point in time is defined as the optimal value.

As discussed in Chapter 2, Section 3, by employing this type of calculation method, it is possible to omit the stroke-volume-per-beat measurer such as in FIG. 54. Accordingly, this embodiment offers an advantage in that the cuff becomes unnecessary.

3. Model of Pressure Wave at Proximal Portion of Aorta

Figure 75:
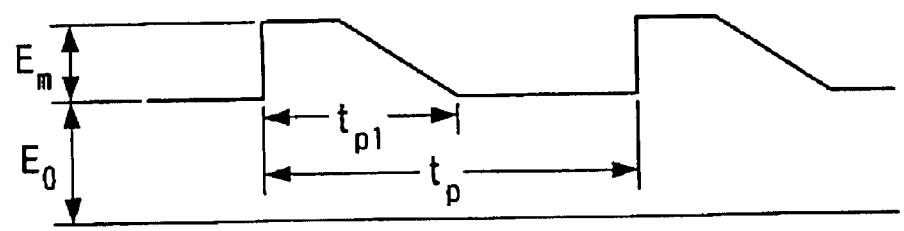
FIG. 75 is another waveform diagram modeling the blood pressure waveform at the proximal portion of the aorta in a human being.

A trapezoidal wave, rather than a triangular wave, may be employed to model the pressure waveform at the proximal portion of the aorta. An example of such a wave is shown in FIG. 75. A trapezoidal wave more closely approximates the actual pressure wave than does a triangular wave, thus making it possible to obtain more accurate circulatory parameters.

4. Other Methods for Calculating Circulatory Parameters

The circulatory parameters have been obtained from calculations using several equations. However, it is also acceptable to use a circuit simulator or the like to simulate each of the response waveforms of the model when each of the circulatory parameters are varied within a specific range, and then select and output the circulatory parameters which best coincide with the actually measured radius artery blood pulse waveform. In this case, it is possible to use a more complicated model which is closer to reality for the electric model of the circulatory system and the model of the pressure waveform at the proximal portion of the aorta. As a result, measurement accuracy is improved even further.

Part 2' Calculation Method Based on Distortion in Blood Pulse Wave (1) Overview

As a general rule, in the above analysis method based on an electric model, each of the values of the circulatory parameters are calculated based on the measured results for both the radius artery blood pulse waveform and the stroke volume per beat. This method is somewhat inconvenient with respect to activities outdoors and the like, in that it is necessary to use a cuff for the detection of stroke volume per beat in order to obtain measurements of good accuracy. However, there is available another method in which only the radius artery blood pulse waveform is measured, and each of the values of the circulatory parameters is obtained from these measured results.

(2) Calculation Method

It is understood that there is a strong relationship between the distortion obtained from the radius artery blood pulse waveform and each of the values of the circulatory parameters. Thus, blood pulse wave distortion d can be obtained from the following equation using the results of a spectral analysis of the blood pulse wave. The calculation of waveform spectrum information is as described in Chapter 3, Section 2.

$$\text{distortion } d = \sqrt{(I_2^2 + I_3^2 + \ldots + I_n^2)}/I_1$$

wherein, I1 is the amplitude of the fundamental wave, and I2, I3, . . . , are the amplitudes of the 2nd, 3rd, . . . , nth order harmonic waves.

Figure 76A:
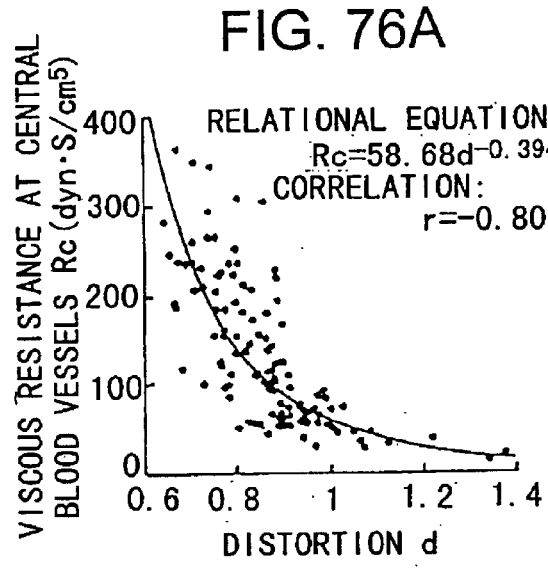
FIG. 76A is a diagram showing the correlation coefficient between the distortion rate d and resistance Rc in blood vessels at the center of the circulatory system.
Figure 76B:
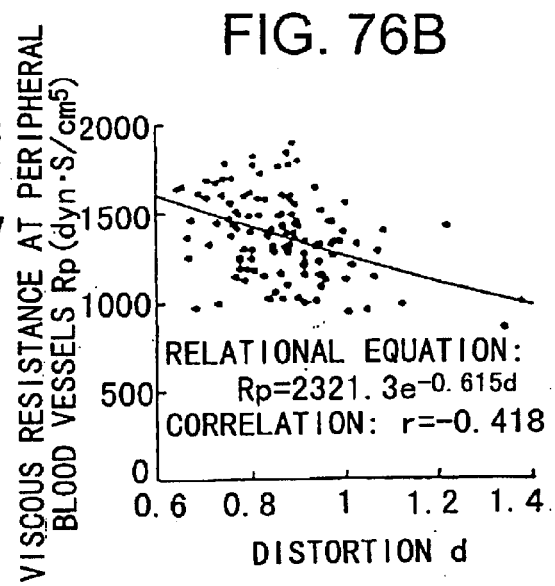
FIG. 76B is a diagram showing the correlation coefficient between the distortion rate d and resistance Rp at peripheral blood vessels.
Figure 76C:
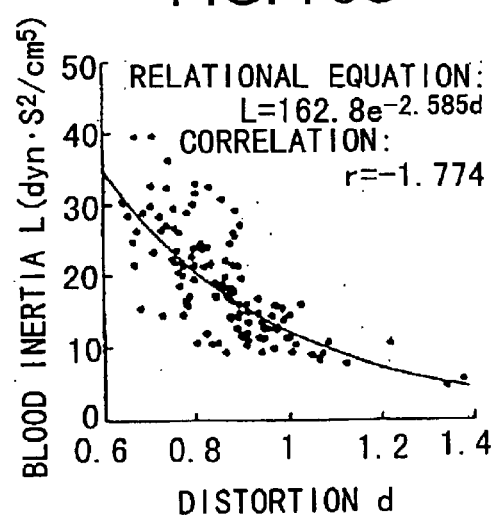
FIG. 76C is a diagram showing the correlation coefficient between the distortion rate d and blood inertia L.
Figure 76D:
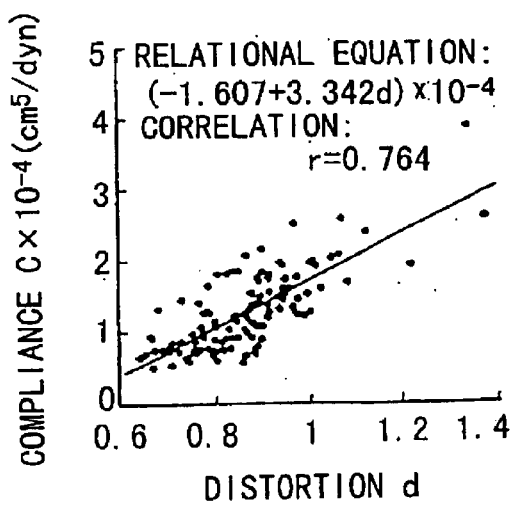
FIG. 76D is a diagram showing the correlation coefficient between the distortion rate d and compliance C.

Next, the values of each of the elements is obtained from the relative equation between distortion d and each of the values of the circulatory parameters. FIGS. 76A through D show the results of an examination of the above described correlation using test subject 120 as an example. FIG. 76A shows the relationship between resistance Rc at central blood vessels and distortion d. Obtaining a relational equation for Rc and d yields $Rc = 58.68 d^{-0.394}$, with the correlation r equal to −0.807. Further, FIG. 76B shows the relationship between the blood vessel resistance Rp at the periphery of the body and distortion d. Obtaining a relational equation for Rp and d yields $Rp = 2321.3 \, e^{-0.615d}$, with the correlation r equal to −0.418. FIG. 76C shows the relationship between inertia L and distortion d. Obtaining a relational equation yields $L = 162.8 e^{-535d}$, with the correlation r equal to −1.774. FIG. 76D shows the relationship between compliance C and distortion d. Obtaining the relational equation between C and d yields $C = (-1.607 + 3.342d) \times 10^{-4}$, with the correlation r equal to 0.764.

(3) Representative Blood Pulse Waveform and Distortion

Figure 1A:
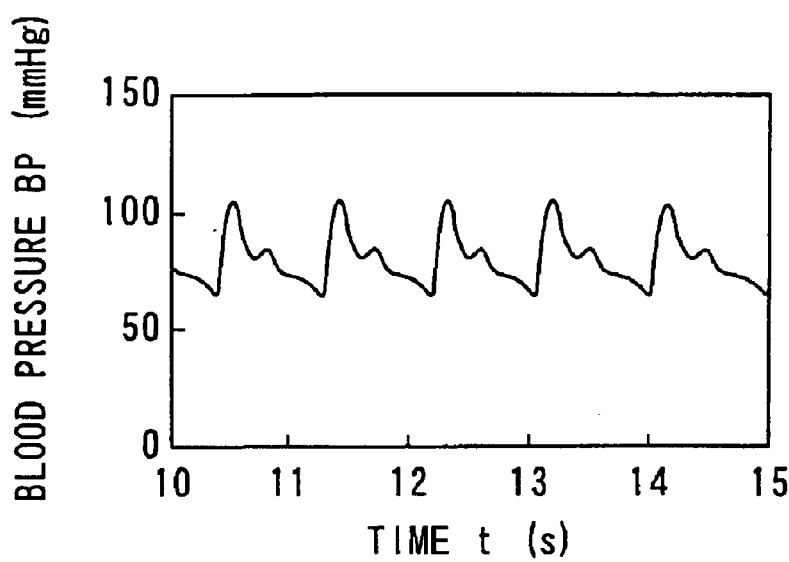
FIG. 1A is a waveform diagram of a Ping mai, a typical blood pulse waveform.
Figure 1B:
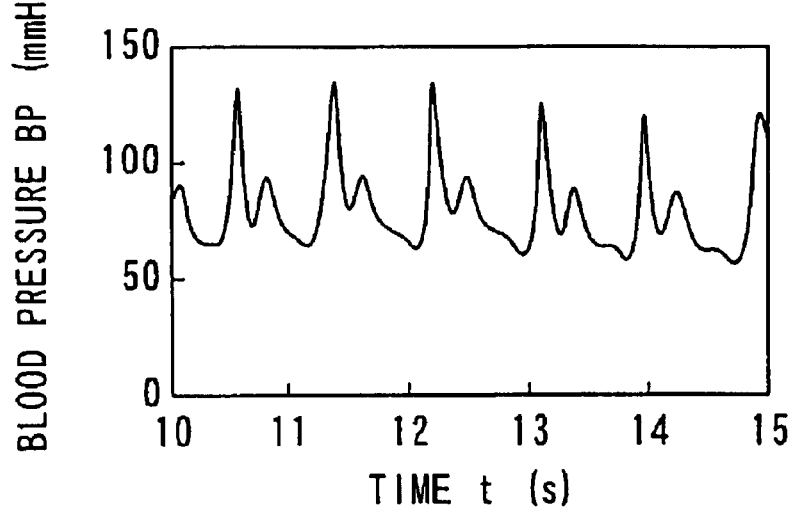
FIG. 1B is a waveform diagram of a Hua mai, a typical blood pulse waveform.
Figure 1C:
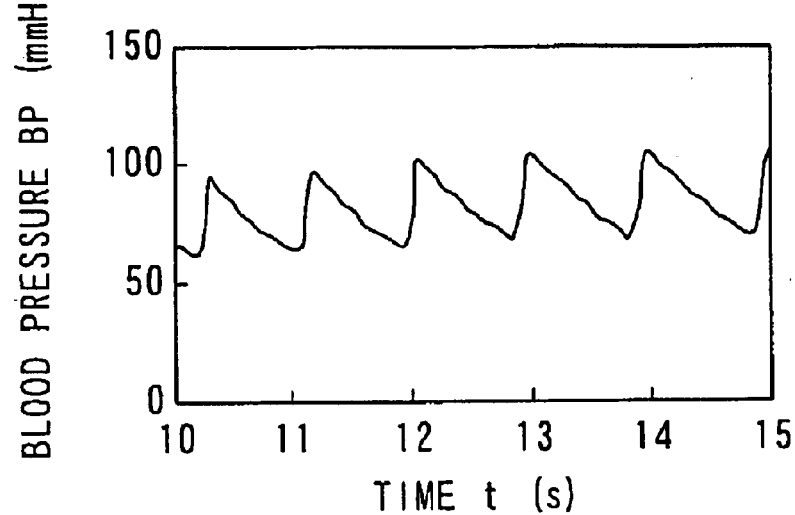
FIG. 1C is a waveform diagram of a Xuan mai, a typical blood pulse waveform.
Figure 77:
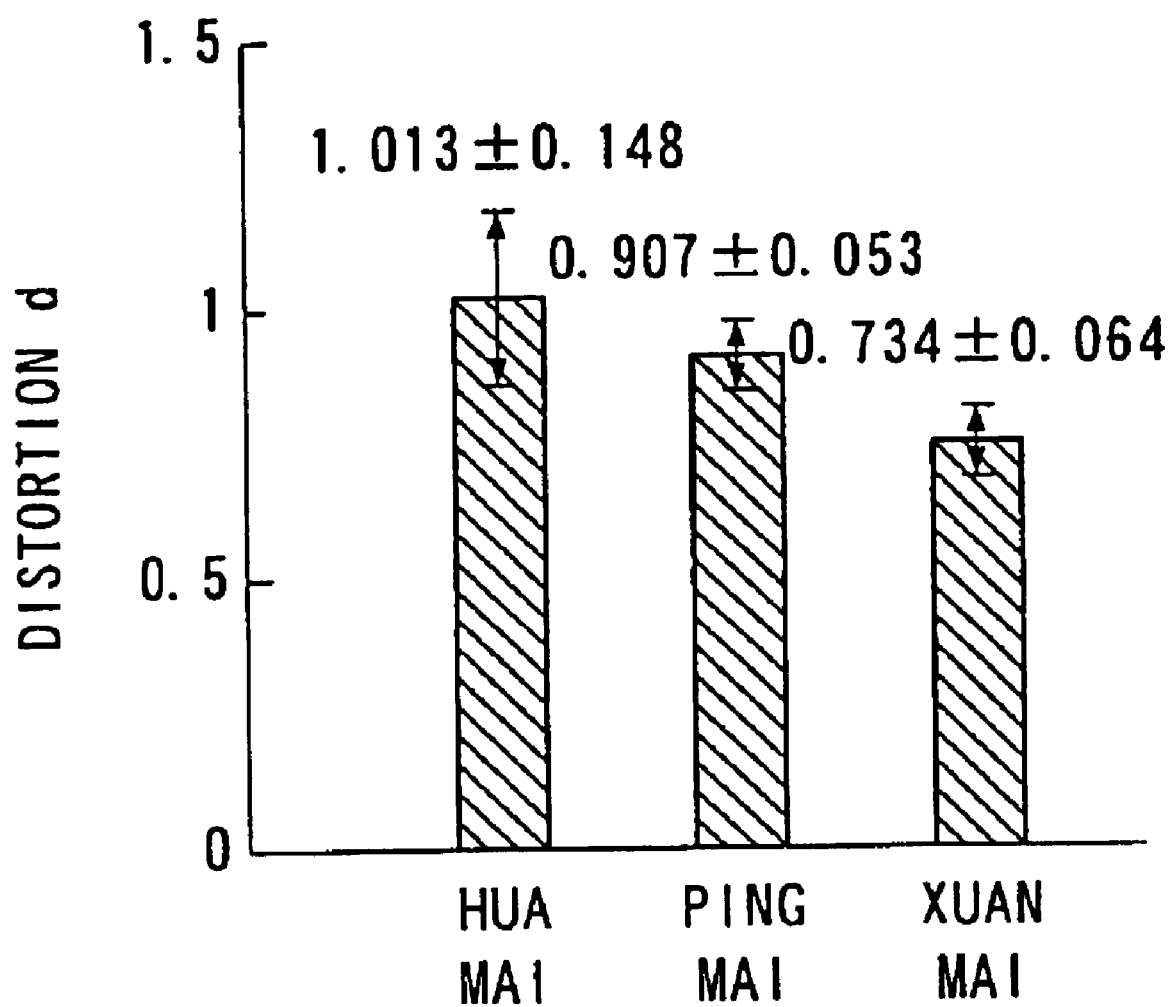
FIG. 77 is a diagram showing the relationship between the distortion rate d and three types of blood pulse waves.

FIG. 77 shows the relationship between distortion and a Ping mai, Hua mai, and Xuan mai, the typical blood pulse waveforms (see FIGS. 1A through C). FIG. 77 shows the results of analysis on 35 examples of a Ping mai, 21 examples of a Hua mai and 22 examples of a Xuan mai. In this figure, the Ping mai demonstrates a distortion centered on 0.907 with a deviation of 0.053 up or down; the Hua mai demonstrates a larger distortion centered on 1.013 with a deviation of 0.148 up or down; and the Xuan mai demonstrates the smallest distortion averaging 0.734 with a deviation of 0.064 up or down. When the size relationship between the distortion in Ping mai, Hua mai, and Xuan mai was tested in a t-test, the level of significance with 0.05 or less, confirming a significant level of difference.

Figure 78:
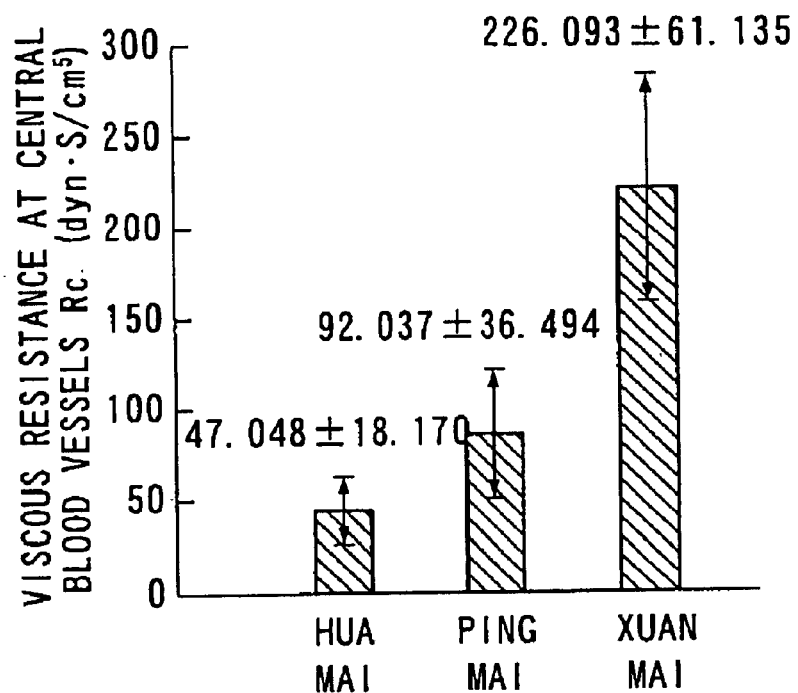
FIG. 78 is a diagram showing the relationship between the resistance Rc in blood vessels at the center of the circulatory system and three types of blood pulse waves.
Figure 79:
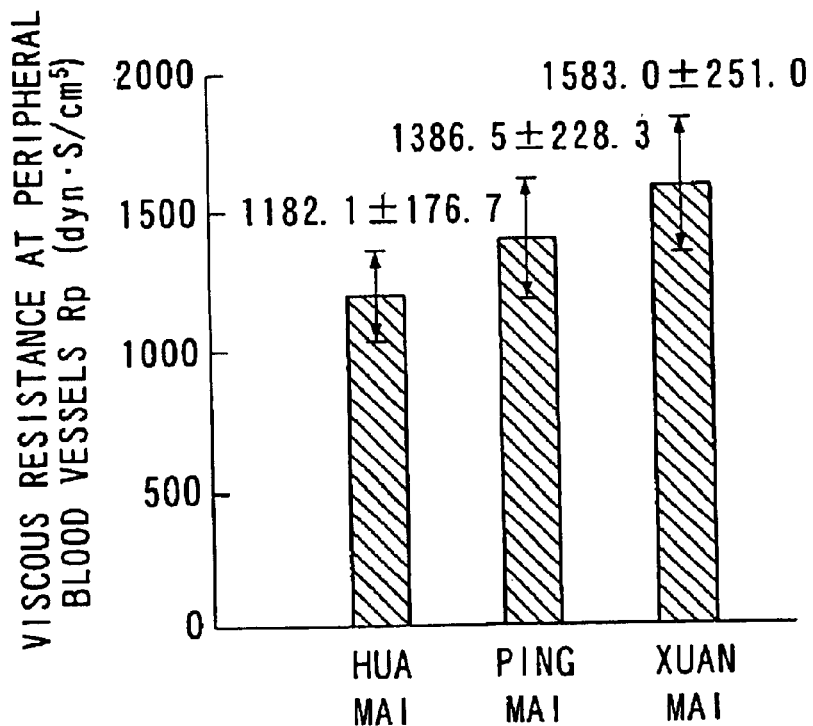
FIG. 79 is a diagram showing the relationship between the resistance Rp at peripheral blood vessels and three types of blood pulse waves.
Figure 80:
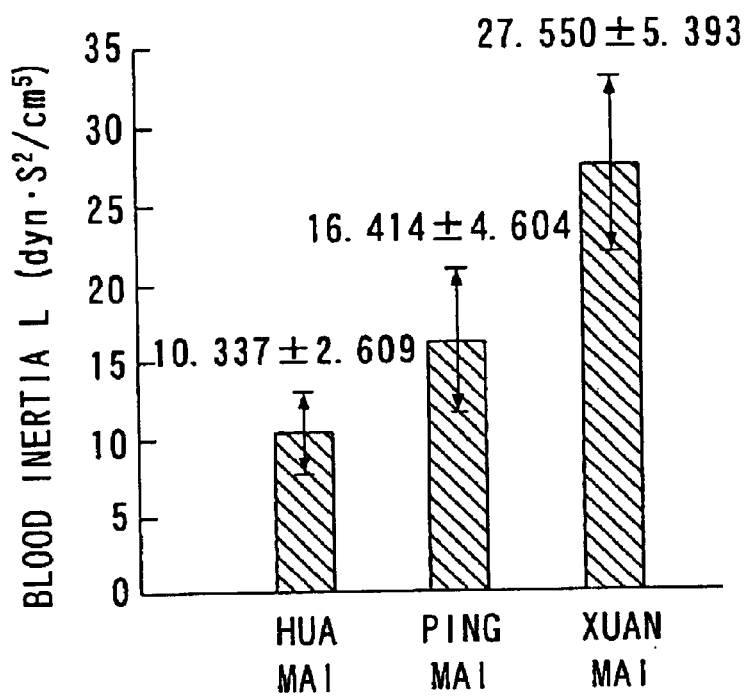
FIG. 80 is a diagram showing the relationship between the blood inertia L and three types of blood pulse waves.
Figure 81:
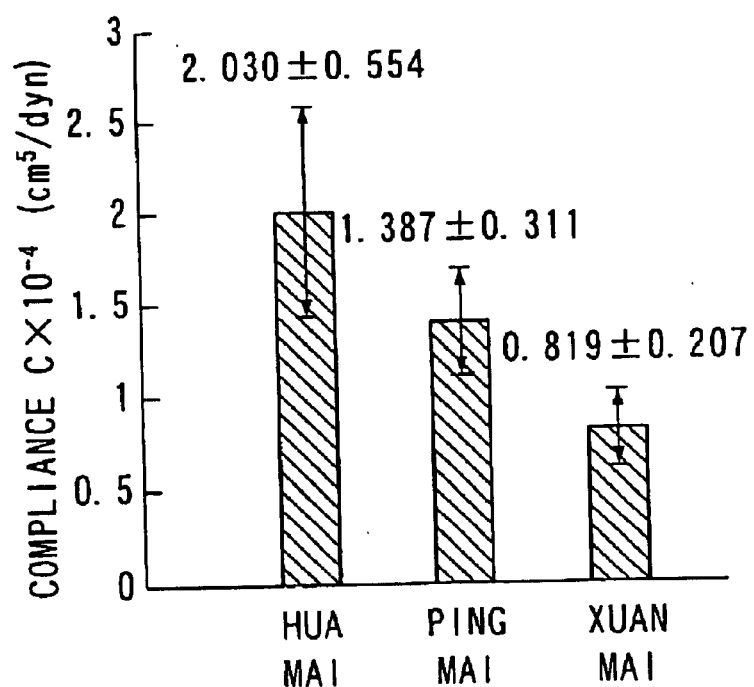
FIG. 81 is a diagram showing the relationship between compliance C and three types of blood pulse waves.

FIGS. 78 through 81 show the relationship between each of the circulatory parameters and the Ping mai, Hua mai, and Xuan mai. FIG. 78 shows the relationship between central blood vessel resistance Rc and the 3 blood pulses. As shown in the figure, the blood vessel resistance of the Hua mai is the smallest at 47.048±18.170 dyn·s/cm$^5$ (the same units apply below), followed by the Ping mai at 92.037±36.494, and the Xuan mai, which had the largest resistance at 226.093±61.135. Further, FIG. 79 shows the relationship between peripheral blood vessel resistance Rp and the 3 blood pulses. As shown in the figure, the blood vessel resistance of the Hua mai is the smallest at 1182.1±176.7, followed by the Ping mai at 1386.5±228.3, and the Xuan mai, which had the largest resistance at 1583.0±251.0. FIG. 80 shows the relationship between inertia L of the blood and the 3 blood pulses. As shown in the figure, the inertia of the Hua mai is the smallest at 10.337±2.609, followed by the Ping mai at 16.414±4.604, and the Xuan mai, which had the largest inertia at 27.550±5.393. FIG. 81 shows the relationship between compliance C and the three blood pulses. As shown in this figure, the compliance of the Hua mai is the largest at 2.030±0.554×10$^{-4}$ cm$^5$/dyn (the same units apply below), followed by the Ping mai at 1.387±0.311, and the Xuan mai, which had the smallest compliance at 0.819±0.207.

Accordingly, the order of the size relationship is reversed only in the case of compliance. If the compliance values are inverted, then the same order in the size relationship between the blood pulses can be achieved as for those of the other parameters. Further, the size relationship between these circulatory parameters and the 3 blood pulses demonstrated a level of significance of 0.05 or less in a t-test.

Figure 82:
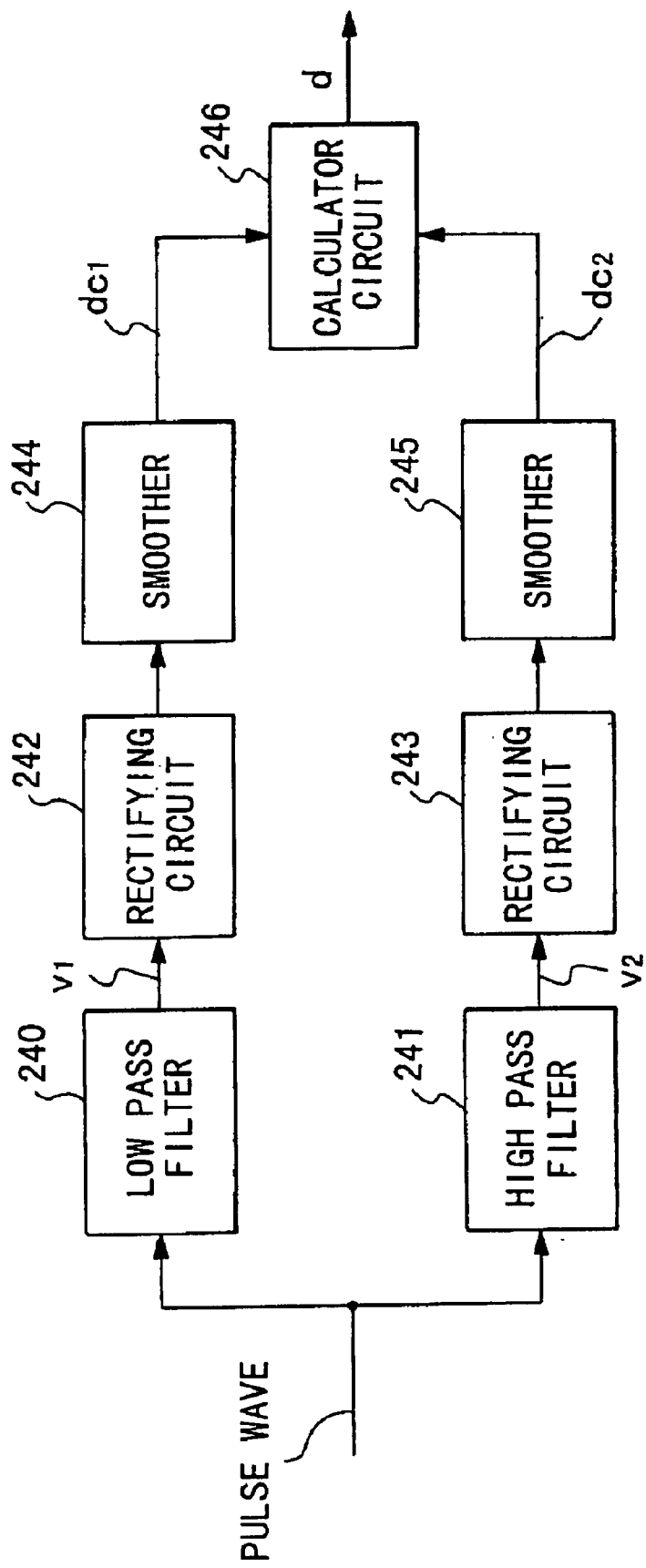
FIG. 82 is a block diagram showing another example of the structure of the distortion calculating means.

(4) Modifications 1. (I2+I3+ . . . +In)/I1, or the like, may be employed to define the definition of the distortion 2. The correlation relationships equation may be stored as a table in memory, in place of calculations using correlation equations 3. Distortion d can be obtained using a method employing the circuit shown in FIG. 82.

Namely, the blood pulse waves are input into a low pass filter 240 and a high pass filter 241, and low frequency signal component v1 and high frequency signal component v2 are output. Next, each output signal v1 and v2 is rectified at rectifying circuits 242, 243 and smoothed at smoothing circuits 244, 245, to obtain direct current signals dc1 and dc2. These DC signals dc1 and dc2 are divided at division circuit 246, to obtain distortion d=dc2/dc1.

4. The circulatory parameters are not limited to those described above. Rather, a variety of other models may be considered which would provide the same results. In particular, the correlational equation for obtaining circulatory parameters is not limited to the above. Rather, other experimental equations may be employed to the same affect.

Part 3 Calculation Method Based on Blood pulse Wave Distortion, and High Harmonic Phase and Amplitude of Blood pulse Wave Spectrum The circulatory parameters are obtained from the distortion gotten from the blood pulse wave, and high harmonic phase and amplitude of the frequency spectrum of the blood pulse wave.

First, the amplitudes I1, I2, I3, . . . , of the blood pulse wave's fundamental wave and high harmonic waves and the phases P2, P3, P4, . . . for the high harmonic fundamental wave are obtained using a Fourier analysis of the waveform of the read out blood pulse wave (hard ware suitable for this purpose is exemplified by the devices explained in Chapter 3, Section 2). Next, the distortion d of the blood pulse wave is determined by the following equations from obtained amplitude values $I_1, I_2, I_3, \ldots$ $$d=\sqrt{(I_2^2+I_3^2+\ldots+I_n^2)}/I_1$$

Next, each circulatory parameter value is determined from a regression formula for distortion d, phase P2, P3, . . ., and each of the values for the circulatory parameters. This regression formula is shown below.

$$R_c(dyn\ s/cm^5)=-Xd-179.00Xd+2.275XP_5+2.295XP_230\ 726.74$$

$$(R^2=0.86, P<0.00001,=106)$$

$$R_p(dyn\ s/cm^5)6.90XP_5-391.5Xd+192.3$$

$$(R^2=0.49, P<0.00001, n=106)$$

or, $$R_p(dyn\ s/cm^5)0.68XP_2-788.10Xd+1957.3$$

$$(R^2=0.30, P=0.008,=106)$$

$$L(dyn\ s^2/cm^5)=-31.40Xd+0.16P_5+11.50$$

$$(R^2=0.74, P<0.00001, n=106)$$

$$C(cm^5/dyn)=2.34Xd-0.007P_5+0.69$$

$$(R^2=0.74, P<0.00001,=n106)$$

Where, $R^2$ is the decision coefficient, P is the significance level, and n is the sampling number.

These regression formulae are obtained by measuring the radius artery blood pulse waveform in a number of test subjects, using Fourier analysis on the measured blood pulse wave to determine the fundamental wave and the high harmonic wave amplitude and phase, obtaining the stroke volume per beat and the circulatory parameters from the radius artery blood pulse waveform for each subject, and then calculating the correlation between the obtained amplitude, phase and parameters obtained for each subject.

SECTION 2: Analysis of Physiological State Based on Tidal Wave in Blood pulse Wave (Calculation of LF, HF, [LF/HF], RR50)

Part 1 Indicators Showing Tidal Wave in Blood pulse Wave

LF, HF, [LF/HF], and RR50 are information (i.e., indicators relating to physiological state) relating to the tidal wave in a blood pulse wave. An explanation will now be made of the significance of these indicators.

Figure 83:
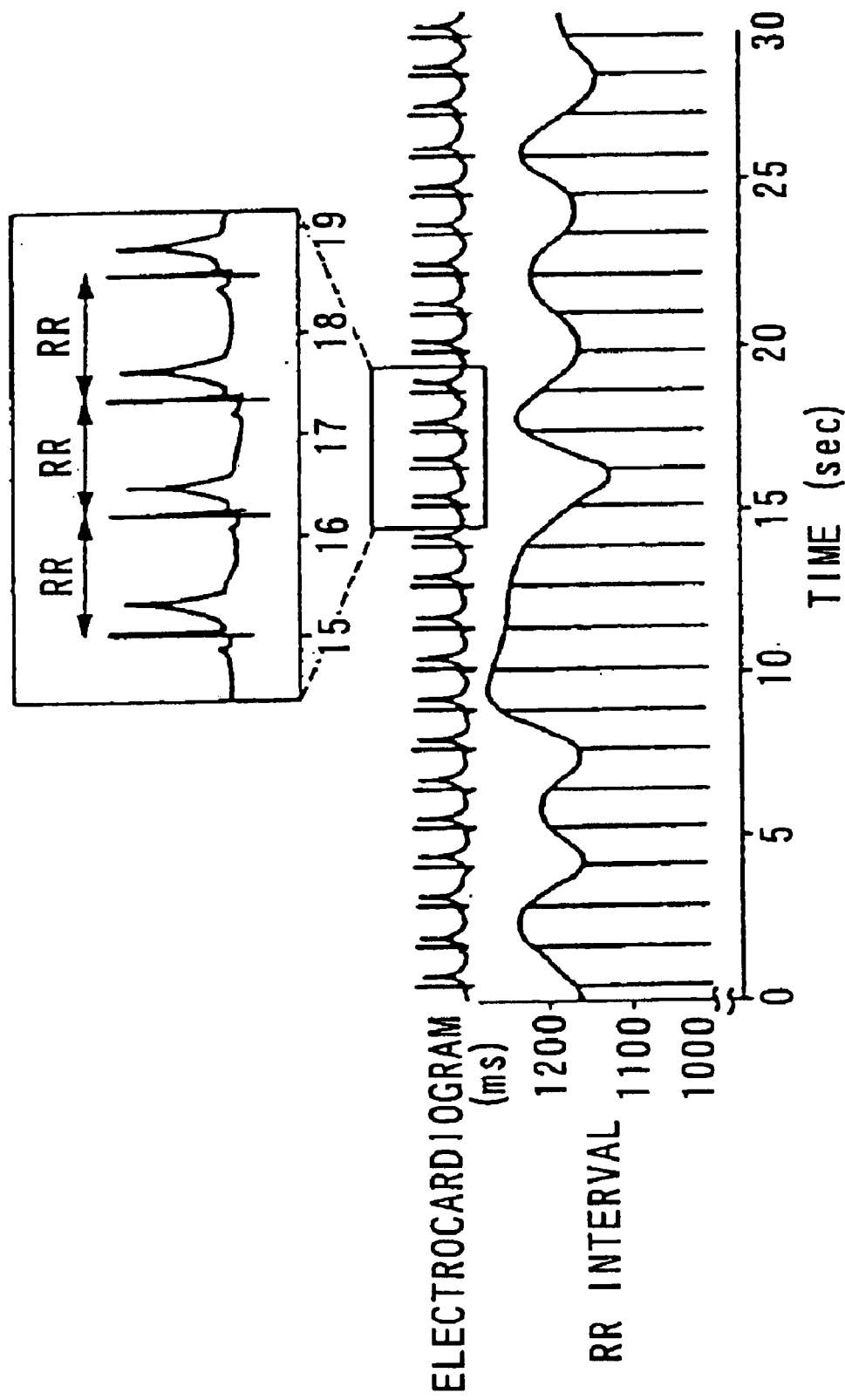
FIG. 83 is a diagram showing the relationship between an electrocardiogram and the RR interval.

In an electrocardiogram, the interval between the R wave of one heart beat and the R wave of the next heart beat is referred to as the RR interval. This RR interval is a numerical value which serves as an indicator of the functioning of the autonomic nervous system in the human body. FIG. 83 shows heart beat and the RR interval obtained from the waveform of this heartbeat in an electrocardiogram. As may be understood from this figure, an analysis of the measured results in an electrocardiogram reveals that the RR interval varies over time.

Figure 84:
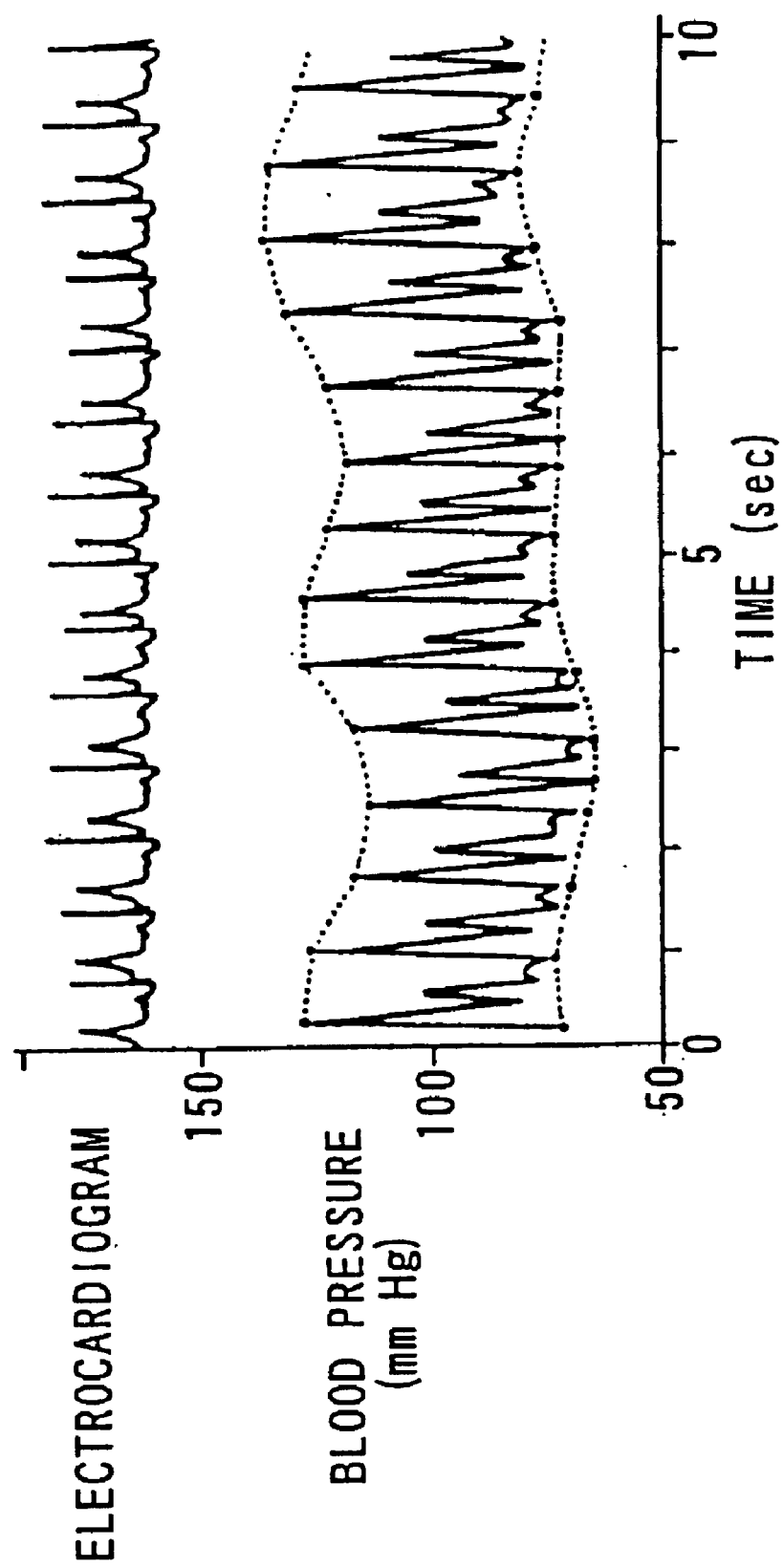
FIG. 84 is a diagram showing the relationship between an electrocardiogram and the blood pulse wave.

On the other hand, variation in blood pressure measured at the radius artery or the like, is defined as the variation in blood pressure at each beat from contraction to relaxation of the heart, and corresponds to variation in the RR interval in an electrocardiogram. FIG. 84 shows the relationship between the electrocardiogram and blood pressure. As may be understood from this figure, the blood pressure during each contraction and relaxation in a heart beat can be measured as the maximum value of arterial pressure, and the minimum value immediately preceding this maximum value in each RR interval.

By carrying out spectral analysis of variations ranging from heart beat to blood pressure, it may be understood that the variations are composed of waves having a plurality of frequencies. These may be classified into the following three types of variation components.

Figure 85A:
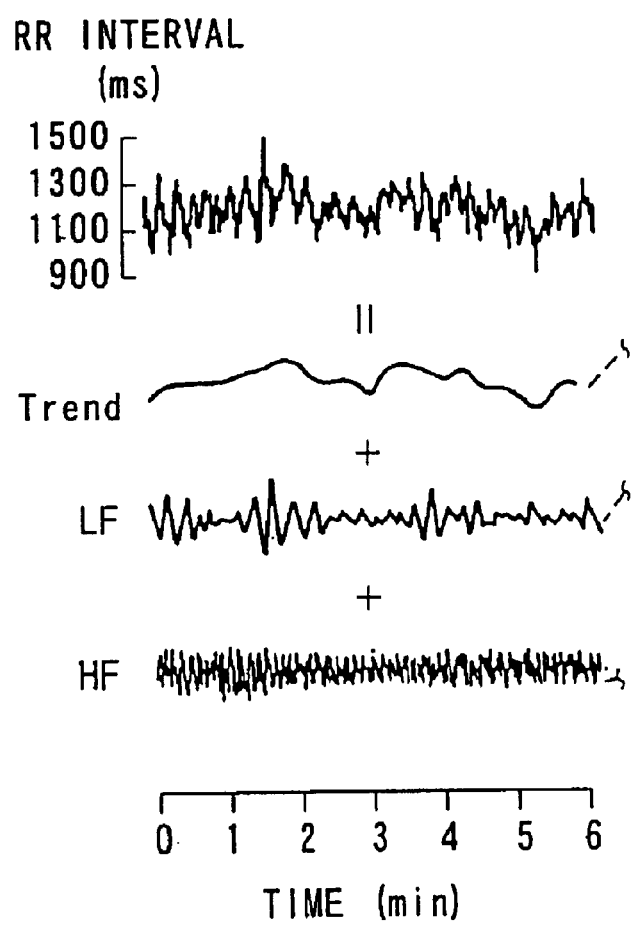
FIG. 85A is a diagram showing the relationship between fluctuations in the RR interval and the frequency components which compose these fluctuations.
Figure 85B:
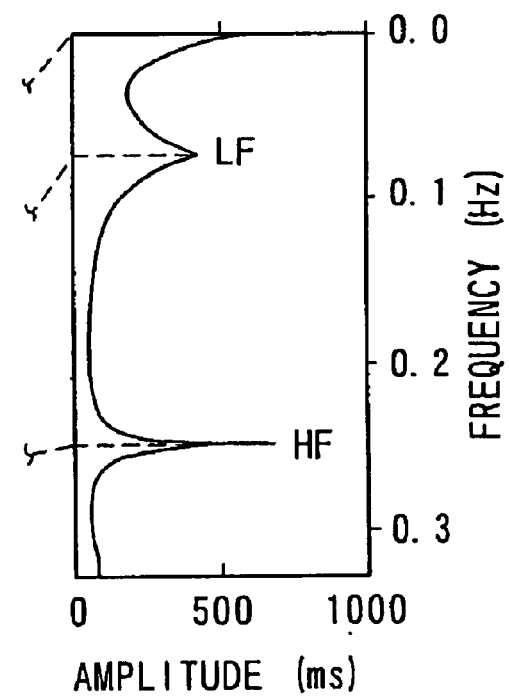
FIG. 85B is a diagram showing the results of spectral analysis of the fluctuations in the RR interval.

1. HF (high frequency) component which is the variation coinciding with respiration
2. LF (low frequency) component which varies with a periodicity of around 10 seconds
3. Trend which varies with a frequency which is lower than the measurement limits The RR interval between neighboring blood pulse waves is obtained for each measured blood pulse wave, and the discrete value of the obtained RR interval is interpolated using a suitable method (for example, 3rd order spline interpolation) (see FIG. 83). An FFT operation is carried out on the curved lined following interpolation, followed by spectral analysis. As a result, it is possible to pick out the variation component as a peak on the frequency axis. FIG. 85A shows the waveform of variation in the RR interval of a measured blood pulse wave and the waveform of each of the components of variation in the case where the waveform of variation is segregated into the three frequency components noted above. FIG. 85B shows the results of spectral analysis on the waveform of variation in the RR interval shown in FIG. 85A.

As may be understood from this figure, peaks are apparent at two frequencies near 0.07 Hz and 0.25 Hz when a subject is in a state of repose. The former frequency value is the LF component, while the latter is the HF component. The TREND component cannot be read in the figure because it is below the limit for measurement.

The LF component shows the degree of tension in the sympathetic nervous system. The larger this component, the greater the increase in tension (or the state of arousal). On the other hand, the HF component indicates the degree of tension in the parasympathetic nervous system. The larger the amplitude of this component, the more relaxed (or sedate) the state.

The amplitude values for the LF and HF components will vary according to the individual. Accordingly, with this in mind, the proportion LF/HF, which is the ratio of the amplitudes of the LF and HF components, is useful to estimate the degree of tension in the subject. When the value of LF/HF is large, than the degree of tension is high, while when LF/HF is small, the degree of tension is low indicating the subject is relaxed.

RR50 is defined by the fixed number at which the absolute value of the blood pulse wave interval corresponding to the RR interval for two consecutive heart beats varies by 50 milliseconds or more, when measurements of blood pulse wave are carried out over a fixed period of time. The larger the value of RR50, the more sedate the subject is, while the smaller the value of RR50, the more aroused the subject is.

When calculating RR50, frequency analysis of the blood pulse wave is not absolutely necessary since only the RR interval (blood pulse wave interval) is essential.

Part 2 Calculation Methods for Each Indicator

These indicators can be calculated from blood pulse waveforms in the order such as explained below.

(1) Calculation of Blood pulse Wave Interval

First, the waveform of the blood pulse wave over a fixed period of time (30 seconds or a minute, for example) is taken up. The peak information collection processing explained in Chapter 3, Section 1 is carried out to effect detection of peaks in the all of the blood pulse waveforms taken up during the measured time interval. The time of adjacent blood pulse wave peaks and the time interval of both (hereinafter, referred to as RR interval) are calculated.

(2) Calculation of LF, HF and LF/HF

The value of the obtained RR interval is discrete along the time access. Accordingly, a curved line such as shown in FIG. 85A is obtained by interpolation between neighboring RR intervals using a suitable interpolation method. Next, a spectrum such as shown in FIG. 85B is obtained by carrying out FFT processing on the interpolated curved line. Processing to collect peak information is carried out in the same manner as carried out on the blood pulse waveform, to obtain the frequencies in the spectrum corresponding to the aforementioned maximum value and the maximum value. The maximum value obtained in the low frequency region is defined as the LF component, while the maximum value obtained in the high frequency region is defined as the HF component. Further, the amplitudes of these components are obtained and the amplitude ratio LF/HF is calculated.

(3) Calculation of RR50

The time difference in neighboring RR intervals is sequentially obtained based on the RR interval obtained above. Next, a check is made of each of these time differences to confirm whether or not the time difference exceeds 50 milliseconds, and the fixed number of time differences exceeding 50 milliseconds is counted and set as RR50.

Section 3: Correction of Physiological State Based on Measurement of Physical Activity The preceding sections have concerned the various physiological states which can be obtained from blood pulse wave and the methods of blood pulse wave analysis to obtain these states.

It is known that physiological state can vary depending on the activity of a subject. For example, the measured value of [LF/HF] will vary considerably depending on whether a test subject is moving or in a state of repose. Therefore, an approach may be considered in which the physiological state obtained from the blood pulse wave is corrected in response to the physical activity of the test subject. A concrete discussion of this follows below.

Namely, in the first method, an acceleration sensor is attached to the test subject or to the device, and the blood pulse wave is measured along with the value of the acceleration sensor. When the results of the acceleration sensor confirm that the subject is moving, the measured values for physiological state are suitably corrected based on the measured value of the acceleration sensor to convert to values under normal conditions (i.e., when the subject is in repose).

As a second method, constant measurements are made of physiological state obtained from the blood pulse wave and of the value of the acceleration sensor. These measured values are then stored in memory. When measuring the physiological state at the current time, memory is searched for a measured value closest to the value measured by the acceleration sensor at the current point. The stored physiological state which was stored together with the acceleration sensor value which was searched out and found is set as the current physiological state.

By means of the above-described methods, even in the case where the test subject is engaged in an activity which effects physiological state, it is possible to obtain a physiological state measurement which coincides with the subject's physical activity, based on past similar states of activity.

A "state of repose" as used here means movement in the vicinity of the blood pulse wave sensor which is measured by the acceleration sensor and found to be below some fixed limit value (for example, 0.1 G). More specifically, when, for example, the test subject is waving his arm, the blood pulse wave cannot be measured. Accordingly, measurements obviously cannot be made during sports activity, while activities such as walking inside a room or outside are also not suitable for measurements.

Figure 86A:
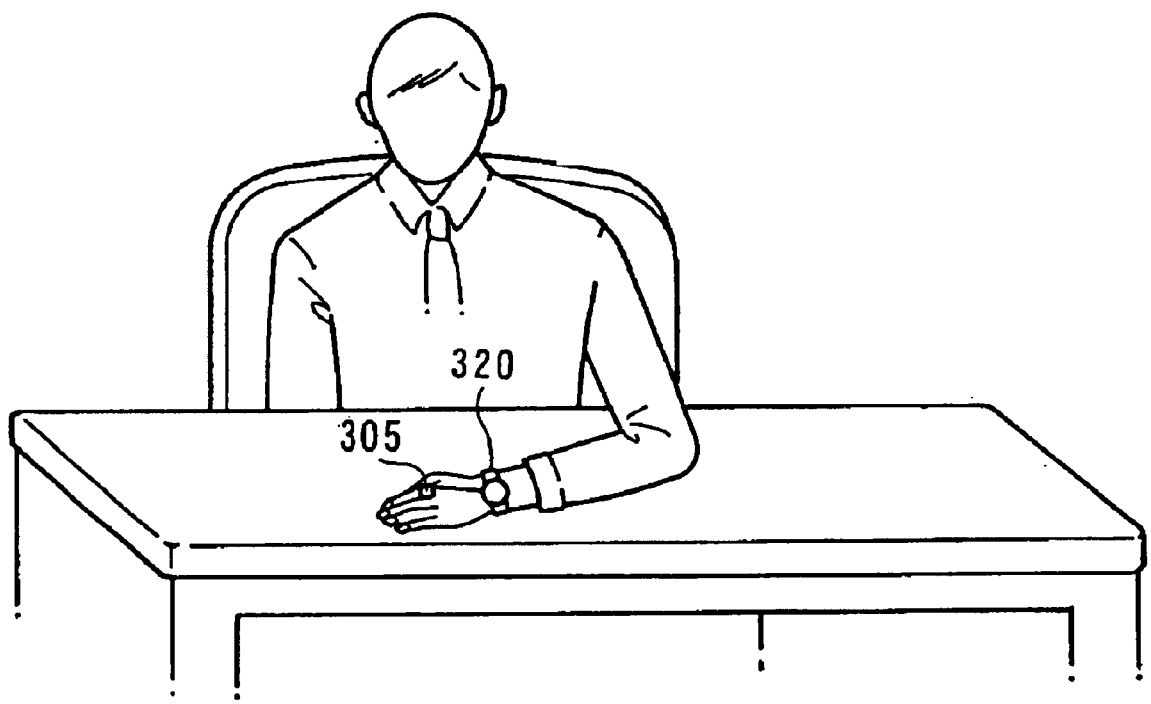
FIGS. 86A and 86B are a diagram showing desirable arrangements in which to carry out blood pulse wave measurements.
Figure 86B:
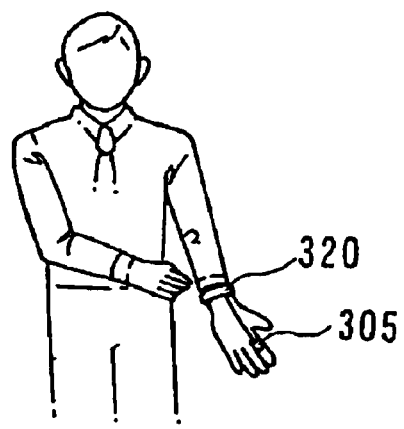

Thus, for example, assuming the user is in a room, he may move to an area where there are a desk and a chair, sit in the chair as shown in FIG. 86A, and place the arm with the watch on the desk, taking care not to move his hand. While this is the ideal arrangement, the device may also be employed in the case where the user is exercising outside. In this case, exercise is suspended and breathing is allowed to return to normal in order to carry out the measurements. Similarly, if the user is taking a walk, then this activity is suspended. Next, the user assumes a position such as shown in FIG. 86B, for example, and carries out the necessary operations by pressing buttons on wristwatch 320 with the opposite hand while trying not to move the arm on which the watch is worn.

In the case of an embodiment in which a blood pulse wave sensor 305 is attached to a necklace or pair of eye glasses, the user may be either seated in a chair or standing, so long as there is little movement. In other words, no problem is present in measurement, provided that any movement is of a degree which does not apply vibration on blood pulse wave sensor 305.

(Modification)

In addition to obtaining the spectrum of the blood pulse wave using FFT, a variety of other frequency analysis methods applicable in this chapter may be considered, including DFT (discrete Fourier Transfer), MEM (Maximum Entropy Method), the wavelet method, and the like.

CHAPTER 5 INTERFACE METHOD

In the various devices which will be discussed in detail in the next chapter, indicators or data from a human being are provided or input to a device, while notification from the device to the human being is carried out via various embodiments. The means for information inputting or notifying may require a specialized apparatus depending on the application of the device. However, provided that the means is achieving of reaching a variety of objectives, then it may be considered in the discussion herein that the device may be realized without concern for the means employed. For example, a buzzer may be sounded, a message displayed on a display, or a sound made to provide a warning to the user. In other words, any means may be used so long as it satisfies the objective of providing warning to the user.

This chapter will concern specific examples of these means. As a general rule, multiple variations of the devices explained in the next chapter are possible, since any one of the input means and notifying means discussed hereinafter may be employed.

Section 1: Input Means

When giving instructions from the human being to the device, or inputting information, the following equipment may be employed.

1. keyboard
2. pointing device mouse, touch screen, tablet, tracking ball, etc.
3. various memory media Many of the various devices available for the storage of data can be used as input means. Floppy disks, magnetic disks, optical magnetic disks and the like may be cited as examples of such devices. In addition, a variety of other media such as magnetic drums, magnetic tapes, cassette tapes, CD-ROM and the like may also be considered.

4. other

In the case where the input of sound or image data is a consideration, then microphones or scanners may be employed.

Section 2: Output Means (Means for Notification to Human Being)

The means described below are available for providing notification from the device to the human being. These means may be classified based on the five senses. Further, these means may be used alone or in plurality.

As will be explained below, it is possible to design a device which can be optimally used by a person whose is physically impaired. Namely, by employing a notifying means which does not rely on the sense of sight, for example, a person who is blind can readily understand the notification, while by employing a means which does not rely on the sense of sound, notification can be carried out for a person who is deaf. Further, by employing a means which relies on sound or touch, it not necessary for the user to intentionally glance at the LCD on his wrist watch during exercise, etc. Thus, an additional advantage is provided in improving the ease of use of the device.

Part 1 Means Relying on Sense of Sound

There are available a variety of notifying means relying on the sense of sound, these including means designed to inform the user of the results of the analysis or diagnosis of blood pulse wave, or to issue a warning to a person. Means such as the following may be considered, for example. These means are frequently embedded in some sort of portable device such as a wrist watch or the like. In this case, some of the normal components assembled as part of the watch may be diverted.

1. buzzer
2. piezo-electric device
3. speaker
4. As a specialized example, a means may also be considered in which the person to be notified is provided with a portable pager, and notification is carried out by a device.

When carrying out notification to a user using this kind of equipment, it is frequently desired to communicate some sort of information along with the notice. In this case, information such as volume levels may be changed as shown below in response to the details of the information to be communicated.

1. pitch
2. volume
3. tone
4. sound
5. type of music (program, etc.)

Part 2 Means Relying on Sense of Sight

A means relying on sight may be employed when the objective is to inform the user of various measured results or messages from the device, or to provide a warning. The following equipment may be considered as such types of means.

1. display device

These include CRTs (cathode ray tube display device) and LCDs (liquid crystal display). The lens projector (see FIG. 29) explained in Chapter 2, Section 1, Part 6 is also available as one type of specialized display device.

2. printer
3. X-Y plotter
4. lamp

Further, the following variations may also be considered when providing notification.

Figure 87:
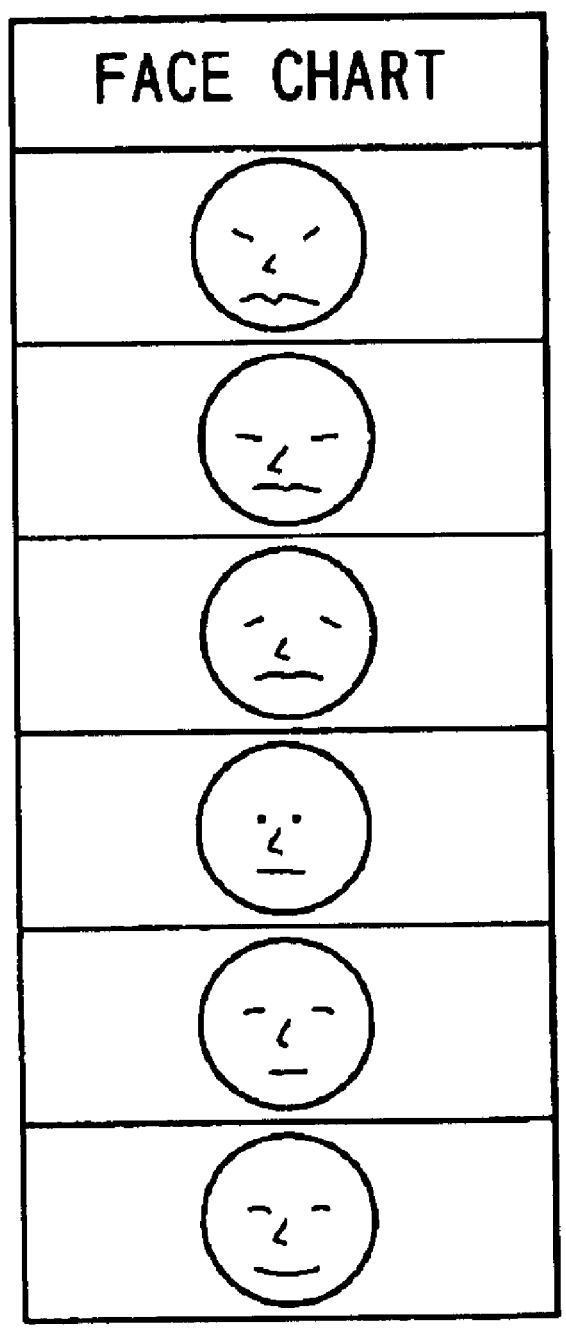
FIG. 87 is a diagram showing a face chart employed as a notifying means.

1. separate analog or digital displays in the case of notification involving numerical values
2. display using graph
3. addition of contrast to a display color
4. bar graph display where providing notification of a numerical value as is applying a grade to a numerical value
5. circular graph
6. a face chart When providing notification by applying a grade to a numerical value, a face chart may be displayed such as shown in FIG. 87 in response to the grade. In this figure, 6 grades are assumed.

Part 3 Means Relying on Sense of Touch

A means relying on the sense of touch may also be considered as a notifying means, examples thereof including the following.

1. electrical stimulation

A form memory alloy projecting outward from the rear surface of a portable device such a wrist watch is provided, with electricity passed through this form memory alloy.

2. mechanical stimulation

A retractable projection (such as a needle-shaped object which is not very pointed) may be formed to the rear of a portable device such as a wrist watch, and stimulation may be administered via this projection.

Figure 88:
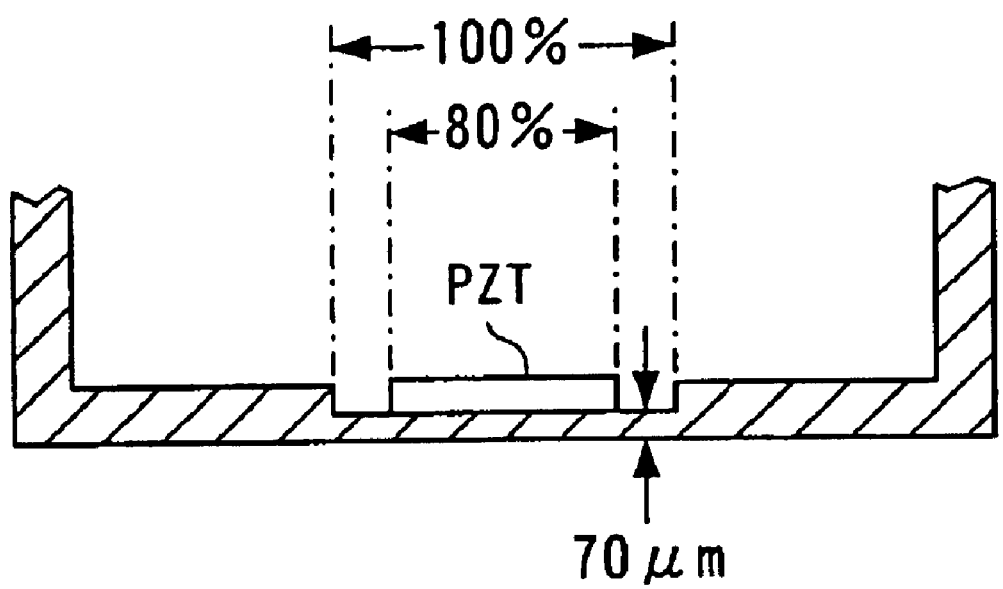
FIG. 88 is a section view of a wrist watch which internally incorporates the notifying means, in the case where notification is carried out by means of vibration using a piezo element.

Additionally, if the contents of the notification are simple, then the following embodiment may be employed which uses mechanical vibration to notify the user. A conventionally known vibration alarm which communicates vibration by rotating a eccentric load may be provided in a unitary or separate fashion to the main body of a portable device. Further, as shown in FIG. 88, a thin part of 70 $\mu$m in thickness may be formed to one portion of the inner side of the bottom surface of the main body of a portable device, and a piezoelement PZT attached thereto. When an alternating current of a suitable frequency is impressed on this piezoelement, the piezoelement PZT vibrates, with this vibration communicated to the user wearing the portable device. Additionally, the piezoelement may have a thickness of 100 $\mu$m, with a diameter length which is 80% of the length of the diameter of the concavity. When the diameter is set to be 80% in this way, it is possible to increase the sound of the notification sound.

By using the preceding mechanisms to change the strength, duration, frequency and the like of the vibration in response to the contents of the notification, it is possible to achieve a notification which is rich in variation.

Part 4 Means Relying on Sense of Smell

A mechanism for emitting a fragrance or the like may be provided to a device as a means relying on the sense of smell. A correspondence can be formed between the notification details and the odor, with the device emitting a fragrance in response to the notification contents. The micropump discussed in Chapter 6, Section 2, Part 1, or the like, is optimally employed for the mechanism for emitting fragrance or the like.

Section 3: Communication Means

Each of the devices explained in detailed in Chapter 6 below can be provided with an I/O (input/output) interface means for carrying out communication with an external piece of equipment such as a personal computer. As a result, the various types of information measured in the body are sent to the external device and the indicator or setting contents sent from the external equipment is taken up by the device.

Figure 89:
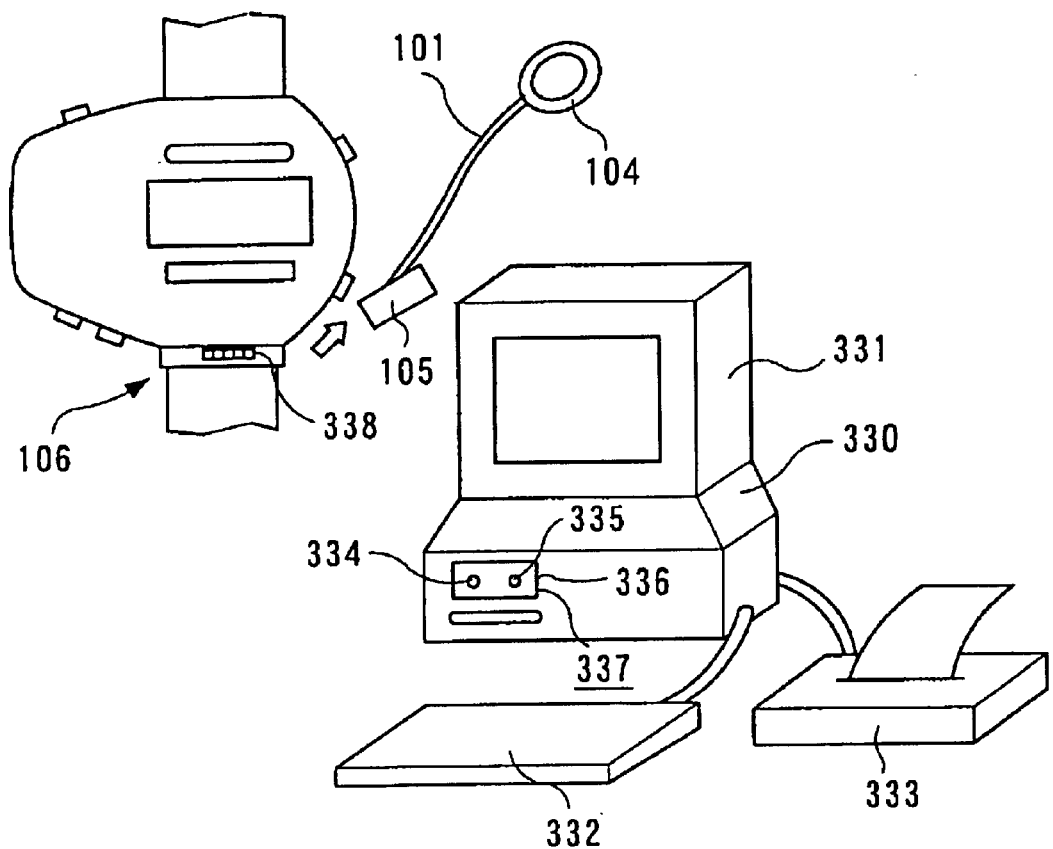
FIG. 89 is a diagram showing a wrist watch incorporating the device according to the present invention, and a personal computer which carries out optical communication with the device.

An explanation of the communication means for carrying out communication with an external piece of equipment will now be explained with reference to FIG. 89. As shown in the figure, the personal computer is composed of a main body 330, display 331, key board 332, and printer 333. Since this is an ordinary personal computer, an explanation of the internal structure thereof will be omitted with the exception of the following points.

Namely, main body 330 contains transmission and receiving controllers (not shown) for sending and receiving photo signal data. The transmission controller has a LED 334 for transmitting an photo signal, and the receiving controller has a phototransitor 335 for receiving an photo signal. An infrared type device using near infrared (for example, medium wavelengths of around 940 nm) is employed for LED 334 and phototransistor 335, and carry out optical transmission from a transmission window 337 which is provided to the front surface of main body 330, via a visible light cutting filter 336 which blocks visible light.

The device connected to the personal computer has the following structure. The wrist watch shown in FIG. 32 will be employed for the explanation here, however, a necklace, eye glasses or a variety of other portable equipment may also be employed for the device without problem. As described above, a connector 105 is formed in a detachable manner to device main body 100 of the wrist watch. Accordingly, a communication connector 338 such as shown in FIG. 89 may be attached in place of a connector cover to the connector portion from which the connector 105 has been removed. Similarly, the LED, phototransistor, and interface for optical communication are incorporated to communication connector 338 on the computer side. Further, an optical interface (not shown) for optical communications may be provided inside device main body 100 of the wrist watch.

In order to send the various information stored in the computer's RAM or hard disk to the wrist watch from the computer, a transfer command is charged from key board 332, for example. As a result, the information in the personal computer is output via LED 334 and communication window 337 as near infrared light. The near infrared light is thus sent to the optical interface via communication connector 338 at the wrist watch.

When various information such as the measured values of the physiological state is sent to the personal computer from the wrist watch, the direction of communication is the reverse of that described above. In other words, the portable device user operates the button switches provided on the wrist watch in order to set the device to the mode for transferring data. As a result, the information which the processor inside the device is to transfer is read out from RAM or the like, and sent to the optical interface. Thus, the measured value is converted to an photo signal, sent from communication connector 338, and transferred to the personal computer via communication window 337 and phototransistor 335.

When carrying out optical communication as above, in the case where it is not possible to identify whether or not the device has transmitted the information, it sometimes occurs that information which should be received by a different device is mistakenly received. Therefore, the I/O interface means employs identification information showing which equipment sent the information when information is sent or received.

Figure 90:
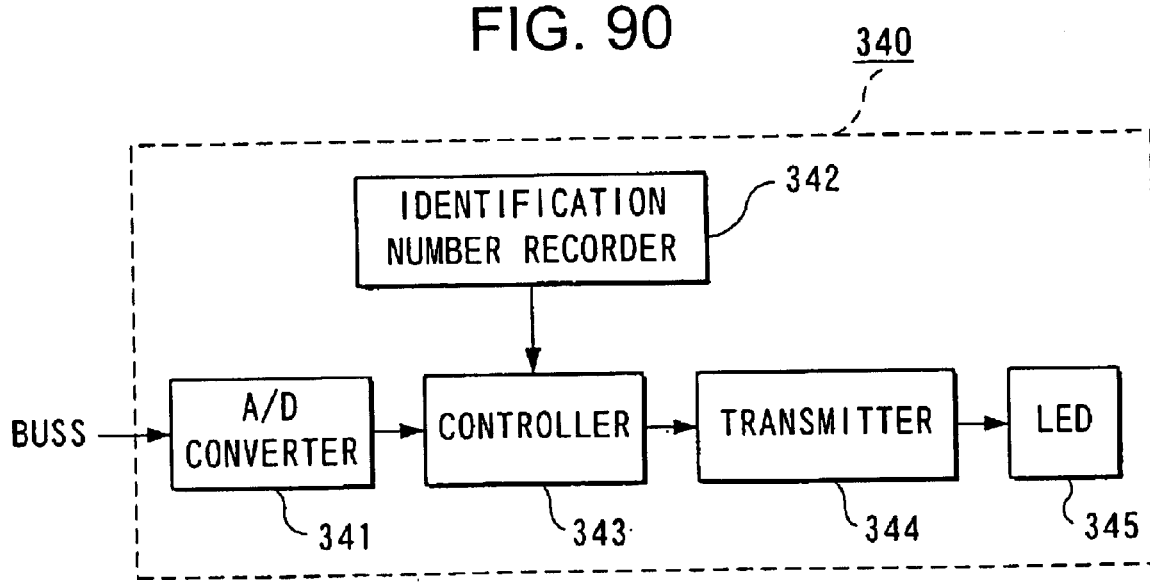
FIG. 90 is a detailed block diagram of the transmission device provided inside an input/output interface incorporated in the device according to the present invention.

An explanation will now be made using FIG. 90 of the structure for preventing contention when a plurality of equipments are sending photo signals. Transmission device 340 shown in the figure is stored in an I/O interface means. Further, in this figure, information from a processor in the portable device or personal computer is placed in a bus.

A/D converter 341 converts various information signals sent from the bus into digital signals by sampling at a fixed time interval.

Identification number recorder 342 records an identification number for identifying the device from which the photo signal was sent. This identification number is carried by the photo signal together with the aforementioned information when the information is sent outside transmission device 340. The identification number stored in identification number recorders 342 inside transmission device 340 are assigned different numbers depending on the settings at the time of export. Accordingly, the setting is designed so that unique numbers are assigned to all devices, including the portable device, the personal computer, and any other devices.

Controller 343 is a circuit for controlling each part within transmission device 340. Transmitter 344 houses a drive circuit for driving LED 345 for sending an photo signal. By driving LED 345, the transmission data created by controller 343 is converted to an photo signal and sent out from the device.

By making communication with an external device possible as described above, it is possible to transfer information from the portable device to an external device. At the same time, it is also possible to carry out a variety of settings or instructions from the external device to the portable device.

An explanation will now be made of the information transfer between the portable device and an external device using specific examples. In the following discussion, the waveform of the blood pulse wave measured in the portable device is displayed on a display 331 (see FIG. 89) which is provided to an external piece of equipment. Further, the type of blood pulse waveform displayed on display 331 may be any one of the Ping mai, Hua mai, or Xuan mai described above. The type of blood pulse waveform measured is transferred from the portable device to the external device after begin compressed at the portable device.

In order to realize the above, the waveforms of blood pulse waves measured in the body are analyzed at the portable device, and a determination of the waveform type (Ping mai, Hua mai, Xuan mai) is made. In order to carry out this determination, one method among others which may be considered is one in which the correlation relation between the blood pulse wave distortion (or circulatory parameters) and the Ping mai, Hua mai, and Xuan mai is checked in advance, the distortion (or circulatory parameters) in the blood pulse wave is calculated from the measured blood pulse waves, and the type of blood pulse wave is determined.

Next, the type of blood pulse wave is encoded with a character mark, for example. The encoded information is transferred to the external device using optical communication, the transfer taking place via the respective I/O interface means provided to both the portable device and the external device. At the external device, a determination is made as to whether the blood pulse wave is Ping mai, Hua mai, or Xuan mai based on the relayed encoded information. The blood pulse waveform corresponding to the type of blood pulse wave determined is read out from the ROM which is stored in the external device, and is shown on display 331.

In addition to showing the blood pulse waveform on display 331 as described above, the name corresponding to the waveform type (i.e., Ping mai, Hua mai, Xuan mai) may also be displayed in letters, or in symbols or icons indicating the waveform type.

As explained above, if the device is designed so as to realize communication between a portable device and an external device using compressed information, it becomes possible to reduce the amount of information to be transferred. Communication using this type of compressed information is entirely equivalent to the case where transferring information from an external device to a portable device.
(Modifications)

1. In practical application, the communication connector 338 may be connected to an external device using a cable, or communication may be carried out in a wireless fashion using radio or the optical signals explained above.

CHAPTER 6 DIAGNOSIS AND CONTROL OF PHYSIOLOGICAL STATE

The various means used by the device explained in this chapter are not limited to just one example. Rather, a variety of modifications are possible. For example, in the case of a design employing a wrist watch type device as a blood pulse wave detector, a necklace or eyeglass type blood pulse wave detector may be substituted. Further, in the case of a device employing circulatory parameters as a measure of physiological state, the circulatory parameters may be obtained based on an electric model, or based on distortion, without imparting an effect on the result.

Section 1: Diagnosis of Physiological State

The device in this section carries out various diagnoses of physiological state obtained from an analysis of blood pulse waves, and reports these results to the diagnostician or test subject.
Part 1 Diagnostic Device Using Cyclic Variations in Physiological State This device accurately detects changes in physiological state while referencing the cyclical changes which have occurred on a daily, monthly, and annual basis in the body in the past, and then diagnosis the condition of a patient.

Embodiment 1

Figure 91:
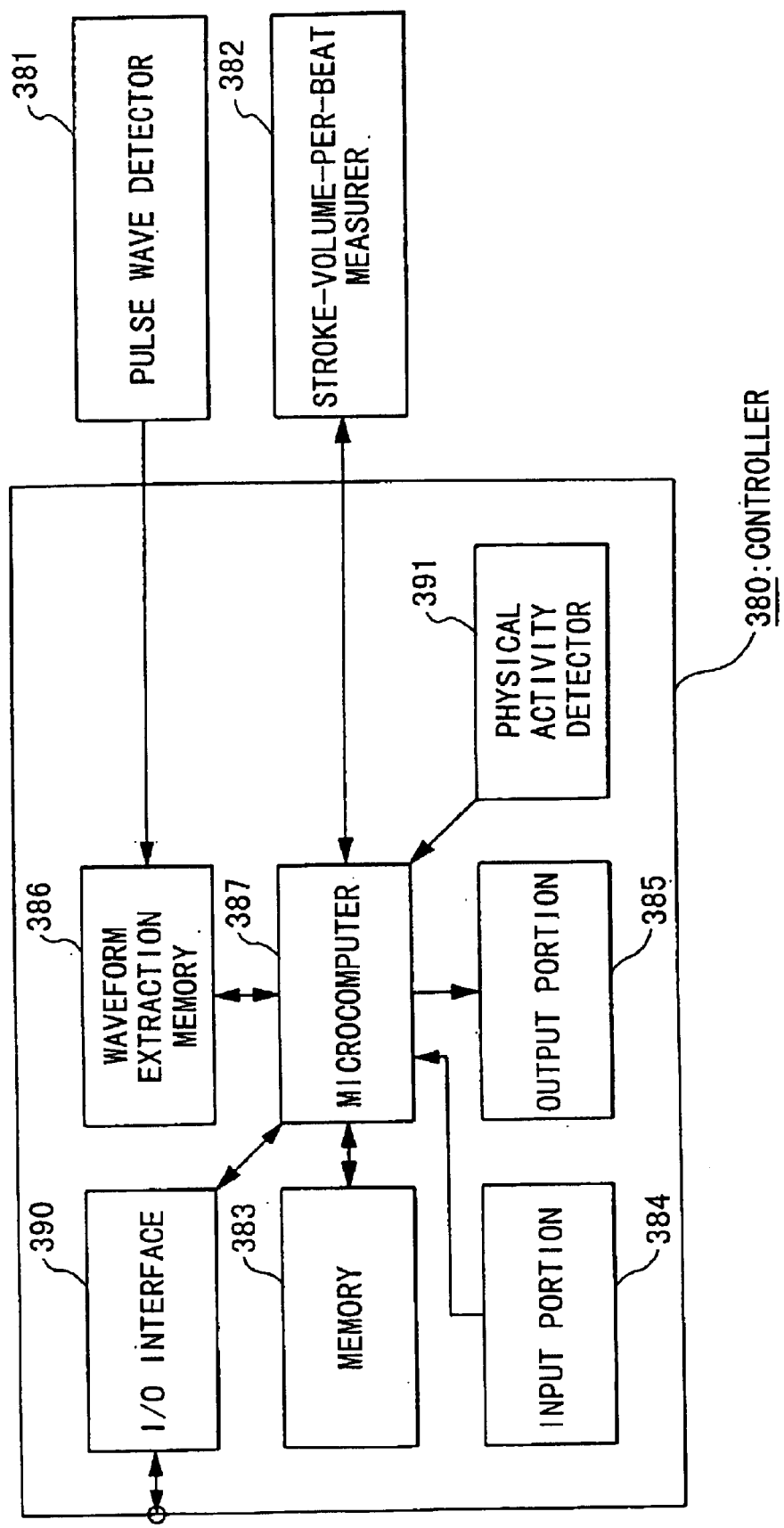
FIG. 91 is a block diagram showing the first structure of the diagnostic device according to the present invention.

As explained above, the circulatory state in the human body varies on a daily basis, with these variation also differing between individuals. The devices according to the present embodiment pick up changes in the state of health of a patient after sufficiently referencing the daily variation in the circulatory state, and provide this information to the diagnostician. In other words, the circulatory parameters are collected from a patient daily, at a plurality of times throughout the day. Each time the parameters are collected, a determination is made as to whether or not these current parameters are within the range of variation exhibited in parameters collected at the same time of the day over a fixed period of time in the past. When the current parameters fall outside the range of variation exhibited in the past, the device then provides notification of this fact.
Structure of the Device FIG. 91 is a block diagram showing the structure of the device according to the present embodiment. In this figure, blood pulse wave detector 381 is a means provided for measuring the radius artery waveform in the patient. Stroke-volume-per-beat measurer 382 measures the stroke volume per beat, and outputs an electric signal indicating this result. The structure, operation and arrangement for measurement of blood pulse wave detector 381 and stroke- volume-per-beat measurer 382 are as described in detail in Chapter 2.

Next, an explanation of each of the parts making up controller 380 will be made. Memory 383 is a non-volatile memory composed of a battery backed-up RAM, or the like, and is employed as temporary memory for the control data when microcomputer 387 controls each of the parts of controller 380. Further, circulatory parameters measured at a plurality of different times are recorded in a specific i;3q recording area of memory 383 for each patient.

Input portion 384 is provided for inputting commands to microcomputer 387, and is composed, for example, of a keyboard.

Output portion 385 is composed of a printer, display device, and the like. These devices are under the control of microcomputer 387, and carry out the recording and display of information such as circulatory parameters and the like obtained from the patient.

Waveform extraction memory 386, which is also under the control of microcomputer 387, takes up a blood pulse wave signal output from blood pulse wave detector 381, and extracts and records the blood pulse wave for a single blood pulse from the signal taken up. Waveform extraction memory 86 is discussed in detail in Chapter 3, Section 1, Part 2.

Microcomputer 387 carries out the control of each of the parts inside controller 380 in accordance with commands input via input portion 384. Microcomputer 387 houses a watch circuit, and carries out the following processing at one of a plurality of preset times:

1. measurement of radius artery blood pulse wave and stroke volume per beat
2. calculation of circulatory parameters
3. determination of whether or not current circulatory parameters are within the range of variation exhibited by parameters measured at the same time of the day over a fixed period of time in the past
4. alarm output when an irregular result is obtained in the determination Physical activity detector 391 is one example of a physical activity detector means for picking up the physical activity of the device's user. The measured value of physical activity is converted to a digital signal and sent to microcomputer 387.
Operation of the Device The operation of the present embodiment will now be explained with reference given to the flow chart shown in FIG. 92.

Figure 92:
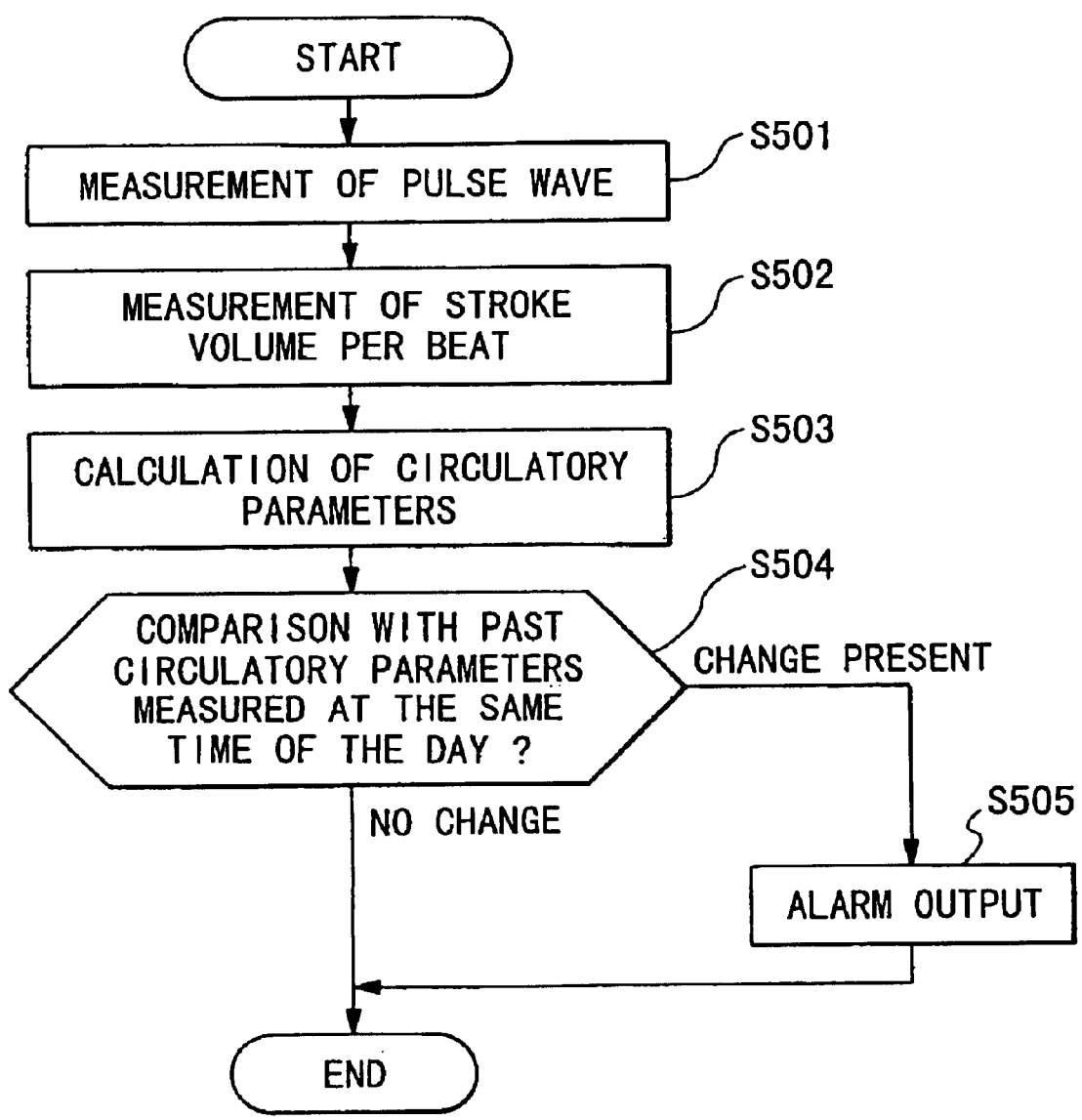
FIG. 92 is a flow chart showing the operation of this same device.

As above, microcomputer 387 in this embodiment is provided with a watch circuit. The processing shown in FIG. 92 is carried out when the current time indicated by the watch circuit coincides with one of a plurality of preset times (for example, 6:00, 8:00, 10:00, 12:00, . . . ).

The process first proceeds to step S501, where microcomputer 387 uses blood pulse wave detector 381 and waveform extraction memory 386 to carry out processing to collect the radius artery waveforms as explained in Chapter 3, Section 1, and then collects peak information of the blood pulse wave.

When measuring the blood pulse waves here, microcomputer 387 reads the outputs of physical activity detector 391 and stores this output in memory 383. A determination is made as to whether or not the output value of physical activity detector 391 indicates that the user is in a state of repose. Since there is a concern that the measurement of the blood pulse waves will be not be accurate if the user is not in a state of repose, microcomputer 387 provides notification to the user using output portion 385. The blood pulse waves are then measured after confirming that the user is in a reposed state suitable for carrying out measurements Next, the process proceeds to step S502, where microcomputer 387 measures the patient's stroke volume per beat by controlling stroke-volume-per-beat measurer 382.

At the next step, step S503, microcomputer 387 carries out calculation of circulatory parameters. Namely, the first initiation point of the waveform of a single beat at which extraction of waveform parameters is to be carried out by microcomputer 387 is obtained, and the waveform value of the blood pulse wave of the one beat from which the peak addresses of this initial point begins is read out from waveform extraction memory 386. The values of each of the elements in the lumped four parameter model are then calculated based on the thus read out waveform of a single beat and the stroke volume per beat measured in step S502. The calculated values are then written in memory 383 as the circulator parameters at the current time.

The stroke volume per beat is measured when calculating the circulatory parameters, in order to employ the method explained in Chapter 4, Section 1, Part 1. However, the methods explained in Chapter 4, Section 1, Parts 2 or 3 may also be employed.

The process next proceeds to step S504, where microcomputer 387 determines whether or not the current circulatory parameters obtained in step S503 are within the limits of variation shown by circulatory parameters obtained at the same time of the day over a fixed period of time in the past which are stored in memory 383. A more detailed explanation of this processing follows.

Namely, if the current time is 8:00 am, then microcomputer 387 references circulatory parameters measured at 8:00 am on the previous day, 2 days prior and 3 days prior, and calculates an average value E (i.e., moving average value) and a standard deviation a for the circulatory parameters. Microcomputer 387 then determines whether or not the current circulatory parameters are within the range of E±3σ.

When even one of the current parameters is found to be outside the range of E±3σ in the above determination, then the process proceeds to step S505, an alarm is outputted via output portion 385 and the processing terminates. Conversely, when all of the current parameters are inside the range of E±3σ in the above determination, then the processing terminates without an alarm being output.

The present embodiment enables rapid detection in the case where a severe change in circulatory parameters occurs which is not within the range of daily variation for a given patient. In other words, when there is a change in the physical condition on the present day from the physical condition over the recent past several days, the device according to the present embodiment can provide notification of this fact to the patient.

The preceding explanation provided that an alarm would sound when the current circulatory parameters were not within a specified range of an average value for parameters obtained over a fixed period of time in the past. However, it is also possible to design the device to provide notification when the physical condition is good, rather than to issue a warning when an anomaly in the parameters is present. Using the preceding example, in the case where the current circulatory parameters are, for example, within the range of E±3σ, the device notifies the user (diagnostician, etc.) that the current physical condition is good and is not exhibiting any change from the recent past.

By providing notification of his current good physical state, the user receives psychological reassurance, thereby improving his quality of life.

Embodiment 2

The preceding embodiment detected anomalies in physiological state based on changes in circulatory parameters. However, it is also possible to detect anomalies based on daily variation in the blood pulse wave spectrum. Accordingly, in this embodiment, the current blood pulse wave spectrum is detected, and compared to spectrums obtained in the past at the same time of the day. Based on these results, then, an anomaly in physical condition is detected.

Structure of the Device

Figure 93:
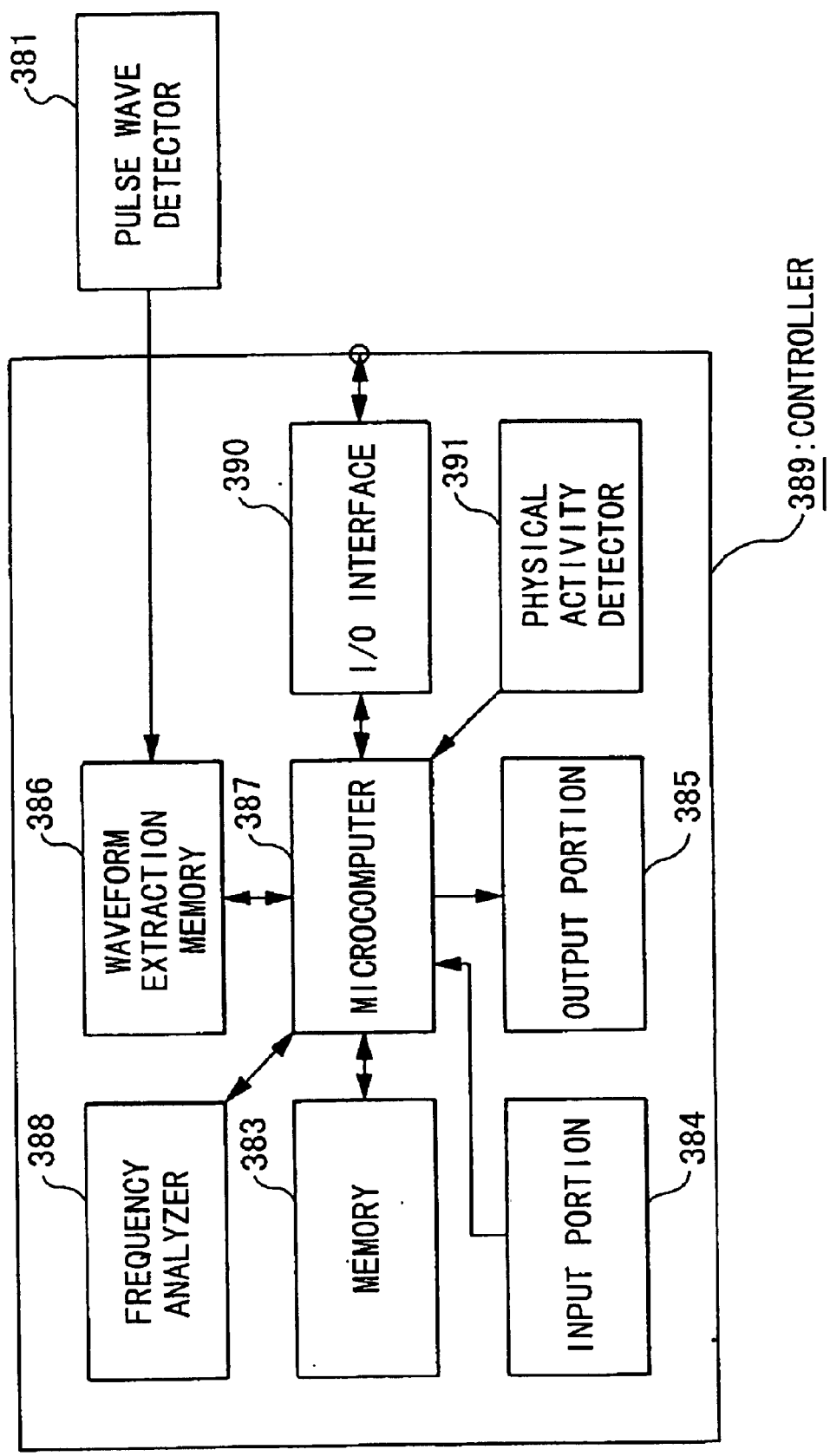
FIG. 93 is a block diagram showing the second structure of the same device.

FIG. 93 is a block diagram showing the structure of the device according to this embodiment. The device in this figure differs from that shown in FIG. 91 in that it is not provided with a stroke-volume-per-beat measurer 382, but is provided with a frequency analyzer 388.

Frequency analyzer 388 receives blood pulse waveform values in beats via microcomputer 387, and then repeatedly carries out high-speed regeneration of the received waveform values. Frequency analysis is carried out at each beat, to calculate the spectrum which forms the blood pulse wave. The detailed structure and operation of frequency analyzer 388 are disclosed in Chapter 3, Section 2, Part 2.

Operation of the Device

The operation of the device will be explained for each of the parts differing from the first embodiment.

As a result of the control of waveform extraction memory 386 and frequency analyzer 388 by microcomputer 387, the amplitudes H1 to H6 and the phases θ1 to θ6 of each spectrum of the blood pulse waves is detected from frequency analyzer 388. Next, the detected values are stored in memory 383, and standard date for detecting an anomaly in physical condition is formed based on this stored data in the same way as in Embodiment 1.

As discussed above, rather than detecting all of amplitudes H1 to H6 and phases θ1 to θ6, it is also possible to detect only one component, phase θ4 for example, which particularly displays a change in physical state. Further, as in Embodiment 1, it is also acceptable to issue a notice when the physical condition is good.

Embodiment 3

In each of the preceding embodiments, the measurement of physiological state was carried out at preset times. In contrast, this embodiment enables measurements to be carried out at times other than those specified. Namely, in order to carry out an accurate diagnosis, it is preferable to carry out measurements of the radius artery blood pulse wave or the like at a specific time each day. However, since this may be difficult, the present embodiment makes it possible to take measurements at times other than those specified. This may be exemplified as follows.

1. The diagnostic device notifies the patient with a chime or the like when it is time to carry out measurements 2. The patient responds to this notification as quickly as possible, by attaching a cuff or the like and inputting a command to the device via input portion 384 to measure the radius artery blood pulse wave 3. The device carries out the processing shown in the flow chart in FIG. 92 in the same manner as in the preceding embodiments. However, in this case, in step S503, the actual time of measurement is written in memory 383 together with the circulatory parameters. In this way, the circulatory parameter collection times stored in memory vary according to the day. Accordingly, determination processing is carried out as follows in step S504.

If, for example, measurements are carried out at 8:20 am, then the parameters collected at around that time (before and after 8:20) are read out from among the parameters stored in memory from the previous day. Next, in the case where these circulatory parameters are plotted on a 2 dimensional coordinate system in which the horizontal axis is time and the vertical axis is the circulatory parameter value, the interpolated curve (for example, secondary curve) between each plot is obtained. The value on this interpolated curve at 8:20 am is then determined. The same processing is then carried out for circulatory parameters obtained 2, 3, . . . , days prior, and each of the circulatory parameters at 8:20 am over a past prespecified period of time is obtained using interpolation calculations. The average value E and standard deviation σ are then determined for the circulatory parameters obtained in this way using interpolation calculations. A determination is then carried out in the same way as in the preceding embodiments.

As a result, even in the case where past parameter values for the current time are not recorded in the recording means, it is possible to obtain the parameter value for the current time using interpolation calculations. Accordingly, processing can still be carried out even in the case where it is difficult to carry out measurements of physiological state at regular times.

Additionally, as in the first embodiment, it is also possible to provide notification when the physical condition is good.

Embodiment 4

In this embodiment, a diagnosis is carried out based on the mode of change in the circulatory parameters. Namely, a judgment is made not on the circulatory parameters themselves, but on whether the mode of change in the circulatory parameters is in line with the mode of change exhibited by parameters measured at the same time of the day over a prespecified period of time in the past.

The processing in this embodiment is carried out in accordance with the flow chart shown in FIG. 92. However, in this embodiment, during the late night hours when measurement of the radius artery blood pulse wave or the like is not carried out, microcomputer 387 reads out the circulatory parameters for each time that were recorded during that day from memory 383. Microcomputer 387 determines which of the following categories each of the circulatory parameters falls under, applies the results of this determination to the circulatory parameter, and then rewrites the parameters with this additional information in memory 383.

B: minimum, or bottom, value
U: rising, or upward trending, value
T: maximum, or top, value
D: falling, or downward trending, value In the determination made in step S504 in FIG. 92, a determination is made as to whether the change from the prior to the current circulatory parameters is rising or falling. A decision is then made as to whether or not the results of the determination are in line with changes in circulatory parameters measured at the same time over a prespecified period of time in the past.

In other words, where focusing on the trend in circulatory parameter change at 8:00 am, for example, assume that all of the parameters collected over the past 10 days demonstrate an upward trend U at 8:00 am. In this case, when the circulatory parameters obtained at 8:00 am on the current day are rising as compared to circulatory parameters obtained in the immediately preceding measurement at 6:00 am, then this change is viewed to be normal and in line with the mode of change over the past 10 days. Conversely, when the circulatory parameters obtained at 8:00 am on the current day are falling as compared to circulatory parameters obtained immediately before at 6:00 am, then this change is viewed to be abnormal and opposite the mode of change over the past 10 days. Accordingly, in this case, the processing proceeds to step S505 in FIG. 92 and an alarm is output.

In this embodiment then, it is possible to catch unnatural changes in the physiological state.

In the preceding explanation, notification was carried out in the case where the mode of change in the circulatory parameters at the current time was opposite the mode of change exhibited by the parameters in the past. However, as in the first embodiment, it is also possible to provide notification to the user that his physical condition is good in the case where the mode of change in the current parameters is identical to the mode of change demonstrated by the parameters in the past.

Embodiment 5

In this embodiment, diagnosis is carried out based on the time of generation of maximum and minimum values in the parameters. In other words, in this embodiment it is possible to catch unnatural movements in the current parameters based on the times at which maximum and minimum values were generated in the parameters in the past.

In the fourth embodiment, the mode of change, i.e., rising, falling, etc., was determined for each of the parameters obtained on the current day. However, in this embodiment, the times at which maximum and minimum values are generated in the parameter obtained on the current day is determined and written in memory 383. For example, ranges are determined for the times at which maximums and minimums are generated over the past 5 days, and the interval therebetween is obtained.

The following remarks may be made about each of the ranges obtained in this way.

1. The interval between the range of times at which a minimum value is generated and the range of times at which the adjacent maximum value is generated is the interval during which the parameter should be rising. If the parameter is rising in this interval, then the condition is normal, while if the parameter is falling in this interval, the condition is abnormal.

2. The interval between the range of times at which a maximum value is generated and the range of times at which the adjacent minimum value is generated is the interval during which the parameter should be falling. If the parameter is falling in this interval, then the condition is normal, while if the parameter is rising in this interval, the condition is abnormal.

In this embodiment, when the current time is associated with one the intervals as described above, then the determinations noted in 1 and 2 above are carried out on the parameters at that time.

Parameter maximum/minimum collection times may be employed for the maximum/minimum value generation times. In addition, a daily variation curve may be obtained for the parameters using rhythm analysis, and maximum/minimum value generation times on this daily variation curve may be employed.

Thus, unnatural changes in the physiological state can be caught by means of the present embodiment.

In the preceding explanation, when the current time is within the interval for minimum value generation or the interval for maximum value generation, notification is carried out in the case where the mode of change in the circulatory parameters at the current point in time is opposite the mode of change exhibited by the circulatory parameters in the past. However, a design is also possible in which notification is given to the user that his condition is good when the mode of change in the circulatory parameters at the current point in time is the same as that observed in the past.

Embodiment 6

In this embodiment, the device is employed in the diagnosis of an internal step out.

When a test subject occupies a time isolation chamber in which all time references are absent, the subject's regulating functions run freely, operating on a 25 hour cycle. However, after a long period in an isolation chamber, sleep-awake rhythms and rectal temperature rhythms may dissociate, with the former operating on a 30 hour cycle and the latter operating on a 25 hour cycle. This phenomenon is referred to as internal step out.

In recent times, however, there are frequent situations of time isolation in daily life which invite the occurrence of internal step out. Working the late shift or traveling far distances between different time zones (i.e., jet lag) are examples of an irregular lifestyle.

When internal step out occurs, it may give rise to ailments such as autonomic ataxia or the like. Accordingly, early detection is necessary when internal step out has occurred.

Rectal temperature rhythms are ordinary synchronized with the circulatory parameters. Using embodiment 1 described above, it is possible to detect the rhythm of daily variation in the circulatory parameters which reflect the rectal temperature rhythms. Accordingly, by detecting a disturbance in the rhythm of daily variation, it is possible to see symptoms of the internal step out.

In this case, this approach offers an advantage in that it enables diagnosis without employing a measurement of deep body temperature.

In each of the embodiments described above, diagnosis can be carried out after taking into consideration the cyclical changes which occur naturally in physiological state. Thus, accurate detection of unnatural changes can be effected. Moreover, since it is also possible to know how the circulatory parameters change before and after exercise or bathing, it is also possible to know the effect of mental training depending on the blood pulse wave type.

(Modifications)

1. A sound source such as a metronome may be supplied to the device, and the patients breathing regulated using a 0.25 Hz metronome sounding prior to carrying out measurements.

2. The parameters obtained daily up until the current point in time are recorded in memory 383. Using an X-Y plotter as an output device, controller 380 (or 389) controls X-Y plotter to plot a curve for the daily variation in the parameters. Further, in response to a command from the user, daily variation curves for several days worth of parameters may be superimposed and plotted. As a result, it is possible to visually pick up changes in the patient's condition.

3. In response to a command by the user, the correlation between daily variation curves of parameters from several days is obtained and output. As a result, it is possible to catch any changes in biorhythms.

4. A design is also possible in which once parameter collection is finished each day, and the daily variation curve for that day's parameters is confirmed, the correlation between that daily variation curve and the previous day's daily variation curve is obtained. This is carried out on a daily basis. By detecting a break in the correlation, it is possible to detect a break in the biorhythms as above.

5. In Embodiment 1, circulatory parameters obtained from measurements may be corrected after taking into consideration the variation which occurs throughout the year. For example, in the case of compliance C, correction to reduce the measured result by a fixed ratio may be carried out in the summer, while correction to increase the measured result by a fixed ratio may be carried out in the winter. As a result, the accuracy of the diagnosis is improved.

6. In embodiments 1 and 2 above, an alarm sounded when the measured value of the current circulatory parameters deviated by more than a fixed amount from the average for past measured values. However, it is also possible to provide an analog (or digital) display of the parameter value.

Figure 94:
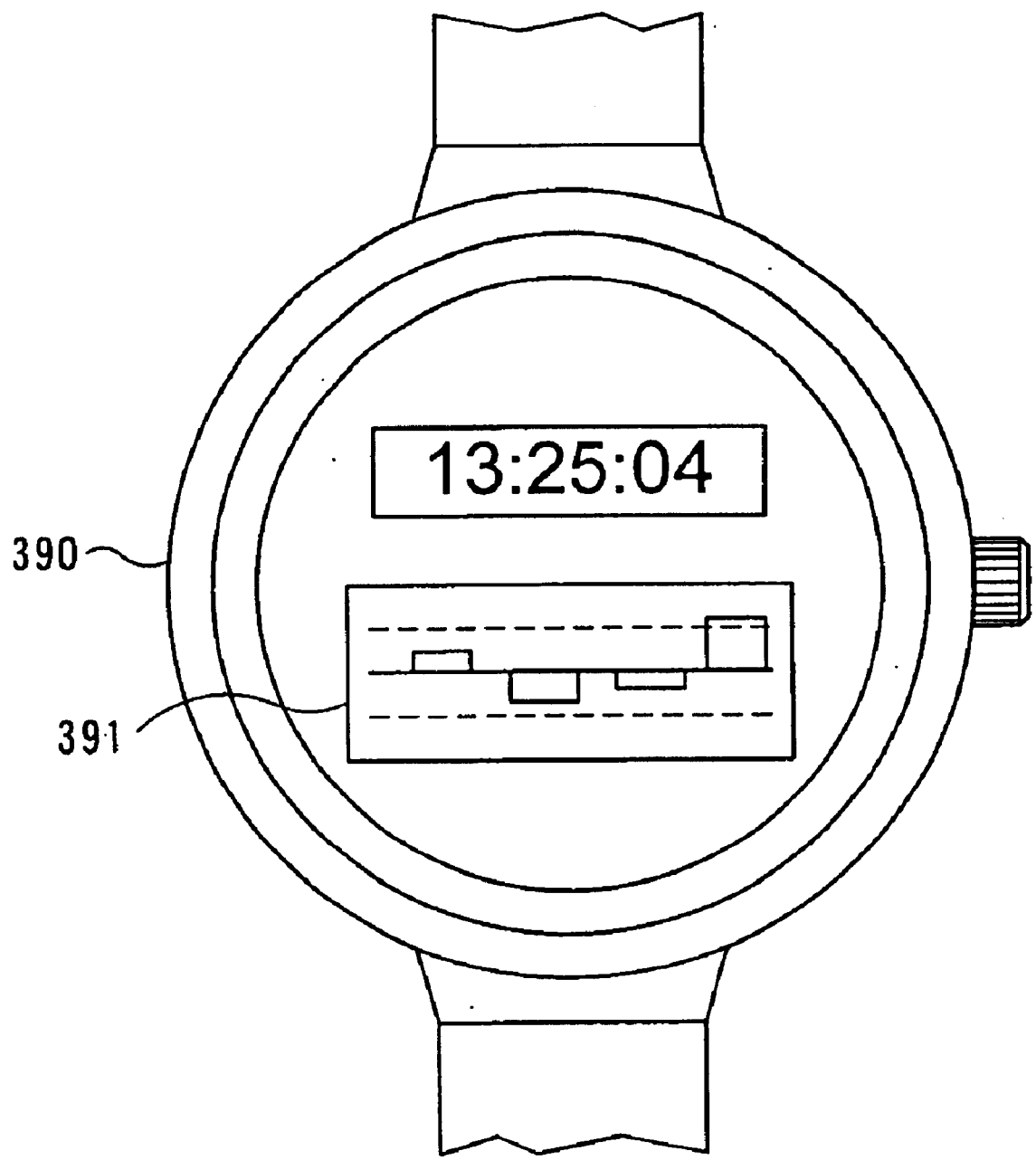
FIG. 94 is a diagram showing an example of the display of circulatory parameters in the same device.

In FIG. 94, controller 389 shown in FIG. 93 is incorporated in an LCD watch 390, a blood pulse wave detector 381 (not shown) is attached to the rear of the watch band, and a display 391 is attached to a face. The difference between the current measured values and the average for past measured values of the circulatory parameters Rc, Rp, L and C is displayed by means of a bar graph on display 391. The broken line in FIG. 94 indicates the level at which attention becomes necessary. Finally, the plus/minus display as shown in the figure, or an absolute value display may also be employed.

By means of this structure, the circulatory parameters can be measured at fixed intervals (for example, 15 minutes), and the measured result displayed. Thus, it is possible for the user to always be able to confirm his physiological condition. Previously, it was only possible to know one's own physical condition by measuring body temperature. By attaching this device to the arm, however, it is possible to know one's physical condition at any time more accurately than provided using body temperature. Accordingly, this should be extremely advantageous to buy business people.

Figure 95:
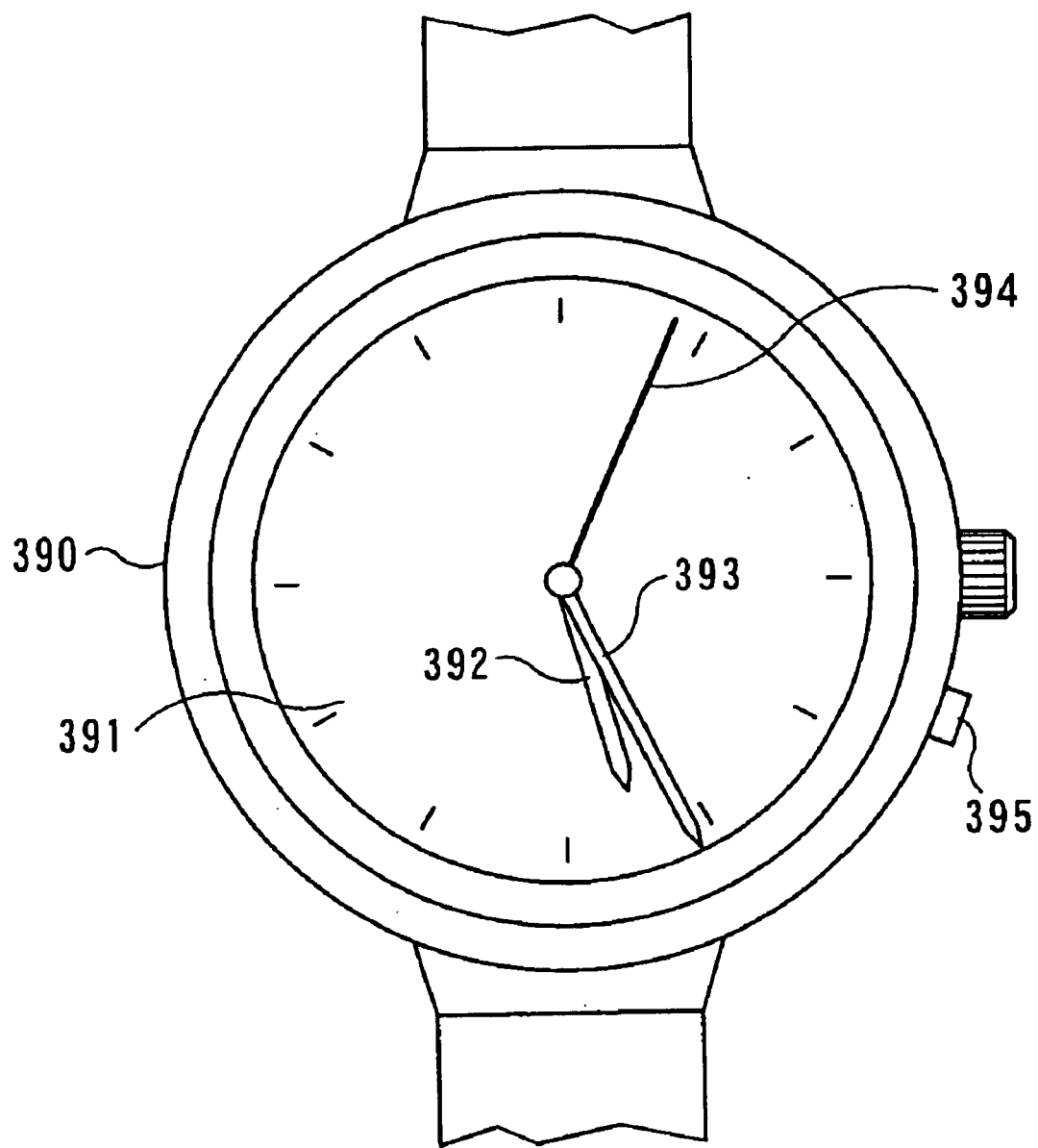
FIG. 95 is a diagram showing another example of the display of circulatory parameters in the same device, with this embodiment employing a watch hand for the display.

As shown in FIG. 95, a hand display may be used in place of the bar graph display. Namely, the hour hand 392, minute hand 393 and second hand 394 shown in this figure may be employed, with the current measured value for the circulatory parameters assigned to hour hand 393 and the average of past measured values assigned to minute hand 393. Display can then be carried out by moving hour hand 392 and minute hand 393 in response to the current and past values. In the case shown in FIG. 95, when the hour hand is at 12:00, the value is set to 0. As the value of the circulatory parameters becomes larger, the hour hand is driven in the clockwise direction. The hour hand 392 is closer to the 6 o'clock position than the minute hand 393, indicating that the current value of the circulatory parameters is slightly larger than the average value for circulatory parameters collected in the past. Incidentally, the number 395 in the figure is a mode setting button for changing between the wrist watch mode and the mode for displaying the current measured value and average value for circulatory parameters collected in the past.

Additionally, other hands may be provided in addition to the hour, minute, and second hands.

Figure 96:
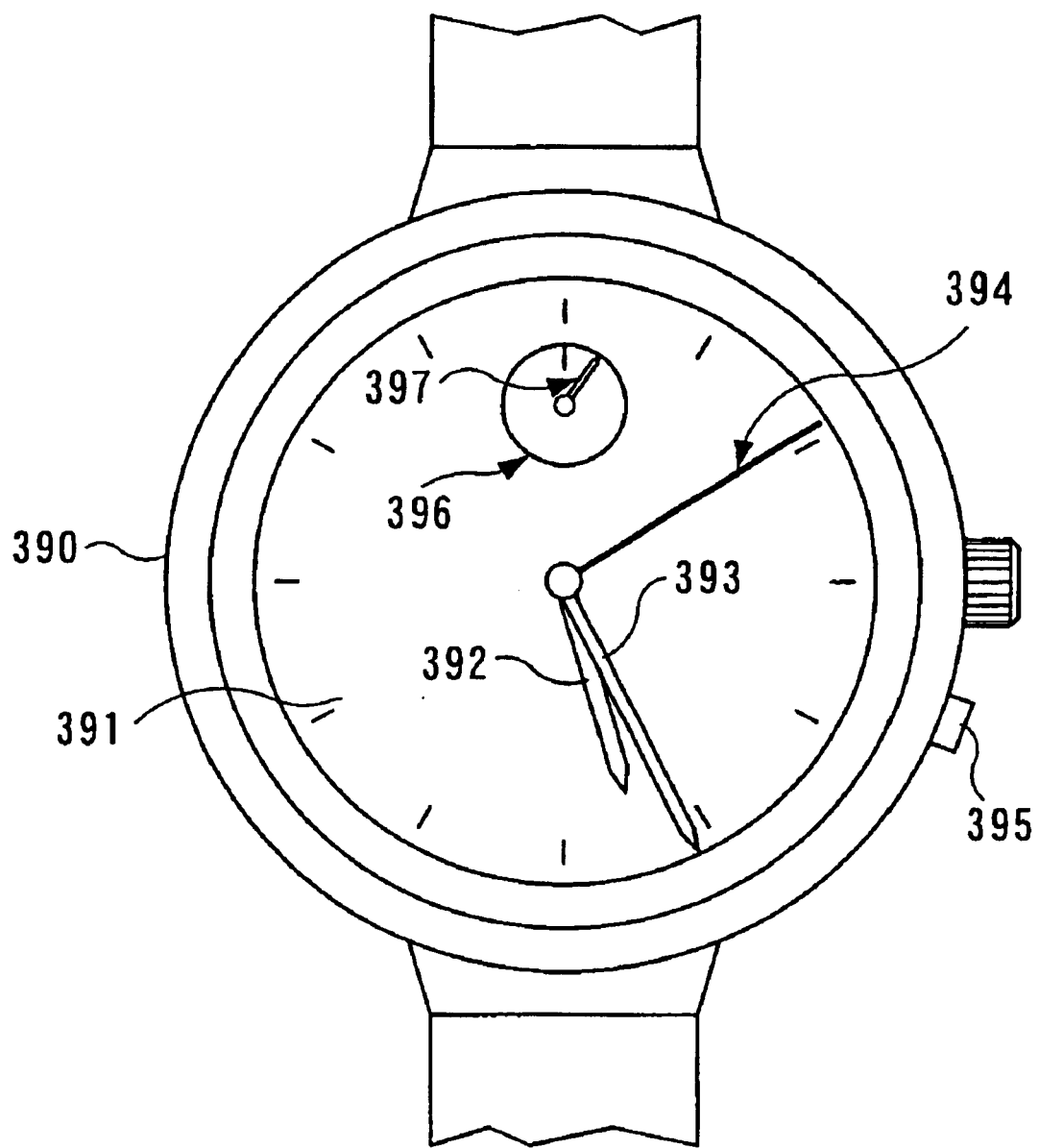
FIG. 96 is a diagram showing another example of the display of circulatory parameters in the same device, with a special display provided in this embodiment to display the circulatory parameters.

An embodiment such as shown in FIG. 96, in which only one hand is employed is also acceptable. In this figure, parts which are the same as those shown in FIG. 95 are assigned the same numeric symbol and an explanation thereof is omitted. This embodiment is designed to display the difference in the current value based on the average value of circulatory parameters collected in the past. For this purpose, a display surface 396 which is smaller than display 391 is provide to display 391, while a small hand 397 is attached to display 396. The 12 o'clock position on this display corresponds to the average value of circulatory parameters collected over a fixed period of time in the past, while small hand 397 indicates the current value of the circulatory parameters. This embodiment is designed to display the current value of the circulatory parameters based on the average value in the past the past using the position of small hand 397. In other words, if the current value exceeds the average value obtained in the past, then the small hand 397 turns in the clockwise direction. If the current value falls below the average value obtained in the past, then small hand 397 rotates in the counter-clockwise direction.

The rotational direction of small hand 397 may be reversed from that described above. In the case of circulatory parameters and the like which are composed of a plurality of indicators, a plurality of small hands may be provided in a number corresponding to the number of indicators to be displayed. Further, it is also acceptable to provide displays for each indicator, with one small hand provided to each display. When using the device as an ordinary wrist watch, display 396 can be used to display the date and day as in the case of a commercially available wrist watch. In this case, mode setting button 395 can be used to switch between an ordinary wrist watch mode and a mode for displaying the circulatory parameters.

7. In place of the display of the above-described circulatory parameters, it is also acceptable to display the difference between the current phase and amplitude of the blood pulse wave and the average values therefor. The difference between the sum of parameter components Rc, Rp, and L and the past average value for the sum of these components may also be displayed. In this case, a smaller value for the sum of these parameters Rc, Rp, and L indicates a good physical condition, while a large value for parameter C indicates a good condition. Accordingly, it is desirable to display the sum of the other parameters excluding C.

As a result, it is possible to accurately know the state of the body on the current day.

8. In each of the above-described embodiments, the average of data collected over the past three days or a week may be used as the standard data for making a determination of the physical condition. Additionally, it is also acceptable to use data collected on a day when the physical condition is good for the standard data.

In this case, however, it is necessary to take into consideration the annual variation in the parameters, and correct the data depending on the season. Further, since ambient temperature is believed to be one major factor behind this annual variation, it is also acceptable to correct the standard data based on the air temperature.

9. The preceding embodiments were explained using a lumped four parameter model, however, it is also acceptable to employ an electric model. Also, physiological conditions other than circulatory parameters may be employed, such as the tidal wave indicator explained in Chapter 4, Section 2.

10. A design also acceptable wherein, after the user has assumed a state of repose prior to measuring the blood pulse waves, he may use input portion 384 to notify this fact to the device. In this case it is also convenient to provide the user with a means of determining whether his position is suitable for making blood pulse wave measurements. This can be accomplished by informing the user of the suitability of his position as determined by the output value of physical activity detector 391.

It is also acceptable to design microcomputer 387 to constantly detect for a reposed state using physical activity detector 391, and then carry out detection of the blood pulse way only when the user is in a state of repose for a specified interval of time.

Moreover, rather than waiting for the user to enter a state of repose, measurement of blood pulse wave and physical activity can be carried out over a specific period of time, with the measured values then stored together in memory 383. Based on the stored results of the physical activity measurements, only the blood pulse wave measurement taken when the user was in a state of repose for a specified period of time may be selected, and user to obtain the blood pulse wave information.

Part 2 Diagnostic Device Using Tidal Wave in Blood Pulse Wave

Embodiment 1

The device according to this embodiment collects indicators of physiological state every day at a specific time, and displays the current measured value and the moving average of the measurements over the past several days on a portable device such as a wrist watch. As a result, the user is able to know the state of his health from the displayed results. Further, by displaying the transition over time in the measurements, the user may be made aware of recent changes in his physical health. The present embodiment employs the indicators LF, HF, LF/HF, RR50 and blood pulse rate, which were explained in Chapter 4, Section 2, as indicators of physiological state.

Structure of the Device

Figure 97:
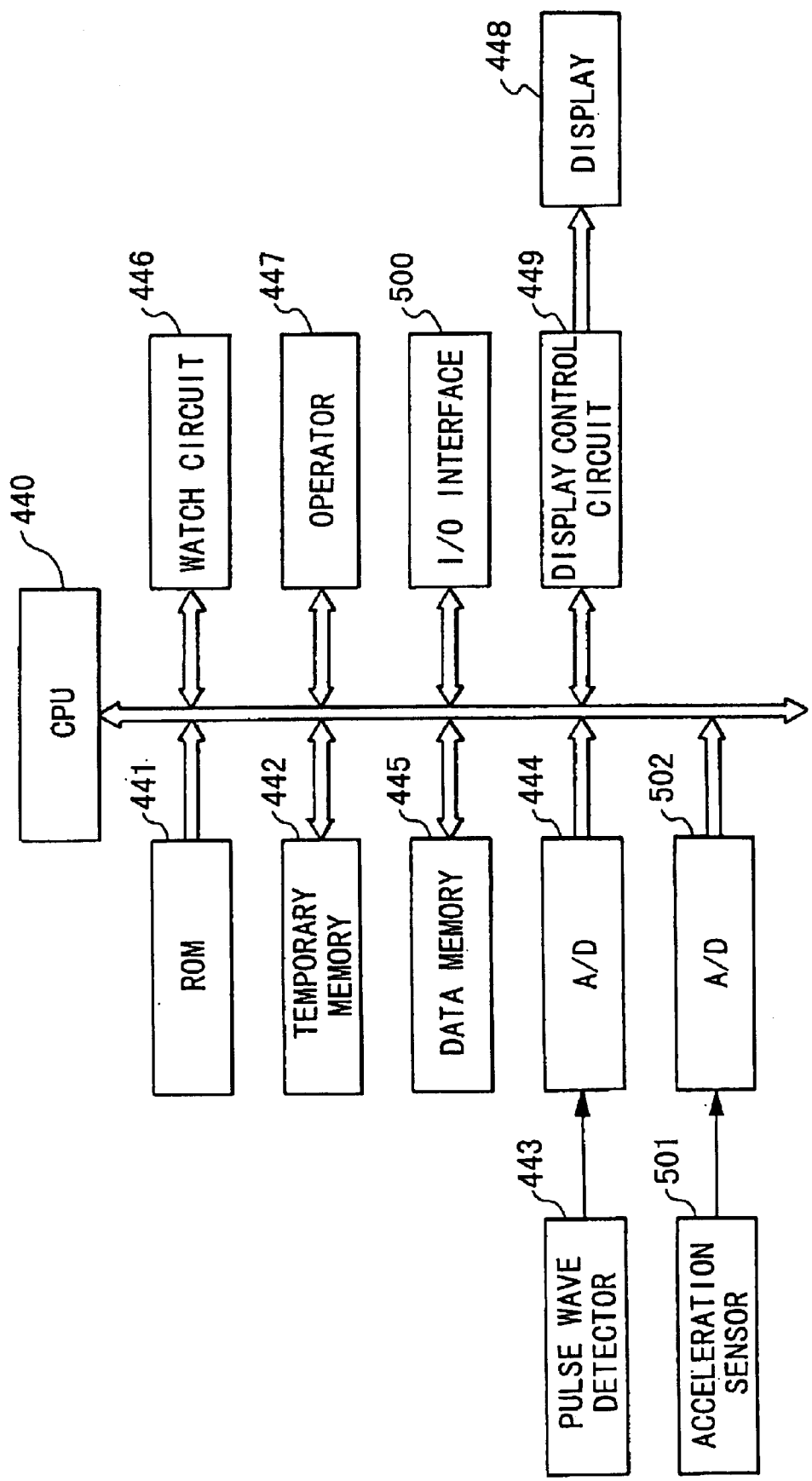
FIG. 97 is a block diagram showing the structure of a diagnostic device according to the present invention which utilizes the tidal wave in the blood pulse wave.

FIG. 97 is a block diagram showing the structure of the device according to the present embodiment. In this embodiment, the user wears wrist watch 450 shown in FIG. 98, which incorporates the device of this embodiment. An embodiment in which a pressure-type blood pulse wave detector was incorporated in a wrist watch was explained in Chapter 2, Section 1, Part 4.

In FIG. 97, CPU 440 is the central portion for controlling each circuit inside the device. The function of CPU will be explained below under "Operation of the Device". Control programs and control data for CPU 440 are stored in ROM 441. Temporary memory 442 is one type of RAM which is used as an operational area when CPU 440 is carrying out calculations. Blood pulse wave detector 443 constantly measures the blood pulse wave at the user's radius artery, and outputs the measured result as an analog signal. A/D converter 444 quantifies the analog signal, converts it to a digital signal and outputs it. Data memory 445, which is a non-volatile memory composed of battery backed-up RAM or the like, stores LF, HF, LF/HF, RR50 and blood pulse rate values from the past several days and blood pulse wave data taken up by CPU 440 from A/D converter 444. Watch circuit 446 generates the time of day which is displayed on wrist watch 450, and is provided with a mechanism for interrupting CPU 440. Namely, in response to an indication from CPU 440, time circuit 446 sends an interrupt signal to CPU 440 when a specific time of the day is detected or after the elapse of a specified period of time. Operator 447 is formed of a variety of buttons which are provided to wrist watch 450. Operator 447 detects the depression of these buttons and outputs the type of button depressed. Display 448 is a display apparatus suitable for the various types of display provided on a wrist watch. Display control circuit 449 receives display information created by CPU 440, and assembles display data from the display information for relay to display 448.

I/O interface 500 carries out communication with external devices, and is equivalent to the I/O interface explained in Chapter 5, Section 3. By employing I/O interface 500, information about physiological state (for example, LF, HF, LF/HF, RR50, and blood pulse rate data from a prespecified number of days in the past that is stored in data memory 445) can be transferred to an external device.

Acceleration sensor 501 is one example of a physical activity detection means for picking up the physical activity of the device's user. A/D converter 502, which has the same structure as A/D converter 444, converts the output from acceleration sensor 501 into a digital signal and relays the digital signal to a bus.

The device of the present embodiment has two modes: an Ordinary Use Mode, during which the device is used as a regular wrist watch, and an Analysis Mode, during which the device displays the results of analysis of the blood pulse wave.

Figure 98:
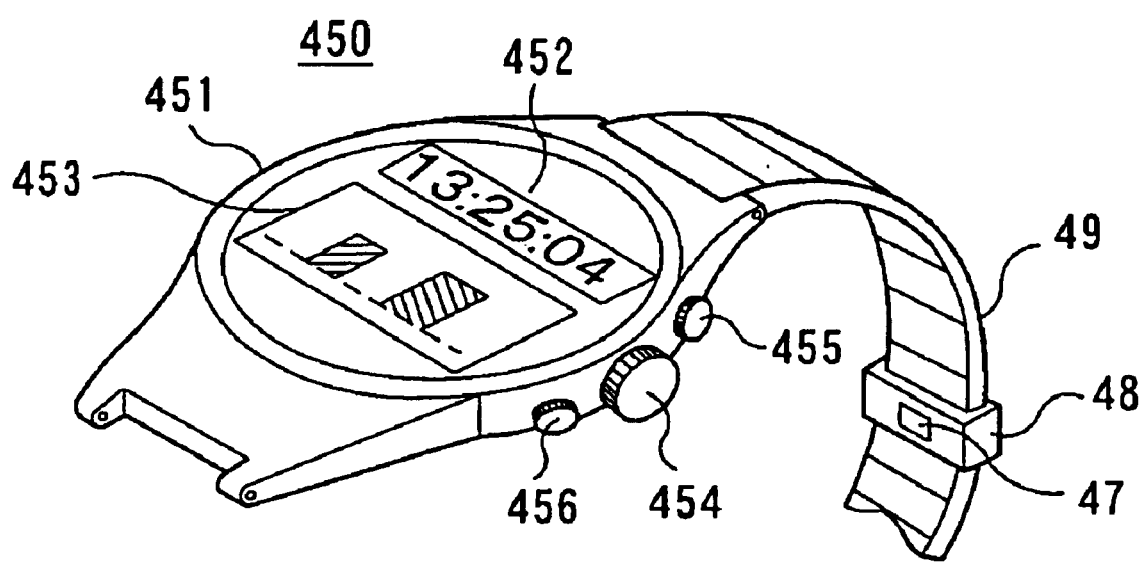
FIG. 98 is a perspective view of a wrist watch 450 incorporating the same device.

In FIG. 98, the number 451 indicates the main body of a wrist watch which is provided with a time display 452 and a figure display 453 on the upper surface thereof. Time change button 24, mode switching button 25, and display switching button 26 are provide to the right lateral surface of the watch main body 451. The current time, which is sent from CPU 440, is constantly displayed on time display 452. The day and date are displayed on figure display 453 when the device is in the Ordinary Use Mode, while the results of the analysis of the blood pulse wave is displayed in graph form when the device is in the Analysis Mode. Time change button 454 is a watch stem employed to adjust the time or set an alarm. Mode switching button 455 is for switching between the Ordinary Use Mode and the Analysis Mode. Each time this button is depressed, switching between the two modes occurs. The Ordinary Use Mode is initialized when a power source is inserted. Display switching button 456 is used to switch the details of the display on figure display 453 when in the Analysis Mode.

Further, any one of the blood pulse wave analysis results below can be displayed as a graph on figure display 453.

1. current value and moving average of LF/HF
2. current value and moving average of LF and HF
3. current value and moving average of RR50
4. current value and moving average of blood pulse rate
5. transition in LF/HF over fixed period of time in the past
6. transition in LF and HF over fixed period of time in the past
7. transition in RR50 over fixed interval of time in the past
8. transition in blood pulse rate over fixed interval of time in the past Each time display switching button 456 is depressed, the results of the analysis in the preceding 1 to 8 are sequentially displayed on figure display 453. Further, in the case where a graph of the transition in blood pulse rate over a fixed period of time in the past (number 8 above) is displayed, a single depression of display switching button 456 will again bring up the display of the current value and moving average of LF/HF (number 1 above).

In the present embodiment, the value of the moving average is calculated based on measurements made over the past one week. Thus, the "fixed period of time" as stated in 4 to 8 above is assumed to be one week as well.

Operation of the Device (1) Pre-processing

In order to carry out blood pulse wave measurements at fixed intervals of time (for example, 2 hours), CPU 440 directs watch circuit 446 to generate an interrupt signal every two hours starting from 12:00 am, for example, upon introduction of the power source, etc.

(2) Measurement and Analysis of Blood pulse Waves

When watch circuit 446 generates an interrupt signal to CPU 440 at 2:00 pm, CPU 440 reads out the output from acceleration sensor 501 via A/D converter 502, and records this output in temporary memory 442. Next, a determination is made as to whether or not the output value of acceleration sensor 501 indicates the user is in a state of repose. Since the blood pulse wave measurements may not be accurate if the user is not in a suitable state of repose, CPU 440 notifies the user by means of a display message on display 448. Next, once confirmation is made that the user is in a suitable state of repose, CPU 440 carries out blood pulse wave uptake processing for a fixed period of time only (30 sec, for example). In order to do this, CPU 440 indicates a 30 second monitoring time to watch circuit 446.

Blood pulse wave detector 443 constantly measures the blood pulse wave at the user's radius artery. The measured results are converted to a digital signal by A/D converter 444, and output. CPU 440 takes up this digital signal and stores the signal in data memory 445 along with the current time (2:00 pm) read out from watch circuit 446. CPU 440 repeats the uptake processing. After 30 seconds, an interrupt signal is sent by watch circuit 446 to CPU 440, and the processing halts. Blood pulse waveforms obtained over a 30 second time interval in the above processing are then stored in data memory 445.

Next, CPU 440 analyzes the waveforms of the blood pulse waves stored in data memory 445, and calculates LF, HF LF/HF and RR50. The method for calculating these indicators is explained in detail in Chapter 4, Section 2. Further, CPU 440 converts the number of peaks in the blood pulse wave observed during one measured time interval to a one minute time interval and sets this as the blood pulse rate. Subsequently, these values are stored in data memory 445 together with the time at which the blood pulse waves were measured (2:00 pm).

(3) Display of Measured Results

When the user depresses mode switching button 455, the mode switches from the Ordinary Use Mode to the Analysis Mode.

When a notification that mode switching button 455 has been depressed is received from operator 447, CPU 440 sends a command to display control circuit 449 to clear figure display 453. As a result, the display of the day and date on figure display 453 is cleared.

1. Collection of Current Values of Physiological State

Next, CPU 440 carries out the measurement of blood pulse wave and analysis of physiological state in the same order as the processing described in the above "(2) Measurement and Analysis of Blood pulse Wave". Namely, blood pulse waveforms collected over a 30 second interval only are taken up in data memory 445. These blood pulse waveforms are then analyzed, and the current values of LF, HF, LF/HF, RR50, and blood pulse rate are calculated. These values are then stored in temporary memory 442.

2. Interpolation Processing

CPU 440 obtains the current time from watch circuit 446, and then obtains the times for the preceding and proceeding blood pulse wave measurements relative to the current time. Because the device has been set as described above to take blood pulse wave measurements at 2 hour intervals starting from 12:00 am, then, for example, if the current time is 1:30 pm, the preceding and proceeding blood pulse wave measurement times are 12:00 pm and 2:00 pm, respectively.

Next, LF, HF, LF/HF, RR50 and blood pulse rate values measured at 12:00 pm and 2:00 pm are read out from data memory 445 for each day over a fixed period of time in the past. The 12:00 and 2:00 values for each of LF, HF, LF/HF, RR50 and blood pulse rate are interpolated from the data to estimate the current values. CPU 440 then obtains an average value for each of LF, HF, LF/HF, RR50 and blood pulse rate for the week's worth of data.

When interpolating the data, a wider range of information, i.e., not merely information from the preceding and proceeding measurement times, is necessary. However, the necessary information can be read out from data memory 445, with interpolation then carried out.

3. Graph Display

Figure 99:
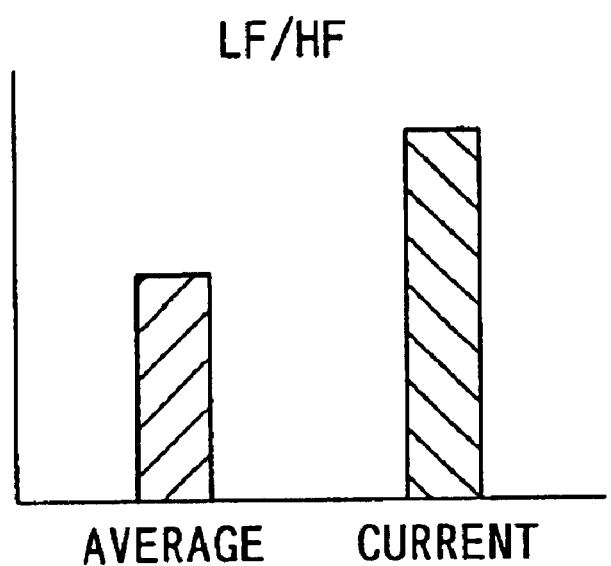
FIG. 99 is a bar graph of LF/HF displayed on figure display 23 in the same device.

A bar graph such as shown in FIG. 99 is created from the moving average value for LF/HF and the current value of LF/HF (from above, 1:30 pm). When the art display information in the graph is sent to display control circuit 449, the average value of LF/HF over the past week and the current value of LF/HF are displayed on figure display 453 of display 448 (screen 1).

When the user subsequently depresses display switching button 456, CPU 440 creates display information for the graph as discussed below, and sequentially displays the graph on figure display 453.

(a) First Button Press (screen 2)

Figure 100:
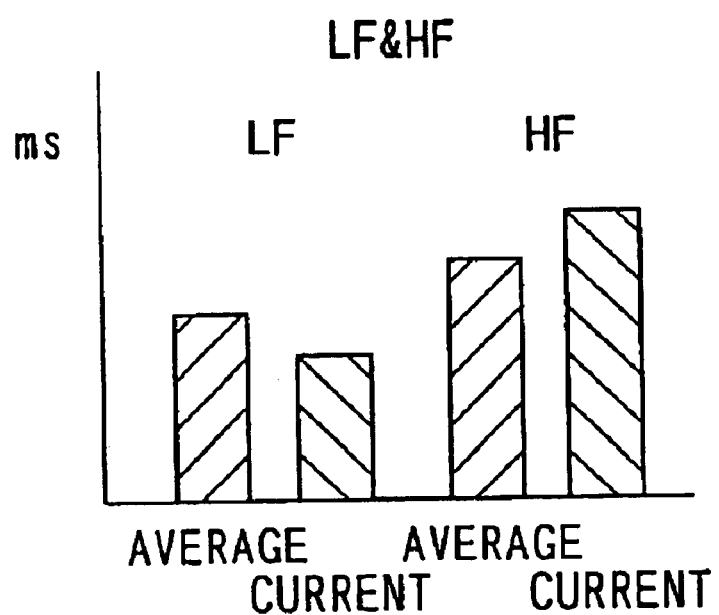
FIG. 100 is a bar graph of LF and HF displayed on figure display 23 in the same device.

As shown in FIG. 100, the average values of LF and HF over the past week and the current values of LF and HF are displayed as a bar graph.

(b) Second Button Press (screen 3)

Figure 101:
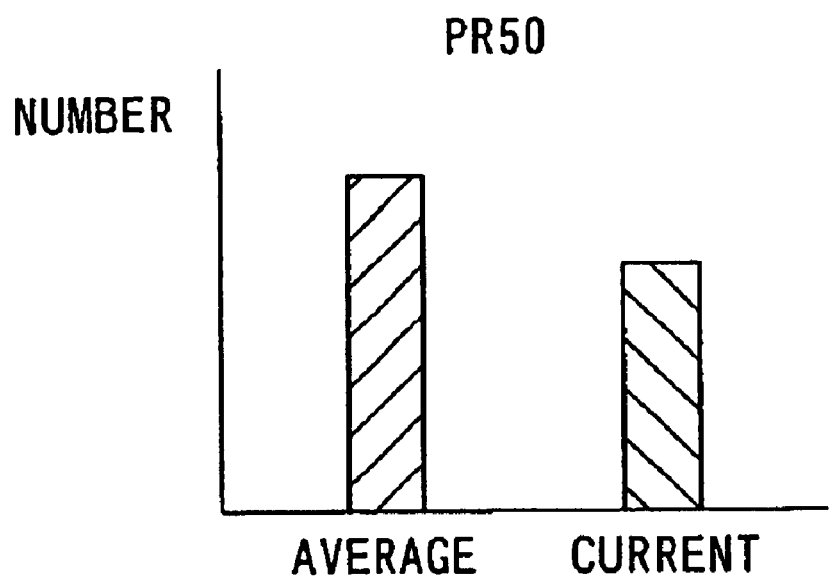
FIG. 101 is a bar graph of RR50 displayed on figure display 23 in the same device.

As shown in FIG. 101, the average value of RR50 over the past week and the current value of RR50 are displayed as a bar graph.

(c) Third Button Press (screen 4)

Figure 102:
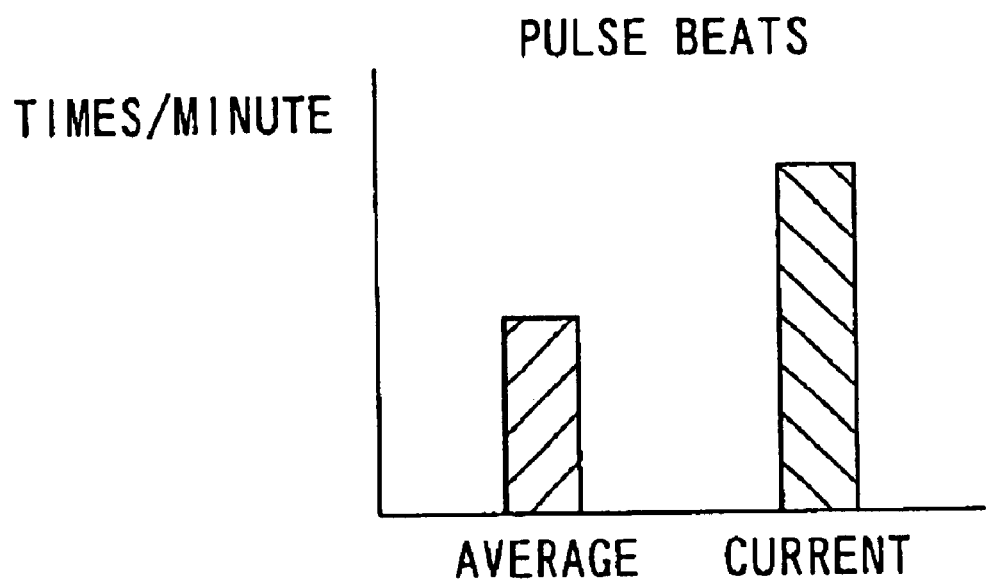
FIG. 102 is a bar graph of blood pulse rate displayed on figure display 23 in the same device.

As shown in FIG. 102, the average value of blood pulse rate over the past week and the current value of blood pulse rate are displayed as a bar graph.

(d) Fourth Button Press (screen 5)

Figure 103:
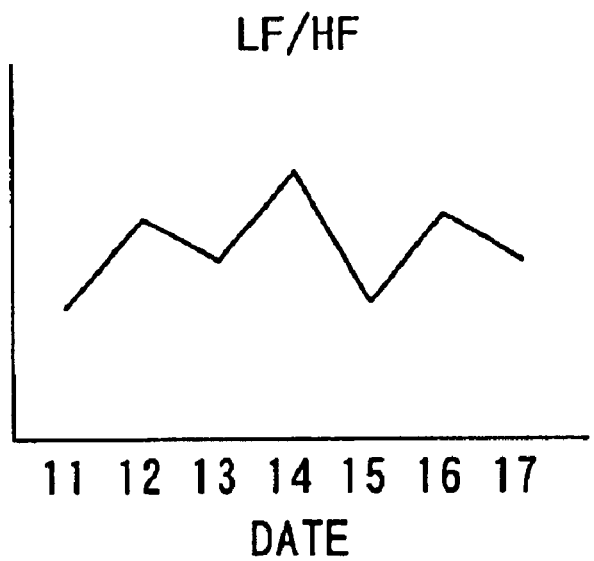
FIG. 103 is a line graph showing the movement in LF/HF over the past week displayed on figure display 23 in the same device.

The kinked line graph shown in FIG. 103 is displayed using the values of LF/HF over the past week.

(e) Fifth Button Press (screen 6)

Figure 104:
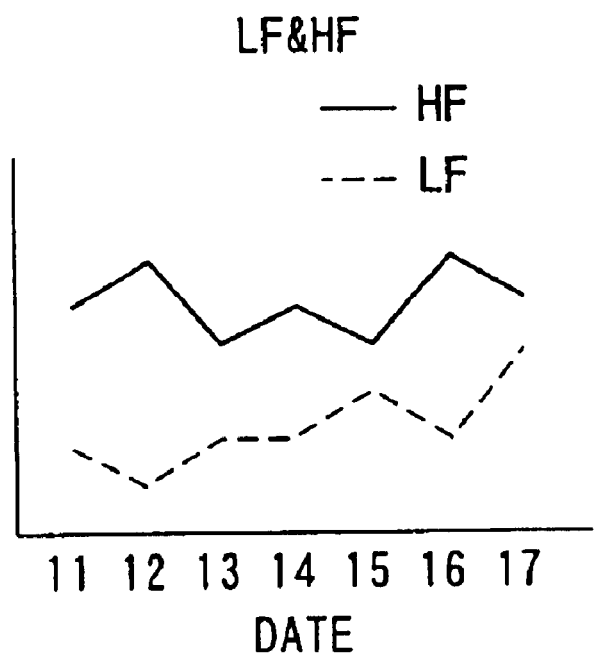
FIG. 104 is a line graph showing the movement in LF and HF over the past week displayed on figure display 23 in the same device.

The two kinked line graphs shown in FIG. 104 are displayed using the values of LF and HF over the past week.

(f) Sixth Button Press (screen 7)

A kinked line graph of the same type as shown in FIG. 103 is displayed using the values of RR50 over the past week, with RR50 replacing LF/HF in FIG. 103

(g) Seventh Button Press (screen 8)

A kinked line graph of the same type as shown in FIG. 103 is displayed using the values of blood pulse rate over the past week, with blood pulse rate replacing LF/HF in FIG. 103.

(h) Eighth Button Press (screen 9)

The initial bar graph shown in FIG. 99 is again displayed. If display switching button 456 is depressed again subsequently, the graphs for each of the 8 screens as described above are displayed.

If the user depresses mode switching button 455 again, the device returns to the Ordinary Use Mode. In this case, CPU 440 sends out a command to display control circuit 449 to clear figure display 453. Next, the day and date are newly obtained, and displayed on figure display 453. When mode switching button 455 is depressed when the device is in the Analysis Mode, display of the above graphs is suspended, the device shifts to the Ordinary Use Mode, and the day and date are displayed.

This embodiment provides for a design in which the present invention is incorporated in a wrist watch which may be worn continually. Thus, the test subject, etc., is able to easily confirm the state of his health at any time. In other words, by displaying a comparison of the current indicator and an average value for indicators obtained at the same time of the day over a fixed period of time in the past, the user may know at a glance whether or not his current physical condition is markedly deviating from his condition during a prespecified period of time in the past, after taking into consideration cyclic variations in physiological state. By displaying the transition in the indicator over a prespecified period of time in the past, it is possible for the user to confirm at a glance any recent changes in his health.

Accordingly, the user becomes accustomed to consulting with a doctor or health facility when he notices a change in his condition following a regular or chance inspection of the indicators measured by the device. Thus, more efficient health management becomes possible.

Embodiment 2

This embodiment will be explained using the fingertip plethysmogram instead of the radius artery blood pulse wave.

Structure of the Device

The functional portions of the device in this embodiment are entirely equivalent to those in Embodiment 1. However, the blood pulse wave detection means and the wrist watch structure differ here from Embodiment 1. Namely, the composition and structure of blood pulse wave detector 443 in FIG. 97 differ in this embodiment from Embodiment 1.

Figure 105:
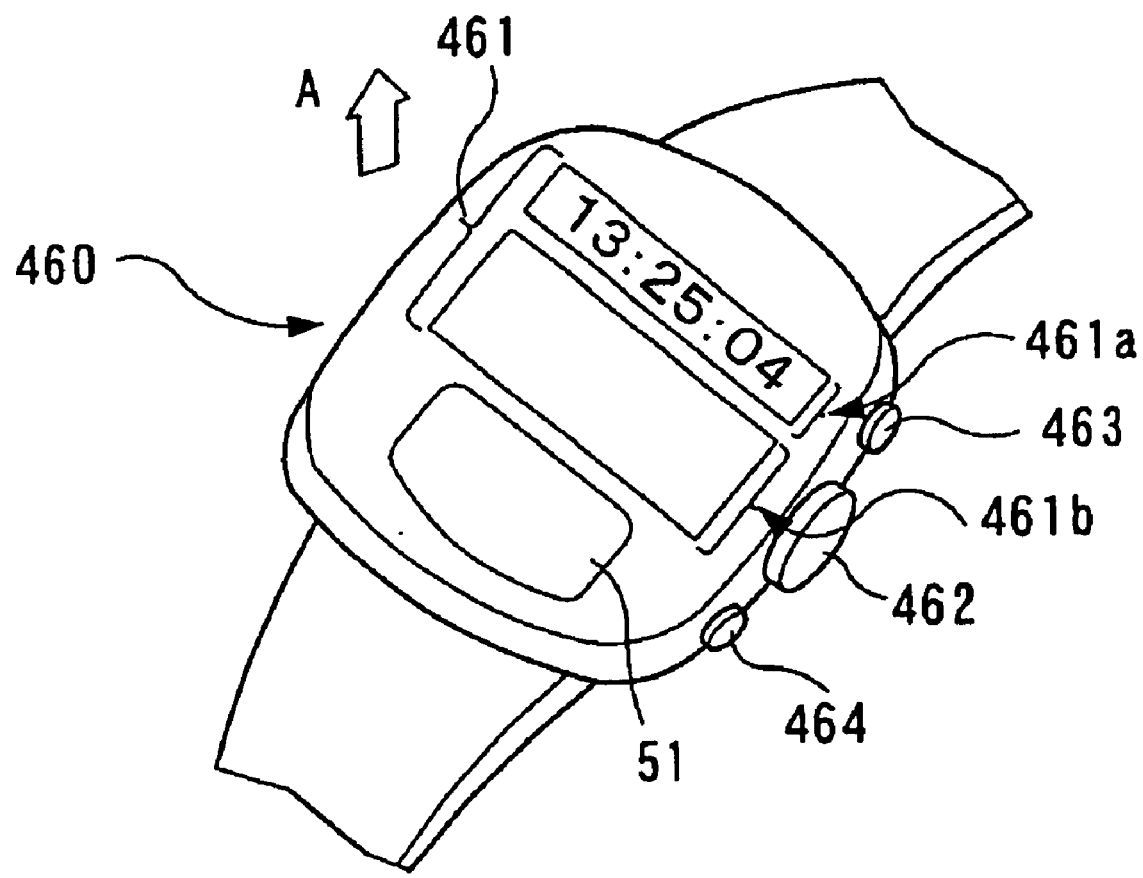
FIG. 105 is a perspective view of a wrist watch according to another embodiment of the present invention.

This embodiment employs a push-type blood pulse wave detector explained in Chapter 2, Section 1, Part 5. FIG. 105 shows the mechanical structure of the wrist watch according to the present embodiment. In this figure, a watch main body 460 is provided with an LCD display 461, finger contact pad 51, time change button 462, analysis mode button 463 and display switching button 464.

LCD display 461 is equivalent to the display 448 shown in FIG. 97, and is formed of a time display 461*a* and figure display 461*b*. The current time is displayed in time display 461*a* when the device is in either the Ordinary Use Mode or the Analysis Mode. In other words, the current time continues to be displayed even when the device is in the Analysis Mode, so that the current time is always available to the user. Figure display 461*b*, on the other hand, displays day and date information when the device operates in the Ordinary Use Mode, but displays measurement and analysis information and messages when the device operates in the Analysis Mode.

Time change button 462 is for setting the time on the wrist watch and for other such setting operations. Analysis mode button 463 is used to set initiation and termination of blood pulse wave analysis functions. Display switching button 464 performs the same function as the display switching button 456 in Embodiment 1, changing the details of the display on figure display 461*b* when the device is operating in the Analysis Mode.

The press pressure which should be applied to finger contact pad 51 is preset to be either 67, 83, 100, 117, or 133 g/cm$^2$. In the following explanation, the push-pressure is set to the optimal pressure for blood pulse wave detection. In the following, this will be 83 g/cm$^2$. Since the push-pressure is adjusted according to the force with which the user applies his fingertip to the finger contact pad 51, measurements will be difficult to carry out if an acceptable range is not provided for each of the above press pressures. Thus, the acceptable range for each of the press pressures noted above is ±2 g/cm$^2$.

CPU 440 sends to the display control circuit 449 shown in FIG. 97 message data to guide the user through the steps of the analysis, graphic data used to direct the user's pushing pressure on finger contact pad 51 to a suitable level, and the like. Display control circuit 449 forms display data from this display information and outputs it to figure display 461*b*.

Figure 106:
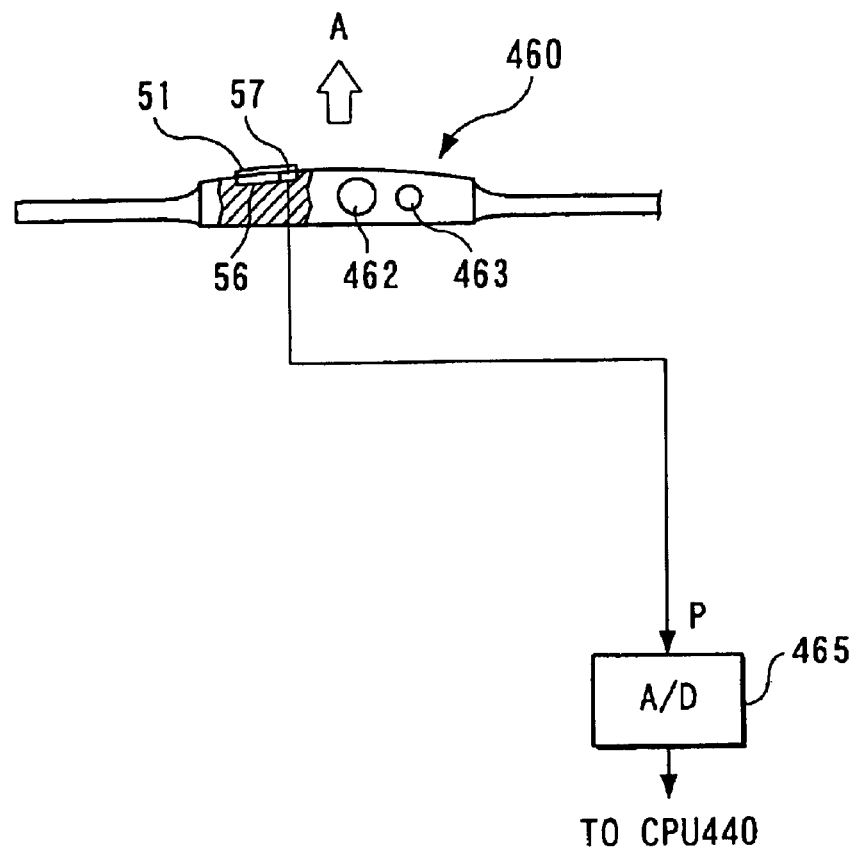
FIG. 106 is a diagram showing the internal structure of the device according to the same embodiment.

As shown in FIG. 106, pressure signal P, which is the output of distortion gauge 57, is converted to a digital signal at A/D converter 465 and sent to CPU 440.

Operation of the Device (1) Pre-processing

In order to carry out blood pulse wave measurements at a fixed time every day, when a power source or the like is introduced, CPU 440 directs watch circuit 446 to generate an interrupt signal every two hours starting from 8:00 am until 10:00 pm, for example. Because the blood pulse wave measurements are carried out in this embodiment by having the user press his finger against a finger contact pad, the measurement time is not set for the nighttime hours, (2) Measurement of Blood pulse Waves In order to measure blood pulse waves during a fixed time interval (for example, 2 hours), when the power source or the like is introduced, CPU 440 directs watch circuit 446 to generate an interrupt signal every 2 hours starting from 12:00 am, for example.

1. Uptake of Blood pulse Waveforms

When watch circuit 446 generates an interrupt signal to CPU 440 at 2:00 pm, for example, CPU 440 uptakes the blood pulse wave during the prespecified period of time in the same manner as performed in Embodiment 1.

First, CPU 440 informs the user that it is time for blood pulse wave measurement. CPU 440 displays a message such as "measuring blood pulse" or the like on figure display 461*b*. After seeing the message, the user presses analysis mode button 463, making the device operational. If the analysis mode button 463 is pressed again at this point, the watch returns to its ordinary operation, while if analysis mode button 463 is pressed while analysis is ongoing, the analysis operation is suspended and the watch returns to its ordinary operations.

Figure 107A:
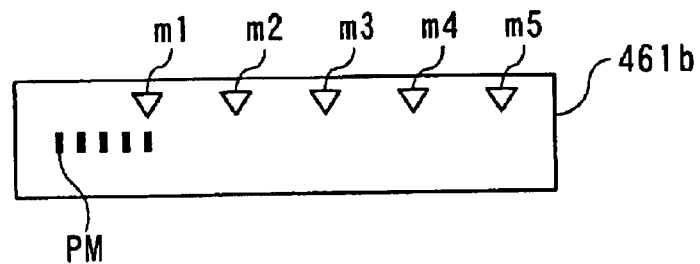
FIGS. 107A to B are figures showing examples of the guidance messages in the same embodiment.

Next, when there is a notice from operator 447 that analysis mode button 364 has been depressed, CPU 440 displays the message "press until 2" on figure display 461*b*. After seeing the message, the user places his finger on finger contact pad 51, thereby altering the resistance value of distortion gauge 57 housed in the watch. CPU 440 detects this change in pressure from the output from A/D converter 465, and switches figure display 461b to a graphic display such as shown in FIG. 107A. The inverted triangles labeled m1 to m5 in this figure signify the measurement points corresponding to, in order from the left, 67, 83, 100, 117 and 133 g/cm$^2$.

Figure 107B:
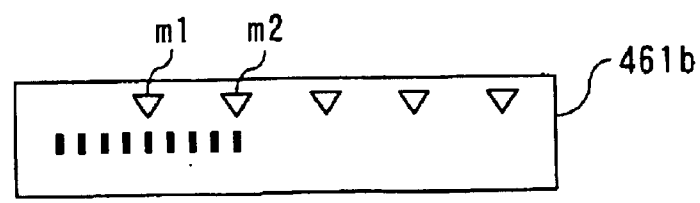
Figure 108:
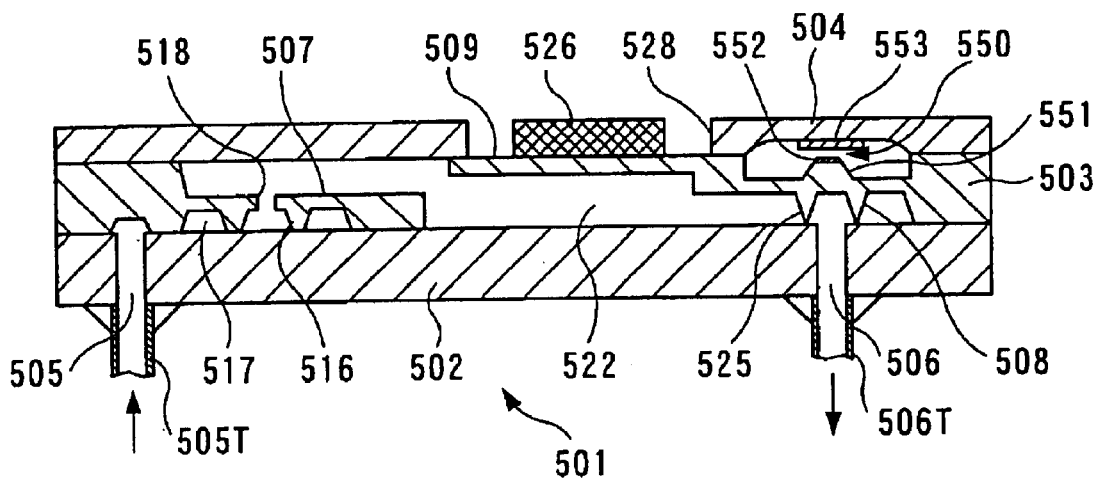
FIG. 108 is a section view showing the structure of micro pump 501 of the present invention.

As the user then increases the pushing pressure of his finger gradually, bar-like marks indicated by the symbol PM (see FIG. 107A) are displayed sequentially from the left, the number of marks displayed corresponding to the actual extent of the push- pressure. Using these marks for reference, the user pushes his second finger against finger contact pad 51 until the display of the PM mark reaches the position marked by m2, which indicates the second measurement point (see FIG. 107B).

Once the PM mark is displayed through the m2 position, this indicates that the current push-pressure is within the acceptable range (83±2 g/cm$^2$) of measurement for the second measurement point. In contrast, if the push-pressure is slightly outside this range, the PM mark preceding the targeted PM mark will flicker.

Once it is detected that the push-pressure has remained within the acceptable range for measurement for given short period of time, CPU 440 terminates the graphic display on figure display 461*b*, and in its place displays a "remain still" message.

If the user moves his finger during this short period of time, causing the push-pressure to deviate from the acceptable range for measurement, a "please retry" message is displayed on figure display 461*b*. The display on figure display 461*b* switches to the above-described graphic display again, so that the user must adjust the push-pressure of his finger until the PM marks are again displayed up to the m2 position.

Once the push-pressure is constant, blood pulse wave measurement is carried out. The measurement operation is the same as in Embodiment 1. CPU 440 sets a prespecified time in time circuit 446, and the blood pulse wave signal from A/D converter 444 is taken up in data memory 445 during this time period only.

(3) Analysis of Blood pulse Waveform

Next, CPU 440 sequentially calculates LF, HF LF/HF, RR50 and blood pulse rate in the same manner as Embodiment 1, and stores these values in data memory 445 together with the time of measurement.

In this way, the regular measurement of physiological state is carried out.

(4) Display of Measured Results

When the user depresses analysis mode button 463 in order to know his current physical condition, CPU 440 clears figure display 461b. Since the button is depressed at a time which does not correspond to the regular blood pulse wave measurement time, CPU 440 recognizes that the depression of the button is an indication of the user's intent user intent.

1. Collection of Current Values of Physiological State

CPU 440 carries out the measurement of blood pulse waves and the analysis of blood pulse waveforms as described in "(2) Measurement of Blood pulse Waves" and "(3) Analysis of Blood pulse Waveform" above. Namely, the fingertip plethysmogram over a fixed time interval is taken up in data memory 445, and the current values of LF, HF, LF/HF, RR50 and blood pulse rate are calculated from the waveform analysis of the blood pulse wave.

2. Interpolation Processing

CPU 440 interpolates the values for the physiological state in the past in the same manner as in Embodiment 1 above, and then calculates the physiological state at the same time of the day as the current time. The moving average for each physiological state is obtained.

3. Graph Display

When the user depresses display switching button 464, the physiological state graphs shown in FIGS. 99 to 104 are displayed on figure display 461b, in the same order as set forth in Embodiment 1.

As explained above, by means of the preceding embodiments, it is possible for a user to check his physical condition any time he wishes by displaying the results of an analysis thereof. Further, since both the current state and the moving average of the physiological state over a prespecified period of time in the past are displayed together, it is possible for the user to quantitatively know how his current state of health compares to his regular health condition. Moreover, since the transition in the physiological state can be displayed, the user may know at any time how the condition of his health has changed recently.

(Modifications)

1. The device according to the first embodiment may be incorporated in an accessory or a pair of eye glasses.

2. The display of the graphs shown in FIGS. 99 to 104 may be carried out at the regular time for measurement of the blood pulse wave.

3. In each of the above embodiments, graphs were used to display the analyzed results with a view toward direct visualization. However, a numeric display may also be employed, for example.

4. A design may also be provided in which each of the maximum and minimum values in physiological state over the past one week are detected, and a buzzer is sounded or a warning display is provided when the current value is larger than the maximum value or smaller than the minimum value. As a result, it is possible to provide a warning to the user when his current physiological state differs markedly from his recent physiological state.

Further, it is also possible to provide a design in which, in accordance with the diagnostic device in Part 1, the user is notified that his physical state is good when the current physiological state values are smaller than the maximum value obtained for the past one week, or larger than the minimum value obtained for the past one week, such that a good physical state is indicated. By providing this kind of notification, the user receives psychological reassurance, contributing to an improvement in his quality of life.

5. The physiological state of an individual differs between the afternoon and evening. Accordingly, a design may be provided in which the maximum and minimum values for the afternoon and the maximum and minimum values for the evening are obtained. The current value is then compared to the afternoon maximum and minimum values or the evening maximum and minimum values, as appropriate to the current time of the day. As a result, it is possible to obtain an even more accurate analysis of the state of health.

6. In the preceding embodiments, the blood pulse waves were measured and the current physiological state was calculated following the depression of mode switching button 455. As a substitute method, however, the blood pulse waveforms may be taken up constantly in data memory 445, and the waveform over a fixed period of time (for example 30 seconds) constantly stored in data memory 445. Further, rather than again measuring the blood pulse waves when mode switching button 455 is depressed, the physiological state is calculated from the stored blood pulse waveforms. As a result, the time from when the user depresses the button until the display of the results can be considerably reduced.

7. A design may be provided so that when the user detects an anomaly, the results of the spectral analysis of variations in the RR interval are displayed as a graph so that a physician or other health profession may render a diagnosis.

8. In the above-described embodiments, the information displayed on figure display 453 could be changed by the depression of display switching button 456 by the user. However, it is also acceptable to automate this operation so that the display of information is carried out in order at a fixed time interval (5 seconds, for example). As a result, the need to operate a button in order to view the different information is eliminated.

9. It is also acceptable to design the device so that the user may use operator 447 to inform the device that he has assumed a state of repose in preparation for blood pulse wave measurement. In this case, it is convenient to display on display 448 the suitability of conditions for blood pulse wave measurements as determined from the output value of acceleration sensor 501, so that the user may make a determination of whether or not he is in a suitable state of repose.

Further, a design is also acceptable in which CPU 440 constantly carries out detection for a state of repose using acceleration sensor 501, with blood pulse wave detection carried out only when the state of repose is during a prespecified period.

A design may also be provided in which, rather than waiting for a state of repose, the measurement of blood pulse waves and of physical activity is carried out over a prespecified period of time, and these measured values are stored together in data memory 445. Based on the stored measured results for physical activity, only the results for blood pulse waves measured when the user was in a state of repose for a fixed interval of time are selected to obtain the blood pulse wave information.

10. As explained in the preceding device, a watch hand such as in FIG. 95 may be employed instead of a bar graph to provide notice to the user in the cases of FIGS. 99 through 102 (i.e., LF/HF, LF, HF, RR50 and blood pulse rate indicators) as well.

Section 2: Control of Physiological State

In this section, a variety of devices for controlling physiological state through the administration of a drug, the emission of a fragrance, or the like will be explained. These devices diagnose the physiological state from the results of an analysis of the blood pulse waves, and carry out the control of physiological state based on the results of this diagnosis.

In the drug administration and drug emission devices which will be explained below, a micropump may be used as a common drive means when administering a drug or emitting a fragrance. Accordingly, before the various devices are explained, the micropump and the drive for driving it will first be explained.

Part 1 Micropump (1) Micropump Structure

FIG. 8 is a sectional diagram of micropump 501 which has a sandwich structure consisting of base plate 502, thin film 503 and surface plate 504.

Base plate 502 consists of a glass base having a thickness of 1 mm, for example, and is provided with input and output ports 505 and 506, respectively. Tubes 505T and 506T are bonded to these ports by means of an adhesive agent such that there is no leakage therefrom.

Film 503 consists of a Si base having a thickness of 0.3 mm, for example. An entrance valve 507 and an output valve 508, and a diaphragm therebetween have been formed to thin film 503 by means of an etching method. A pump chamber 522 and a pump flow system connected thereto is formed below diaphragm 509. A piezo disk type piezo element 526 is bonded to the upper portion of diaphragm 509 as a drive means.

Entrance valve 507 is formed to cover base 502. A communicating hole 518 is formed in the approximate center of the upper surface of entrance valve 507, while a valve 516 is formed projecting downward so as to surround communicating hole 518. The tip of valve 516 extends until base 502. A chamber 517 is formed by the lateral side of entrance valve 507 and valve 516. Chamber 517 connects to input port 505 via a flow system not shown. Output valve 508 is formed of a cap-shaped valve 525 which covers entrance to output port 506.

Surface plate 504, which consists of the same type of glass plate as base 502, is adhered on to thin film 503 using an anode bonding method: The upper wall of one portion of the flow path of the aforementioned pump flow system is formed by surface plate 504. A window 528 is formed in the spot corresponding to diaphragm 509 on surface plate 504. Piezo element 526 is adhered to the surface of diaphragm 509 which is exposed through window 528. The thickness of surface plate 504 is approximately 1 mm.

Operation detection switch 550 will now be explained. Operation detection switch 550 is provided to detect the behavior of the partition of output valve 508, and consists of projection 551 projecting outward from the top portion of the partition, electrode 552 adhered to the surface of projection 551, and rear electrode 553 which is adhered on the bottom of upper surface plate 504 opposite electrode 552.

As will be explained below, an output blood pulse from an oscillation circuit 564 is impressed on electrodes 552 and 553 via the condenser C and resistor R shown in FIG. 109. Various interface materials may be employed for electrodes 552 and 553, such as Pt-Ir, W, Ta, Ni, Pt, Pd, Mo, Ti, polycrystal Si, $WSi_2$, CP1, CP2 and the like.

(2) Structure of the Drive

Figure 109:
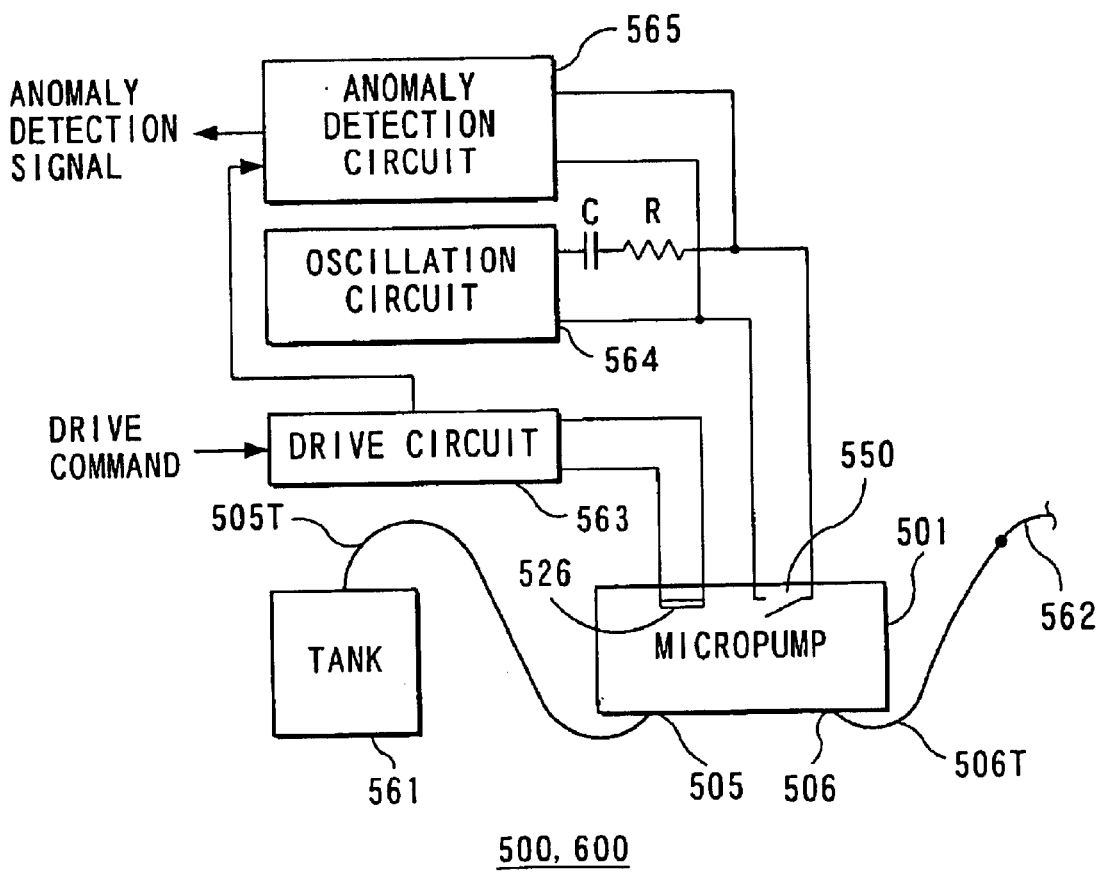

FIG. 109 shows the structure of the drive for driving micropump 501. In this figure, the entire circuit indicated by the numeric symbol 500 (600) forms the drug administrator or fragrance emitter inside the device.

In FIG. 109, 501 is a micropump as explained above. An input port 505 is inserted into a tank 561 via a tube 505T, while output port 506 is connected to tube 506T.

In the case where the device is employed to administer a drug, tube 506T is joined to an injection needle 562 as shown in the figure for that purpose. On the other hand, when the device is employed to emit a fragrance, the tip of tube 506T is instead disposed near a jet opening (explained below) for emitting a fragrance.

When drive circuit 563 receives a drive command from an external device such as a microcomputer, it generates a fixed level (around 100 V) drive blood pulse which is supplied to piezo element 526, the drive means of micropump 501.

Oscillation circuit 564 generates a plurality of blood pulses which have periods which are shorter than the blood pulse width of the drive blood pulse. The generated blood pulses are impressed on operation detection switch 550 of micropump 501 via condenser C and resistor R. Operation detection switch 550 is designed to enter an ON state for a fixed period of time only, each time fluid is expelled from output port 506 of micropump 501. Accordingly, when micropump 501 is operating normally, a drive blood pulse is impressed on to it, with the pressure at either end of operation detection switch 550 falling each time expulsion of fluid is carried out.

Anomaly detection circuit 565 adjusts the voltage at both ends of operation detection switch 550. When the level of the voltage obtained due to this adjustment does not change over time with respect to the drive blood pulse, an anomaly detection signal is output. This anomaly detection signal is sent to a microcomputer or the like which controls the micropump.

(3) Operation of Micropump and Drive

Figure 110:
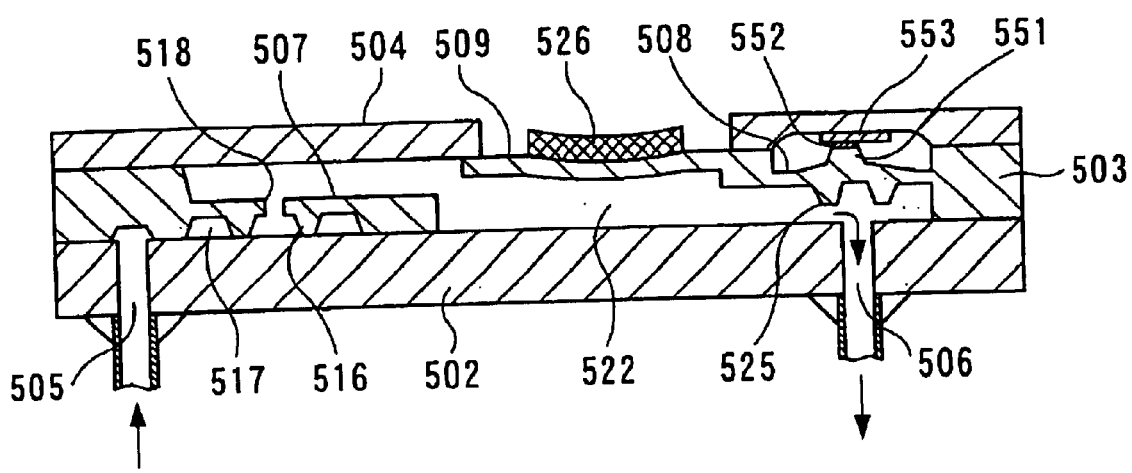

First, drive circuit 563 generates a fixed level (about 100 V) drive blood pulse when it receives a drive command from a microcomputer or the like provided external to the micropump. The generated drive blood pulse is supplied to piezo element 526 of micropump 501. When this drive blood pulse is impressed, piezo element 526 deforms as shown in FIG. 110, bending toward diaphragm 509. As a result, the pressure inside pump chamber 522 increases, causing the partitioning wall of output valve 508 to be lifted upward and valve 525 to move away from base 502. The fluid (drug, fragrance, etc.) inside pump chamber 522 flows to output port 506 through the opening between valve 525 and base 502, and is emitted via 506T in the case where the device is used to emit a fragrance, or administered via injection needle 562 in the case where the device is employed to administer a drug.

Figure 111:
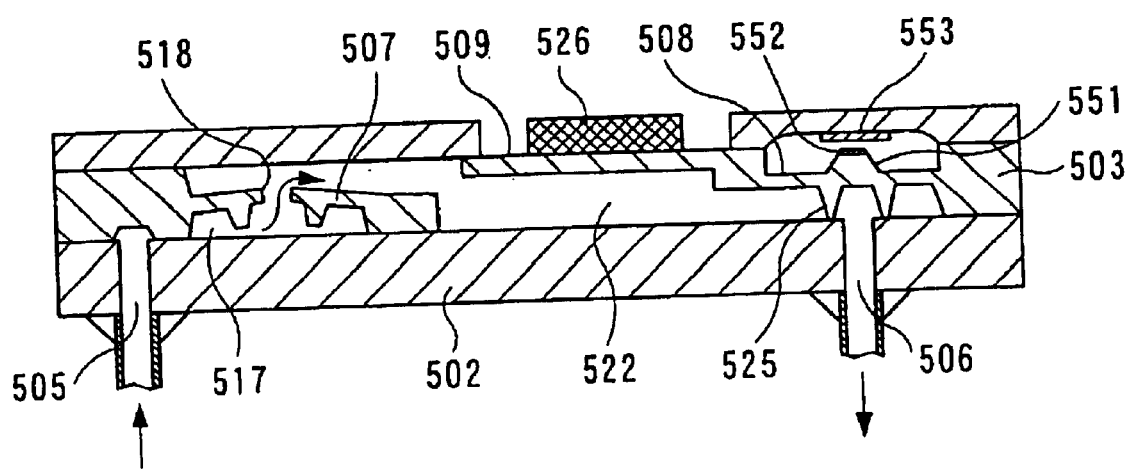

When the drive blood pulse falls, diaphragm 509 returns to its original shape as shown in FIG. 111, giving rise to a negative pressure in pump chamber 522. As a result, valve 525 of output valve 508 is pressed against base 502, sealing output port 506 as a result. Conversely, when the partitioning wall of input valve 507 is lifted upward, valve 516 moves away from base 502. As a result, fluid flows from input port 605, and is siphoned up into pump chamber 522 via communicating hole 518 and the space between valve 516 and base 502. Thereafter, the expulsion and uptake of the fluid is repeated as above each time a drive blood pulse is impressed.

During the operation of micropump 501, the voltage at the ends of operation detection switch 550 is monitored by anomaly detection circuit 565. If the fluid is not expelled smoothly due to clogging of the tube or needle, there will be a deviation from the normal relationship between the timing for drive blood pulse generation and the timing for when operation detection switch 550 enters an ON state. When anomaly detection circuit 565 detects this deviation, an anomaly detection signal is output to the microcomputer, etc.

Part 2 Drug Administration Control Device

The behavior of the circulatory system in individuals suffering from high blood pressure, heart failure or other types of circulatory system related diseases is frequently unstable. As a result, constant monitoring is necessary to ensure that the patient's condition does not become critical. There are a variety of factors which can influence the behavior of the circulatory system, these including α receptors, β receptors, choline receptor, ACE receptor, and the like. By administering circulatory acting agents such as α blockers, β blockers, calcium blockers, and ACE inhibitors to the patient, it is possible to control the condition of the circulatory system to stabilize its behavior.

Because the administration of a circulatory acting agent when the patient's condition has deviated from a normal state must be carried out in a timely manner, the health professional must constantly monitor the patient's condition. Accordingly, this is a labor intensive activity. Further, in the case of a patient whose condition is serious, the administration of circulatory acting agents is carried out so often as to almost be considered constant. For these patients it becomes necessary for them to remain bedridden just to receive their medication.

The device of the present invention was developed in view of the above described circumstances. This device monitors the state of a patient's circulatory system, and carries out the administration of a drug as necessary based on the results of this monitoring, thereby stabilizing the state of the patient's circulatory system with respect to blood pressure, etc. In order to do this, this device determines whether or not the patient's condition is one which requires medication, and then administers a circulatory acting agent, such as an α blocker or β blocker, as necessary based on the results of the determination. A "circulatory acting agent" as noted here includes drugs and hormones which act either directly or indirectly on the circulatory system.

Embodiment 1
Summary of the Device

The drug administration control device according to this embodiment employs the previously described LF, HF, [LF/HF], and RR50 as the physiological state in order to observe changes in the blood pulse wave. The organism's state of arousal or sedation obtained from these various values is employed in the control of drug administration.

In other words, LF, HF, [LF/HF] and RR50 are calculated by measuring the patient's blood pulse wave at regular intervals. When the patient is in a sedate state as determined from these physical states, then α blocker is administered to the patient to calm the state of excitation of the α receptors. Conversely, when the patient is in an aroused state, β blocker is administer to calm the state of excitation of the β receptors. In this way, the circulatory state with respect to blood pressure and the like is stabilized.

Structure of the Device

Figure 112:
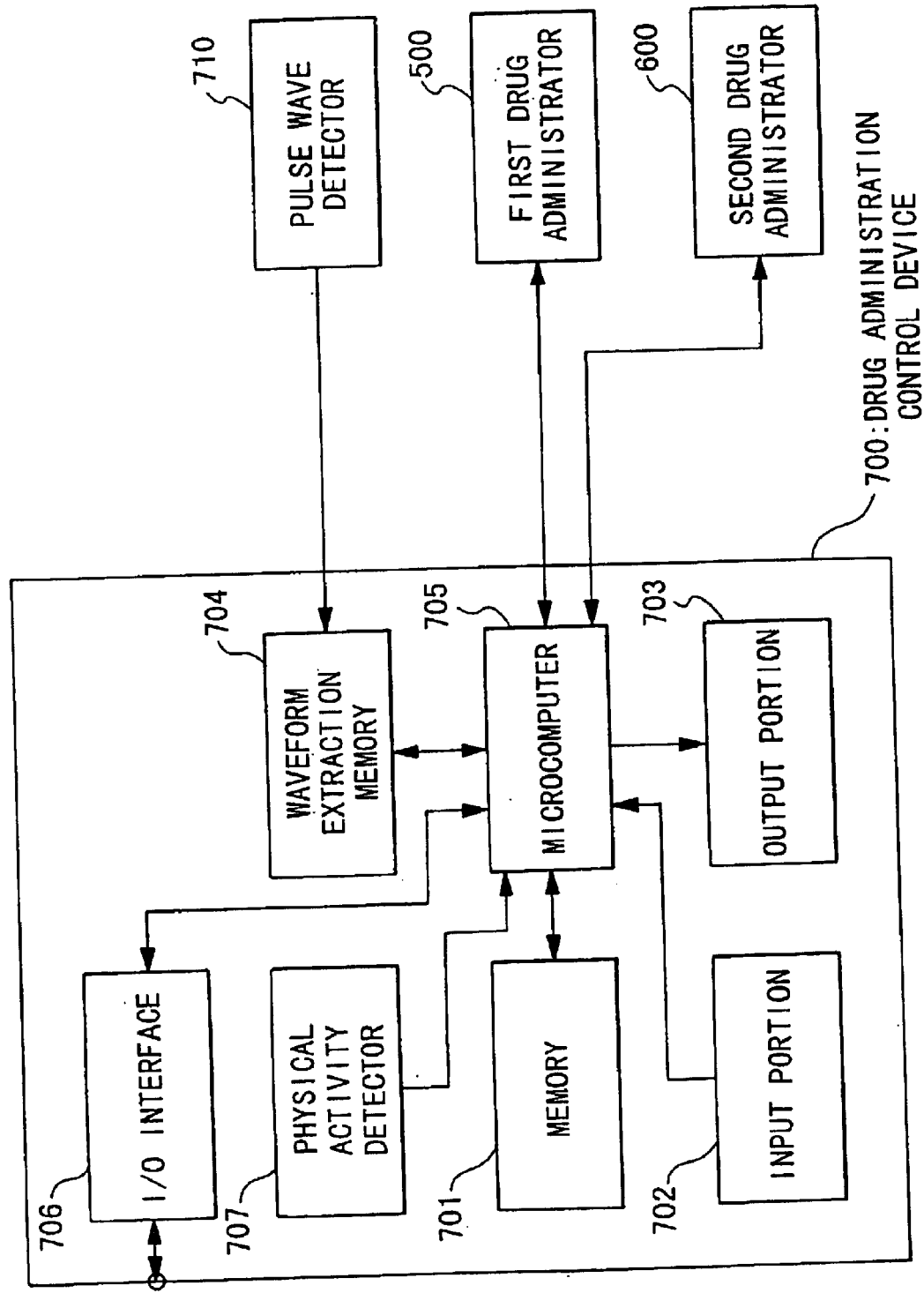

FIG. 112 is a block diagram showing the structure of drug administration control device 700 in this embodiment. Memory 701 is formed of a battery backed-up RAM or the like, and is a non-volatile memory. Memory 701 is employed for temporary storage of control data when microcomputer 705 controls each of the parts in drug administration control device 700. The desirable value (the value at a time when the patient was in good health, for example, or an average value determined from a number of healthy test subjects) in the case of the patient to be medicated for at least one of LF, HF, [LF/HF] and RR50 is stored in advance in a specific recording area of memory 701.

In addition to controlling the administration of a drug by using physiological state in which the details are fixed as above, drug administration control device 700 can also extract the physiological state from the blood pulse wave obtained from a patient, and use the physiological state formed in this way to control administration of a drug. The physiological state formed in this way is stored in a specific recording area of memory 701.

Input portion 702 is an input means provided for inputting commands to microcomputer 705, and is, for example, formed of a keyboard.

Output portion 703 is an output means formed of a printer, display device or the like. It is under the control of microcomputer 705, and carries out the recording of the physiological state obtained from the patient, the recording of the administration of a drug, the display of a blood pulse wave, and the like.

Waveform extraction memory 704 is under the control of microcomputer 705, and uptakes blood pulse wave signals output from blood pulse wave detector 710, and extracts and records the blood pulse wave of a single beat from the uptaken signal. The details of waveform extraction memory 704 are discussed in Chapter 3, Section 1, Part 2.

Microcomputer 705 controls each part inside this device 700 in accordance with compounds input via input portion 702. Microcomputer 705 houses a watch circuit, and carries out each of the processing described below each time a fixed period of time has elapsed when the device is in the operational mode for controlling administration of a drug.

1. Control of processing to uptake a blood pulse wave signal and to extract the blood pulse wave of one beat by waveform extraction memory 704

Peak information is stored in the internal memory each time a blood pulse wave peak is detected by waveform extraction memory 704.

2. Frequency analysis of blood pulse wave and determination of patient condition Based on the above peak information, the waveform values of the blood pulse wave of continuous beats are read out from waveform extraction memory 704, and the physiological state is calculated. The obtained physiological state and the desirable physiological state stored in advance in memory 701 are compared, and a determination is made whether or not the patient is in a sedate state.

3. Control of administration of drug

Based on the above determination, if the patient is deemed to be in an aroused state and his blood pressure has reached a value such that administration of a drug is necessary, then a drive command is supplied to the second drug administrator 600, with β blocker than being administered. Conversely, if the patient is deemed to be in a sedate state and his blood pressure has reached a value such that administration of a drug is necessary, then a drive command is supplied to the first drug administrator 500, with a blocker than being administered to the patient.

First drug administrator 500 and second drug administrator 600 are formed of a micropump, described in Part 1, and a drive. First drug administrator 500 is for administering blocker, while second drug administrator 600 is for administering blocker. The tank 561 shown in FIG. 109 is filled with a liquid α or β blocker.

I/O interface 706, which is explained in detail in Chapter 5, Section 3, is provided to carry out communication with an external device. By employing an I/O interface 706, the information about physiological state and the like which is stored in memory 701 can be transmitted to an external device.

Physical activity detector 707 is an example of a physical activity detector which picks up the physical activity of the device users. Physical activity detector 707 converts the measured value of the user's physical activity to a digital signal, and sends it to microcomputer 705.

Device Operation
(1) Administration of a Drug Using a Fixed Physiological State

When the device user has not indicated any particular mode, drug administration control device 700 controls the administration of a drug to the patient as explained below based on a fixed physiological state pre-stored in memory 701. In the case where tank 561 is exchanged when administering a drug, the user inputs a command indicating this fact via input portion 702. Microcomputer 705 receives this command and, as a result, writes the initial value of the remaining volume (equivalent to capacity of a full tank) of α and β blocker in memory 701.

As described above, microcomputer 705 houses a watch circuit which generates timer interrupt signals each time a fixed period of time has elapsed. As a result of the generation of timer interrupt signals, microcomputer 705 exercises the timer interrupt routine shown in FIG. 113.

First, the processing proceeds to step S721, where microcomputer 705 carries out processing to collect waveforms and the peak information therefor. The details of this operation are discussed in Chapter 3, Section 1. When measuring the blood pulse wave here, microcomputer 705 reads out and records the output of physical activity detector 707 in memory 701. Microcomputer 705 then determines whether or not the output value of physical activity detector 707 indicates that the user is in a state of repose. Since there is a concern that the measurement of the blood pulse wave may not be accurate if the user is not in a state of repose, microcomputer 705 uses output portion 703 to notify the user if he not sufficiently reposed. Thereafter, the user confirms that he is in a state of repose, after which the blood pulse waves are measured.

The processing then proceeds to step S722, where microcomputer 705 carries out waveform read out processing and analysis of the blood pulse waveform. In other words, microcomputer 705 analyzes the blood pulse waveform stored in memory 701, and calculates LF, HF, {LF/HF] and RR50. The details of this operation are described in Chapter 3, Section 1 and Chapter 4, Section 2.

Next, the processing then proceeds to step S723, where microcomputer 705 stores the physiological state obtained in Step S272 together with the information indicating the current day and time.

Next, the processing proceeds to step S724, where microcomputer 706 references the output of the time circuit and the time of previous administration of the drug which is stored in memory 701, and then determines whether or not a specific period of time has elapsed since the previous administration. If the results of this determination are YES, then the processing proceeds to Step 725, while if the results are NO, the timer interrupt routine terminates. Determination is carried out in this way so as to avoid continuous administration of the same blocker prior to the administered gent taking effect.

The processing next proceeds to Step S725, where the current measured physiological state and the physiological state stored in advance in memory 701 are compared. If the results of this comparison exceed a prespecified range such that the patient is in a sedate state, the processing proceeds to Step S726. The patient's blood pressure blood pulse wave is measured by blood pulse wave detector 710, to obtain a blood pressure value. When the blood pressure value is such that the administration of a drug is necessary, a drive command is generated and sent to first drug administrator 500 a specified number of times, with the quantity of blocker is to be administered calculated based on the number of times the drive command was generated. On the other hand, if the results of the aforementioned comparison exceed a specific range such that the patient is in an aroused state, the processing proceeds to step S727. As in step S726, when the patient's blood pressure value is such that the administration of a drug is necessary, a drive command is sent to second drug administrator 600 a specified number of times, based on which the quantity of β blocker to be administered is calculated. When the physiological state does not coincide with either of these situations described above, i.e., the state is normal, the timer interrupt routine is terminated.

When a drive command is generated by microcomputer 705, the first drug administrator 500 and the second drug administrator 600 administer their respective blockers to the patient via the tube 506 and injection needle 562 shown in FIG. 109. As a result of receiving anomaly detection signals from these administrators, microcomputer 705 executes an alarm display on output portion 703 prompting the user to exchange injection needle 562.

Next, once steps S726 and S727 are completed, the processing proceeds to step S728, where the dose of the pharacological substance to be administered is calculated based on the number of times a drive order was generated. The dosage, the type of blocker (α or β blocker) to be administered, and the time of administration are then stored in memory 701 as recorded information relating to the administration of the drug. This information stored in memory 701 can be output from output portion 703 in accordance with the commands input from the input portion 702. By referring to this recorded information relating to the administration of the drug, the health professional can see any changes or the like which have taken place in the patient. In step S708, the amount remaining of the blocker used in the current administration of the drug is read out from memory 701 and the current dose is subtracted from this remainder and stored as the new remainder in memory 701. Once this remaining amount falls below a prespecific value, microcomputer 705 sends a warning output command to output portion 703. Output portion 703 uses an alarm display or the like to prompt the user to change tank 561. In this way, tank 561 can be changed before the drug is used up.

The timer interrupt routine is completed as above. Thereafter, the routine is repeated again after the elapse of a fixed period to time.

(2) Parameter Recording/Automatic Operating Mode

The user may enter commands via input portion 702 to set the operational mode to a parameter recording mode/ automatic operational mode. In the operational mode, the physiological state is created based on blood pulse waves obtained from the patient. The thus created physiological state can then be used to carry out control of drug administration. The operation of this operational mode will now be explained.

Figure 114:
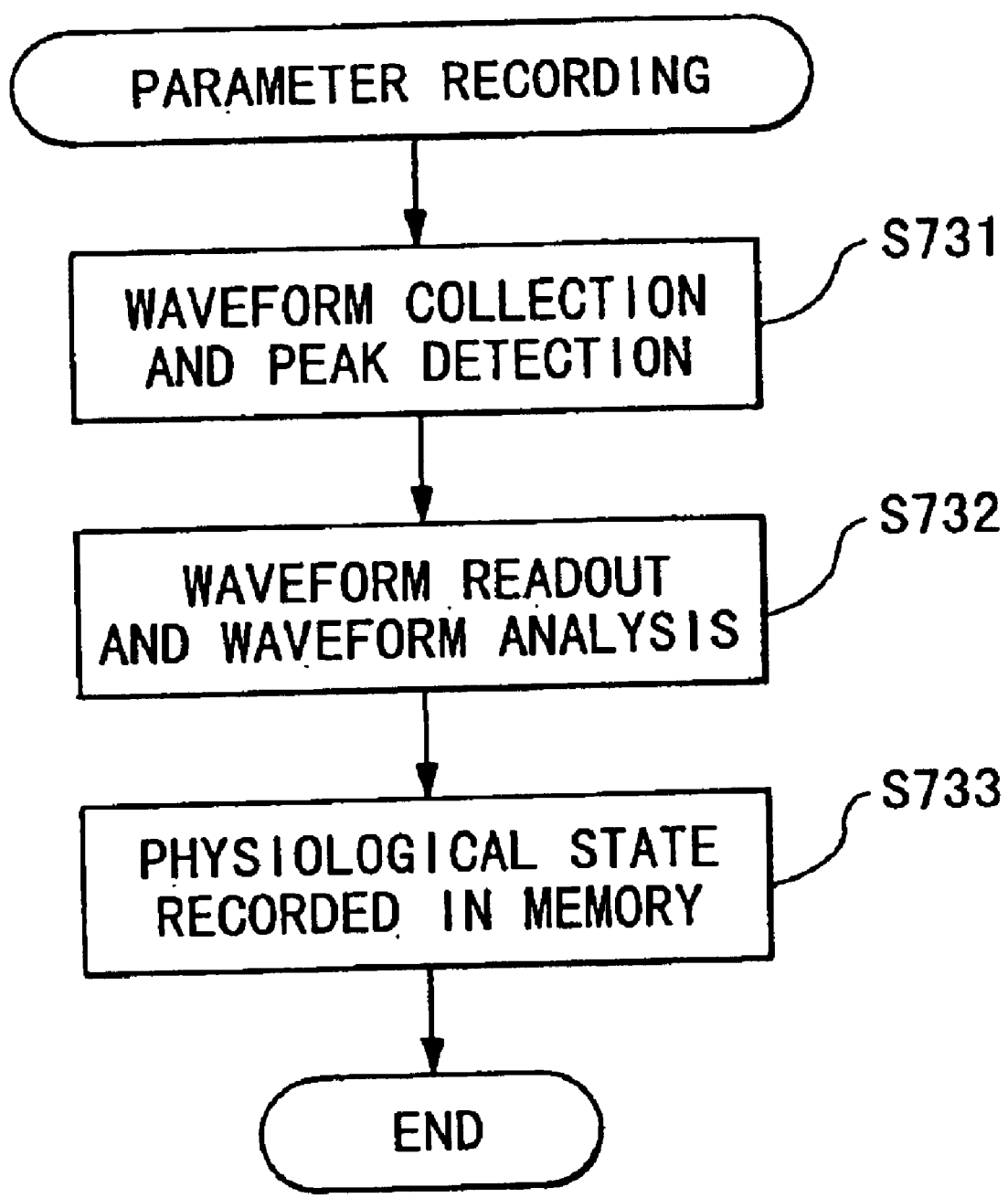

When initiating control of the administration of the pharmacological substance in the operational mode, it is necessary to obtain the physiological state. When the patient has reached a point where an α or β block has become necessary, the health professional inputs a command to input portion 702 to create the physiological state. As a result, the pattern recording routine shown in the flow chart in FIG. 114 is carried out by microcomputer 705.

Figure 113:
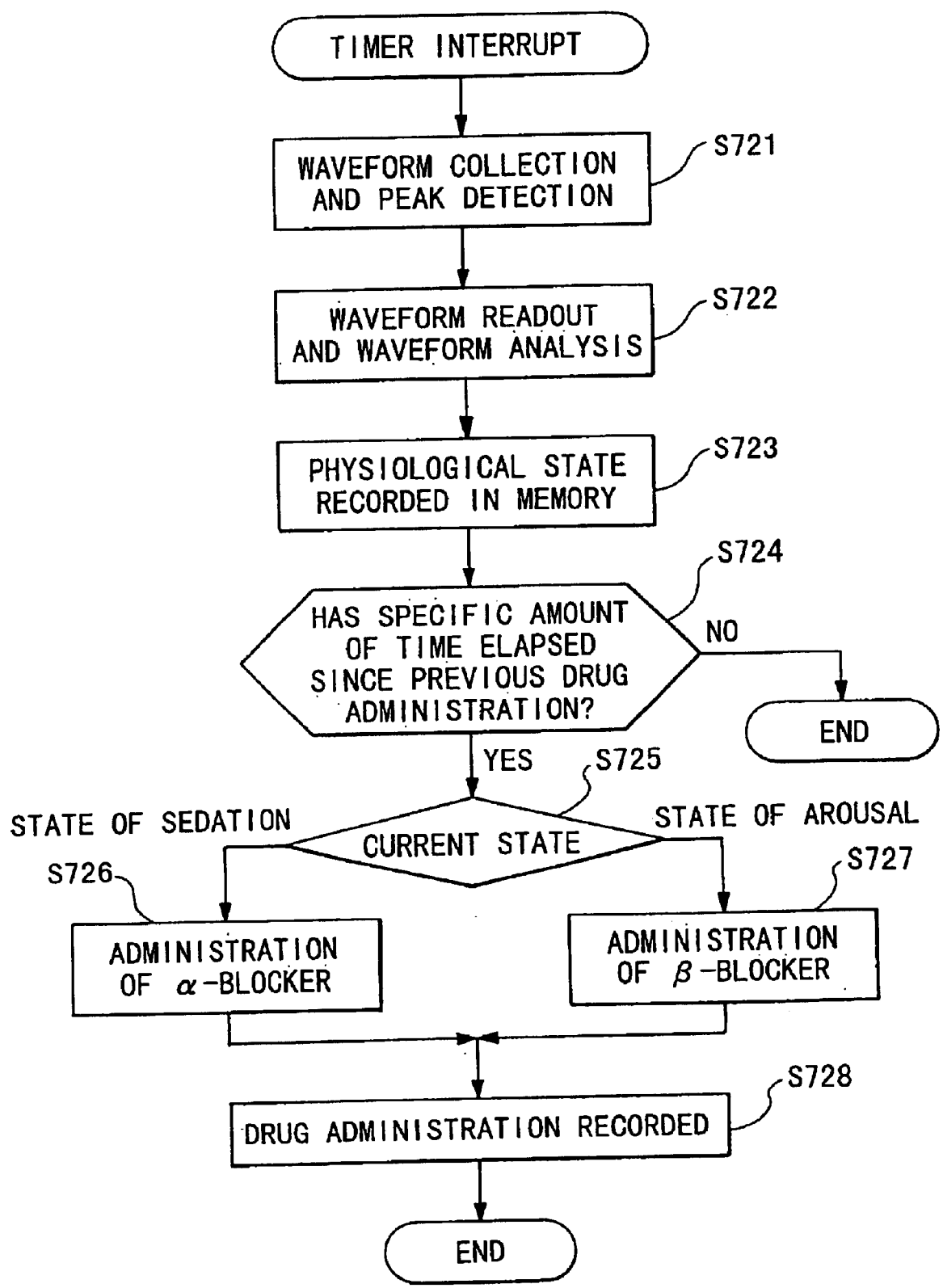

Next, the processing proceeds to step S731, and wave form collection and peak detection processing are carried out. Next, in step S732, the physiological state is calculated by carrying out wave form extraction processing and waveform analysis over a prespecified period of time. Next, in step S733, the physiological state obtained in step S732 is recorded in memory 701. The details of the processing in each of these steps are equivalent to steps S721, S722, and S723 in the timer interrupt routine (FIG. 113). Accordingly, a detailed description thereof will be omitted.

After creating the physiological state in memory 701 in this way, a command to start control of administration of the drug is input via input portion 702. As a result, the timer interrupt routine is carried out over a fixed period of time, as described above. However, in this case, control of the administration of the drug is carried out based on the physiological state obtained from the patient in this way, rather than on a fixed value physiological state stored in advance in memory 701.

Embodiment 2

The device according to this embodiment is designed to enable separation of the device for controlling administration of a drug into a portable portion and a stationary portion.

Structure of the Device

Figure 115:
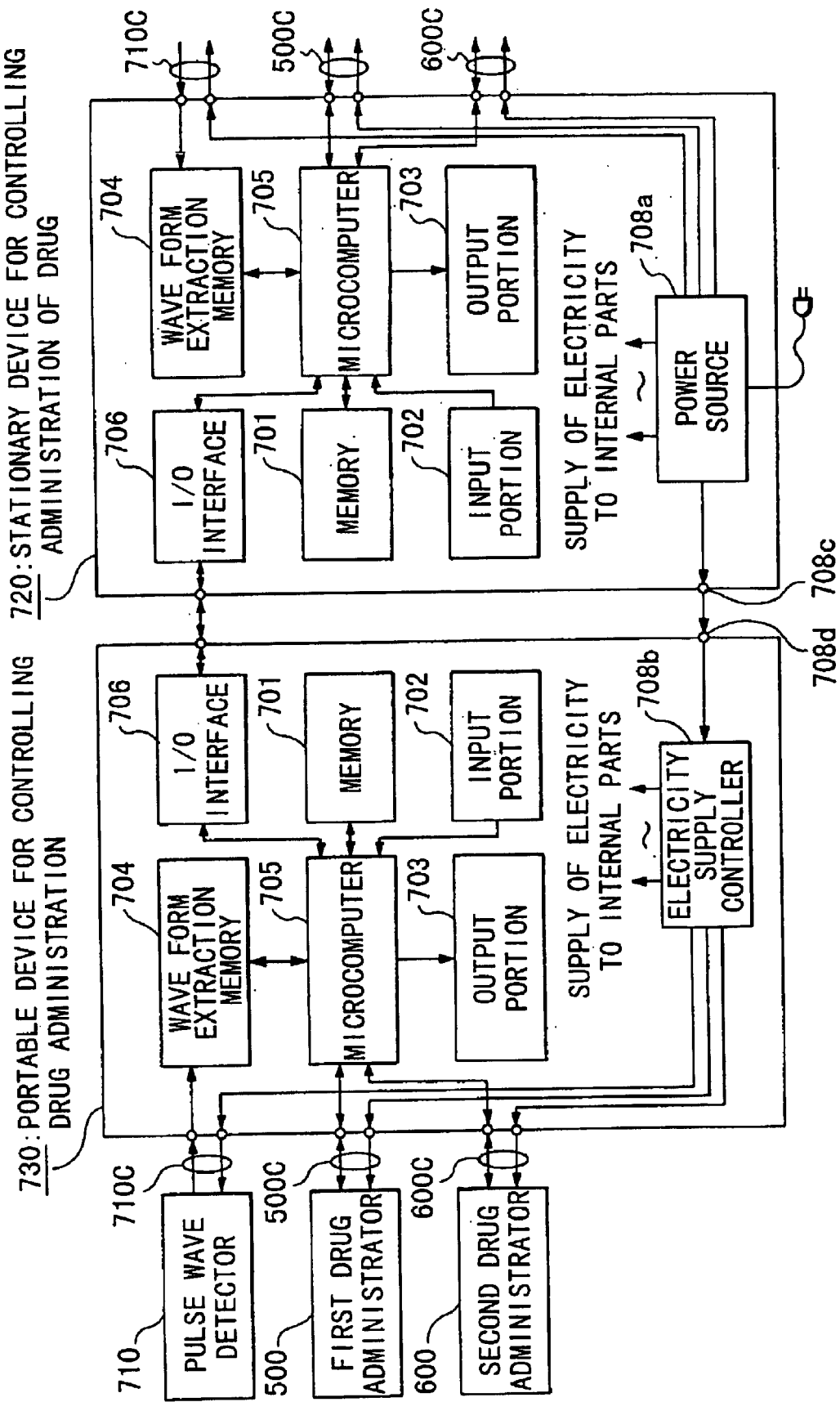

The design of the device for controlling administration of a drug according to this embodiment is shown in FIG. 115.

In this figure, numeral 720 is a stationary device for controlling administration of a drug which is fixed in place next to a hospital bed, for example, while numeral 730 indicates a portable device for controlling administration of a drug which the patient carries with him. Both of these devices have a construction similar to the device 700 for controlling administration of a drug which is shown in FIG. 112. The same numeric symbols have been applied to parts in common with those of device 700, and an explanation thereof has been omitted. Accordingly, the following explanation will address only those parts in devices 720 and 730 which differ from device 700.

An I/O interface 706 (explained already) is provided to both stationary device 720 and portable device 730 for controlling administration of a drug, so that their respective microcomputers 705 can carry out communications there between. As explained above, the I/O interface is provided with a mechanism for assigning identification numbers for each type of communication information. Accordingly, in this embodiment, when communication is carried out in a wireless fashion, stationary device 720 for controlling administration of a drug can communication with a plurality of portable devices 730 for controlling administration of a drug by employing time-sharing.

Each of the external devices of blood pulse wave detector 710, first drug administrator 500 and second drug administrator 600 can be attached to stationary device 720 or portable device 730 for controlling administration of a drug using cables 710C, 500C and 600C, respectively. Each of these cables house a signal line and an electrical supply line. The sending and receiving of signals between the devices for controlling administration of a drug and each of the external devices is carried out via the signal line, while the supply of electricity is carried out via the electrical supply line.

Portable device 730 for controlling administration of a drug has a battery (not shown) which is charged with electricity via a charging terminal 708d. Portable device 730 for controlling administration of a drug also has an electrical supply controller 708b which supplies electricity from this battery to the parts inside the device and supplies electricity to each of the outside devices via each of the electric supply lines in the cables. Since portable device 730 for controlling administration of a drug operates using the battery as a power source, it is necessary to conserve power. Thus, the control of the supply of electric power from electrical supply controller 708b is carried out by microcomputer 705. In other words, under the control of microcomputer 705, the supply of electric power from electrical supply controller 708b to each of the parts in the device is carried out only for the necessary interval of time, such as when the above described timer interrupt routine is carried out. At all other times, then, electric power is supplied only to microcomputer 705. Further, the supply of electric power to blood pulse wave detector 710 is carried out only when the A/D converter inside waveform extraction memory 704 is carrying out sampling of the waveform values, while the supply of electric power to first drug administrator 500 and second drug administrator 600 is carried out only in the steps for performing drug administration during the timer interrupt routine. Electrical supply controller 708b is provided with a voltage monitoring circuit (not shown) for outputting an alarm signal when the battery's output voltage drops below a prespecified value. This alarm signal is supplied at microcomputer 705 which then drives a warning means, such as light generating or alarm sound generating device (neither are shown in the figures), to provide a warning.

Stationary device 720 for controlling administration of a drug has an electrical source 708a. Electrical source 708a supplies power to the internal parts of the device as well as the blood pulse detector and other external devices using a commercially available electrical source. The output voltage of electrical source 708a is output to voltage output terminal 708c. By connecting charging terminal 708d of the portable device 730 for controlling administration of a drug to this terminal 708c, the battery inside portable device 730 can be charged.

The operation of either of devices 720 and 730 for controlling administration of a drug when used alone is equivalent to that described in the first embodiment above. Accordingly, an explanation thereof has been omitted here.

Operation of the Device

This embodiment's devices 720 and 730 for controlling administration of a drug give and receive information via I/O interface 706. Accordingly, the following type of application is possible.

1. Blood pulse wave detector 710, first drug administrator 500, second drug administrator 600 and portable device 730 for controlling administration of a drug are connected to stationary device 720 for controlling administration of a drug. As charging of the battery in portable device 730 for controlling administration of a drug is carried out, the physiological state of the patient is collected by stationary device 720 for controlling administration of a drug, and stored in memory 701.

2. The physiological state recorded in memory 701 in stationary device 720 for controlling administration of a drug is read out from microcomputer 705, and sent via I/O interface 706 to portable device 730 for controlling administration of a drug. This information is written to memory 701 via I/O interface 706 and microcomputer 705 inside portable device 730 for controlling administration of a drug.

3. Blood pulse wave detector 710, first drug administrator 500, and second drug administrator 600 are connected to portable device 730 for controlling administration of a drug. A command to initiate control of drug administration is input, and the timer interrupt routine explained in the first embodiment above is carried out regularly, with the administration of the drug controlled based on the physiological state taken up from stationary device 720 for controlling administration of the drug. During this time, the patient may leave his bed and move around. In addition, if the output voltage of the battery inside portable device 730 for controlling administration of the drug falls below a prespecified value, then an alarm signal will be generated and a warning will be generated by microcomputer 705 after it receives this alarm signal.

4. After the elapse of a prespecified period of time, or upon receiving an alarm display indicating that it is time to change tank 561, the patient returns to his hospital room. Portable device 730 for controlling administration of a drug is connected to stationary device 720 for controlling administration of a drug. While the battery inside portable device 730 for controlling administration of a drug is being charged, the record of drug administration (i.e., the times of administration and the types of blocker administrated through the present time) which is recorded in memory 701 inside portable device 730 is sent to stationary device 720 for controlling administration of a drug. This record of drug administration is added to the records of drug administration which have recorded through the current point in time in memory 701 inside stationary device 720 for controlling administration of a drug.

In this way, the recorded information concerning administration of the drug remains in memory 701 of the stationary device 720 for controlling administration of a drug. Thus, the health professional can note any changes in the patient's condition by outputting via output portion 703 this recorded information on administration of the drug. As necessary, the health professional may then recreate the setting for a desirable physical state in stationary device 720 for controlling administration of a drug, and then relay this to portable device 730 for controlling administration of a drug. Thereafter, when the patient so desires, control of administration of a pharmacological substance may be carried out by portable device 730 for controlling administration of a drug in the same order as prescribed in the preceding number 2. and 3. above.

In this embodiment, the device can be employed in a portable manner, while, in addition, the conservation of unnecessary power may also carried out. Thus, the device may be used over a long period of time. Further, since an alarm is sounded when the battery's output voltage falls, failure of the device to operate due to a dead battery is prevented. Additionally, since information on the record of drug administration can be carried out with external devices, the administration of the drug can be carried out continuously by a plurality of drug administration control devices, with recording of the administration of the drug taking place.

Embodiment 3

In the above embodiments, for example, a determination was made as to whether or not a drug should be administered based on the use of the tidal wave information of the blood pulse wave as the physiological state. In contrast, in this embodiment, values for each of the elements in a lumped four parameter model which models a patient's circulatory system are obtained based on the blood pulse waves obtained from the patient, with these results used as the physiological state.

In this embodiment, microcomputer 705 reads out the blood pulse wave per beat from waveform extraction memory 704 in step S722 in FIG. 113. Microcomputer 705 then calculates the values of each of the elements forming the above-described model, and employs these calculated results as the physiological state. In step S725, the values of each of the elements for indicating states of arousal or sedation respectively, which are stored in advance as the physiological state, are compared to the aforementioned physiological state to enable a determination of the condition of the patient.

Embodiment 4

Although two blockers were employed in the preceding embodiment, it is also acceptable to use just one. Alternatively, three or more blockers may be used. For example, when it is only necessary to administer an α blocker, then second drug substance administrator 600 may be omitted from the construction shown in FIG. 112, with only first drug substance administrator 500 employed. The steps subsequent to step S725 in the timer interrupt routine regularly carried out by microcomputer 705 are altered, so that when the result of the determination in step S724 is YES, a determination is then made as to whether or not the patient is in a state of sedation currently. When a YES result is obtained here, an α blocker is administered, with the administration of the drug recorded. When a NO result is obtained, the timer interrupt routine is concluded without administration of a drug.
(Modifications)

1. Device 700 for controlling administration of a drug (or portable device 730 for controlling administration of a drug in Embodiment 2) may be incorporated in an accessory or a pair of eyeglasses.

2. In the preceding embodiments, an α or β blocker is administered when the waveform parameters of the blood pulse wave satisfy certain conditions. However, it is also permissible to store the blood pulse waves as is for the states which require administration of an or blocker as is in memory, compare these stored blood pulse waves with measured blood pulse waves, and carry out control of administration of the drug according to the results of this comparison.

3. In the preceding embodiments, a fixed quantity of an or blocker was administered one time in the case where the patient was in a state of arousal or sedation. However, it is not necessary to limit administration to this form. Namely, nifedipin or the like may be administered. In this case, the administration of a drug may be carried out over several times according to a preset control program, i.e., a fixed quantity of drug may be administered at a given time when a state of arousal or sedation is detected, and then administered again in a fixed quantity after the elapse of a prespecified period of time.

4. Although administration of a drug was carried out by means of an injector in the above embodiments, the administration means of the present invention is not limited thereto. For example, percutaneous, intravenous, intrarterial, intra-abdominal, oral, and rectum administering methods, among others, for administering drugs may be employed.

5. The drug administration device of this embodiment is not limited to the control of administration of a drug acting on the circulatory system. Rather, other applications are also possible. For example, the device may be employed in the administration of prostaglandin (an arterial dilator) in the case of occlusive arteriosclerosis. In addition, this device may also be employed for automatically controlling the speed of an intravenous drip, or the administration of heparin during dialysis, for example.

6. In the preceding embodiments, a micropump employing silicon micromachining was used, however, the present invention is not limited thereto. For example, a syringe-type, rotary-type, balloon-type, or other types of fluid supplementation pumps may be employed for the micropump.

7. In the preceding embodiments, detection was made of the need for administering a drug based on the subject's physiological state, and a final determination was then carried based on blood pressure measurements. However, it is also acceptable to carry out the final determination based on a direct measurement of the internal pressure of the blood vessels.

8. In the preceding embodiments, a determination was made as to whether or not to administer a drug based on the blood pulse waves obtained from the patient, and, when necessary, the administration of the day was automatically carried out. However, the present invention is not limited to the case where administration of a drug is automatically carried out. For example, a device may be designed in which the micropump, etc., which is the administration means in the preceding embodiments, is omitted and each of the indicators of physiological state obtained from the patient is displayed or output. In this case, the health professional makes a decision as to whether or not to carry out administration of a drug based on the display or output details.

9. A comprehensive determination of the state of arousal or sedation may be made by incorporating any one of LF, HF, [LF/HF] or RR50, or two or more of these as the physiological state indicators.

10. The current states of arousal or sedation, i.e., the values of the current indicator of the blood pulse wave tidal wave, the circulatory parameter Rp or the like, may be displayed on the display surface of the watch.

11. When administering a drug, detection of the blood pulse waveform may be carried out, with administration of the drug synchronized with the blood pulse output of blood sent from the heart (blood pulse cycle), so that the administration of the drug is carried out between successive blood pulse intervals (i.e., between successive blood pulse waves). As a result, the administration of the drug can be carried out when the blood vessel pressure of the hypodermic tissue is low.

12. In the measurement of blood pulse wave, the user may confirm on his own that he has assumed a state of repose and then may inform the device of this fact using input portion 702. In this case, it is convenient to provide the user with notification that conditions are suitable for measurements to be made based on the output value of physical activity detector 707, so that he can determine whether or not he is in a audible state of repose.

Microcomputer 705 may also be designed to constantly carry out detection for a state of repose using physical activity detector 707, and then carry out blood pulse wave detection only at specific time when a state of repose is present.

Blood pulse wave measurements and physical activity measurements may be carried out over a prespecified period of time, without waiting for a state of repose to be present. These measured values are then stored together in memory 701. Based on the restlt of the stored measurements of physical activity, the blood pulse wave measurement results at a point in time when the user was in a state of repose during a specific period of time are selected to obtain blood pulse wave information.

13. In each of the preceding embodiments, it is also acceptable to detect the effect of the drug and inform the patient there of. Namely, after directing administration of a drug, microcomputer 705 then measures the blood pulse waves from the patient, calculates the physiological state, and makes a determination as to whether or not the obtained physiological state requires administration of a drug. If an effect from the drug administered is noted, a determination is made that subsequent administration is not necessary and this fact is then output from output portion 703.

Part 3 Drug Emission Device

There has been an increasing awareness of the need for relaxation in today's stressful times. Accordingly, there is a desire for a relaxation method which can easily be employed during one's daily life. The use of fragrances with a sedating effect has long been know as one such means for relaxation. One method employed since ancient times, for example, uses incense to calm or soothe, while contemporary examples include air control devices which blow air into which a fragrance has been mixed.

While it is desirable to provide periods of relaxation at a suitable frequency so that stress does not accumulate, today's busy person readily neglects to do so. Since there is little sense in making a special effort to force oneself to relax, a means of relaxation which does not require this sort of effort has been desired.

While an appropriate level of relaxation is necessary to avoid the accumulation of stress, it is not appropriate to constantly be in a state of relaxation. Namely, in order to have a healthy lifestyle, it is necessary to be in sedate when one is supposed to rest, but be in an alert or aroused state when one is supposed to work. Thus, it desirable to switch between these states appropriately.

This device attempts to respond to the above-stated demands, by automatically emitting a fragrance with an appropriate timing which does not require the attention of the device user. In this way, the states of arousal or sedation are controlled so that relaxation can be carried out.

Preliminary Examination

The present inventors carried out the following preliminary examinations when designing this device. Additionally, while a variety of drugs may be employed in this device, the following explanation will employ the case where a fragrance is used.

Confirmation of the Effect of Fragrance

Physiological states such as arousal and sedation are closely related to the circulatory state parameters. It is known that when the human body changes from a state of sedation to a state of arousal, or vise-versa, these changes appear in changes in the circulatory parameters. Accordingly, the present inventors confirmed the effect of fragrance by studying the behavior of the circulatory parameters in a human being when the subject sniffed the fragrance.

(1) Method of Measurement

Seven men ranging in age from 23 to 39 were employed as test subjects. The stroke volume per beat, the waveform at the radius artery and other measurements were made in each subject before, during and after the subject sniffed lavender aroma oil and sandalwood aroma oil.

(2) Method of Analysis

A lumped four parameter model was assumed for the circulatory parameters in the human body, and confirmation was made of the change over time which each of the elements in the model demonstrated.

(3) Results of Measurements

Figure 116A:
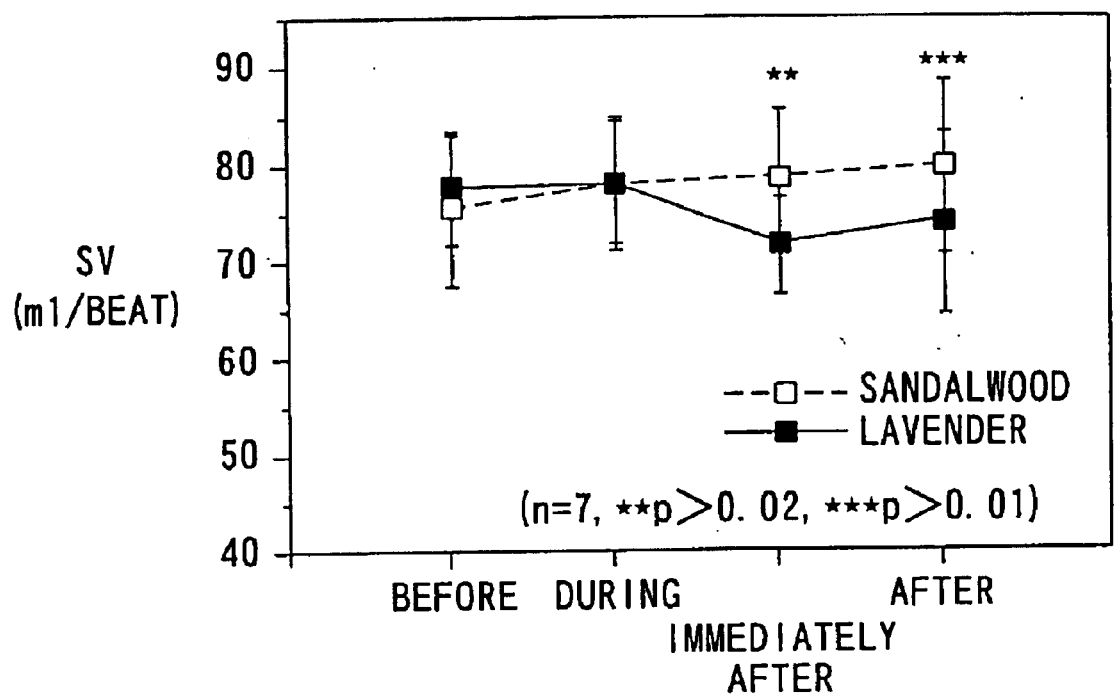
Figure 116B:
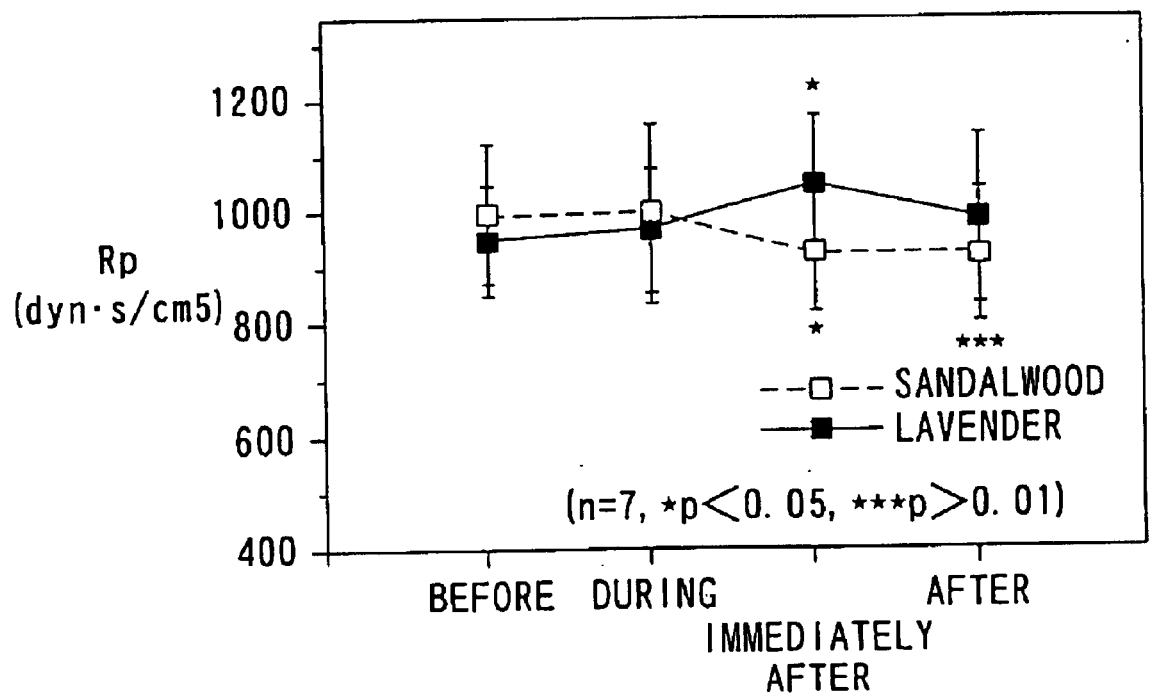

Changes in the circulatory parameters due to the effect of the fragrance were confirmed in this experiment. Of the data obtained in this experiment, data on stroke volume per beat SV and blood vessel resistance Rp are shown in FIGS. 116A and 116B. In these figures, indications of when the measurements were taken are shown along the horizontal axis. Here, "BEFORE" indicates that measurements were taken prior to sniffing the fragrance; "DURING" indicates that measurements were taken after the subject had been sniffing the fragrance for 6 minutes; "IMMEDIATELY AFTER" indicates that measurements were taken after 3 minutes had passed since the subject stopped sniffing the fragrance; and "AFTER" indicates that measurements were taken after 6 minutes had passed since the subject stopped sniffing the fragrance.

As shown in FIGS. 116A and 116B, a significant increase in blood vessel resistance Rp (namely, transition to a sedate state) due to sniffing the lavender fragrance could be confirmed, while a significant increase in stroke-volume-per-beat SV and a significant decrease in blood vessel resistance Rp (namely, transition to an aroused state) due to sniffing of a sandalwood fragrance could be confirmed.

In this way, then, it was confirmed by these preliminary investigations that lavender has a sedating effect, while sandalwood has an arousing effect.

Confirmation of Rhythmic Variation in Circulatory Parameters

It is known that human beings cycle through states of arousal or sedation according to regular rhythms on a daily basis. The present device is concerned with controlling the physical state of the human body to a desirable result by emitting fragrances. When investigating the means by which to realize this objective, it is necessary to grasp the past behavior of the physical condition in the case where no manipulation is being carried out. Therefore, the present inventors studied the changes over time in the circulatory parameters and other physiological conditions as described above, and were thereby able to confirm the rhythmic changes which occur in the conditions in the human body.

Summary

Based on the results of the above investigation, points which should be taken into consideration when designing the present device may be summarized as follows.

1. Since different fragrances have different effects, it is necessary to decide the type of fragrance based on the desired effect.

2. The amplitude of the rhythm of daily changes is very large. Accordingly, even where controlling the physical condition in a human being using fragrances, it is necessary to consider the rhythm of the daily changes, rather than just controlling emission of the fragrance based on the current values of the circulatory parameters.

3. The values of the circulatory parameters exhibit considerable variation across individuals. Accordingly, it is necessary to control the emission of the fragrance based on the rhythm of daily changes in the circulatory parameters of the individual user.

Embodiment 1

From the above preliminary investigation, the inventors confirmed that human subjects pass through phases of arousal and sedation throughout the day according to a regular rhythm. Some individuals whose biorhythms provide desirable transitions between the states of arousal and sedation are fortunate to be able to maintain these rhythm over long periods of time. However, these regulating rhythms can be disturbed by a variety of causes. When this happens, it is necessary to "reset" the rhythms to their natural state. Further, some individuals may become overly aroused or overly sedate. Accordingly, it is necessary to provide them with a means to avoid this. Finally, individuals who tend to become overly sedate and individuals who tend to become overly aroused also require a means to shift back into a more appropriate state.

The device of this embodiment regularly measures the circulatory parameters of the user and releases fragrance as necessary based on the results of these measurements. As described above, circulatory parameters vary rhythmically in a regular manner throughout the day. Accordingly, the need for fragrance emission cannot be determined solely on the circulatory parameters at a particular point in time. Therefore, regulation of fragrance emission is carried out based on the current values of each of the circulatory parameters taking into consideration the rhythmic changes that occur in the circulatory state. Further, how rhythm changes for arousal and sedation are most desirably manipulated varies according to the user. Therefore, the inventors made it possible for the user to select the desired control mode to determine when fragrance emission should be performed.

FIGS. 117 through 123 show each of the modes for regulating fragrance emission which are possible in the present embodiment. In these figures, the solid line indicates the natural changes over time in the states of arousal and sedation in the subject, while the dotted line shows changes over time in the subject's state when regulated by fragrance emission. An explanation will now be made of each of the modes for regulating fragrance emission shown in these figures.

1. Mode 1

Figure 117:
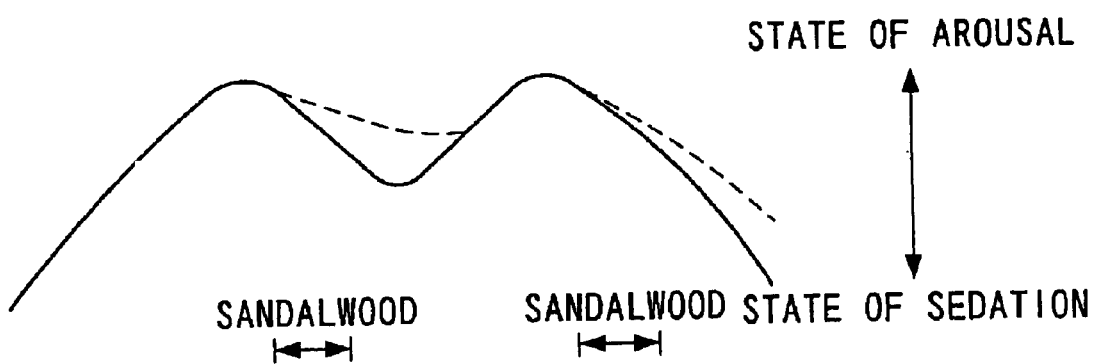

Mode 1 controls against the transition to a sedate state by releasing sandalwood (which has a stimulating effect) during a time period in which the user begins to move into a sedate state (FIG. 117). This mode is desirable for users who do not wish to become overly sedate.

2. Mode 2

Figure 118:
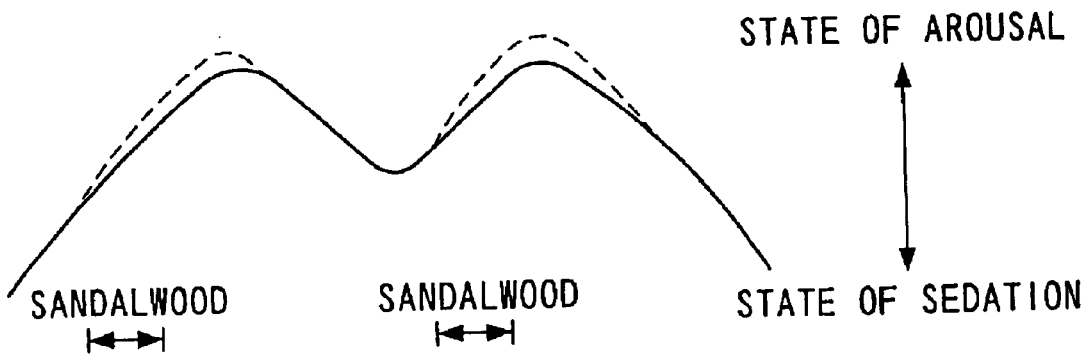

Mode 2 promotes transition to an aroused state by releasing sandalwood (which has a stimulating effect) during a time period when the user begins to move into an aroused state (FIG. 118). This mode is desirable for users who wish to speed up transition from a sedate to an aroused state.

3. Mode 3

Figure 119:
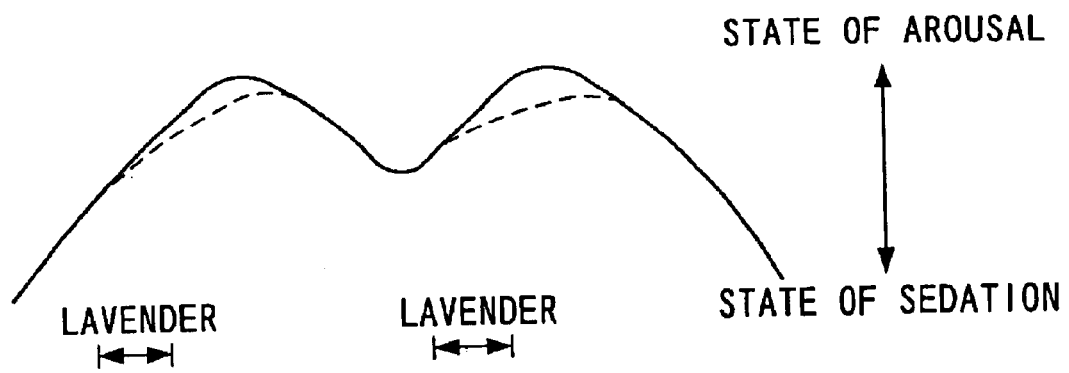

Mode 3 controls against the transition to an aroused state by releasing lavender (which has a sedating effect) during the time period when the user begins to move into an aroused state (FIG. 119). This mode is desirable for users who wish to avoid entering a state of excessive arousal.

4. Mode 4

Figure 120:
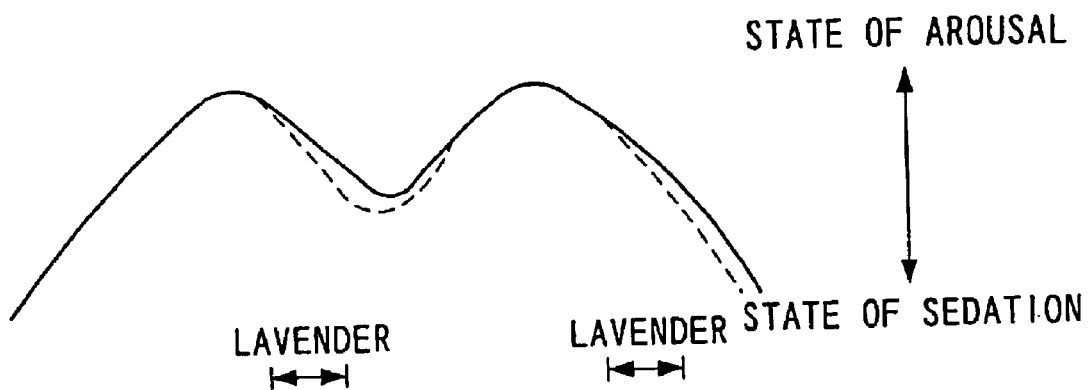

Mode 4 promotes transition to a sedate state by releasing lavender (which has a sedating effect) during the time period when the user begins to move into a sedate state (FIG. 120). Thus mode is desirable for users who wish to speed up transition from an aroused state to a sedate state.

5. Mode 5

Figure 121:
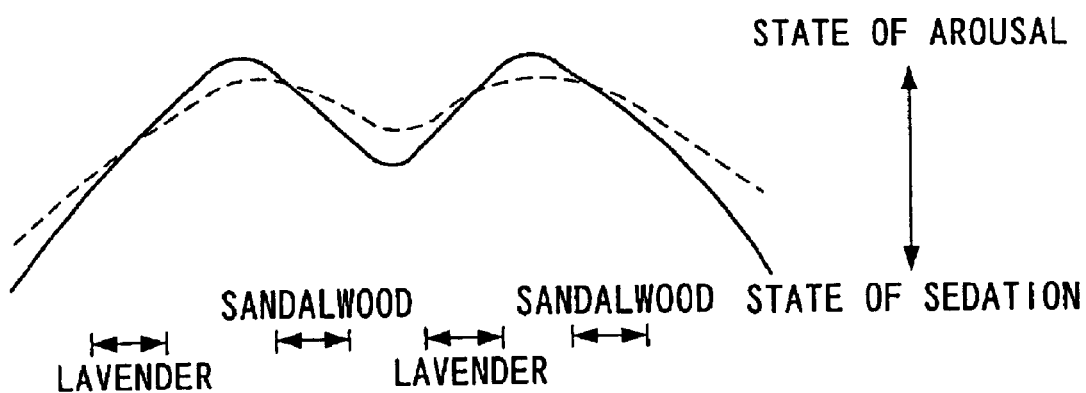

Mode 5 controls against the transition to an aroused state by releasing lavender during the time period when the user begins to move into an aroused state, and controls against transition to a sedate state by releasing sandalwood during the time period when the user begins to move into a sedate state (FIG. 121). This mode is desirable for users who need to maintain a constant state.

6. Mode 6

Figure 122:
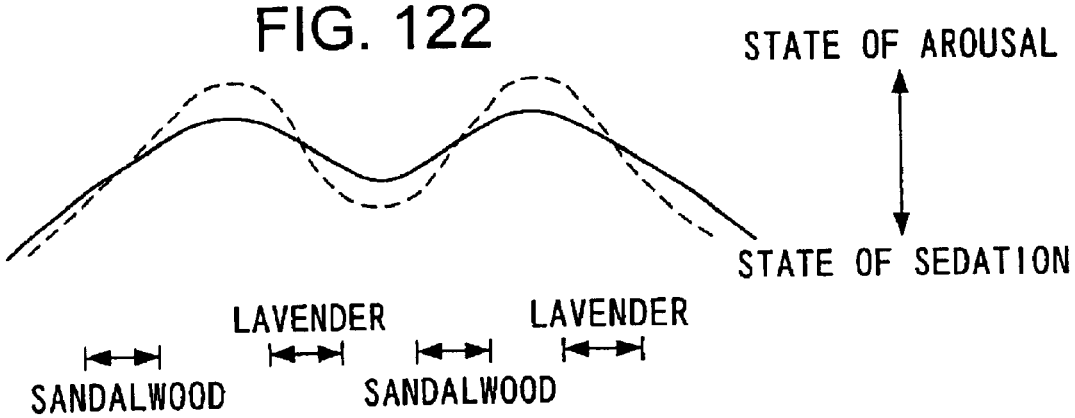

Mode 6 promotes transition to an aroused state by releasing sandalwood during the time period when the user begins to move into an aroused state, and promotes transition to a sedate state by releasing lavender during the time period when the user begins to move into a sedate state (FIG. 122). This mode is optimal for users who wish to modulate biorhythms.

7. Mode 7

Mode 7 releases fragrance to regulate a change in the state of arousal or sedation in the case where this change is opposite the biorhythm fluctuations which have occurred in the past. Namely, when a transition to a sedate state is confirmed during the time periods TA and TC during which the user would ordinarily be moving into a state of arousal, mode 7 provides for the release of sandalwood to control against transition to a sedate state. Similarly, when transition to an aroused state is confirmed during the time periods TB and TD during which the user would ordinarily be moving into a state of sedation, mode 7 provides for the release of lavender to control against transition to an aroused state (see FIG. 123). Accordingly, this mode is effective in controlling against abrupt transition to states of sedation or arousal.

Structure of the Device

FIG. 124 is a block diagram of the functional structure of the device of this embodiment.

Blood pulse detector 750 is a provided to measure the radial artery waveforms of the subject, while first and second fragrance emitting means 500 and 600 are provided to release lavender and sandalwood, respectively. Detailed explanations of these were provided in Part 1 above.

The device of this embodiment has a battery 760 and an electrical supply controller 761 which carries out the intermittent supply of electricity. Electrical supply controller 761 supplies the output voltage from battery 760 to each of controller 740, blood pulse detector 750, first fragrance emitting means 500 and second fragrance emitting means 600 only when necessary (i.e., when controller 740 is performing calculations, or when the fragrance emitting means are releasing fragrances). Because the voltage of battery 760 is intermittently supplied to each part, it is possible to keep electrical consumption down to a low level. Thus, it is possible to operate the device over a long period of time. Further, the output voltage of battery 760 is monitored by a microcomputer inside controller 740 which will be explained below. Therefore, when the output voltage falls below a prespecified level, a warning to that effect is provided. Accordingly, the user is alerted that the battery needs to be replaced.

Figure 125A:
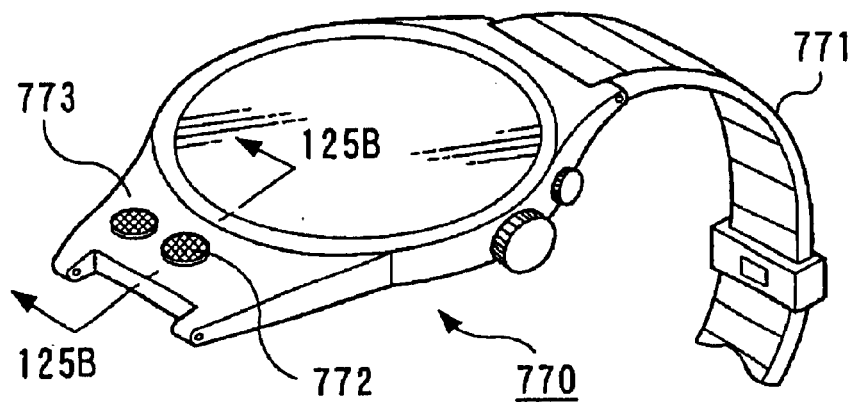
Figure 125B:
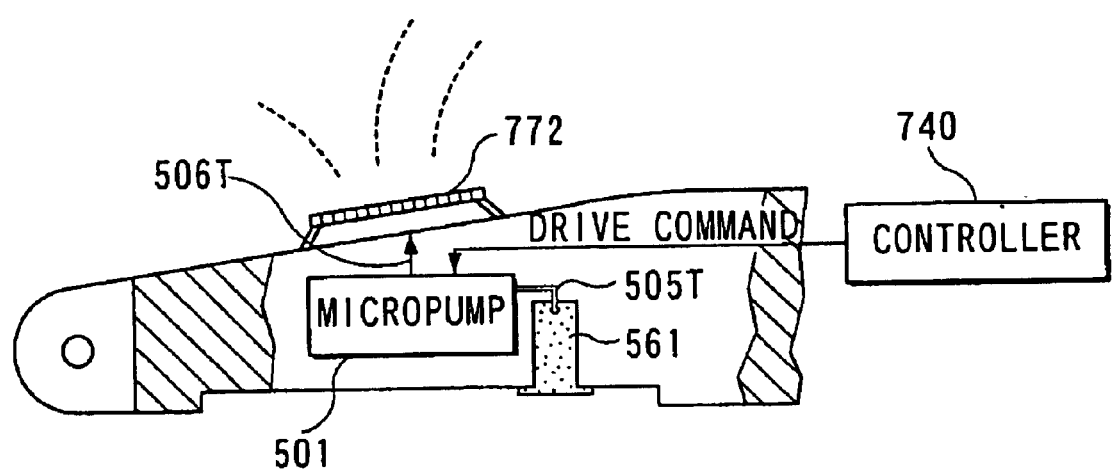

FIGS. 125A and 125B show the complete structure of the device of this embodiment. FIG. 125A is a perspective view showing the outside of the device, while FIG. 125B is a cross-sectional view along the line A–A' in FIG. 125A. As shown in these figures, in this embodiment, an arrangement incorporated into a wrist watch having the pressure-type blood pulse wave sensor explained in Chapter 2, Section 1, Part 4 is employed.

The structure in cross-section of the area of attachment of watch band 771 in watch main body 770 is as shown in FIG. 125B. Tank 561 and micropump 501 explained in Part 1 are contained therein. These form first fragrance emitting means 500 shown in FIG. 124. Micropump 501 siphons up lavender fragrance from tank 561 via a tube 505T in accordance with a drive order sent from controller 740. The fragrance thus taken up is jetted to the outside via tube 506T from jet hole 772 which is formed in the surface of watch main body 770.

Figure 123:
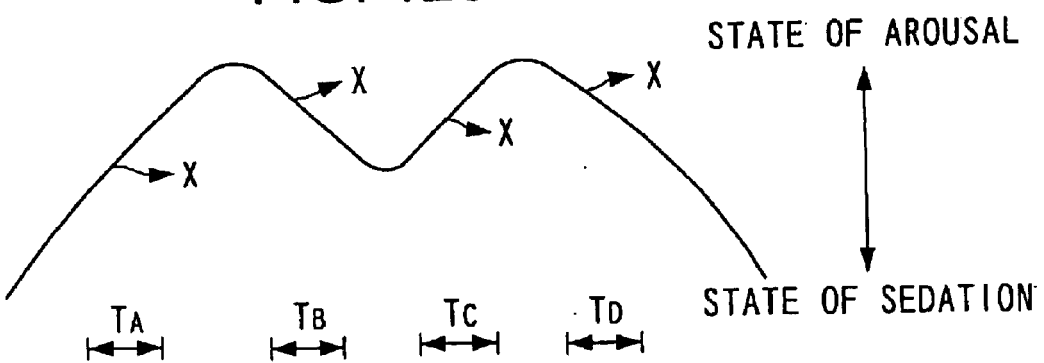

Additionally, a structure corresponding to the second fragrance emitting means 600 shown in FIG. 123 is also provided in watch main body 770, but is omitted from the figure for simplicity. The sandalwood fragrance which is siphoned up by second fragrance emitting means 600 is jetted to the outside from jet hole 773.

Next, with reference again being made to FIG. 124, the structure of controller 740 will be explained. Memory 741 is a non-volatile memory composed of random access memory or the like and is supplied with a back-up battery. Microcomputer 745 is used to temporarily store control data for regulating the rest of the parts in the device. Further, the prespecified memory area in memory 741 stores circulatory parameters measured at a plurality of different times.

Input portion 742 is provided for inputting various commands to microcomputer 745 such as the commands to set one of modes 1 through 7 explained above. Input portion 744 is formed by a watch stem, button or the like provided to watch main body 700 shown in FIG. 125A, for example.

Output portion 743 is formed of a liquid crystal display device, alarm device or the like provided to watch main body 770.

Under the regulation of microcomputer 745, waveform extraction memory 744 receives detection signals from blood pulse detector 750, and extracts and stores the blood pulse-wave for one beat from the signal taken up. Further details on this are provided in Chapter 3, Section 1, Part 2.

Microcomputer 745 regulates each part within controller 740 according to commands input via input portion 742. Further, microcomputer 745 contains the watch circuit. After each elapse of a fixed period of time, microcomputer 745 carries out the following timer interruption process.

1. Control of Blood pulse Wave Signal Uptake by Waveform Extraction Memory 744 and Blood pulse Wave Extraction for One Beat Peak information is obtained as each peak in a blood pulse is detected by waveform extraction memory 744, and is written into the internally housed memory.

2. Calculation of Circulatory Parameters

Based on the peak information obtained in number 1. above, the waveform values of the blood pulse waves for one beat are read out from waveform extraction memory 744. Based on these blood pulse waves, then, the circulatory parameters of the user are obtained. This embodiment employs the method for obtaining parameters from the blood pulse wave distortion, and the high harmonic phase and amplitude of the blood pulse wave spectrum which was discussed in Chapter 4, Section 1, Part 3. The thus obtained circulatory parameters were then stored in memory 741 along with information indicating the time of measurement of the blood pulse wave.

By repeating the above processing at fixed intervals, the circulatory parameters over time are stored in memory 741.

Microcomputer 745 references circulatory parameters obtained over a fixed interval of time in the past which are stored in memory 741, and uses this data to regulate fragrance emission by first fragrance emitting means 500 and second fragrance emitting means 600. An explanation of the details of this regulation will be omitted here, but will be explained below when the operation of the embodiments is explained.

First fragrance emitting means 500 and second fragrance emitting means 600 are formed of a micropump and a drive therefor. First fragrance emitting means 500 emits lavender fragrance, while second fragrance emitting means 600 emits sandalwood fragrance. In this embodiment, tank 561 shown in FIG. 109 may be filled with lavender or sandalwood.

I/O interface 755, which is provided to carry out communication with external devices, was explained in detail in Chapter 5, Section 3. By employing this I/O interface 755, the physiological states or the information on the record of fragrance emission, which are stored in memory 741, can be transferred to an external device.

Physical activity detector 756 is one example of a means for detecting the physical activity of the device's user. Physical activity detector 756 converts the measured value of physical activity into a digital signal and sends it to microcomputer 745.

Operation of the Device
(1) Regular Measurement of Circulatory Parameters

As explained above, a regular timer interruption is carried out to microcomputer 745. As a result, the following processing is executed by microcomputer 745 as a timer interrupt routine.

To begin with, processing is carried out to collect the blood pulse waveform and the peak information therefor. A detailed explanation of this processing is provided in Chapter 3, Section 1.

When measuring the blood pulse wave, microcomputer 745 reads out the output from physical activity detector 756 and stores the output in memory 741. Microcomputer 745 then determines whether or not the values output from physical activity detector 756 indicate that the user is in a state of repose. Since there is a concern that the blood pulse wave measurements will be inaccurate if the user is not in a state of repose, microcomputer 745 notifies the user using output portion 743. The blood pulse waves are then measured once microcomputer 745 confirms that the user is in a state of repose suitable for measuring the blood pulse waves.

Next, microcomputer 745 executes waveform readout and the calculation of circulatory parameters. Namely, microcomputer 745 reads out the waveform value of the blood pulse wave of a single beat from waveform extraction memory 744, and uses a FTT process to obtain the blood pulse wave spectrum (amplitude and phase information).

The value of one parameter, inductance L for example, in the lumped four parameter model is then calculated based on this spectrum. The other parameters are then calculated based on the value of inductance L and the waveform of a blood pulse wave of a single beat. Microcomputer 745 then writes the thus obtained circulatory parameters in memory 741 together with information indicating the current time and date.

(2) Regulation of Fragrance Emission

The operation to regulate fragrance emission differs in the case where one of modes 1 through 6 are selected, and in the case where mode 7 is selected. The operation in each case will be explained below.

1. Selection of One of Modes 1 Through 6

When one of these modes is selected, once a prespecified time late at night is reached, microcomputer 745 carries out processing to determine when to release fragrance. Namely, microcomputer 745 reads out past circulatory parameters obtained over a fixed time interval (a specific number of days) which have been stored in memory 741, and calculates the transition average for the times when a specific parameter (for example, resistance RP) reaches its maximum and when it reaches its minimum. Based on the results of these calculations, microcomputer 745 obtains the time periods during which the user moves from a sedate to an aroused state (periods TA and TC in FIG. 123), and the time periods during which the user moves from an aroused to a sedate state (periods TB and TD in FIG. 123). Next, microcomputer 745 sets fragrance emission commands so that the appropriate fragrance of the selected mode will be released at a specified time of the day (for example, at the middle of the time period) in the time period determined as above. For example, when the selected mode is mode 5, microcomputer 745 carries out the following four kinds of time interval settings for fragrance emission.

driving of second fragrance emitting means 600 at a prespecified time of the day in time period TA driving of first fragrance emitting means 500 at a prespecified time of the day in time period TB driving of second fragrance emitting means 600 at a prespecified time of the day in time period TC driving of first fragrance emitting means 500 at a prespecified time of the day in time period TD Then, at the specified times throughout the day, microcomputer 745 sends out a drive order to the fragrance emitting means. When a drive order is generated by microcomputer 745, the first and second fragrance emitting means 500, 600 emit their corresponding fragrance from jet holes 772 and 773, respectively, to the outside. The fragrance is siphoned up from tank 561 to micropump 501. If microcomputer 745 receives an anomaly detection signal from first or second fragrance emitting means 500, 600, it carries out the display of an alarm on output portion 743. As a result, when fragrance emission is not carried out in a normal fashion, the user is immediately informed of this fact so that prompt adjustment, etc., of the emitting means can be performed.

Once fragrance emission is complete, the quantity of fragrance emitted is computed based on the number of times a drive command was generated. The release quantity and the type of fragrance emitted are written in memory 741 as release memory information. Further, a total is obtained for the amount of fragrance emitted until that point in time for each fragrance, and is also written in memory 741. When this total exceeds a prespecified value, microcomputer 745 sends a warning output order to output portion 743. Output portion 743 then alerts the user to change tank 561 by means of a light on an alarm lamp or the like. In this way, the user is alerted when it is time to refill the fragrance.

2. Selection of Mode 7

Microcomputer 745 reads out circulatory parameters recorded in memory 741 at prespecified times late at night in this mode, as well. Based on this readout, microcomputer 745 determines the time periods in which the user transitions from a sedate to an aroused state (periods TA and TC), and from an aroused to a sedate state (periods TB and TD) (see FIG. 123). In this mode, fragrance emission is carried out in the thus determined time periods based on the observation of changes over time in circulatory parameters and the observed results.

Namely, microcomputer 745 regularly measures the circulatory parameters during one of the periods TA, TB, TC and TD throughout the day. Microcomputer 745 then determines whether the circulatory parameters just obtained are increasing or decreasing versus their previously obtained values. Next, microcomputer 745 determines whether the change over time in the circulatory parameters is opposite that which normally should be occurring in the user's circulatory parameters at that period of the day. If microcomputer 745 determines that the change occurring over time in the circulatory parameters is opposite that which normally occurs, then fragrance is released to regulate this irregular change.

For example, resistance RP normally declines during the aforementioned period TA as the user moves from a sedate to an aroused state. A declining resistance RP during this period would be normal, indicating that no adjustment of the user's internal state is necessary. An increasing RP during this period, however, is opposite the change in this circulation parameter which normally occurs in the user. In this case, then, microcomputer 745 sends a drive order to second fragrance emitting means 600 to release sandalwood fragrance. The increase in resistance RP, and thus the transition to a sedate state, is thereby controlled against. In contrast, resistance RP ordinarily increases during period TB. Thus, when RP is declining during this period, microcomputer 745 sends a drive order to first fragrance emitting means 500 to release lavender fragrance, thereby halting the decrease in resistance RP.

In this way, the control of fragrance emission is carried out based on changes over time in circulatory parameters. Control or promotion of the state of sedation or arousal of the user is automatically carried out with optimal timing using this fragrance emission. As a result, it is possible to control the condition of the user over time in accordance with desired rhythm changes.

Embodiment 2

In contrast to the drug releasing device of embodiment 1 wherein regulation of fragrance emission was carried out based on the shape of the blood pulse waveforms, in this embodiment fragrance emission is controlled based LF, HF, and [LF/HF]. The following explanation will be carried out using [LF/HF] as a representative example of these indicators. However, control is carried out in the same way when LF or HF are employed, with the exception that the type of fragrance to be emitted in the case of HF is reversed.

Structure of the Device

The structure of this embodiment is identical to that of the first embodiment.

Operation of the Device (1) Regular Measurement and Spectral Analysis of Blood pulse Wave As explained above, regular (at 2 hour intervals, for example) timer interruptions are generated with respect to microcomputer 745. At these times, then, microcomputer 745 carries out the following time interrupt routine.

To begin with, as in Embodiment 1, the waveforms and the peak information of these waveforms are collected. In this embodiment, this blood pulse wave uptake processing is carried out at every measurement, for example, every 30 seconds. Next, the uptaken blood pulse waveforms and [LF/HF] are calculated and stored together with the time at which these measurements are made in memory 741.

The above-described regular measurement and the spectral analysis of blood pulse wave are carried out every two hours.

(2) Regulation of Fragrance Emission

As in embodiment 1, in this embodiment as well, the operation to regulate fragrance emission differs in the case where one of modes 1 through 6 are selected, and in the case where mode 7 is selected. The operations for each case will be explained below.

1. Selection of one of modes 1 through 6

Microcomputer 745 determines the period of fragrance emission at a prespecified time late at night. Namely, microcomputer 745 reads out from memory 741 the [LF/HF] values for a fixed number of past days (the past week, for example), and obtains an average [LF/HF] value in each time period. Next, microcomputer 745 calculates the time of day when the average value of [LF/HF] reaches its maximum and minimum values.

Next, based on these calculated results, microcomputer 745 obtains the time periods during which the user moves from a sedate to an aroused state, and from an aroused to a sedate state. Microcomputer 745 then sets fragrance emission commands so that the appropriate fragrance of the selected mode will be released at a specified time of day (for example, at the middle of the time period) in the time periods obtained.

Subsequently, once the designated time of day is reached, microcomputer 745 carries out fragrance emission by driving first fragrance emitting means 500 or second fragrance emitting means 600. When fragrance emission is complete, as in Embodiment 1, the volume of fragrance emitted is calculated and stored in memory 741 along with the type of fragrance emitted as release recording information. In addition, the cumulative total for the quantity emitted is obtained for each fragrance and stored in memory 741.

2. Selection of Mode 7

As in number 1. above, microcomputer 745 determines the average value of [LF/HF] over a period of a week from [LF/HF] values stored in memory 741. Next, microcomputer 745 calculates the times of the day at which this average value reaches its maximum and minimum. Next, based on the thus obtained times of the day, microcomputer 745 obtains the time periods during which the user transitions from a sedate to an aroused state and from an aroused to a sedate state. Next, during the following day, microcomputer 745 carries out regulation of fragrance emission based on monitoring of changes over time in the [LF/HF] during the obtained time period and the results of this monitoring.

In other words, microcomputer 745 regularly measures the value of [LF/HF], and determines whether the current [LF/HF] value is increasing or decreasing from its previous value. Next, microcomputer 745 determines whether the changes over time in these values is opposite those which normally occur during the time period associated with the time of the day at which the regular measurement was made. If the change is determined to be opposite that which normally occurs, fragrance is released to regulate this anomalous change.

For example, a decreasing [LF/HF] value in a time period during which the user should be moving from a sedate to an aroused state is opposite the change over time which normally occurs. Accordingly, microcomputer 745 sends a drive command to second fragrance emitting means 600 to release sandalwood fragrance, thereby causing the user to move into a state of arousal. Further, if the [LF/HF] value is increasing during a time period in which the user should be moving from an aroused to a sedate state, microcomputer 745 sends a drive command to first fragrance emitting means 500 to release lavender fragrance, thus moving the user into a sedate state.

Embodiment 3

The device of this embodiment resembles that of Embodiment 2 in that the emission of fragrance is carried out based on information regarding the blood pulse tidal wave. However, this embodiment differs in that it employs RR50 as the physiological state.

Structure of the Device

The structure of this embodiment is identical to that of the first and second embodiments.

Operation of the Device (1) Regular Measurement of Blood pulse

As described above, periodic, (for example, at two hour intervals) timer interruptions are generated with respect to microcomputer 745. As these times, then, microcomputer 745 carries out the following timer interrupt routine.

First, as in Embodiment 2, the waveforms and the peak information of these waveforms are collected and recorded. Once one measurement phase is ended, microcomputer 745 carries out peak detection on each blood pulse of the blood pulse wave obtained during the measurement period. RR50 is calculated and stored in memory 741 together with the time at which measurements were made.

The above described regular measurements of blood pulse wave are carried out at two hour intervals throughout the day.

(2) Control of Fragrance Emission

With the exception that the operation to regulate fragrance emission here employs RR50 instead of [LF/HF] values, the operation of this embodiment is identical to that of the second embodiment. As explained above, a larger [LF/HF] value indicates a more aroused state, while a smaller [LF/HF] value indicates a more sedate state. In contrast, in the case of RR50 values, a larger value indicates a more sedate state, while a smaller value indicates a more aroused state. Accordingly, the selection standards for fragrance emission in fragrance emission control are opposite those in the second embodiment.

(Modifications)

1. The present device may be incorporated in an accessory or pair of eye glasses.

2. The previous embodiments employed two fragrance emitting means, however, a device that releases only one type of fragrance may also be constructed.

3. In the mode 7, fragrance is released when circulatory parameters during a specified time period are changing in a way which is opposite the change which has occurred in the past during that time period (i.e., rising when they should be falling, etc.), however this mode may be modified.

Namely, in place of, or addition to, mode 7, a mode may be provided wherein fragrance is released when circulatory parameters are measured during a specific time period that are outside dispersion limits (for example, average value E±3s, where s is standard deviation) determined from parameter values over the preceding several days, this fragrance being one which will cause the circulatory parameters to return to within the dispersion limits.

4. The previous embodiments employed lavender and sandalwood as the fragrances to modify circulatory parameters. However, whether a particular fragrance is appropriate will differ to some degree according to individual differences. Accordingly, depending on the user, fragrances other than sandalwood and lavender may be more appropriate to generate effects of sedation and arousal. Therefore, when using the device according to these embodiments, it is desirable to first confirm the type of fragrance most appropriate to set in first fragrance emitting means 500 or second fragrance emitting means 600.

The preceding explanation employed the case where lavender and sandalwood were employed as examples of drugs. However, provided that a correlation relationship such as described above is present with the physiological state, then fragrances other than lavender and sandalwood may be employed, or substances other than fragrance may be used.

5. Two manual switches may be added to the above embodiments, so that lavender is released when the first switch is operated, and sandalwood is released when the second switch is operated.

6. The phase of a high harmonic wave, the fourth harmonic wave for example, with respect to the fundamental wave can be detected using spectral analysis of the blood pulse wave, and control of fragrance emission can be carried out based on this value.

In other words, the inventors were able to confirm in testing that changes occur in each phase of the second, third and fourth higher harmonic waves, and in the amplitude of the third higher harmonic wave when subjects are stressed. For example, in the case of a physical stress such as immersing one hand in water at a temperature of 4° C., the inventors confirmed from an examination of the blood pulse waves of 8 test subjects that changes occurred in the phases of the second, third and fourth higher harmonic waves, and in the amplitude of the third higher harmonic wave 95% of the time. Further, in the case of a psychological stress such as requiring the subjects to repeatedly subtract 9 from 1000, the inventors confirmed from an examination of the blood pulses of 8 test subjects that changes occurred in the phase of the fourth higher harmonic wave 95% of the time.

7. The number of heart beats may be employed instead of RR50 in Embodiment 3. As is commonly known, a negative correlation is observed between RR50 and the number of heart beats. Accordingly, by carrying out control of fragrance emission where the selection of fragrance is opposite that of the third embodiment (i.e., identical to the second embodiment), the same effects can be obtained as described above. Further, the various values of body temperature, blood pulse number or the like obtained from the waveform from the electrocardiogram may be employed.

8. Emission of the fragrance or other drug may be carried out according to a keyed input by the user.

9. It is also acceptable to design the device so that, after the user has assumed a state of repose prior to measuring the blood pulse waves, he may use input portion 742 to notify this fact to the device. In this case it is also convenient to provide the user with a means of determining whether his position is suitable for making blood pulse wave measurements. This can be accomplished by informing the user of the suitability of his position as determined by the output value of physical activity detector 756.

It is also acceptable to design microcomputer 745 to constantly detect for a reposed state using physical activity detector 756, and then carry out detection of the blood pulse way only when the user is in a state of repose for a specified interval of time.

Moreover, rather than waiting for the user to enter a state of repose, measurement of blood pulse wave and physical activity can be carried out over a specific period of time, with the measured values then stored together in memory 741. Based on the stored results of physical activity measurements, only the blood pulse wave measurement taken when the user was in a state of repose for a specified period of time may be selected, to obtain blood pulse wave information.

10. In each of the preceding embodiments, it is acceptable to detect the effect of a drug, such as a fragrance, and then inform the user of this fact. Namely, after directing emission of a fragrance, microcomputer 745 measures blood pulse waves in the user, calculates the physiological state, and then determines whether or not the thus obtained physiological state (which will differ depending on the above described modes) has reached a desired state. Once an effect is noted, microcomputer 745 determines that it is not necessary to emit any more fragrance, and informs the user of this fact via output portion 743.

11. When emitting a drug, it is permissible to carry out detection of the blood pulse waveform, and emit the drug to the organism in between successive blood pulse outputs (i.e., between successive waveforms) of blood from the heart (i.e. blood pulse cycle). In this way, emission of a pharmacological agent can be carried out when the internal pressure of the hypodermic tissue is low, improving the efficiency of the emission so as to be extremely effective.

Part 4 Doze Prevention Device

Some examples of applications will now be explained in which diagnosis and control are carried out based on the physiological state (indicators of blood pulse wave fluctuation), while taking into consideration the regular changes therein. The doze prevention device which will be explained below is not a device for directly controlling the physiological state, but is a device for controlling external equipment (an automobile, for example). Further, this explanation will be made from the perspective of "control".

In recent years, numerous accidents have occurred due to drivers dozing off while operating an automobile. A variety of devices have been proposed to prevent this from occurring. One example which may be considered is a device attached to the steering wheel. In this device, conductors are attached to the left and right sides of the steering wheel, and measurements of the driver's resistance are made by having both of the driver's hands in constant contact with the conductor. If the driver dozes off and his hand falls from the steering wheel, the resistance value between the conductors changes. As a result, it is perceived that the drive has dozed off, and a warning sound is issued to the driver. In this way, it becomes possible to prevent an accident from occurring due to dozing off by the driver.

Other devices may employ changes in heart beats obtained from measurements in the electrocardiogram of the driver, or changes in the driver's respiration.

However, in the method described above in which conductors are attached to the steering wheel, it is not possible to accurately monitor for a doze state when the driver is driving with just one hand, or is wearing gloves. Additionally, in the methods employing changes in heart beat or respiration, the devices used are large, and thus not convenient for the driver to carry about with him.

The device described here is intended to resolve these problems by detecting a doze state based on an analysis of the alertness level of the human body from the activity of the blood pulse waves obtained therefrom.

Embodiment 1

The doze prevention device of the present embodiment detects doze states based on the correlation relationship which exists between the information included in the blood pulse wave and the level of alertness in the human body. In this case, a number of measured quantities obtained from the blood pulse wave are employed as indicators to determine the level of alertness in the human body. LF, HF, [LF/HF] and RR50 will be employed as specific examples below. From the above correlation relationship, the physiological state becomes more sedate as the doze state becomes deeper. RR50, for example, is believed to become gradually larger as the doze state progresses. Accordingly, it is possible to detect a doze state by detecting the change in these indicators.

Structure of the Device

FIG. 126 is a block diagram showing the structure of this device. The device's user (for example, an automobile driver or train operator) wears the wrist watch 790 shown in FIG. 127, with the device shown in FIG. 126 incorporated inside this wrist watch 790.

In FIG. 126, CPU 781 is a central part for controlling each circuit inside the device. The function of CPU 781 will be explained below.

Control programs and control data for CPU 781 are stored in ROM 782.

Temporary memory 783 is one type of RAM which is used as an operational area when CPU 781 is carrying out calculations.

Blood pulse wave detector 784 constantly measures the blood pulse wave at the user's radius artery, and outputs the measured result as an analog signal.

A/D converter 785 quantifies the analog signal, converts it to a digital signal and outputs it.

Data memory 786, which is a non-volatile memory composed of battery backed-up RAM or the like, stores LF, HF, LF/HF, and RR50 values that were calculated based on the blood pulse wave, and on data such as blood pulse waveforms uptaken by CPU 781 from A/D converter 785.

Watch circuit 787 generates the time of day which is displayed on wrist watch 790. CPU 781 reads out the time from time circuit 787 in order to know the current time.

Operator 788 is provided with a variety of buttons which are provided to wrist watch 790. Operator 788 detects the depression of these buttons and outputs the type of button depressed.

Buzzer 789 generates a warning sound directed at the user, based on commands to start or stop the sounding operation from CPU 781. In practical application, this buzzer 789 may be an alarm mechanism attached to a commercially available digital-type wrist watch.

I/O interface 850 carries out communication between the device of the present invention and an external device, and is equivalent to the I/O interface explained in Chapter 5, Section 3. By employing I/O interface 850, information such as the values of LF, HF, LF/HF, and RR50 stored in data memory 786 can be transferred to an external device.

Acceleration sensor 851 is one example of a physical activity detection means for picking up the physical activity of the device's user. A/D converter 852, which has the same structure as A/D converter 785, converts the output from acceleration sensor 851 into a digital signal and relays the digital signal to a bus.

The wrist watch shown in FIG. 127 has two modes: an Ordinary Use Mode, during which the device is used as a regular wrist watch, and a Monitoring Mode, during which the device detects the doze state of the user and issues a warning.

In this figure, the numeral 791 is the main body of a wrist watch which is provided with a time display 792 on the upper surface thereof for displaying time and date in the same way as a regular wrist watch. Time change button 794 (stem) for adjusting the time and mode switching button 795 are provided to the right lateral surface of the watch main body 790. Mode switching button 795 is provided for switching between the Ordinary Use Mode and the Monitoring Mode. Each time this button is depressed, switching between the two modes occurs. The Ordinary Use Mode is initialized when a power source is inserted.

Additionally, as explained in Chapter 2, Section 1, Part 4, the numbers 47, 48, and 49 indicate a pressure-type blood pulse wave sensor, a fastener, and a wrist watch band, respectively.

Operation of the Device

An explanation will now be made of the case where detection of a doze state is carried out using RR50 as the above described indicator.

(1) Shift to Monitoring Mode

The device user depresses mode switching button 795 of wrist watch 790 before beginning operation of a motor vehicle, for example. Operator 788 detects the depression of the button and sends a message to CPU 781 that switching button 795 has been depressed. CPU 781 switches the device from the current ordinary use mode to the monitoring mode, thereby enabling the function for monitoring for a doze state during driving.

(2) Uptake of Blood pulse Waveform

Blood pulse wave detector 784 is constantly measuring the blood pulse wave at the radius artery of the user. This measured result is converted to a digital signal at A/D converter 785, and output to a common bus. CPU 781 reads out this digital data during a prespecified interval of time once the monitoring mode is enabled from depression of the button as described above. The read out digital data is stored in data memory 786 together with the current time read out from watch circuit 787.

However, the following may be carried out in order to measure the blood pulse wave even more accurately. Namely, CPU 781 reads out and takes up the output of acceleration sensor 851 via A/D converter 852, and stores this output in temporary memory 783. CPU 781 then make a decision as to whether or not the output value of acceleration sensor 851 indicates that the user is in a state of repose. Since there is a concern that the measurements of the blood pulse wave will not be accurate if the user is not in a state of repose, a buzzer 789 or the like is employed by CPU 781 to inform the user in this case. Blood pulse wave measurements are then carried out once it is confirmed that the user is in a state of repose.

(3) Analysis of the Blood pulse Waveform

CPU 781 then analyzes blood pulse waveforms stored in data memory 786 from a prespecified period of time in the past, and calculates the RR50. The calculated RR50 value is then stored in data memory 786 together with the current time of day read out from watch circuit 787.

(4) Determination of Alertness State and Control of Warning Sound

CPU 781 next calculates RR50, and determines whether or not the user is in doze state based on the calculated value. Namely, CPU 781 checks the size relationship between the calculated RR50 value and a predetermined standard value, and determines that the user is in a doze state if the calculated RR50 value is larger than the standard value. CPU 781 then sends a sound warning command to buzzer 789, which then generates a warning sound to bring the user to an alert state.

As the user becomes more alert, the RR50 value gradually falls until it eventually becomes less than the aforementioned standard value. Upon detecting this, CPU 781 sends a stop alarm sounding command to buzzer 789, and the generation of the warning sound from buzzer 789 ends.

Alternatively, a user who has returned to a state of alertness may depress the mode switching button 795. When CPU 781 receives notice from operator 788 that mode switching button 795 has been depressed, it switches the device from the monitoring mode to the ordinary use mode. At the same time, CPU 781 sends a command to buzzer 789 to stop sounding the alarm, so that the generation of the warning sound ends.

Embodiment 2

In the above Embodiment 1, a warning was carried out when the current RR50 value exceeded a fixed standard value. However, it is preferable to take into consideration the regular variation in the indicators of the blood pulse tidal wave. The following explanation of the device according to this embodiment will also employ RR50 as the indicator of physiological state.

Structure of the Device

The structure of the device in this embodiment is equivalent to that of the first embodiment. However, indicators of the blood pulse tidal wave which are collected over a fixed interval of time are sequentially stored in data memory 786.

Operation of the Device (1) Shift to Monitoring Mode

When the device user depresses mode switching button 795, CPU 781 switches the device to the monitoring mode and sets watch circuit 787 to generate interrupt signals at fixed time intervals.

(2) Regular Period of Measurement of RR50

Each time an interrupt signal enters CPU 781 from watch circuit 787, CPU 781 uptakes the radius artery blood pulse wave from blood pulse wave detector 784 via A/D converter 785, calculates RR50 and stores it in data memory 786.

(3) Determination of Alertness State and Control of Warning Sound

Once the above processing is finished, CPU carries out a determination of the doze state. Namely, CPU 781 reads out RR50 values from a fixed period of time in the past, one week for example, and calculates the average transition in the RR50 over the past week. If the current RR50 value exceeds this average value by a prespecified value, CPU 781 determines that the user is in a doze state, and generates a warning sound from buzzer 789.

The subsequent operations are equivalent to those in Embodiment 1. Namely, the user awakens and becomes more alert, or the user depresses the mode switching button 795 so that CPU 781 changes the device to the ordinary use mode, stopping the generation of the warning sound.

As a result, the doze state of a user can be determined based on his daily RR50 level. Thus, misdetection or failure to detect a doze state becomes extremely unlikely, making this device excellent from the perspective of safety.

Embodiment 3

In the preceding embodiments, a warning sound was issued to the driver when a doze state was detected. However, in place of warning the driver, a wireless connection may be affected between the device and the automobile so that when a doze state in the driver is detected, a command is output to the car brakes to apply braking pressure to the vehicle.

Structure of the Device

The structure of the device according to this embodiment is shown in FIG. 128. The same numeric symbols have been applied to parts in this figure which have equivalent functions to those shown in FIG. 126, and an explanation thereof is omitted here.

Transmitter 800 which is provided to wrist watch 790 amplifies the electric signal sent from CPU 781 so that it is suitable for transmitter antenna 801. Transmitter antenna 801 converts this electric signal to radio waves and outputs the radio waves.

The driver is seated in vehicle 810. Receiving antenna 811 receives the radio waves sent from transmitter antenna 801 and converted them to an electric signal. Receiving antenna 812 amplifies this electric signal and outputs the amplified signal to following controller 813. Following controller 813 controls receiver 812, brake device 814 and the various devices inside vehicle 810 which are not shown in the figure. Brake device 814 regulates the control operations of vehicle 810 in accordance with commands from controller 813.

Operation of the Device

In the same sequence as in the preceding embodiments, CPU 781 measures the driver's blood pulse waveforms in the monitoring mode, and analyzes the results to detect whether the driver is in a doze state. CPU 781 send the brake control command signal to transmitter 800. This control command passes through transmitter 800 and is converted to radio waves at transmitter antenna 801, and is then emitted outside watch 790. The radio waves are received by receiving antenna 811 which is provided to one side of vehicle 810, and are converted to an electric signal. This electric signal is amplified at receiver 812 and sent to controller 813. Controller 813 receives the electric signal from receiver 812 and analyzes this command. When controller 813 confirms that the electric signal is a brake control command, it relays the control command to brake device 814. As a result, brake device 814 halts vehicle 810 by applying the brake.

As explained above, by means of each of the preceding embodiments, it is possible to detect a doze state in a user using the relatively simple method of blood pulse wave detection. Thus, it is possible to realize a device which is not large, but which may be embodied so as to permit free portability thereof. Further, this device is additionally advantageous in that it may be incorporated in a wrist watch or other portable device so that it does not interfere with driving or other activities.

(Modifications)

1. This device may incorporated into an accessory or pair of eye glasses.

2. In the preceding embodiment, a determination of the user's state of alertness was made based on the RR50 value. However, in place of the RR50 value, it is also possible to employ LF, HF or LF/HF. Namely, the smaller the amplitude of the LF component, the larger the amplitude of the HF component, or the smaller the value of [LF/HF], the more sedate is the physiological state. In this case, when determining the level of alertness of the user in the processing in (4)of Embodiment 1 above, a determination that the user is in a doze state may be made when the amplitude of LF falls below a standard value, the value of HF exceeds a standard value, or the value of [LF/HF] falls below a standard value.

3. There need not be only one volume to the warning sound. Rather, the volume may increase or decrease in accordance with the difference between the calculated RR50 value and the standard value.

4. LF, HF, [LF/HF], and RR50 values need not be considered separately. Rather, any number or all of these may be considered when making a determination of whether or not to carry out a warning sound.

5. In Embodiment 3, a warning means such as a buzzer 789 or the like may be issued to the driver together with the operation to apply the brake and stop the car.

6. An even greater effect can be obtained by carrying out a warning using a buzzer or the like, while also jetting a fragrance having a stimulating effect like that employed in the fragrance emitting control described above.

7. It is also acceptable to design the device so that, after the user has assumed a state of repose prior to measuring the blood pulse waves, he may use operator 788 to notify this fact to the device. In this case it is also convenient to provide the user with a means of determining whether his position is suitable for making blood pulse wave measurements. This can be accomplished by informing the user of the suitability of his position as determined by the output value of acceleration sensor 851.

It is also acceptable to design CPU 781 to constantly detect for a reposed state using acceleration sensor 851, and then carry out detection of the blood pulse wave only when the state of repose occurs for a prespecified interval of time.

Moreover, rather than waiting for the user to enter a state of repose, measurement of blood pulse wave and physical activity can be carried out over a specific period of time, with the measured values then stored together in memory 786. Based on the stored results of the physical activity measurements, only the blood pulse wave measurement taken when the user was in a state of repose for a specified period of time may be selected, to obtain blood pulse wave information.

8. While the above Embodiment 3 explained the case where an automobile was operated, the present embodiment may of course be suitably employed in other types of vehicles. In addition, rather than providing the notifying means in a portable device, it is also permissible to carry out notification by controlling the horn, etc. provide to the vehicle.

9. Each of the previous embodiments were explained using the case where s warning was carried out after detecting a doze state. However, it is also acceptable to calculate the level of alertness of the user, and inform the user that the level is sufficiently high enough when the information is applicable. As a result, the user's attention is alerted each time notification is made, reinforcing the his awareness to remain alert.

While the invention has been described in conjunction with several specific embodiments, it is evident to those skilled in the art that many further alternatives, modifications and variations will be apparent in light of the foregoing description. Thus, the invention described herein is intended to embrace all such alternatives, modifications, applications and variations as may fall within the spirit and scope of the appended claims.

What is claimed is:

1. A device for controlling a physiological state, comprising:
   a measuring means for measuring an indicator of a physiological state related to arousal or sedation in a patient and a blood pulse waveform in the patient;
   an administering means for administering a drug to the patient;
   a recording means for recording blood pulse waveforms corresponding to a physiological state in which drug administration is necessary; and
   a drug administration control means for comparing the blood pulse waveform measured by the measuring means and the blood pulse waveforms stored in the recording means, and for issuing a command to carry out administration of a drug based on the result of the comparison.

2. A device for controlling a physiological state, comprising:
   a measuring means for measuring an indicator of a physiological state related to arousal or sedation in a patient;
   an administering means for administering a drug to the patient;
   a drug administration control means for issuing a command to the administering means for drug administration when the indicator of the physiological state satisfies specific conditions; and
   a means for detecting the output of a drug administration command, for determining from the point of this detection whether or not the indicator of physiological state has reached a state which does not satisfy the specified conditions, and for providing notification when the indicator of the physiological state has reached a state which does not satisfy the specified conditions.

3. A device for controlling a physiological state according to claim 2, wherein the administering means comprises an infuser of the drug.

4. A device for controlling a physiological state according to claim 2, wherein the administering means comprises an emission of the drug.

5. A device for controlling a physiological state, comprising:
   a measuring means for measuring an indicator of a physiological state related to arousal or sedation in a patient;
   an administering means for administering a drug to the patient;
   a blood pulse detector for detecting a blood pulse cycle of blood sent from the patient's heart; and
   a drug administration control means for issuing a command to the administering means for drag administration when the indicator of the physiological state satisfied specific conditions,
   wherein the drug administration control means issues a command to administer a drug to the administering means during the time interval from one blood pulse beat to the next blood pulse beat in synchronization with the blood pulse cycle.

6. A device for controlling a physiological state according to claim 5, wherein the administering means comprises an infuser of the drug.

7. A device for controlling a physiological state according to claim 5, wherein the administering means comprises an emission of the drug.

8. A device for controlling a physiological state, comprising:
   a measuring means for measuring an indicator of a physiological state;
   a recording means for storing the indicator measured, up until a current point in time;
   a control means for selecting a time period in which the indicator is changing according to a specified trend, and for outputting a command to administer a drug during the time period; and
   an administering means for administering the drug in accordance with the command; and wherein the control means selects a time period in which the indicator is changing according to a specified trend, and outputs a command to administer a drug during the time period.

9. A device for controlling a physiological state, comprising:
 a measuring means for measuring an indicator of a physiological state;
 a recording means for storing the indicator measured, up until a current point in time;
 a control means for selecting a time period in which the indicator is changing according to a specified trend, and for outputting a command to administer a drug when the trend of the change differs from a trend demonstrated by the indicator during a past time period; and
 an administering means for administering a drug in accordance with the command; and
 wherein the control means selects a time period in which the indicator is changing according to a specified trend, and outputs a command to administer a drug when the trend of the change differs from a trend demonstrated by the indicator during a past time period.

10. A device for controlling a physiological state, comprising:
 a measuring means for measuring an indicator of a physiological state;
 a recording means for storing the indicator measured, up until a current point in time;
 a control means for determining when a drug is to be administered based on a rhythm of variation displayed by the indicator over a specified period of time, and for outputting a drug emission command at a determined time;
 an administering means for administering the drug in accordance with the drug emission command; and
 a means for detecting an output of the drug emission command, determining from the point of this detection whether or not the indicator of the physiological state indicates a first state which does not require emission of a drug, and providing notification when the indicator of the physiological state has reached the first state.

11. A device for controlling a physiological state, comprising:
 a measuring means for measuring an indicator of a physiological state;
 a recording means for storing the indicator measured, up until a current point in time;
 a control means for outputting a drug emission command based on a current indicator of the physiological state and on a rhythm of variation in the indicator over a specified period of time;
 an administering means for administering a drug in accordance with the drug emission command; and
 a means for detecting an output of the drug emission command, determining from the point of this detection whether or not the indicator of the physiological state indicates a first state which does not require emission of a drug, and providing notification when the indicator of the physiological state has reached the first state.

12. A device for controlling a physiological state, comprising:
 a measuring means for measuring an indicator of a physiological state;
 a recording means for storing the indicator measured, up until a current point in time;
 a control means for determining in advance a time when a drug is to be administered based on circulatory indicators measured by the measuring means over a specific number of days in the past, and for outputting a drug emission command at the determined time; and
 an administering means for administering the drug in accordance with the drug emission command.

13. A device for controlling a physiological state according to claim 12, wherein the administering means comprises an infuser of the drug.

14. A device for controlling a physiological state according to claim 12, wherein the administering means comprises an emission of the drug.

15. A device for controlling a physiological state, comprising:
 a measuring means for measuring an indicator of a physiological state;
 a recording means for storing the indicator measured, up until a current point in time;
 a control means for outputting a drug emission command at a time determined in advance based on a current indicator of the physiological state and on circulatory indicators measured by the measuring means over specific number of days in the past; and
 an administering means for administering a drug in accordance with the drug emission command.

16. A device for controlling a physiological state according to claim 15, wherein the administering means comprises an infuser of the drug.

17. A device for controlling a physiological state according to claim 15, wherein the control means selects a specified time period, and outputs a command to administer a drug when the indicator during the specified time period deviates a fixed amount above a moving average obtained in the past for the indicator.

18. A device for controlling a physiological state according to claim 15, wherein the administering means comprises an emission of the drug.

19. A device for controlling a physiological state according to claims 12 or 15, further comprising a first notification means for obtaining an amount of drug administered, and providing notification when the summed value of the administered amount reaches a specified amount.

20. A device for controlling a physiological state according to claim 19, comprising a second notification means for monitoring whether or not the emission of the drug is being carried out normally, and providing notification when an anomaly is present.

21. A device for controlling a physiological state according to claim 20, the device being portable, and comprising a battery and operating based on voltage supplied from the battery, and comprising an electricity supply control means intermittently supplying the voltage output from the battery to elements in the device.

22. A device for controlling a physiological state according to claim 21, further comprising a third notification means for providing notification when the voltage output from the battery falls below a specified voltage.

23. A device for controlling a physiological state according to claims 12 or 16, further comprising a blood pulse detection means for detecting in a body a blood pulse cycle blood output from a heart, wherein the control means issues a command to administer a drug during a time interval from one blood pulse beat to a next blood pulse beat in synchronization with the blood pulse cycle.

* * * * *

UNITED STATES PATENT AND TRADEMARK OFFICE
CERTIFICATE OF CORRECTION

PATENT NO. : 6,890,304 B1
DATED : May 10, 2005
INVENTOR(S) : Kazuhiko Amano et al.

It is certified that error appears in the above-identified patent and that said Letters Patent is hereby corrected as shown below:

Column 114,
Line 60, please change "claims 12 or 16" to -- claims 12 or 15 --.

Signed and Sealed this

Twenty-fifth Day of October, 2005

JON W. DUDAS
*Director of the United States Patent and Trademark Office*